(12) United States Patent
Mazed et al.

(10) Patent No.: US 9,823,737 B2
(45) Date of Patent: Nov. 21, 2017

(54) AUGMENTED REALITY PERSONAL ASSISTANT APPARATUS

(71) Applicants: Mohammad A Mazed, Chino Hills, CA (US); Sayeeda Mazed, Chino Hills, CA (US)

(72) Inventors: Mohammad A Mazed, Chino Hills, CA (US); Sayeeda Mazed, Chino Hills, CA (US)

( * ) Notice: Subject to any disclaimer, the term of this patent is extended or adjusted under 35 U.S.C. 154(b) by 331 days.

(21) Appl. No.: 14/120,835

(22) Filed: Jul. 1, 2014

(65) Prior Publication Data

US 2016/0004298 A1 Jan. 7, 2016
US 2016/0334866 A9 Nov. 17, 2016

Related U.S. Application Data

(63) Continuation-in-part of application No. 13/448,378, filed on Apr. 16, 2012, and a continuation-in-part of
(Continued)

(51) Int. Cl.
| | |
|---|---|
| *G09G 3/00* | (2006.01) |
| *G06K 9/00* | (2006.01) |
| *H04N 5/225* | (2006.01) |
| *G06T 19/00* | (2011.01) |
| *G06F 3/01* | (2006.01) |
| *G10L 15/26* | (2006.01) |
| *H04N 5/33* | (2006.01) |
| *G06F 3/041* | (2006.01) |
| *G06F 19/00* | (2011.01) |
| *H04W 4/02* | (2009.01) |
| *A61B 90/00* | (2016.01) |

(Continued)

(52) U.S. Cl.
CPC .............. *G06F 3/011* (2013.01); *G06F 3/013* (2013.01); *G06F 3/017* (2013.01); *G06F 3/041* (2013.01); *G06F 19/70* (2013.01); *G06K 9/00268* (2013.01); *G06K 9/00671* (2013.01); *G06T 19/006* (2013.01); *G09G 3/00* (2013.01); *G09G 3/001* (2013.01); *G10L 15/26* (2013.01); *H04N 5/225* (2013.01); *H04N 5/33* (2013.01); *A61B 2090/365* (2016.02); *G09G 3/346* (2013.01); *G09G 2380/08* (2013.01); *G10L 15/00* (2013.01); *H01L 2224/48091* (2013.01); *H04W 4/02* (2013.01)

(58) Field of Classification Search
CPC ......... G06T 19/006; G06T 2207/20212; G06T 2207/20221; G06K 9/00671; H04N 2201/3245; A61B 2090/365
USPC .................................................. 345/632, 633
See application file for complete search history.

(56) References Cited

U.S. PATENT DOCUMENTS

| 7,751,896 B2* | 7/2010 | Graf .................... A61N 1/36046 607/54 |
| 8,768,141 B2* | 7/2014 | Chan ........................ H04N 5/77 386/224 |

(Continued)

*Primary Examiner* — John Villecco

(57) ABSTRACT

Various embodiments of an intelligent augmented reality personal assistant apparatus integrated (or co-packaged) with an eye motion sensor, a microprocessor or an intelligent microprocessor and an intelligent rendering algorithm are disclosed. Such an augmented reality personal assistant apparatus can interpret/analyze/learn activities, communication or contextual information of a user and recommend relevant and useful information to the user.

20 Claims, 80 Drawing Sheets

Related U.S. Application Data application No. 13/663,376, filed on Oct. 29, 2012, now Pat. No. 9,557,271, which is a continuation-in-part of application No. 13/135,832, filed on Jul. 15, 2011, now abandoned, which is a continuation-in-part of application No. 12/573,012, filed on Oct. 2, 2009, now Pat. No. 8,017,147, which is a continuation-in-part of application No. 12/390,302, filed on Feb. 20, 2009, now abandoned, which is a continuation-in-part of application No. 12/169,523, filed on Jul. 8, 2008, now abandoned, application No. 14/120,835, filed on Jul. 1, 2014, which is a continuation-in-part of application No. 12/238,286, filed on Sep. 25, 2008, now abandoned.

(60) Provisional application No. 61/957,343, filed on Jul. 1, 2013, provisional application No. 61/517,204, filed on Apr. 15, 2011, provisional application No. 61/742,074, filed on Aug. 1, 2012, provisional application No. 61/631,071, filed on Dec. 27, 2011, provisional application No. 61/274,306, filed on Aug. 14, 2009, provisional application No. 61/043,059, filed on Apr. 7, 2008.

(51) Int. Cl.
  *G10L 15/00* (2013.01)
  *G09G 3/34* (2006.01)

(56) References Cited

U.S. PATENT DOCUMENTS

| Patent/Pub No. | | Date | Inventor | Class |
|---|---|---|---|---|
| 8,885,422 | B2* | 11/2014 | Ribeiro | G11C 5/02 365/189.17 |
| 9,077,647 | B2* | 7/2015 | Fein | G06F 3/048 |
| 9,326,710 | B1* | 5/2016 | Liu | A61B 5/14546 |
| 9,331,278 | B2* | 5/2016 | Yang | H01L 45/1633 |
| 9,332,935 | B2* | 5/2016 | Etzkorn | A61B 5/682 |
| 2003/0179094 | A1* | 9/2003 | Abreu | A61B 5/0002 340/573.1 |
| 2004/0116794 | A1* | 6/2004 | Fink | A61B 3/16 600/398 |
| 2004/0186366 | A1* | 9/2004 | Leonardi | G02C 7/04 600/398 |
| 2008/0147954 | A1* | 6/2008 | Mouttet | G06F 7/607 710/317 |
| 2009/0163826 | A1* | 6/2009 | Mouttet | G11C 11/54 600/544 |
| 2010/0110372 | A1* | 5/2010 | Pugh | B29D 11/00009 351/159.75 |
| 2010/0169108 | A1* | 7/2010 | Karkanias | G06Q 50/22 705/2 |
| 2011/0076810 | A1* | 3/2011 | Xia | H01L 27/0688 438/129 |
| 2011/0194195 | A1* | 8/2011 | Zalevsky | G02B 5/1895 351/159.04 |
| 2012/0007038 | A1* | 1/2012 | Strukov | H01L 27/0207 257/5 |
| 2012/0019557 | A1* | 1/2012 | Aronsson | G06T 11/00 345/633 |
| 2012/0026776 | A1* | 2/2012 | Yan | G11C 13/0002 365/148 |
| 2012/0075574 | A1* | 3/2012 | Pugh | A61F 9/023 351/158 |
| 2012/0194418 | A1* | 8/2012 | Osterhout | G02B 27/0093 345/156 |
| 2012/0224070 | A1* | 9/2012 | Burroff | H04N 5/23219 348/207.1 |
| 2012/0236623 | A1* | 9/2012 | Qureshi | G11C 13/0007 365/148 |
| 2012/0245444 | A1* | 9/2012 | Otis | A61B 5/1486 600/345 |
| 2013/0009993 | A1* | 1/2013 | Horseman | G06F 19/3418 345/633 |
| 2013/0023106 | A1* | 1/2013 | Pickett | G11C 13/0002 438/382 |
| 2013/0041245 | A1* | 2/2013 | Cerboni | A61B 5/6821 600/398 |
| 2013/0114329 | A1* | 5/2013 | Nickel | H01L 27/101 365/148 |
| 2013/0137076 | A1* | 5/2013 | Perez | G09B 5/06 434/308 |
| 2013/0194540 | A1* | 8/2013 | Pugh | A61F 2/1635 351/159.03 |
| 2014/0009623 | A1* | 1/2014 | Lai | G06F 3/017 348/169 |
| 2014/0139551 | A1* | 5/2014 | McCulloch | G09G 5/377 345/633 |
| 2014/0160157 | A1* | 6/2014 | Poulos | G06F 3/011 345/633 |
| 2014/0160424 | A1* | 6/2014 | Benko | G06F 1/163 351/158 |
| 2014/0176603 | A1* | 6/2014 | Kumar | G06F 3/011 345/633 |
| 2014/0222526 | A1* | 8/2014 | Shakil | G06Q 50/22 705/7.38 |
| 2014/0225918 | A1* | 8/2014 | Mittal | G06F 3/017 345/633 |
| 2014/0247343 | A1* | 9/2014 | Chen | G02B 27/017 348/135 |
| 2014/0306994 | A1* | 10/2014 | Brown | G06T 19/006 345/633 |
| 2014/0368532 | A1* | 12/2014 | Keane | G02B 27/017 345/619 |
| 2015/0128096 | A1* | 5/2015 | Rizvi | G02B 27/017 715/863 |
| 2015/0161344 | A1* | 6/2015 | Chung | H04L 67/10 705/2 |
| 2015/0219899 | A1* | 8/2015 | Mack | G02B 27/0172 345/633 |
| 2015/0235473 | A1* | 8/2015 | Schowengerdt | G06T 19/006 345/633 |
| 2015/0324645 | A1* | 11/2015 | Jang | G06F 3/012 345/633 |
| 2015/0338915 | A1* | 11/2015 | Publicover | H04N 5/23229 345/633 |
| 2015/0358614 | A1* | 12/2015 | Jin | G02B 27/017 348/49 |
| 2016/0003760 | A1* | 1/2016 | Etzkorn | A61B 5/14507 205/122 |
| 2016/0174913 | A1* | 6/2016 | Somanath | A61B 5/747 600/301 |

* cited by examiner

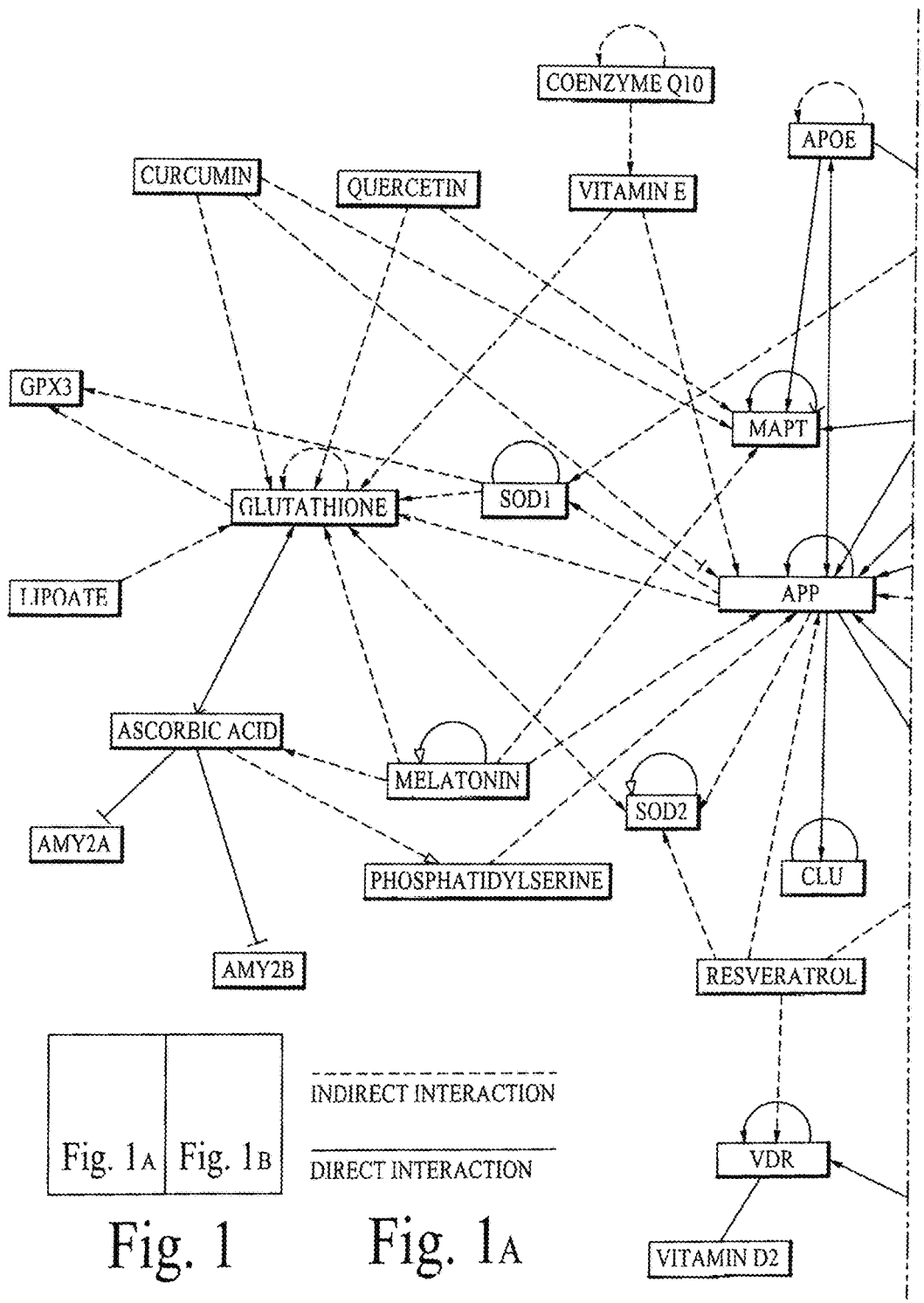

INDIRECT INTERACTION
DIRECT INTERACTION

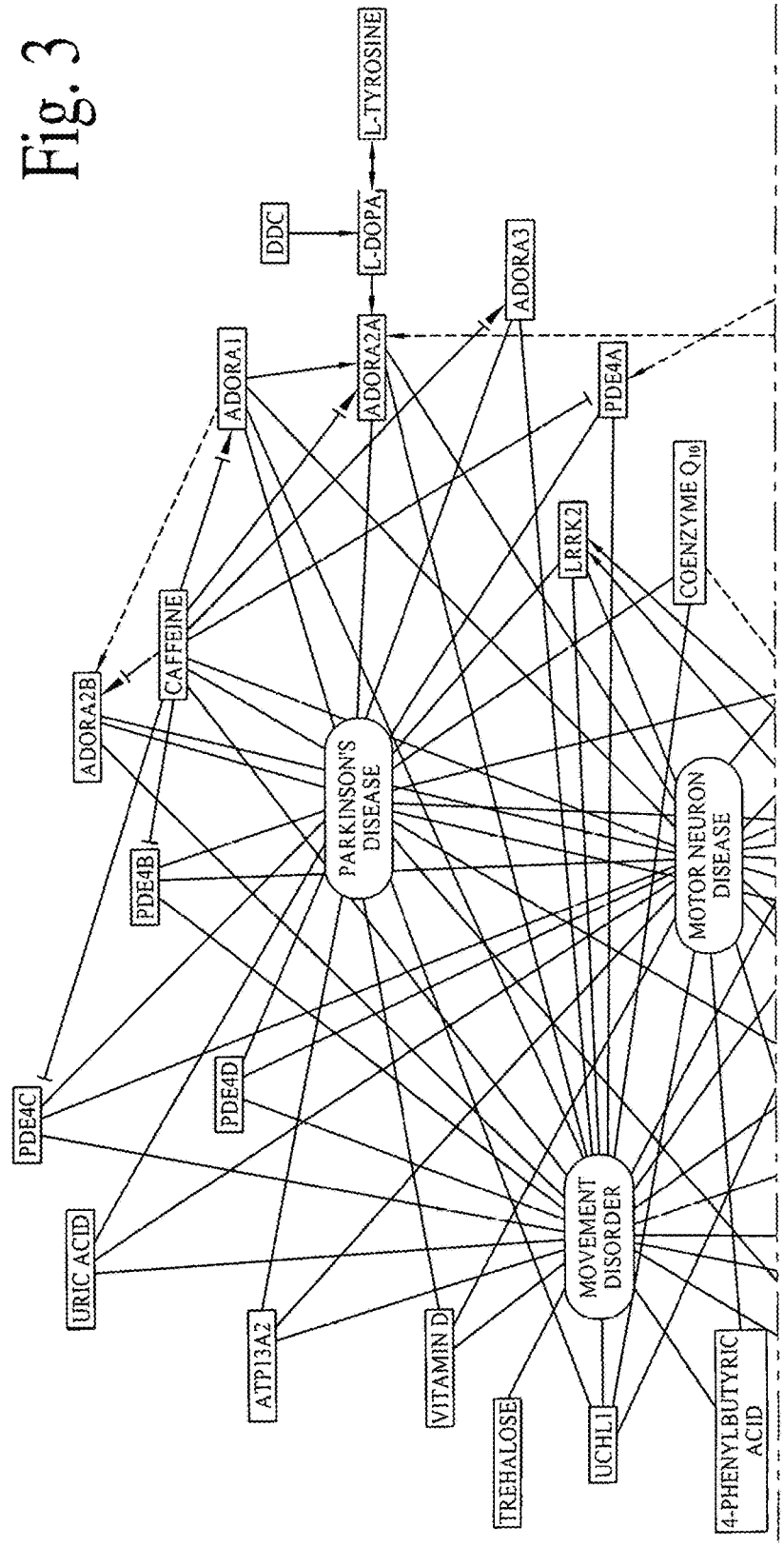

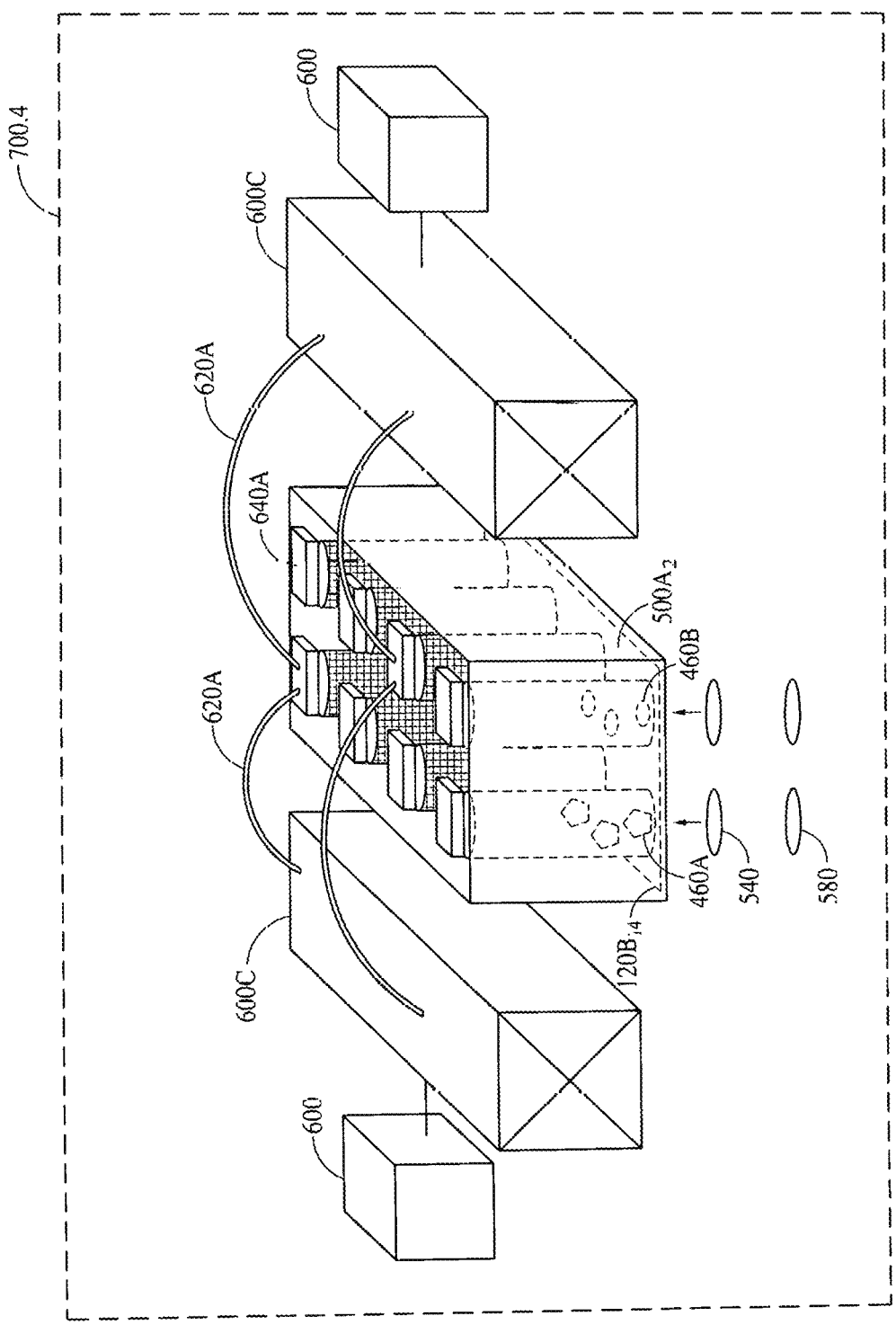
Fig. 12_G

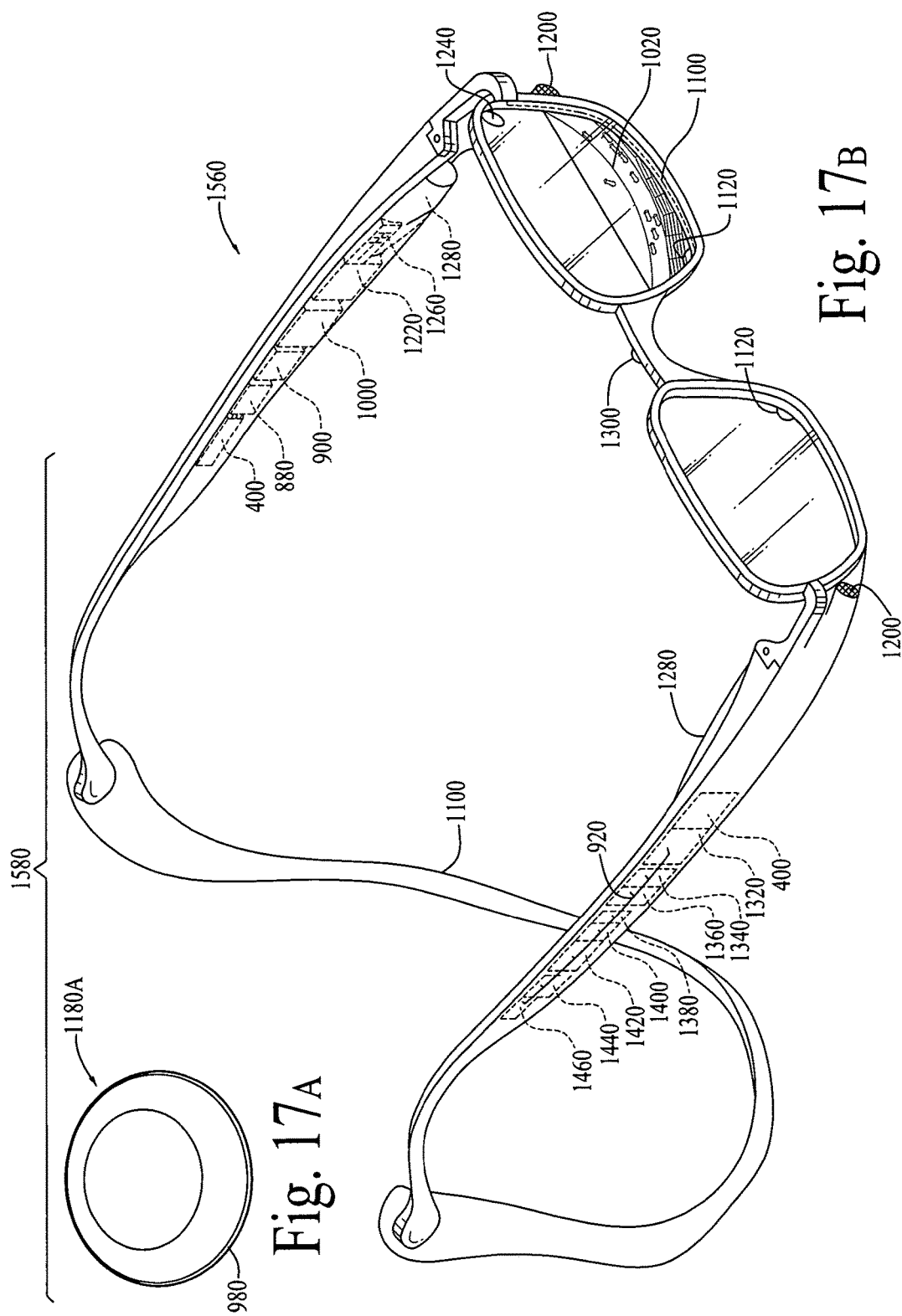

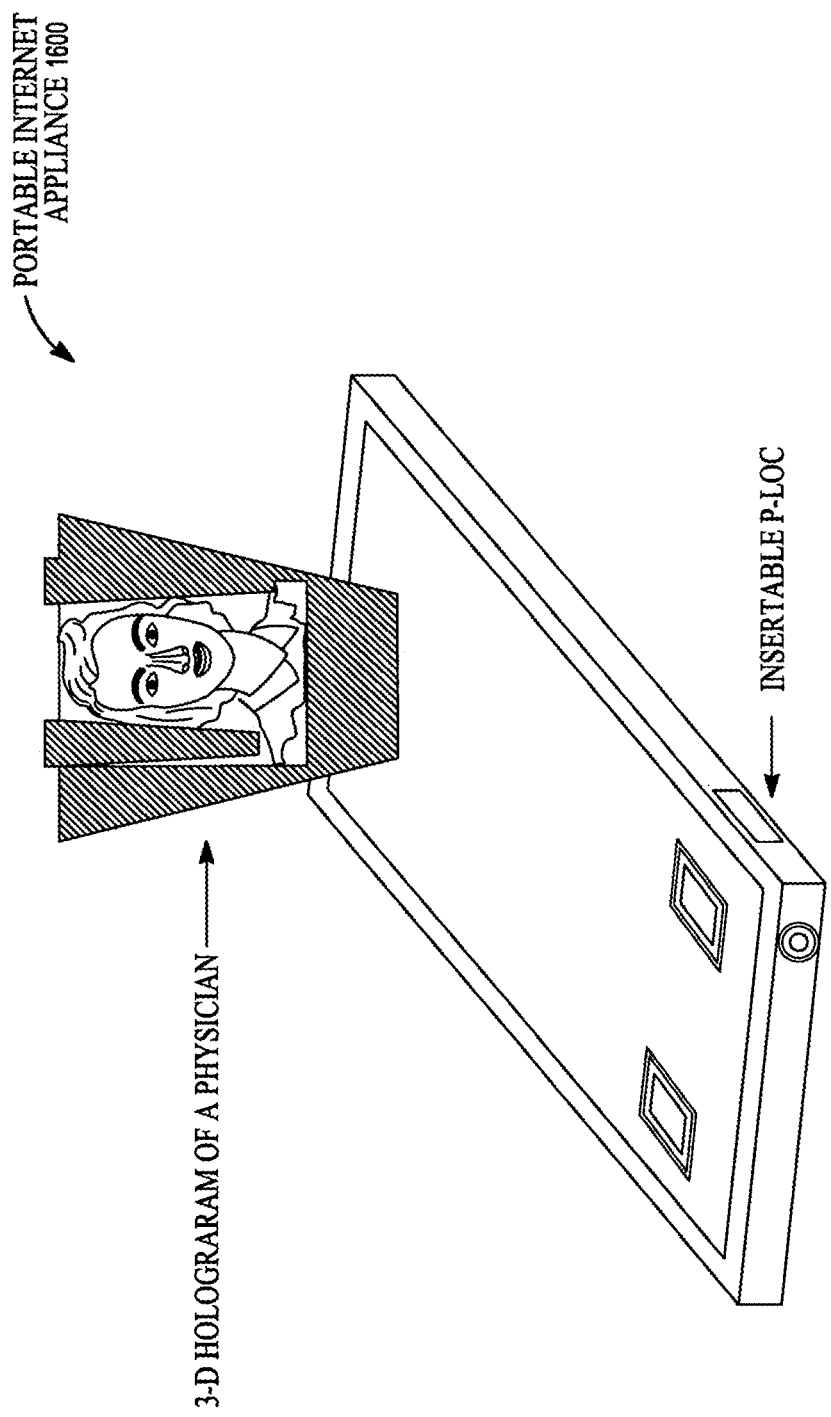

FIG. 25

AUGMENTED REALITY PERSONAL ASSISTANT APPARATUS

CROSS REFERENCE OF RELATED APPLICATIONS

The present application claims priority to: U.S. Provisional Patent Application No. 61/957,343 entitled "AUGMENTED REALITY PERSONAL ASSISTANT", filed on Jul. 1, 2013. The present application is a continuation-in-part (CIP) of U.S. Non-Provisional patent application Ser. No. 13/448,378 entitled "SYSTEM AND METHOD FOR INTELLIGENT SOCIAL COMMERCE", filed on Apr. 16, 2012. Furthermore, the present application is a continuation-in-part (CIP) of U.S. Non-Provisional patent application Ser. No. 13/663,376 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Oct. 29, 2012, (which claims priority to: U.S. Provisional Patent Application No. 61/742,074 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Aug. 1, 2012; U.S. Provisional Patent Application No. 61/631,071 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Dec. 27, 2011; and U.S. Provisional Patent Application No. 61/628,060 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Oct. 24, 2011), which is a continuation-in-part (CIP) of U.S. Non-Provisional patent application Ser. No. 13/135,832 entitled "CHEMICAL COMPOSITION AND ITS DELIVERY FOR LOWERING THE RISKS OF ALZHEIMER'S, CARDIOVASCULAR AND TYPE-2 DIABETES DISEASES", filed on Jul. 15, 2011, which is a continuation-in-part (CIP) of U.S. Non-Provisional patent application Ser. No. 12/573,012 entitled, "NUTRITIONAL SUPPLEMENT FOR THE PREVENTION OF CARDIOVASCULAR DISEASE, ALZHEIMER'S DISEASE, DIABETES AND REGULATION AND REDUCTION OF BLOOD SUGAR AND INSULIN RESISTANCE", filed on Oct. 2, 2009, wherein the Ser. No. 12/573,012 application resulted in an issuance of U.S. Pat. No. 8,017,147 on Sep. 13, 2011. The present application is a continuation-in-part (CIP) of U.S. Non-Provisional patent application Ser. No. 12/238,286 entitled, "PORTABLE INTERNET APPLIANCE", filed on Sep. 25, 2008.

The entire contents of all Non-Provisional Patent Applications and Provisional Patent Applications as listed in the previous paragraph are hereby incorporated by reference.

FIELD OF THE INVENTION

The present invention generally relates to (a) chemical compositions for lowering the risks of Alzheimer's, Cardiovascular and Diabetes diseases, (b) delivery (nanodelivery and molecular coupling) of bioactive compounds and/or bioactive molecules and (c) disease diagnostics (molecular nanodiagnostics).

The present invention also relates to (d) a wearable augmented reality subsystem, (e) a wearable subsystem and (f) a portable internet appliance in healthcare; when connected with ambient/always on sensors.

BACKGROUND OF THE INVENTION

One of the most intriguing discoveries is that many risk factors for Cardiovascular, Type-1 Diabetes and Type-2 Diabetes diseases can be risk factors for Alzheimer's disease (also known as Type-3 Diabetes disease). High blood cholesterol levels are important risk factors for Alzheimer's disease. If blood flow is restricted because of plaque accumulation/buildup in a human brain, less oxygen gets to a human brain and fewer waste residues leave a human brain.

Type-1 Diabetes disease can be caused by autoimmune destruction of insulin-producing cells in the pancreas, resulting in high blood sugar. The drugs that block effector-memory T cells can delay and/or prevent Type-1 Diabetes disease.

Type-2 Diabetes disease can be linked to excessive iron, diseased pancreas and metabolic syndrome/obesity-hence macrophages in fat tissues. The macrophages in fat tissues produce cytokine molecules, which can cause inflammations in the pancreas. Such inflammations in the pancreas can increase the insulin (a hormone needed to convert carbohydrates, foods and glucose into energy needed for daily life) resistance and gradually the pancreas loses its ability to produce insulin. Type-2 Diabetes disease is marked by high levels of blood glucose resulting from defects in glucose production and/or glucose inaction and/or insulin production and/or insulin inaction. Type-2 Diabetes disease and obesity can be linked with cryptochrome, a protein. Cryptochrome can regulate/modulate/synchronize the biological clock and glucose level in a human body. An increased level of cryptochrome can suppress/inhibit the production of enzymes (in the liver) for glucose generation during fasting (gluconeogenesis). Bioactive compounds and/or bioactive molecules that enhance the activity of calcineurin/NFAT can be effective against Type-2 Diabetes disease, wherein the beta cells do not produce enough insulin. Type-2 Diabetes disease is caused by insufficient numbers of insulin-producing beta cells. But Type-2 Diabetes disease not only lacks insulin, but also produces too much glucagon. Normally, about 50% of the insulin produced by the pancreas is immediately destroyed by the liver; but there may be a mechanism to regulate how much insulin enters the bloodstream. Insulin degrading enzyme (IDE) is a protease, an enzyme that chops proteins or peptides into smaller pieces. If insulin degrading enzyme is inhibited, insulin can remain in the blood stream longer. Insulin is involved in a surprisingly wide range of important processes, including memory and cognition, thus insulin degrading enzyme inhibitors may have multiple therapeutic applications. Insulin degrading enzyme is a thiol-sensitive zinc-metallopeptidase.

Both Type-1 and Type-2 Diabetes diseases can lead to serious complications (e.g., high blood pressure, kidney disease and premature death). But people with Type-1 and Type-2 Diabetes diseases can control/manage the diseases to lower the risks of serious complications.

The risk of Alzheimer's disease can be linked with obesity and Type-2 Diabetes disease. SorCS1 transport protein can control how the insulin receptor moves around a cell/neuron. Deficiency in SorCS1 transport protein can increase the risk of developing Alzheimer's disease, because amyloid precursor protein (APP) spends too much time in the region of the neuron wherein amyloid precursor protein is broken down into amyloid beta protein. A human brain has a low antioxidant level and requires a large volume of blood pumped through it to function properly. The biochemical reaction of glucose (in blood) with proteins is known as glycation. Glycation can cause problems in a human brain. The glucose molecule can be split/divided open by enzymes for energy consumption in a human brain and two (2) reactive aldehydes can crosslink with proteins in a human brain-thus leading to a decreased blood flow. Another possible link is leptin, a hormone. Leptin is released by fat cells in a human body and acts on the leptin receptors in a human brain to regulate hunger. There are a number of leptin receptors all over a human body including in the hypothalamus of a human brain. Higher level of leptin can suppress appetite and enhance metabolism. Leptin also plays a key role in modulating insulin. But obesity can create leptin resistance-thus leptin is not transported efficiently in a human brain. Higher levels of leptin in a human brain may lower the risk of developing Alzheimer's disease. Leptin can also reduce the production of amyloid beta protein, wherein amyloid beta protein is involved in Alzheimer's disease. Although obesity is often associated with insulin resistance and Diabetes disease, this is not always the case. However, when T-bet protein is absent, the relationship between fat and insulin resistance can be altered. T-bet is a protein that regulates the differentiation and function of immune cells.

Clinical and epidemiological studies have found that Type-2 Diabetes disease and hyperinsulinaemia, increased the risk of developing Alzheimer's disease. The link between hyperinsulinaemia and Alzheimer's disease may be insulin degrading enzyme. This enzyme degrades both insulin and amylin peptides related to the pathology of Type-2 Diabetes disease along with amyloid-beta peptide, a short peptide found in excess in the Alzheimer's brain.

SUMMARY OF THE INVENTION

Chemical Compositions

The present invention relates to chemical compositions (various embodiments) of bioactive compounds for lowering the risks of Alzheimer's, Cardiovascular and Diabetes diseases.

Furthermore, the present invention relates to a chemical composition of a sugar free sweetener for people with Type-2 Diabetes disease.

Furthermore, the present invention relates to various chemical compositions (various embodiments) of a sugar free super-sweetener for people with Type-2 Diabetes disease.

Passive Delivery

The present invention relates to passive delivery (various embodiments) of bioactive compounds and/or bioactive molecules.

Active Delivery

The present invention relates to active delivery (various embodiments) of bioactive compounds and/or bioactive molecules.

Nanodelivery/Molecular Coupling

The present invention relates to targeted nanodelivery and molecular coupling (various embodiments) of bioactive compounds and/or bioactive molecules.

Diagnostics

The present invention relates to a photonic crystal cavity based integrated optical diagnostics biomodule to detect a disease specific biomarker/an array of disease specific biomarkers.

Furthermore, the present invention relates to various microcapillary based integrated optical diagnostics biomodules to detect a disease specific biomarker/an array of disease specific biomarkers.

Furthermore, the present invention relates to various field effect transistor (FET) based integrated electrical diagnostics biomodules to detect a disease specific biomarker/an array of disease specific biomarkers.

Furthermore, the present invention relates to a nanohole based single molecule DNA/RNA sequencing electrical diagnostics biomodule to detect a disease specific biomarker/an array of disease specific biomarkers.

Furthermore, the present invention relates to an x-ray fluorescence diagnostics biomodule for detection of a disease specific biomarker/an array of disease specific biomarkers.

Furthermore, the present invention relates to a retinal contact lens subsystem to detect a disease specific biomarker/an array of disease specific biomarkers.

Furthermore, the present invention relates to a plasmonic interferometer based integrated optical diagnostics biomodule to detect a disease specific biomarker/an array of disease specific biomarkers.

Diagnostics-Delivery System

The present invention relates to an integrated bioelectronics subsystem to detect a disease specific biomarker/an array of disease specific biomarkers and actively deliver bioactive compounds and/or bioactive molecules.

Furthermore, the present invention relates to a retinal contact lens subsystem to deliver bioactive compounds and/or bioactive molecules.

Lab-On-Chip (LOC) Diagnostics

The present invention relates to various Lab-on-Chip subsystems and their applications in personalized healthcare.

Wearable Augmented Reality Subsystem with Connected Ambient/Always on Sensors

The present invention relates to a wearable augmented reality subsystem with connected ambient/always on sensors and its applications in personalized healthcare.

Wearable Subsystem with Connected Ambient/Always on Sensors

The present invention relates to a wearable subsystem with connected ambient/always on sensors and its applications in personalized healthcare.

Portable Internet Appliance with Connected Ambient/Always on Sensors

The present invention relates to a portable Internet appliance with connected ambient/always on sensors and its applications in personalized healthcare.

BRIEF DESCRIPTION OF THE TABLES

The present invention is better understood upon consideration of the description in conjunction with the following Tables and Figures.

Table-1A and Table-1B, wherein each table illustrates a composition of a mixture of micronutrients. Table-1C illustrates a composition of a mixture of micronutrients for topical use. Table-1D, Table-1E, Table-1F, Table-1G, Table-1H, Table-1I, Table-1J and Table-1K, wherein each table illustrates a composition of a mixture of micronutrients.

Table-2A and Table-2B, wherein each table illustrates a composition of a mixture of antioxidants.

Table-3A illustrates a composition of a multi-serve antioxidant liquid. Table-3B and Table-3C, wherein each table illustrates a composition of a single-serve antioxidant liquid.

Table-3D illustrates a composition of a mixture of botanicals. Table-3E illustrates a composition of a mixture of electrolytes and dextrose.

Table-4 illustrates a composition of a biodegradable plastic material.

Table-5 illustrates a composition of a mixture for expression of beneficial $NrF_2$ protein.

Table-6 illustrates molecular docking score with the mammalian target of Rapamycin (mTOR), utilizing computational chemistry software.

Table-7A, Table-7B, Table-7C and Table-7D, wherein each table illustrates a composition of a mixture for suppressing/inhibiting the mammalian target of Rapamycin.

Table-8A, Table-8B, Table-8C, Table-8D and Table-8E, wherein each table illustrates a composition of a mixture for lowering the risks of Alzheimer's disease.

Table-9 illustrates a composition of a mixture for lowering the risks of Cardiovascular disease.

Table-10A, Table-10B, Table-10C and Table-10D, wherein each table illustrates a composition of a mixture for lowering the risks of Type-2 Diabetes disease.

Table-11 illustrates a composition of a mixture of sugar free sweetener for people with Type-2 Diabetes disease.

Table-12A, Table-12B, Table-12C, Table-12D, Table-12E, Table-12F, Table-12G, Table-12H, Table-12I, Table-12J, Table-12K, Table-12L and Table-12M, wherein each table illustrates a composition of a mixture of sugar free super-sweetener for people with Type-2 Diabetes disease.

Table-13A, Table-13B, Table-13C, Table-13D, Table-13E, Table-13F, Table-13G, Table-13H, Table-13I, Table-13J, Table-13K, Table-13L, Table-13M, Table-13N, Table-13O, Table-13P, Table-13Q, Table-13R, Table-13S, Table-13T, Table-13U, Table-13V and Table-13W, wherein each table illustrates a composition of a mixture of chewable/soluble strip for health.

Table-14A illustrates various compositions of a biodegradable scaffold. Table-14B illustrates various compositions of a biodegradable scaffold, integrated with various nanowire field effect transistors.

Table-15 illustrates a composition of a biodegradable plastic material.

Table-16A illustrates various compositions for a nanostructured mesh. Table-16B illustrates various compositions for a nanostructured mesh, integrated with various nanowire field effect transistors.

BRIEF DESCRIPTION OF THE FIGURES

FIG. 1 illustrates graphical interactions of Alzheimer's disease related genes/proteins with a set of bioactive compounds (e.g., an antioxidant, enzymatic antioxidant, enzyme, micronutrient (mineral/vitamin) and drug) and/or bioactive molecules (e.g., enzyme molecule, protein molecule, small molecule, therapeutic molecule, DNA, gene, ribozyme, RNA, messenger RNA (mRNA), micro RNA (miRNA), piwi-interacting RNA (piRNA) and small interfering RNA (siRNA)), according to comprehensive biological pathway analysis (BPA) software. FIG. 1A illustrates a section of FIG. 1

FIG. 2 illustrates graphical interactions of Alzheimer's, Dementia and Parkinson's disease related genes/proteins with a set of bioactive compounds and/or bioactive molecules, according to a comprehensive biological pathway analysis software.

FIG. 3 illustrates graphical interactions of Alzheimer's, Dementia and Parkinson's disease related genes/proteins with a set of bioactive compounds and/or bioactive molecules, according to comprehensive biological pathway analysis software. FIG. 3A illustrates a section of FIG. 3

FIG. 4 illustrates graphical interactions of Type-2 Diabetes disease related genes/proteins with a set of bioactive compounds and/or bioactive molecules, according to a comprehensive biological pathway analysis software.

FIGS. 12D, 12E, 12F and 12G illustrate (an array of microcapillaries based) integrated optical diagnostics biomodules (various other embodiments) to detect up to two (2) million or more disease specific biomarkers.

FIGS. 17A, 17B, 17C and 17D illustrate a near real-time/real-time wearable bioelectronics subsystem, as an augmented reality personal assistant to eavesdrop on a user's communication and anonymously recommend a solution to the user.

FIG. 20 illustrates an insertable photonics-lab-on-chip into the portable Internet appliance. FIG. 20 also illustrates interactions with a hologram utilizing the portable internet appliance.

FIG. 25 illustrates a social graph of a user.

DETAIL DESCRIPTION OF THE INVENTION

Bioactive Compounds &/or Bioactive Molecules Interactions with Genes/Proteins

Figure 1B:
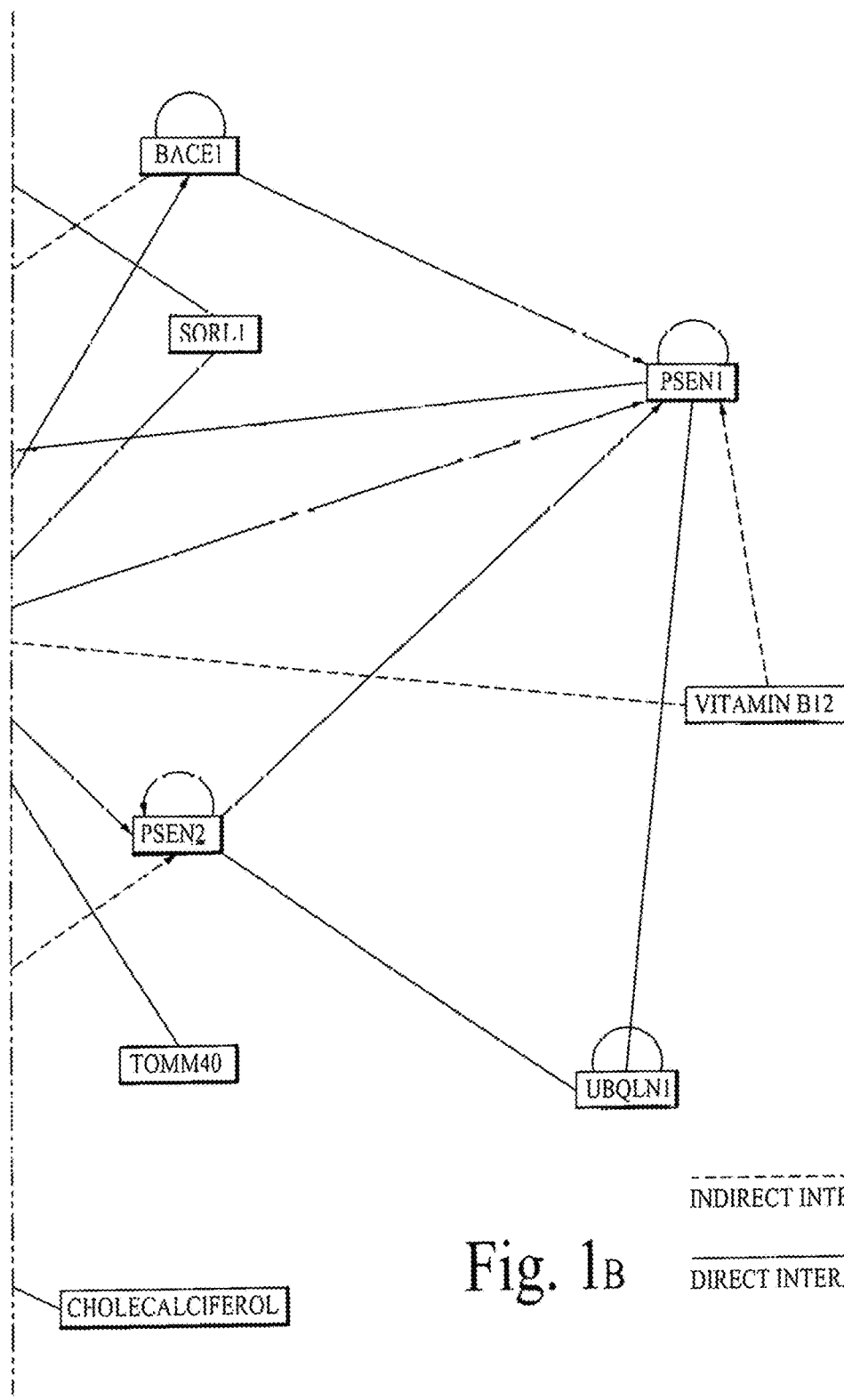
FIG. 1B illustrates a section of FIG. 1, wherein both sections are separated by a dotted line.

FIG. 1 illustrates direct and indirect graphical interactions of Alzheimer's disease related genes/proteins (e.g., APOE, APP, BACE1, CLU, MAPT/TAU, PSEN1, PSEN2, SORL1, TOMM40 and UBQLN1) with a set of bioactive compounds and/or bioactive molecules, utilizing a comprehensive biological pathway analysis software. FIG. 1A illustrates a section of FIG. 1 and FIG. 1B illustrates a section of FIG. 1, wherein both sections are separated by a dotted line.

Figure 2A:
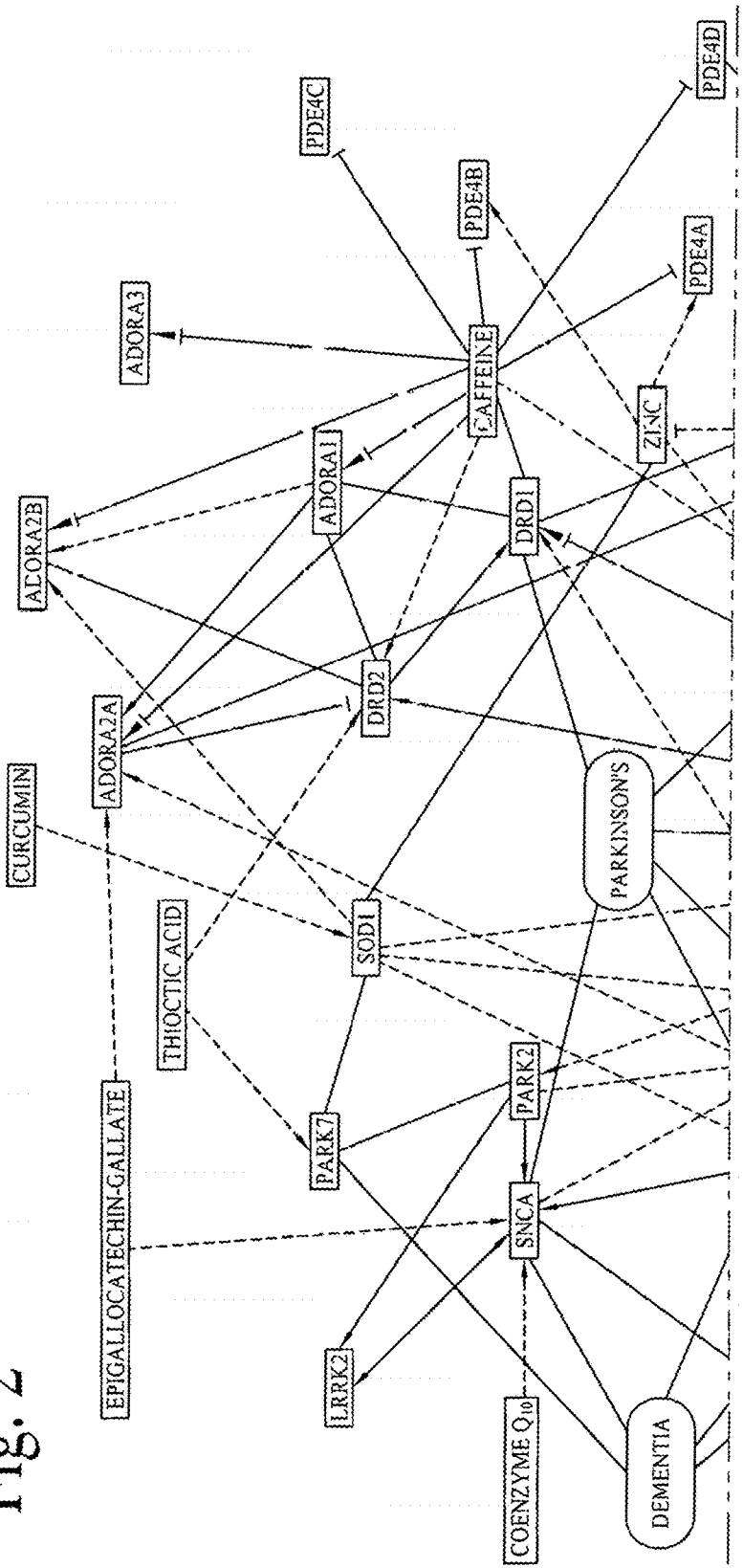
FIG. 2A illustrates a section of FIG. 2
Figure 2B:
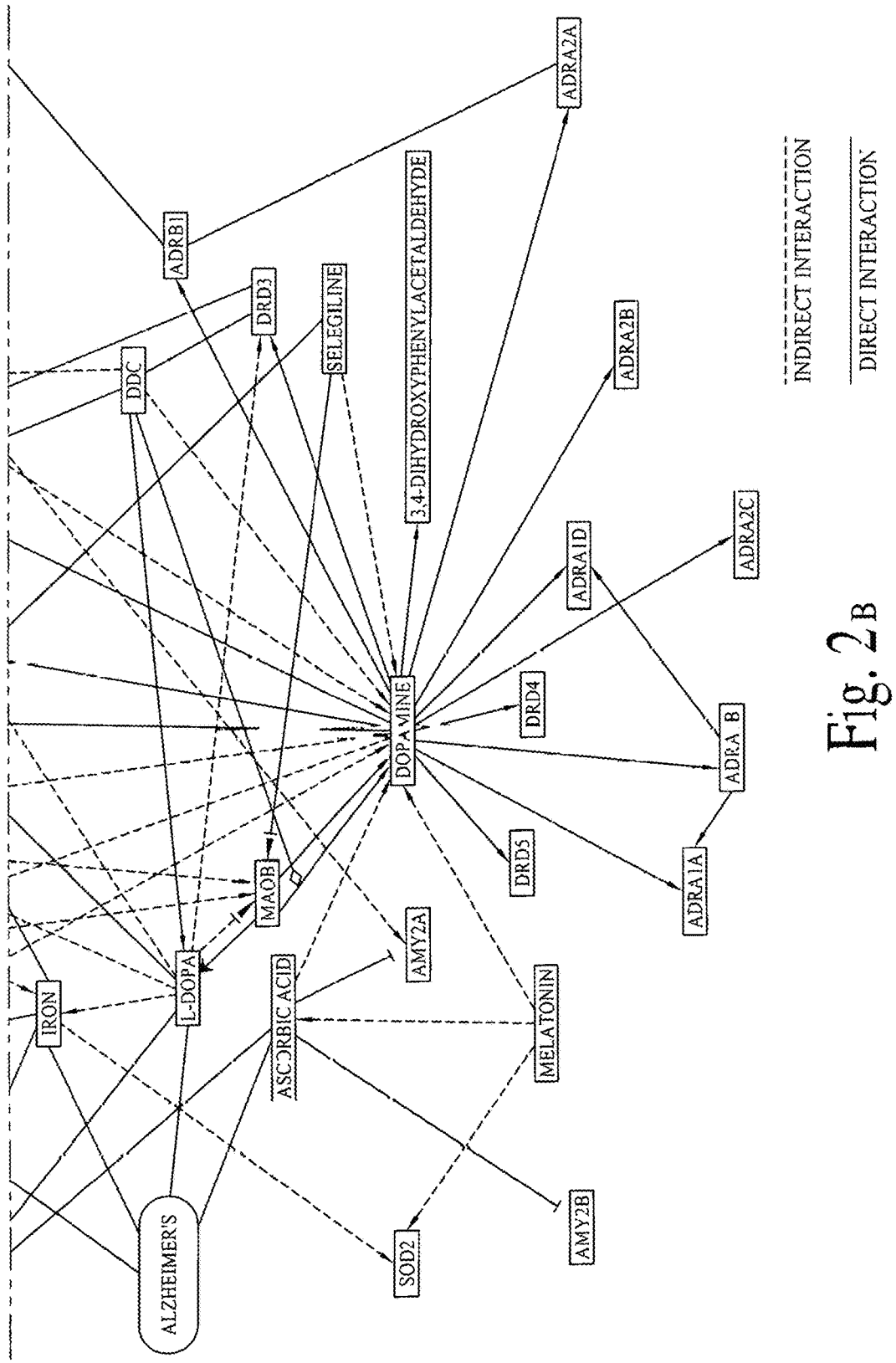
FIG. 2B illustrates a section of FIG. 2, wherein both sections are separated by a dotted line.
Figure 3B:
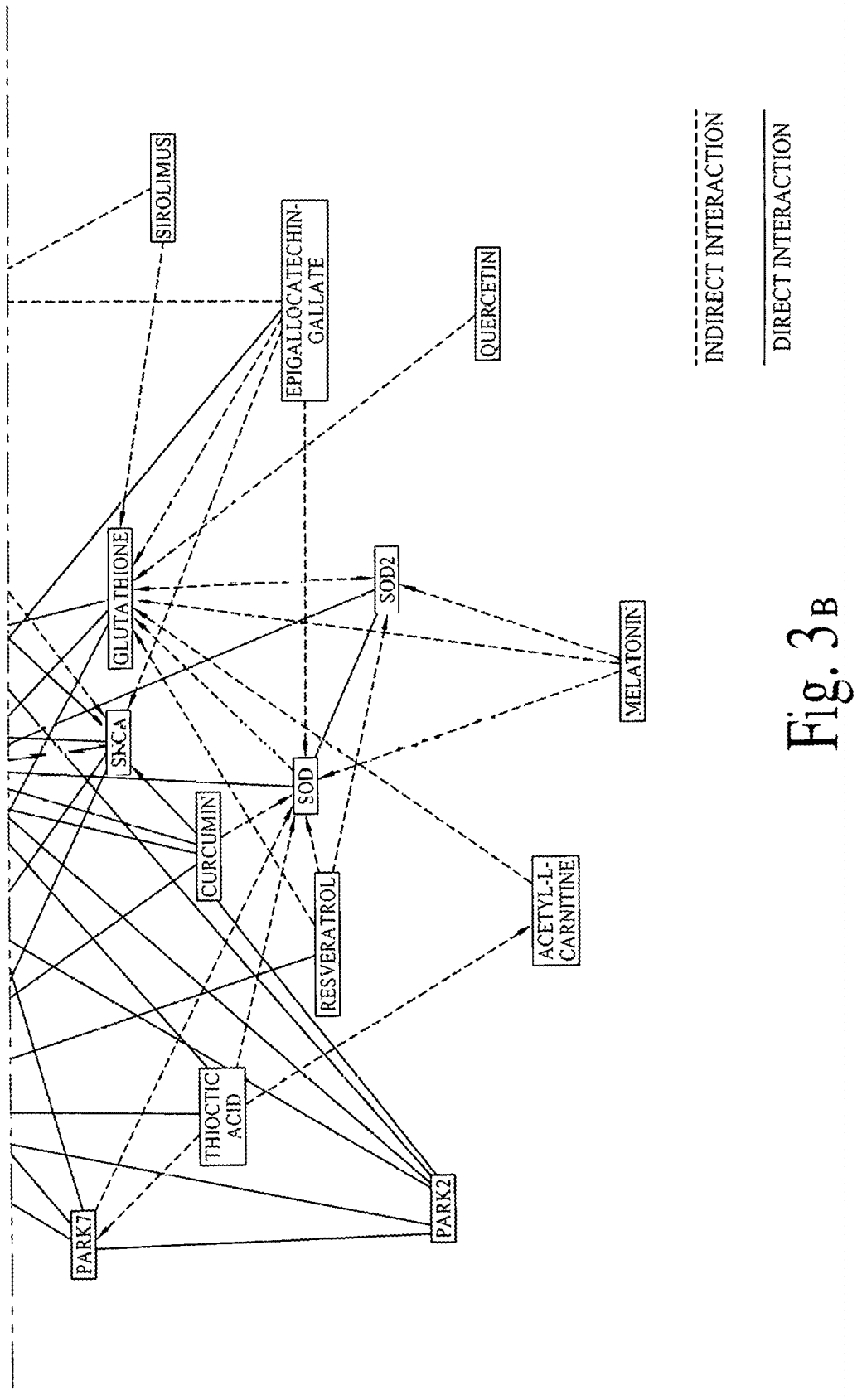
FIG. 3B illustrates a section of FIG. 3, wherein both sections are separated by a dotted line.

FIG. 2 illustrates direct and indirect graphical interactions of Alzheimer's, Dementia and Parkinson's disease related genes/proteins (e.g., DOPAMINE, LRRK2, MAOB, PARK2 and SNCA) with a set of bioactive compounds and/or bioactive molecules, utilizing comprehensive biological pathway analysis software. FIG. 2A illustrates a section of FIG. 2 and FIG. 2B illustrates a section of FIG. 2, wherein both sections are separated by a dotted line. FIG. 3 illustrates direct and indirect graphical interactions of Alzheimer's, Dementia and Parkinson's disease related genes/proteins (e.g., DOPAMINE, LRRK2, MAOB, PARK2 and SNCA) with a set of bioactive compounds and/or bioactive molecules, utilizing comprehensive biological pathway analysis software. FIG. 3A illustrates a section of FIG. 3 and FIG. 3B illustrates a section of FIG. 3, wherein both sections are separated by a dotted line.

Figure 4A:
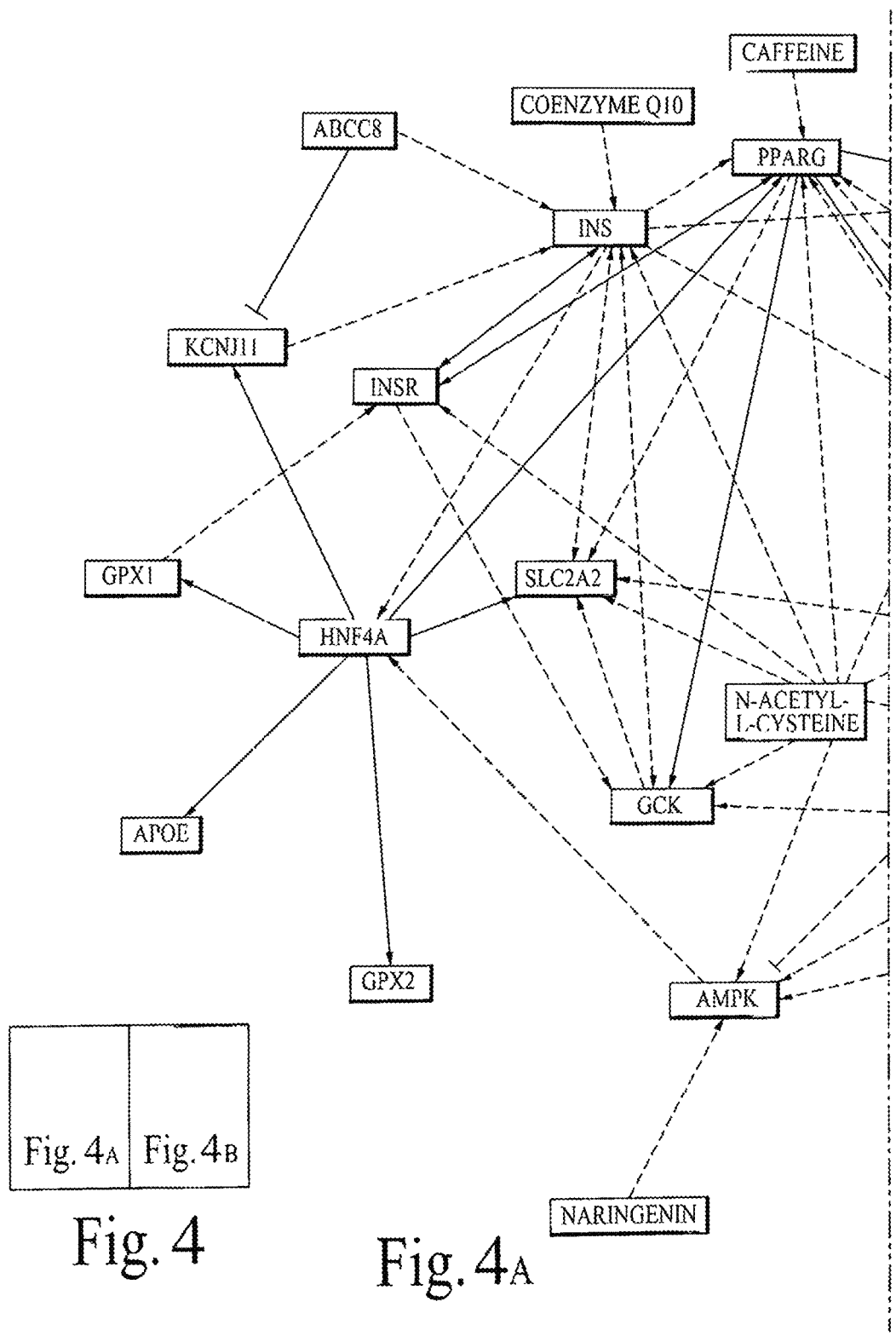
FIG. 4A illustrates a section of FIG. 4
Figure 4B:
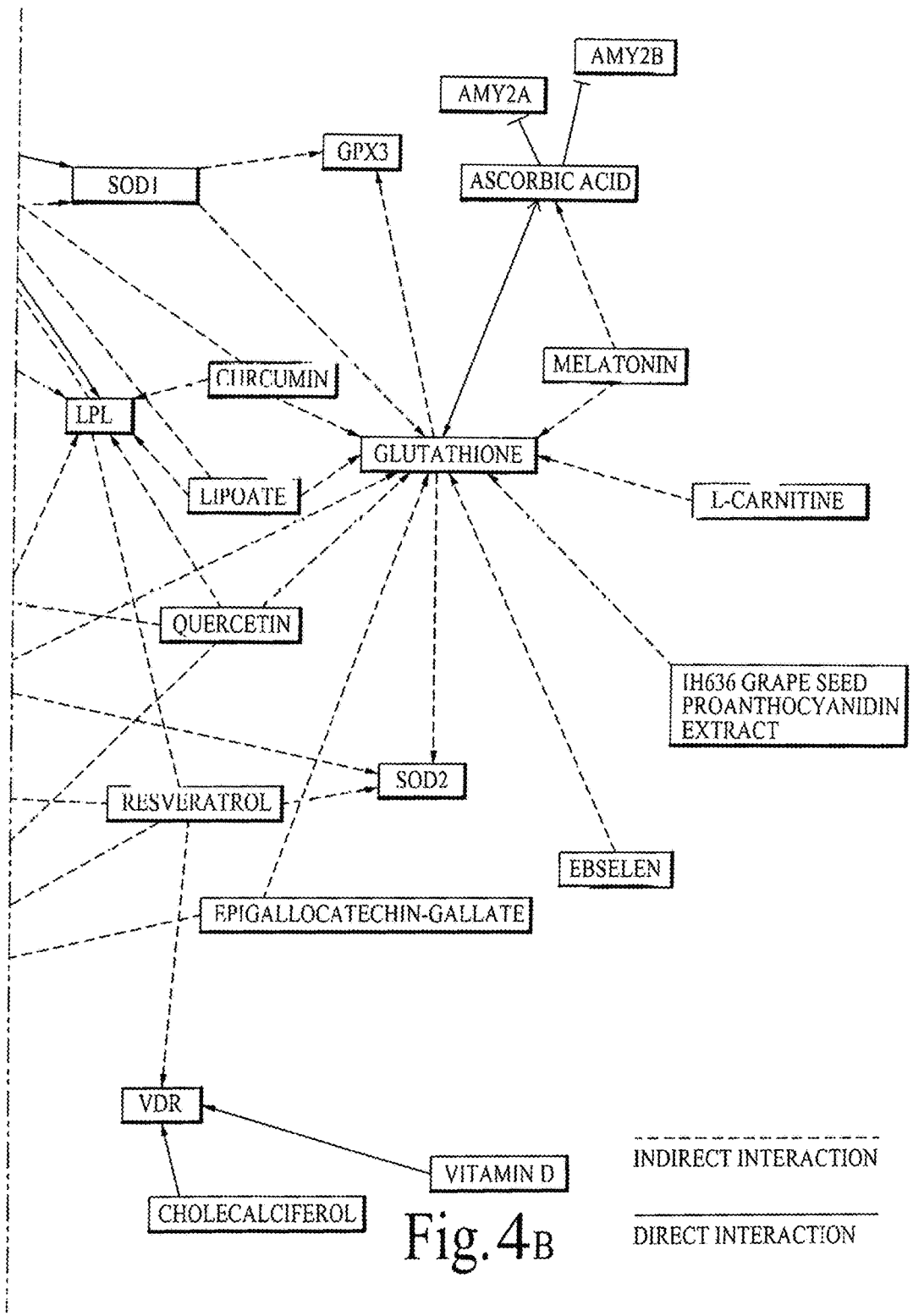
FIG. 4B illustrates a section of FIG. 4, wherein both sections are separated by a dotted line.

FIG. 4 illustrates direct and indirect graphical interactions of Type-2 Diabetes disease related genes/proteins (e.g., ABCC8, GCK, HNF4A, INS, INSR, KCNJ11, LPL, PPARG and SLC2A2) with a set of bioactive compounds and/or bioactive molecules, utilizing comprehensive biological pathway analysis software. FIG. 4A illustrates a section of FIG. 4 and FIG. 4B illustrates a section of FIG. 4, wherein both sections are separated by a dotted line.

Furthermore, Alzheimer's disease related gene/protein APOE is linked with Type-2 Diabetes disease related gene/protein HNF4A.

FIGS. 1A, 1B, 2A, 2B, 3A and 3B are critical to design compositions for lowering the risks of Alzheimer's disease.

FIGS. 4A and 4B are critical to design compositions for lowering the risks of Diabetes disease.

Figure 5A:
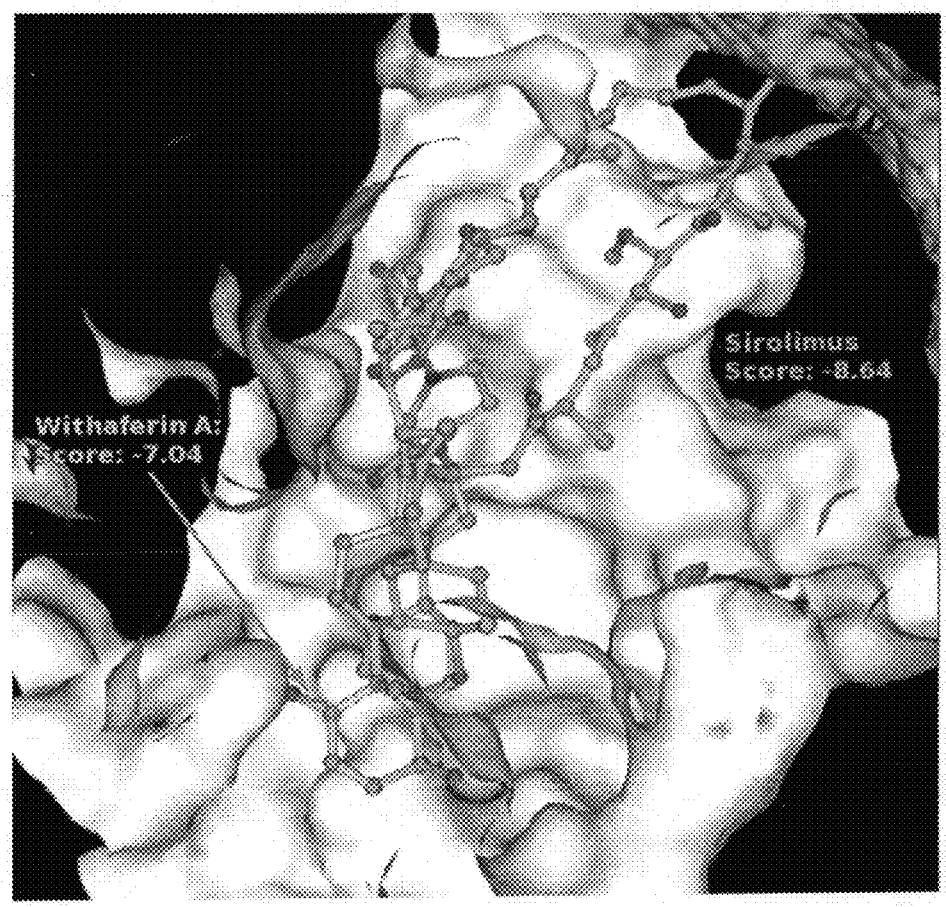
FIGS. 5A and 5B illustrate molecular docking score with the mammalian Target of Rapamycin according to a comprehensive molecular docking analysis software.
Figure 5B:
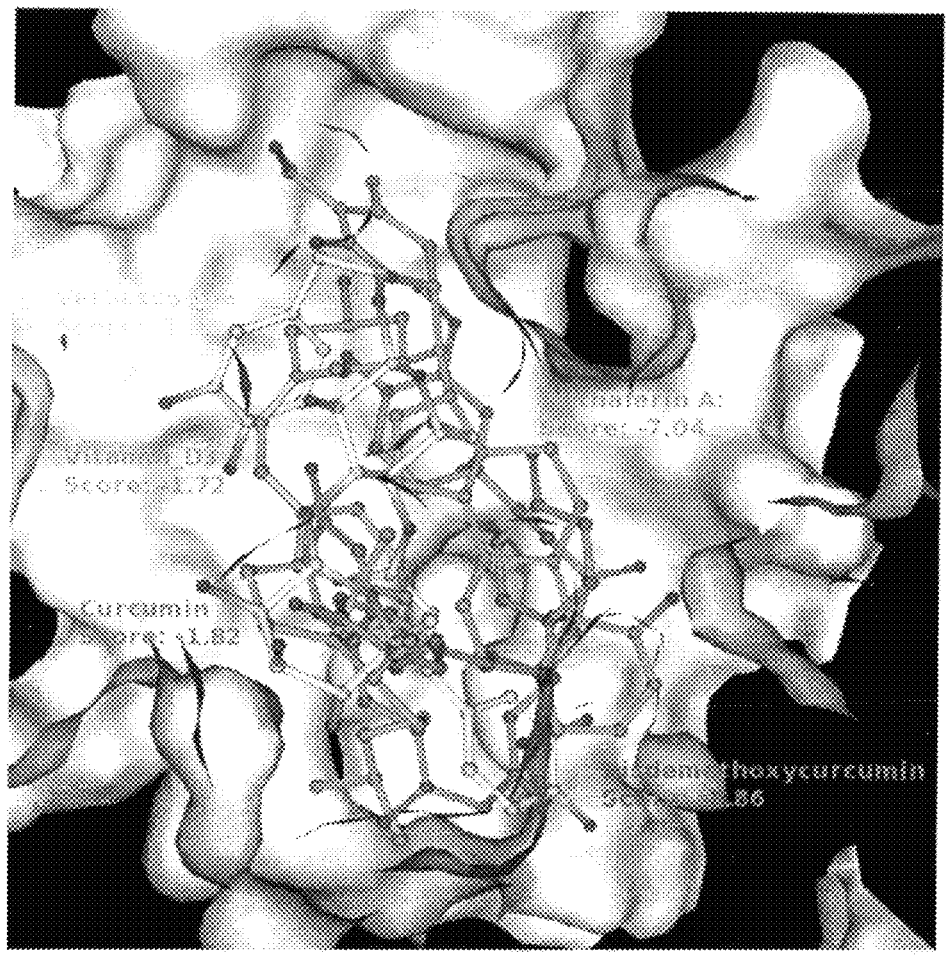

FIGS. 5A and 5B are critical to design compositions for suppressing/inhibiting the mammalian target of Rapamycin.

Compositions

Compositions as described in the Tables below can module (a) gene expression, (b) epigenetic effects and (c) genomic stability.

TABLE 1A

Composition Of A Mixture Of Micronutrients - May Also Include Some Bioactive Compounds From Tables After This Table

| | Unit | +/−50% | WT % |
|---|---|---|---|
| Chemical | | | |
| Pterostilbene (Nanoformulated)[1,2] | Mg | 200 | 4.89% |
| Resveratrol (Nanoformulated)[1,2] | Mg | 200 | 4.89% |
| Mineral | | | |
| Chromium Picolinate | Mg | 0.5 | 0.01% |
| Magnesium L-Threonate | Mg | 400 | 9.78% |
| Selenium (Selenomethionine) | Mg | 0.1 | 0.00% |
| Zinc (L-Opti) | Mg | 15 | 0.37% |
| Vanadium | Mg | 0.01 | 0.00% |
| Nucleotide | | | |
| Nucleotides (DNA) | Mg | 400 | 9.78% |
| Nucleotides (RNA) | Mg | 40 | 0.98% |
| Vitamin | | | |
| Vitamin $B_1$ (Thiamine) | Mg | 10 | 0.24% |
| Vitamin $B_3$ (Nicotinamide) | Mg | 400 | 9.78% |
| Vitamin $B_5$ | Mg | 200 | 4.89% |
| Vitamin $B_6$ (Pyritinol Or Pyridoxal 5'-Phosphate) | Mg | 20 | 0.49% |
| Vitamin $B_9$ (Folate) | Mg | 0.5 | 0.01% |
| Vitamin $B_{12}$ (Methylcobalamin) | Mg | 1 | 0.02% |
| Vitamin C | Mg | 200 | 4.89% |
| Vitamin $D_3$ (Cholecalciferol) | Mg | 0.25 | 0.01% |
| Vitamin $K_2$ | Mg | 2 | 0.05% |
| Other | | | |
| Lactoferrin | Mg | 2000 | 48.91% |
| Total Weight | G | 3.69 | 100.00% |

Mixture of micronutrients contains about 35 billion cumulative (or each live probiotic bacterial component (CFU) at 2.5 billion of: *Lactobacillus acidophilus, Bifidobacterium lacti, Lactobacillus plantarum, Lactobacillus rhamnosus, Lactobacillus casei, Lactobacillus salivarius, Lactobacillus bulgaricus, Bifidobacterium breve, Lactobacillus paracasei, Lactococcus lactis, Streptococcus thermophilus, Lactobacillus brevis, Bifidobacterium bifidum* and *Bifidobacterium longum* can be added with compositions in Table-1A.

Furthermore, live probiotic bacterial components can be encapsulated within a microparticulate system (e.g., chitosan-coated alginate microparticulate system).

TABLE 1B

Composition Of A Mixture Of Micronutrients - May Also Include Some Bioactive Compounds From Tables After This Table

| | Unit | +/−50% | WT % |
|---|---|---|---|
| Botanical | | | |
| *Bacopa monnieri*[+] | Mg | 200 | 1.28% |
| *Emblica officinalis*[+] | Mg | 200 | 1.28% |
| *Vaccinium macrocarpon*[+] | Mg | 800 | 5.12% |
| *Withania somnifera*[+] | Mg | 200 | 1.28% |
| Chemical | | | |
| Acetyl-L-Carnitine | Mg | 200 | 1.28% |
| Alpha-R-Lipoic Acid | Mg | 20 | 0.13% |
| Beta-carotene | Mg | 20 | 0.13% |
| Chlorogenic Acid | Mg | 200 | 1.28% |
| Citicoline (Or L-Alpha Glycerylphosphorylcholine) | Mg | 600 | 3.84% |
| Coenzyme $Q_{10}$ (Nanoformulated)[1,2] | Mg | 1000 | 6.40% |
| Curcumin (Nanoformulated)[1,2,3,4] | Mg | 200 | 1.28% |
| D-Ribose | Mg | 400 | 2.56% |
| Epigallocatechin Gallate | Mg | 200 | 1.28% |
| L-Arginine | Mg | 4000 | 25.62% |
| L-Glutathione (Or Ebselen Or N-Acetyl-L-Cysteine) | Mg | 200 | 1.28% |
| L-Theanine | Mg | 400 | 2.56% |
| Lutein | Mg | 10 | 0.06% |
| Phosphatidylserine | Mg | 200 | 1.28% |
| Pterostilbene (Nanoformulated)[1,2] | Mg | 200 | 1.28% |
| Pyrroloquinoline Quinone (PQQ)[1,2] | Mg | 20 | 0.13% |
| Resveratrol (Nanoformulated)[1,2] | Mg | 200 | 1.28% |
| Touchi | Mg | 200 | 1.28% |
| Trehalose | Mg | 200 | 1.28% |
| Ubiquinol (Nanoformulated)[1,2] | Mg | 400 | 2.56% |
| Zeaxanthin | Mg | 2 | 0.01% |
| Mineral | | | |
| Chromium Picolinate | Mg | 0.5 | 0.00% |
| Magnesium L-Threonate | Mg | 400 | 2.56% |
| Melatonin (Extended Release) | Mg | 3 | 0.02% |
| Omega 3-6-9 Acid (Including Decosahexanoic Acid) (Nanoformulated)[1] | Mg | 400 | 2.56% |
| Potassium | Mg | 400 | 2.56% |
| Selenium (Selenomethionine) | Mg | 0.1 | 0.00% |
| Zinc (L-Opti) | Mg | 15 | 0.10% |
| Zinc Sulfate | Mg | 250 | 1.60% |
| Vanadium | Mg | 0.01 | 0.00% |
| Nucleotide | | | |
| Nucleotides (DNA) | Mg | 400 | 2.56% |
| Nucleotides (RNA) | Mg | 40 | 0.26% |
| Vitamin | | | |
| Vitamin $B_1$ (Thiamine) | Mg | 10 | 0.06% |
| Vitamin $B_3$ (Nicotinamide) | Mg | 400 | 2.56% |
| Vitamin $B_5$ | Mg | 200 | 1.28% |
| Vitamin $B_6$ (Pyritinol Or Pyridoxal 5'-Phosphate) | Mg | 20 | 0.13% |
| Vitamin $B_9$ (Folate) | Mg | 0.5 | 0.00% |
| Vitamin $B_{12}$ (Methylcobalamin) | Mg | 1 | 0.01% |
| Vitamin C | Mg | 500 | 3.20% |
| Vitamin $D_3$ (Cholecalciferol) | Mg | 0.25 | 0.00% |
| Vitamin E | IU | 400 | 2.56% |
| Vitamin $K_2$ | Mg | 2 | 0.01% |
| Other | | | |
| Lactoferrin | Mg | 2000 | 12.81% |
| Live *Lactobacillus plantarum* 299v | Billion | 10 | 0.00% |
| Total Weight | G | 15.61 | 100.00% |

800 mg of L-Tryptophan can be added with compositions in Table-1B.

200 mg of passion fruit tea extract can be added with compositions in Table-1B.

TABLE 1C

Composition Of A Mixture Of Micronutrients For Topical Use - May Also Include Some Bioactive Compounds From Tables Before & After This Table

| | Unit | +/−50% | WT % |
|---|---|---|---|
| Botanical | | | |
| Camellia sinensis (Green Tea) Extract | Mg | 200 | 4.87% |
| Daucus carota Extract | Mg | 200 | 4.87% |
| Emblica officinalis Extract | Mg | 200 | 4.87% |
| Hippophae rhamnoides Oil | Mg | 200 | 4.87% |
| Macrocystis pyrifera Extract | Mg | 200 | 4.87% |
| Prunus amygdalus dulcis (Sweet Almond) Oil | Mg | 200 | 4.87% |
| Solanum lycopersicum | Mg | 200 | 4.87% |
| Chemical | | | |
| Acetyl Hexapeptide | Mg | 200 | 4.87% |
| Arbutin | Mg | 200 | 4.87% |
| Caffeine | Mg | 20 | 0.49% |
| Elastatropin | Mg | 200 | 4.87% |
| Haloxyl | Mg | 200 | 4.87% |
| Hyaluronic Acid | Mg | 200 | 4.87% |
| Hydroxytyrosol | Mg | 200 | 4.87% |
| Hydrolyzed Wheat Protein | Mg | 200 | 4.87% |
| Palmitoyl Pentapeptide-4 | Mg | 200 | 4.87% |
| Quercetin (Nanoformulated)[1,2] | Mg | 200 | 4.87% |
| Resveratrol (Nanoformulated)[1,2] | Mg | 200 | 4.87% |
| Superoxide Dismutase (SOD) (Nanoformulated)[1,2] | Mg | 200 | 4.87% |
| Vitamin | | | |
| Pyrroloquinoline Quinone (PQQ)[1,2] | Mg | 20 | 0.49% |
| Vitamin $B_5$ | Mg | 200 | 4.87% |
| Vitamin E | IU | 400 | 6.49% |
| Total Weight | G | 4.11 | 100.00% |

200 mg of Argan oil can be added with compositions in Table-1C.

200 mg of Coconut (preferably mature coconut) oil can be added with compositions in Table-1C.

200 mg of Marula oil can be added with compositions in Table-1C.

200 mg of Red Raspberry seed oil can be added with compositions in Table-1C.

600 mg of Turmeric oil can be added with compositions in Table-1C.

200 mg of extract of stem cells of *Malus domestica* can be added with compositions in Table-1C.

200 mg of extract of stem cells of leaves of tomato plant can be added with compositions in Table-1C.

Regulatory proteins, called growth factors are biologically active molecules that can stimulate stem cells to grow into specialized cells in the regeneration of human tissue. Suitable amount of growth factors from stem cells can be added. Generally, stem factors contains hundreds of unique growth factors and cytokines that are naturally derived from adult stem cells. The above growth factors can be photo activated/modulated (by a small quantity of reactive molecular species), utilizing a laser/an array of lasers of suitable wavelength and intensity. Furthermore, the above growth factors along with compositions in Table-1C can be nanoformulated/nanoencapsulated (for repairing damaged skin).

Fibroblasts are a type of cell found in the connective tissue, where fibroblasts produce proteins such as collagen, elastin and GAG's which are all critical to repairing skin density and the overall look and quality of the skin. There are at least two distinct types of fibroblasts in the skin: those in the upper layer of connective tissue, which are required for the formation of hair follicles and those in the lower layer, which are responsible for making most of the skin's collagen fibers and repairing damaged skin. Suitable amounts of fibroblasts can be added with composition in Table-1C.

Activators of fibroblasts: 1,3 beta glucan, chlorella, EGF, GHK-copper peptides, niacinamide, R-lipoic acid and retinaldehyde and/or synergistic combination(s) of 1,3 beta glucan, chlorella, EGF, GHK-copper peptides, niacinamide, R-lipoic acid and retinaldehyde can activate fibroblasts and supply nutrients to fibroblasts. Suitable amounts of activators of fibroblasts can be added with compositions in Table-1C.

Furthermore, 1,3 beta glucan, chlorella, EGF, GHK-copper peptides, niacinamide, R-lipoic acid and retinaldehyde and synergistic combination(s) of 1,3 beta glucan, chlorella, EGF, GHK-copper peptides, niacinamide, R-lipoic acid and retinaldehyde can be nanoformulated/nanoencapsulated to activate fibroblasts and supply nutrients to fibroblasts more effectively.

Fibroblast growth factor (FGF) molecules are critical for repairing damaged skin. Fibroblast growth factor molecules can induce expression of Nrf2. Nrf2 regulates the expression of proteins, which are involved in the detoxification of reactive oxygen species (ROS). Suitable amount of fibroblast growth factor can be added with compositions in Table-1C.

Furthermore, zinc finger technology (ZFT) can be utilized to repair DNA damage and assist in the production of proteins and antioxidants within the skin cell. Suitable amounts of zinc finger technology can be added with compositions in Table-1C.

Furthermore, a nanoemulsion system with a high degree of stability can be utilized for transdermal delivery of compositions (described in Table-1C) along with compositions described in the previous paragraphs.

TABLE 1D

Composition Of A Mixture Of Micronutrients - May Also Include Some Bioactive Compounds From Tables Before & After This Table

| | Unit | +/−50% | WT % |
|---|---|---|---|
| Botanicals | | | |
| Boswellia serrata Extract | Mg | 1000 | 12.62% |
| Cayenne Pepper | Mg | 200 | 2.52% |
| Corydalis yanhusuo Root Concentrate | Mg | 200 | 2.52% |
| Curcuma longa Root Extract | Mg | 200 | 2.52% |
| Salix (White Willow) Bark Extract | Mg | 200 | 2.52% |
| Zingiber officinale Root Concentrate | Mg | 200 | 2.52% |
| Chemical | | | |
| Chondroitin Sulfate | Mg | 1000 | 12.62% |
| Curcumin (Nanoformulated)[1,2] | Mg | 200 | 2.52% |
| Dehydrocorybulbine (DHCB) | Mg | 100 | 1.26% |
| Geinstein | Mg | 100 | 1.26% |
| Glucosamine Hydrochloride Or Glucosamine Sulfate | Mg | 2000 | 25.25% |
| Hyaluronic Acid | Mg | 100 | 1.26% |
| Methylsufonlymethane (MSM) | Mg | 1000 | 12.62% |
| S-Adenosyl methionine (SAM) | Mg | 200 | 2.52% |
| Minerals | | | |
| Boron | Mg | 2 | 0.03% |
| Calcium | Mg | 500 | 6.31% |
| Copper | Mg | 1 | 0.01% |
| Magnesium | Mg | 100 | 1.26% |
| Manganese | Mg | 2 | 0.03% |
| Molybdenum | Mg | 0.1 | 0.00% |
| Zinc (L-Opti) | Mg | 15 | 0.19% |

TABLE 1D-continued

Composition Of A Mixture Of Micronutrients - May Also Include Some Bioactive Compounds From Tables Before & After This Table

| | Unit | +/−50% | WT % |
|---|---|---|---|
| Vitamin | | | |
| Vitamin B$_{12}$ (Methylcobalamin) | Mg | 1 | 0.01% |
| Vitamin C | Mg | 200 | 2.52% |
| Vitamin D | IU | 2000 | 0.00% |
| Total Weight | G | 7.92 | 100.00% |

TABLE 1E

Composition Of A Mixture Of Micronutrients - May Also Include Some Bioactive Compounds From Tables Before & After This Table

| | Unit | +/−50% | WT % |
|---|---|---|---|
| Botanicals | | | |
| *Boswellia serrata* Extract | Mg | 1000 | 12.95% |
| *Corydalis yanhusuo* Root Concentrate | Mg | 200 | 2.59% |
| *Curcuma longa* Root Extract | Mg | 200 | 2.59% |
| Salix (White Willow) Bark Extract | Mg | 200 | 2.59% |
| *Zingiber officinale* Root Concentrate | Mg | 200 | 2.59% |
| Chemical | | | |
| Chondroitin Sulfate | Mg | 1000 | 12.95% |
| Curcumin (Nanoformulated)[1,2] | Mg | 200 | 2.59% |
| Dehydrocorybulbine (DHCB) | Mg | 100 | 1.30% |
| Geinstein | Mg | 100 | 1.30% |
| Glucosamine Hydrochloride Or Glucosamine Sulfate | Mg | 2000 | 25.90% |
| Hyaluronic Acid | Mg | 100 | 1.30% |
| Methylsufonlymethane (MSM) | Mg | 1000 | 12.95% |
| S-Adenosyl methionine (SAM) | Mg | 200 | 2.59% |
| Sulforaphane | Mg | 400 | 5.18% |
| Minerals | | | |
| Boron | Mg | 2 | 0.03% |
| Calcium | Mg | 500 | 6.48% |
| Copper | Mg | 1 | 0.01% |
| Magnesium | Mg | 100 | 1.30% |
| Manganese | Mg | 2 | 0.03% |
| Molybdenum | Mg | 0.1 | 0.00% |
| Zinc (L-Opti) | Mg | 15 | 0.19% |
| Vitamin | | | |
| Vitamin B$_{12}$ (Methylcobalamin) | Mg | 1 | 0.01% |
| Vitamin C | Mg | 200 | 2.59% |
| Vitamin D | IU | 2000 | 0.00% |
| Total Weight | G | 7.72 | 100.00% |

TABLE 1F

Composition Of A Mixture Of Micronutrients - May Also Include Some Bioactive Compounds From Tables Before & After This Table

| | Unit | +/−50% | WT % |
|---|---|---|---|
| Botanicals | | | |
| *Boswellia serrata* Extract | Mg | 1000 | 13.30% |
| *Curcuma longa* Root Extract | Mg | 200 | 2.66% |
| Salix (White Willow) Bark Extract | Mg | 200 | 2.66% |
| *Zingiber officinale* Root Concentrate | Mg | 200 | 2.66% |
| Chemical | | | |
| Chondroitin Sulfate | Mg | 1000 | 13.30% |
| Curcumin (Nanoformulated)[1,2] | Mg | 200 | 2.66% |
| Dehydrocorybulbine (DHCB) | Mg | 100 | 1.33% |
| Geinstein | Mg | 100 | 1.33% |
| Glucosamine Hydrochloride Or Glucosamine Sulfate | Mg | 2000 | 26.59% |
| Hyaluronic Acid | Mg | 100 | 1.33% |
| Methylsufonlymethane (MSM) | Mg | 1000 | 13.30% |
| S-Adenosyl methionine (SAM) | Mg | 200 | 2.66% |
| Sulforaphane | Mg | 400 | 5.32% |
| Minerals | | | |
| Boron | Mg | 2 | 0.03% |
| Calcium | Mg | 500 | 6.65% |
| Copper | Mg | 1 | 0.01% |
| Magnesium | Mg | 100 | 1.33% |
| Manganese | Mg | 2 | 0.03% |
| Molybdenum | Mg | 0.1 | 0.00% |
| Zinc (L-Opti) | Mg | 15 | 0.02% |
| Vitamin | | | |
| Vitamin B$_{12}$ (Methylcobalamin) | Mg | 1 | 0.01% |
| Vitamin C | Mg | 200 | 2.66% |
| Vitamin D | IU | 2000 | 0.05% |
| Total Weight | G | 7.52 | 100.00% |

TABLE 1G

Composition Of A Mixture Of Micronutrients - May Also Include Some Bioactive Compounds From Tables Before & After This Table

| | Unit | +/−50% | WT % |
|---|---|---|---|
| Botanicals | | | |
| *Boswellia serrata* Extract | Mg | 1000 | 13.66% |
| Salix (White Willow) Bark Extract | Mg | 200 | 2.73% |
| *Zingiber officinale* Root Concentrate | Mg | 200 | 2.73% |
| Chemical | | | |
| Chondroitin Sulfate | Mg | 1000 | 13.66% |
| Curcumin (Nanoformulated)[1,2] | Mg | 200 | 2.73% |
| Dehydrocorybulbine (DHCB) | Mg | 100 | 1.37% |
| Geinstein | Mg | 100 | 1.37% |
| Glucosamine Hydrochloride Or Glucosamine Sulfate | Mg | 2000 | 27.32% |
| Hyaluronic Acid | Mg | 100 | 1.37% |
| Methylsufonlymethane (MSM) | Mg | 1000 | 13.66% |
| S-Adenosyl methionine (SAM) | Mg | 200 | 2.73% |
| Sulforaphane | Mg | 400 | 5.46% |
| Minerals | | | |
| Boron | Mg | 2 | 0.03% |
| Calcium | Mg | 500 | 6.83% |
| Copper | Mg | 1 | 0.01% |
| Magnesium | Mg | 100 | 1.37% |
| Manganese | Mg | 2 | 0.03% |
| Molybdenum | Mg | 0.1 | 0.00% |
| Zinc (L-Opti) | Mg | 15 | 0.20% |
| Vitamin | | | |
| Vitamin B$_{12}$ (Methylcobalamin) | Mg | 1 | 0.01% |
| Vitamin C | Mg | 200 | 2.73% |
| Vitamin D | IU | 2000 | 0.00% |
| Total Weight | G | 7.32 | 100.00% |

TABLE 1H

Composition Of A Mixture Of Micronutrients - May Also Include Some Bioactive Compounds From Tables Before & After This Table

| | Unit | +/−50% | WT % |
|---|---|---|---|
| Botanicals | | | |
| *Boswellia serrata* Extract | Mg | 1000 | 14.04% |
| *Zingiber officinale* Root Concentrate | Mg | 200 | 2.81% |
| Chemical | | | |
| Chondroitin Sulfate | Mg | 1000 | 14.04% |
| Curcumin (Nanoformulated)[1,2] | Mg | 200 | 2.81% |
| Dehydrocorybulbine (DHCB) | Mg | 100 | 1.40% |
| Geinstein | Mg | 100 | 1.40% |
| Glucosamine Hydrochloride Or Glucosamine Sulfate | Mg | 2000 | 28.09% |
| Hyaluronic Acid | Mg | 100 | 1.40% |
| Methylsufonlymethane (MSM) | Mg | 1000 | 14.04% |
| S-Adenosyl methionine (SAM) | Mg | 200 | 2.81% |
| Sulforaphane | Mg | 400 | 5.62% |
| Minerals | | | |
| Boron | Mg | 2 | 0.03% |
| Calcium | Mg | 500 | 7.02% |
| Copper | Mg | 1 | 0.01% |
| Magnesium | Mg | 100 | 1.40% |
| Manganese | Mg | 2 | 0.03% |
| Molybdenum | Mg | 0.1 | 0.00% |
| Zinc (L-Opti) | Mg | 15 | 0.21% |
| Vitamin | | | |
| Vitamin $B_{12}$ (Methylcobalamin) | Mg | 1 | 0.01% |
| Vitamin C | Mg | 200 | 2.81% |
| Vitamin D | IU | 2000 | 0.00% |
| Total Weight | G | 7.12 | 100.00% |

TABLE 1I

Composition Of A Mixture Of Micronutrients - May Also Include Some Bioactive Compounds From Tables Before & After This Table

| | Unit | +/−50% | WT % |
|---|---|---|---|
| Botanicals | | | |
| *Boswellia serrata* Extract | Mg | 1000 | 14.45% |
| Chemical | | | |
| Chondroitin Sulfate | Mg | 1000 | 14.45% |
| Curcumin (Nanoformulated)[1,2] | Mg | 200 | 2.89% |
| Dehydrocorybulbine (DHCB) | Mg | 100 | 1.44% |
| Geinstein | Mg | 100 | 1.44% |
| Glucosamine Hydrochloride Or Glucosamine Sulfate | Mg | 2000 | 28.90% |
| Hyaluronic Acid | M | 100 | 1.44% |
| Methylsufonlymethane (MSM) | Mg | 1000 | 14.45% |
| S-Adenosyl methionine (SAM) | Mg | 200 | 2.89% |
| Sulforaphane | Mg | 400 | 5.78% |
| Minerals | | | |
| Boron | Mg | 2 | 0.03% |
| Calcium | Mg | 500 | 7.22% |
| Copper | Mg | 1 | 0.01% |
| Magnesium | Mg | 100 | 1.44% |
| Manganese | Mg | 2 | 0.03% |
| Molybdenum | Mg | 0.1 | 0.00% |
| Zinc (L-Opti) | Mg | 15 | 0.22% |
| Vitamin | | | |
| Vitamin $B_{12}$ (Methylcobalamin) | Mg | 1 | 0.01% |
| Vitamin C | Mg | 200 | 2.89% |
| Vitamin D | IU | 2000 | 0.00% |
| Total Weight | G | 6.92 | 100.00% |

TABLE 1J

Composition Of A Mixture Of Micronutrients - May Also Include Some Bioactive Compounds From Tables Before & After This Table

| | Unit | +/−50% | WT % |
|---|---|---|---|
| Botanicals | | | |
| *Boswellia serrata* Extract | Mg | 1000 | 14.66% |
| Chemical | | | |
| Chondroitin Sulfate | Mg | 1000 | 14.66% |
| Curcumin (Nanoformulated)[1,2] | Mg | 200 | 2.93% |
| Geinstein | Mg | 100 | 1.47% |
| Glucosamine Hydrochloride Or Glucosamine Sulfate | Mg | 2000 | 29.32% |
| Hyaluronic Acid | Mg | 100 | 1.47% |
| Methylsufonlymethane (MSM) | Mg | 1000 | 14.66% |
| S-Adenosyl methionine (SAM) | Mg | 200 | 2.93% |
| Sulforaphane | Mg | 400 | 5.86% |
| Minerals | | | |
| Boron | Mg | 2 | 0.03% |
| Calcium | Mg | 500 | 7.33% |
| Copper | Mg | 1 | 0.01% |
| Magnesium | Mg | 100 | 1.47% |
| Manganese | Mg | 2 | 0.03% |
| Molybdenum | Mg | 0.1 | 0.00% |
| Zinc (L-Opti) | Mg | 15 | 0.22% |
| Vitamin | | | |
| Vitamin $B_{12}$ (Methylcobalamin) | Mg | 1 | 0.01% |
| Vitamin C | Mg | 200 | 2.93% |
| Vitamin D | IU | 2000 | 0.00% |
| Total Weight | G | 6.82 | 100.00% |

TABLE 1K

Composition Of A Mixture Of Micronutrients Micronutrients - May Also Include Some Bioactive Compounds From Tables Before & After This Table

| | Unit | +/−50% | WT % |
|---|---|---|---|
| Botanicals | | | |
| *Boswellia serrata* Extract | Mg | 1000 | 15.10% |
| Chemical | | | |
| Chondroitin Sulfate | Mg | 1000 | 15.10% |
| Curcumin (Nanoformulated)[1,2] | Mg | 200 | 3.02% |
| Geinstein | Mg | 100 | 1.51% |
| Glucosamine Hydrochloride Or Glucosamine Sulfate | Mg | 2000 | 30.21% |
| Hyaluronic Acid | Mg | 100 | 1.51% |
| Methylsufonlymethane (MSM) | Mg | 1000 | 15.10% |
| Sulforaphane | Mg | 400 | 6.04% |
| Minerals | | | |
| Boron | Mg | 2 | 0.03% |
| Calcium | Mg | 500 | 7.55% |
| Copper | Mg | 1 | 0.02% |
| Magnesium | Mg | 100 | 1.51% |
| Manganese | Mg | 2 | 0.03% |
| Molybdenum | Mg | 0.1 | 0.00% |
| Zinc (L-Opti) | Mg | 15 | 0.23% |
| Vitamin | | | |
| Vitamin $B_{12}$ (Methylcobalamin) | Mg | 1 | 0.02% |
| Vitamin C | Mg | 200 | 3.02% |
| Vitamin D | IU | 2000 | 0.00% |
| Total Weight | G | 6.61 | 100.00% |

500 mg of avocado soybean unsaponifiables (ASU) can be added to compositions in Table-1 D through Table-1K.

300 mg of black tart cherry extract can be added to compositions in Table-1D through Table-1K.

300 mg of pine bark extract can be added to compositions in Table-1D through Table-1K.

TABLE 2A

Composition Of A Mixture Of Antioxidants - May Also Include Some Bioactive Compounds From Tables Before & After This Table

| Chemical | Unit | +/−50% | WT % |
| --- | --- | --- | --- |
| Acetyl-L-Carnitine | Mg | 200 | 2.12% |
| Alpha-R-Lipoic Acid | Mg | 20 | 0.21% |
| Coenzyme $Q_{10}$ (Nanoformulated)[1,2] | Mg | 200 | 2.12% |
| D-Ribose | Mg | 400 | 4.25% |
| Epigallocatechin Gallate | Mg | 200 | 2.12% |
| Ferulic Acid | Mg | 200 | 2.12% |
| Hyaluronic Acid | Mg | 200 | 2.12% |
| Inositol Hexanicotinate | Mg | 2000 | 21.23% |
| Isothiocyanate Sulforaphane | Mg | 200 | 2.12% |
| L-Arginine | Mg | 4000 | 42.46% |
| L-Analyl-L-Glutamine | Mg | 200 | 2.12% |
| L-Glutamine | Mg | 200 | 2.12% |
| L-Glutathione (Or Ebselen Or N-Acetyl-L-Cysteine) | Mg | 200 | 2.12% |
| Pterostilbene (Nanoformulated)[1,2] | Mg | 200 | 2.12% |
| Quercetin (Nanoformulated)[1,2] | Mg | 200 | 2.12% |
| Resveratrol (Nanoformulated)[1,2] | Mg | 200 | 2.12% |
| Superoxide Dismutase (SOD)* (Nanoformulated)[1,2] | Mg | 200 | 2.12% |
| Ubiquinol (Nanoformulated)[1,2] | Mg | 400 | 4.25% |
| Total Weight | G | 9.42 | 100.00% |

TABLE 2B

Additional Composition Of A Mixture Of Antioxidants - May Also Include Some Bioactive Compounds From Tables Before & After This Table

| Botanical | Unit | +/−50% | WT % |
| --- | --- | --- | --- |
| *Aronia melanocarpa*[+] | Mg | 200 | 12.50% |
| *Citrus limonum*[+] | Mg | 200 | 12.50% |
| *Daucus carota*[+] | Mg | 200 | 12.50% |
| *Hibiscus* spp.[+] | Mg | 200 | 12.50% |
| *Malus domestica*[+] | Mg | 200 | 12.50% |
| *Ribes nigrum*[+] | Mg | 200 | 12.50% |
| *Sambucus nigra*[+] | Mg | 200 | 12.50% |
| *Vaccinium* spp.[+] | Mg | 200 | 12.50% |
| Total Weight | G | 1.60 | 100.00% |

TABLE 3A

Composition Of A Multi-Serve Antioxidant Liquid - May Also Include Some Bioactive Compounds From Tables Before & After This Table

| | Unit | +/−50% | WT % |
| --- | --- | --- | --- |
| Botanicals | | | |
| *Actinidia chinenesis*[+] | G | 25 | 5.49% |
| *Ananas comosus*[+] | G | 25 | 5.49% |
| *Cocos nucifera*[+] | G | 350 | 76.88% |
| *Garcinia mangostana*[+] | G | 25 | 5.49% |
| *Litchi chinensis*[+] | G | 25 | 5.49% |
| *Vitis* spp.[+] | G | 0.75 | 0.16% |
| Chemical | | | |
| Citicoline (Or L-Alpha Glycerylphosphorylcholine) | G | 0.75 | 0.16% |
| Coenzyme $Q_{10}$ (Nanoformulated)[1,2] | G | 0.75 | 0.16% |
| D-Ribose | G | 0.75 | 0.16% |
| L-Analyl-L-Glutamine | G | 0.75 | 0.16% |
| L-Theanine | G | 0.75 | 0.16% |
| Ubiquinol (Nanoformulated)[1,2] | G | 0.75 | 0.16% |
| Total Weight | G | 455.25 | 100.00% |

TABLE 3B

Composition Of A Single-Serve Antioxidant Liquid - May Also Include Some Bioactive Compounds From Tables Before & After This Table

| | Unit | +/−50% | WT % |
| --- | --- | --- | --- |
| Chemical | | | |
| Citicoline (Or L-Alpha Glycerylphosphorylcholine) | G | 0.25 | 0.05% |
| Coenzyme $Q_{10}$ (Nanoformulated)[1,2] | G | 0.25 | 0.05% |
| Creatine | G | 2.0 | 0.44% |
| D-Ribose | G | 0.25 | 0.05% |
| Gamma-Aminobutyric Acid | G | 0.25 | 0.05% |
| Inulin | G | 5 | 1.09% |
| L-Analyl-L-Glutamine | G | 0.25 | 0.05% |
| L-Theanine | G | 0.25 | 0.05% |
| Melatonin (Extended Release) | G | 0.002 | 0.00% |
| Omega 3-6-9 Acid (Including Decosahexanoic Acid) (Nanoformulated)[1] | G | 0.25 | 0.05% |
| Plant Sterol (Nanoformulated)[1] | G | 5 | 1.09% |
| Ubiquinol (Nanoformulated)[1,2] | G | 0.25 | 0.05% |
| Uridine | G | 0.25 | 0.05% |
| Sweetener | | | |
| Erythritol | G | 10 | 2.18% |
| *Stevia rebaudiana*[+] | G | 0.025 | 0.01% |
| Trehalose | G | 0.25 | 0.05% |
| Other | | | |
| Acidified Coconut Water (Or Filter Water) | G | 435 | 94.66% |
| Live *Lactobacillus plantarum* 299v | Billion | 10 | 0.00% |
| Total Weight | G | 459.52 | 100.00% |

TABLE 3C

Composition Of A Single-Serve Antioxidant Liquid - May Also Include Some Bioactive Compounds From Tables Before & After This Table

| | Unit | +/−50% | WT % |
| --- | --- | --- | --- |
| Botanical | | | |
| *Aronia melanocarpa*[+] | G | 0.25 | 0.05% |
| *Citrus limonum*[+] | G | 0.25 | 0.05% |
| *Daucus carota*[+] | G | 0.25 | 0.05% |
| *Hibiscus* spp.[+] | G | 0.25 | 0.05% |
| *Malus domestica*[+] | G | 0.25 | 0.05% |
| *Ribes nigrum*[+] | G | 0.25 | 0.05% |
| *Sambucus nigra*[+] | G | 0.25 | 0.05% |
| *Vaccinium* spp.[+] | G | 0.25 | 0.05% |
| Chemical | | | |
| Citicoline (Or L-Alpha Glycerylphosphorylcholine) | G | 0.25 | 0.05% |
| Coenzyme $Q_{10}$ (Nanoformulated)[1,2] | G | 0.25 | 0.05% |
| Creatine | G | 2.0 | 0.43% |
| D-Ribose | G | 0.25 | 0.05% |
| Gamma-Aminobutyric Acid | G | 0.25 | 0.05% |
| Inulin | G | 5 | 1.08% |
| L-Analyl-L-Glutamine | G | 0.25 | 0.05% |
| L-Theanine | G | 0.25 | 0.05% |

TABLE 3C-continued

Composition Of A Single-Serve Antioxidant Liquid - May Also Include Some Bioactive Compounds From Tables Before & After This Table

|  | Unit | +/−50% | WT % |
|---|---|---|---|
| Melatonin (Extended Release) | G | 0.002 | 0.00% |
| Omega 3-6-9 Acid (Including Decosahexanoic Acid) (Nanoformulated)[1] | G | 0.25 | 0.05% |
| Plant Sterol (Nanoformulated)[1] | G | 5 | 1.08% |
| Ubiquinol (Nanoformulated)[1,2] | G | 0.25 | 0.05% |
| Uridine | G | 0.25 | 0.05% |
| Sweetener |  |  |  |
| Erythritol | G | 10 | 2.17% |
| *Stevia rebaudiana*[+] | G | 0.025 | 0.01% |
| Trehalose | G | 0.25 | 0.05% |
| Other |  |  |  |
| Acidified Coconut Water (Or Filter Water) | G | 435 | 94.25% |
| Live *Lactobacillus plantarum* 299v | Billion | 10 | 0.00% |
| Total Weight | G | 461.52 | 100.00% |

TABLE 3D

Composition Of Botanicals - May Also Include Some Bioactive Compounds From Tables Before & After This Table

|  | Unit | +/−50% | WT % |
|---|---|---|---|
| Botanical |  |  |  |
| *Chamomilla recutita* | Mg | 200 | 6.66% |
| *Humulus lupulus* | Mg | 200 | 6.66% |
| *Lavandula angustifolia* | Mg | 200 | 6.66% |
| *Melissa officinalis* | Mg | 200 | 6.66% |
| *Passiflora incarnate* | Mg | 200 | 6.66% |
| *Valeriana officinalis* | Mg | 200 | 6.66% |
| Chemical |  |  |  |
| Bromelain | Mg | 400 | 13.32% |
| Citicoline (Or L-Alpha Glycerylphosphorylcholine) | Mg | 200 | 6.66% |
| Gamma-Aminobutyric Acid | Mg | 200 | 6.66% |
| L-Theanine | Mg | 200 | 6.66% |
| L-Tryptophan | Mg | 800 | 26.64% |
| Melatonin (Extended Release) | Mg | 3 | 0.10% |
| Other |  |  |  |
| Live *Bifidobacterium longum* | Billion | 10 | 0.00% |
| Live *Lactobacillus helveticus* | Billion | 10 | 0.00% |
| Total Weight | G | 3.00 | 100.00% |

TABLE 3E

Composition Of A Mixture Of Electrolytes & Dextrose - May Also Include Some Bioactive Compounds From Tables Before & After This Table

| Nutrient | Unit Per 8 Fluid Oz |
|---|---|
| Sodium | 10.6 mEq |
| Potassium | 4.7 mEq |
| Chloride | 8.3 mEq |
| Zinc | 1.9 Mg |
| Dextrose | 5.9 G |

Smart Container

Suitable biodegradable material (e.g., silk/plant derived plastic material) can be used as a container.

Lignin (or lignen) is an integral complex chemical compound of the secondary cell walls of plants. A plant derived plastic can be based on lignin (or lignen) as a base material. Furthermore, lignin (or lignen) can be integrated (multi-layered) with chitin (a biopolymer based on the N-acetyl-glucosamine monomer) and/or chitin's variant deacetylated counterpart chitosan and/or fibroin (a protein derived from silk) as a base material.

TABLE 4

Composition Of A Biodegradable Plastic Material

| Composition | Wt % Material A | Wt % Material B | Wt % Material C | Wt % Material D |
|---|---|---|---|---|
| 1 | 80% Lignin | 20% Chitin |  |  |
| 2 | 80% Lignin | 20% Chitosan |  |  |
| 3 | 80% Lignin | 10% Chitin | 10% Chitosan |  |
| 4 | 80% Lignin | 20% Fibroin |  |  |
| 5 | 80% Lignin | 10% Chitin | 10% Fibroin |  |
| 6 | 80% Lignin | 10% Chitosan | 10% Fibroin |  |
| 7 | 80% Lignin | 10% Chitosan | 10% Fibroin |  |
| 8 | 80% Lignin | 5% Chitosan | 5% Chitosan | 10% Fibroin |

A lens/an array of lenses (e.g., utilizing silk material) can be integrated on the interior wall of the container to detect the presence/growth of bacteria/microbes (e.g., bacteria/microbes in a liquid mixture).

Furthermore, the lens/array of lenses (e.g., utilizing silk material) can be integrated with a biological colony counter to estimate/count good/bad bacteria.

One dimensional (1-D)/two dimensional (2-D)/quick response (QR)-codes and/or a radio frequency identification device (RFID) active/passive tag and/or a near field communication tag and/or an ultra-lower power consumption microprocessor (e.g., Ambiqmicro ARM Cortex™-M3 microcontroller or an organic transistor based microprocessor or nano-scaled InAs XOI based microprocessor or Freescale 2 millimeters×2 millimeters KL02 chip-scale package (CSP) (chip-scale package with the components of a micro-scaled computer can be configured with a micro IP/light weight IP address) and/or a memory/storage component (e.g., a printed memristor on a flexible substrate) and a thin-film printed battery/miniature solar cell component can be integrated on an exterior label (covers only a segment of the container's exterior) to (a) deliver information about the product, (b) advertise (e.g., click to view more product (e.g., a drug) information linked with a website and/or click to receive a product coupon in near real-time/real-time), (c) interact (e.g., collective quorum vote on user liking/disliking of the product in near real-time/real-time) with a user's portable internet appliance (e.g., a smart phone/tablet personal computer) and (d) communicate with an inventory management system and/or smart shopping cart, wherein the smart shopping cart is configured (with a removable (about seven (7) inch) display device integrated with a near field communication tag and a near field communication reader) to determine the user's commercial identity/personality on the doorway entrance of the retailer.

In another embodiment, a smart refrigerator containing (food) packages (wherein each package is integrated with a usage indicator microchip) can communicate (wirelessly) with an internet connected home gateway/storage subsystem. Thus, the home gateway/storage subsystem can communicate (wirelessly) with the user's portable internet appliance prior to any shopping.

The user's commercial identity/personality can be enhanced by a collection of inputs from statistically similar users in near real-time/real-time and these inputs can be analyzed by data mining, ANN (artificial neural network), hierarchical cluster analysis and KNN (K-nearest neighbor analysis) and intelligent learning algorithm. These inputs can complement/enhance the user's commercial identity/personality.

Furthermore, these inputs can include the user's facial recognition profile (wherein a facial data is converted into a mathematical code or pattern) to complement/enhance the user's commercial identity/personality.

The exterior label can be integrated with thermochromic ink dot to indicate the temperature of the container.

The exterior label can be placed on a heat-dissipating thermally conducting flexible polymer film. Furthermore, the thermally conducting flexible polymer film can be integrated with a barrier thin-film (e.g., 100 nanometers thick alumina ($Al_2O_3$) fabricated/constructed, utilizing a low-temperature atomic layer deposition (ALD) process).

Humidity, oxygen and water can slowly diffuse into the container to degrade the liquid mixture over time. The barrier thin-film can prevent against humidity, oxygen and water.

The container can be suitably (about 15 degrees centigrade hot-cold side temperature difference) heated or cooled by an array of (embedded superlattice based thin-film Pettier) thermoelectrics, herein the thermoelectrics can be integrated (by utilizing Lithographie-Galvanoformung-Abformung (LIGA), electroforming and MEMS process) on the heat-dissipating thermally conducting flexible polymer film. The thermoelectrics covers only a section of the container's exterior.

Thermal resistance between the thermoelectrics and thermally conducting flexible polymer film is a critical parameter for efficient heating and/or cooling.

The array of thermoelectrics can be electrically powered by an array of printed thin-film batteries/titanium dioxide solar cells (with porphyrin dyes).

TABLE 5

Composition Of A Mixture For Expression Of Beneficial NrF2 Protein - May Also Include Some Bioactive Compounds From Tables Before & After This Table (Except Table-4 and Table-6)

| Botanical | Unit | +/-50% | WT % |
|---|---|---|---|
| Astragalus membranaceus[+] | Mg | 200 | 6.25% |
| Bacopa monnieri[+] | Mg | 200 | 6.25% |
| Camellia sinensis[+] (Black) | Mg | 200 | 6.25% |
| Camellia sinensis[+] (Green) | Mg | 200 | 6.25% |
| Curcuma longa[+] (Or A Curcuminoids Compound)[1,2,3,4] | Mg | 400 | 12.50% |
| Euterpe oleracea[+] | Mg | 200 | 6.25% |
| Hippophae rhamnoides[+] | Mg | 200 | 6.25% |
| Lycium barbarum[+] | Mg | 200 | 6.25% |
| Phyllanthus emblica[+] | Mg | 200 | 6.25% |
| Punica granatum[+] | Mg | 200 | 6.25% |
| Silybum marianum[+] | Mg | 200 | 6.25% |
| Tinospora cordifolia[+] | Mg | 200 | 6.25% |
| Vitis spp.[+] | Mg | 200 | 6.25% |
| Wasabia japonica[+] | Mg | 200 | 6.25% |
| Withania somnifera[+] | Mg | 200 | 6.25% |
| Total Weight | G | 3.20 | 100.00% |

Mitochondria are both generators of and targets for reactive molecular species. Therefore, oxidative stress is intimately linked with mitochondrial dysfunction. The abundant mitochondria in a human brain are major sites of generation and action of reactive oxygen species/reactive nitrogen species (RNS), since a human brain utilizes 20% of the inspired oxygen and 90% of the consumed oxygen to produce energy during oxidative phosphorylation. Thus, a human brain is particularly sensitive to free radical damage/oxidative stress. Mitochondrial turnover is dependent on autophagy (meaning self-eating), which declines with age and is frequently dysfunctional in many neurodegenerative diseases (including Alzheimer's). Autophagy can engage in cross-talk with reactive oxygen species/reactive nitrogen species in both cell signaling and protein damage. The mammalian Target of Rapamycin is an autophagy pathway. The mammalian Target of Rapamycin pathway can function as an inhibitor of the initiation process of autophagy.

Alzheimer's, Cardiovascular and Type-2 Diabetes diseases have misfolded and they all have damaged proteins triggered by pathology at the molecular level. There are about 100,000 different proteins in a human body. After each protein is synthesized, it must be folded into the right shape to be functional. Mistakes can happen, that is why cells have sophisticated housekeeping mechanisms to repair or destroy poorly formed proteins before they can do any harm. Occasionally, a misfolded protein can evade these sophisticated housekeeping mechanisms and accumulates in sufficient quantities to clump together to damage/kill the cell.

One way to treat Alzheimer's, Cardiovascular and Type-2 Diabetes diseases, caused by misfolded proteins is to stimulate the housekeeping mechanisms by activating autophagy (or alternatively suppressing/inhibiting the mammalian Target of Rapamycin pathway).

As a central controller of cell growth and nutrient sensor, the mammalian target of Rapamycin plays a key role in ageing, Alzheimer's, Cardiovascular and Diabetes diseases.

Furthermore, AMPK up regulation (via bioactive compounds and/or bioactive molecules in *Momordica charantia*) activates autophagy via dual mechanisms involving not only by suppressing/inhibiting the mammalian Target of Rapamycin pathway (in particular mTORCI), but also by direct phosphorylation of ULK1 protein.

The bioactive compounds 100 and/or bioactive molecules 100A to suppress/inhibit the mammalian Target of Rapamycin pathway can be encapsulated/caged in the nanoshell 120.

The nanoshell 120 decorated with a targeting ligand, wherein the targeting ligand can recognize/match/bind with adenosine receptors-thus allowing a human body's blood-brain barrier (BBB) to be opened for the passage of the nanoshell 120 to deliver the bioactive compounds 100 and/or bioactive molecules 100A to suppress/inhibit the mammalian Target of Rapamycin pathway in a human brain.

TABLE 6

Molecular Docking Score With mTOR Utilizing Computational Chemistry Software (Also Illustrated in FIGS. 5A and 5B)

| Chemical | Molecular Score |
|---|---|
| Rapamycin/Sirolimus (Known To Suppress/Inhibit mTOR) | -8.64 |
| Withaferin A | -7.04 |
| Cycloastragenol | -2.27 |
| Bisdemethoxycurcumin | -1.86 |
| Curcumin | -1.82 |
| Vitamin $D_3$ | -1.72 |
| Verbascoside | -1.13 |
| Momordin | -0.86 |
| SMER-28 | -0.71 |
| Resveratrol | -0.31 |
| Epigallocatechin gallate | -0.28 |
| Trehalose (Can Induce Autophagy Independent Of mTOR) | -0.25 |
| N,N-dimethylimidodicarbonimidic diamide (Metformin) | -0.11 |

Rapamycin can generate buildup of fatty acids and eventually an increase in insulin resistance leading to Type-2

Diabetes disease. But a combination of rapamycin and metformin can reduce insulin resistance and treat aging related diseases Furthermore, the combination of rapamycin and metformin can be enhanced in its efficacy and synergy by adding one or more chemicals of suitable amount(s): withaferin A, cycloastragenol, bisdemethoxycurcumin, curcumin, vitamin D3, verbascoside, momordin, SMER-28, resveratrol, epigallocatechin gallate and trehalose.

Alternatively, the above combination of rapamycin and metformin can be suitably replaced in its efficacy and synergy by one or more suitable amount(s) of: withaferin A, cycloastragenol, bisdemethoxycurcumin, curcumin, vitamin D3, verbascoside, momordin, SMER-28, resveratrol, epigallocatechin gallate and trehalose with metformin.

TABLE 7A

Composition Of A Mixture For Suppressing/Inhibiting mTOR - May Also Include Some Bioactive Compounds From Tables Before & After This Table

|  | Unit | +/−50% | WT % |
|---|---|---|---|
| Botanical |  |  |  |
| *Momordica charantia*+ | Mg | 200 | 20.00% |
| Chemical |  |  |  |
| Withaferin A (Or A Chemical Derivative Or A Structural Analog Of Withaferin A) (Nanoformulated)[1,2] | Mg | 400 | 40.00% |
| Withanolides (Or A Chemical Derivative Or A Structural Analog Of Withanolides) (Nanoformulated)[1,2] | Mg | 200 | 20.00% |
| Withanosides (Or A Chemical Derivative Or A Structural Analog Of Withanosides) (Nanoformulated)[1,2] | Mg | 200 | 20.00% |
| Total Weight | G | 1.00 | 100.00% |

TABLE 7B

Composition Of A Mixture For Suppressing/Inhibiting mTOR - May Also Include Some Bioactive Compounds From Tables Before & After This Table

|  | Unit | +/−50% | WT % |
|---|---|---|---|
| Botanical |  |  |  |
| *Momordica charantia*+ | Mg | 200 | 12.50% |
| Chemical |  |  |  |
| Bisdemethoxycurcumin (Nanoformulated)[1,2] | Mg | 200 | 12.50% |
| Curcumin (Nanoformulated)[1,2,3,4] | Mg | 200 | 12.50% |
| Cycloastragenol (Nanoformulated)[1,2] | Mg | 200 | 12.50% |
| Withaferin A (Or A Chemical Derivative Or A Structural Analog Of Withaferin A)[1,2] | Mg | 400 | 25.00% |
| Withanolides (Or A Chemical Derivative Or A Structural Analog Of Withanolides) (Nanoformulated)[1,2] | Mg | 200 | 12.50% |
| Withanosides (Or A Chemical Derivative Or A Structural Analog Of Withanosides) (Nanoformulated)[1,2] | Mg | 200 | 12.50% |
| Vitamin |  |  |  |
| Vitamin D3 (Cholecalciferol) | Mg | 0.06 | 0.00% |
| Total Weight | G | 1.60 | 100.00% |

TABLE 7C

Composition Of A Mixture For Suppressing/Inhibiting mTOR - May Also Include Some Bioactive Compounds From Tables Before & After This Table

|  | Unit | +/−50% | WT |
|---|---|---|---|
| Botanical |  |  |  |
| *Momordica charantia*+ | Mg | 200 | 7.66% |
| Chemical |  |  |  |
| 6-Bromo-N-2-propenyl-4-quinazolinamine (SMER-28) | Mg | 10 | 0.38% |
| Bisdemethoxycurcumin (Nanoformulated)[1,2] | Mg | 200 | 7.66% |
| Curcumin (Nanoformulated)[1,2,3,4] | Mg | 200 | 7.66% |
| Cycloastragenol (Nanoformulated)[1,2] | Mg | 200 | 7.66% |
| Epigallocatechin gallate | Mg | 200 | 7.66% |
| Momordin | Mg | 200 | 7.66% |
| Resveratrol (Nanoformulated)[1,2] | Mg | 200 | 7.66% |
| Trehalose | Mg | 200 | 7.66% |
| Verbascoside | Mg | 200 | 7.66% |
| Withaferin A (Or A Chemical Derivative Or A Structural Analog Of Withaferin A) (Nanoformulated)[1,2] | Mg | 400 | 15.33% |
| Withanolides (Or A Chemical Derivative Or A Structural Analog Of Withanolides) (Nanoformulated)[1,2] | Mg | 200 | 7.66% |
| Withanosides (Or A Chemical Derivative Or A Structural Analog Of Withanosides) (Nanoformulated)[1,2] | Mg | 200 | 7.66% |
| Vitamin |  |  |  |
| Vitamin D3 (Cholecalciferol) | Mg | 0.06 | 0.00% |
| Total Weight | G | 2.61 | 100.00% |

TABLE 7D

Composition Of A Mixture For Suppressing/Inhibiting mTOR - May Also Include Some Bioactive Compounds From Tables Before & After This Table

|  | Unit | +/−50% | WT % |
|---|---|---|---|
| Botanical |  |  |  |
| *Cinnamomum zeylanicum*+ | Mg | 200 | 6.67% |
| *Momordica charantia*+ | Mg | 200 | 6.67% |
| *Vitis vinifera*+ (e.g., Seed Extract) | Mg | 200 | 6.67% |
| Chemical |  |  |  |
| Bisdemethoxycurcumin (Nanoformulated)[1,2] | Mg | 200 | 6.67% |
| Curcumin (Nanoformulated)[1,2,3,4] | Mg | 200 | 6.67% |
| Cycloastragenol (Nanoformulated)[1,2] | Mg | 200 | 6.67% |
| Epigallocatechin gallate | Mg | 200 | 6.67% |
| Momordin | Mg | 200 | 6.67% |
| N,N-dimethylimidodicarbonimidic diamide (Or Chemical Derivative Or Structural Analog Of N,N-dimethylimidodicarbonimidic diamide) | Mg | 200 | 6.67% |
| Proanthocyanidins | Mg | 200 | 6.67% |
| Resveratrol (Nanoformulated)[1,2] | Mg | 200 | 6.67% |
| Withaferin A (Or A Chemical Derivative Or A Structural Analog Of Withaferin A) (Nanoformulated)[1,2] | Mg | 400 | 13.33% |
| Withanolides (Or A Chemical Derivative Or A Structural Analog Of Withanolides) (Nanoformulated)[1,2] | Mg | 200 | 6.67% |
| Withanosides (Or A Chemical Derivative Or A Structural Analog Of Withanosides) (Nanoformulated)[1,2] | Mg | 200 | 6.67% |

TABLE 7D-continued

Composition Of A Mixture For Suppressing/Inhibiting mTOR - May Also Include Some Bioactive Compounds From Tables Before & After This Table

|  | Unit | +/−50% | WT % |
|---|---|---|---|
| Vitamin | | | |
| Vitamin $D_3$ (Cholecalciferol) | Mg | 0.06 | 0.00% |
| Total Weight | G | 3.00 | 100.00% |

TABLE 8A

Composition Of A Mixture For Lowering The Risks Of Alzheimer's Disease - May Also Include Some Bioactive Compounds From Tables Before & After This Table

|  | Unit | +/−50% | WT % |
|---|---|---|---|
| Botanical | | | |
| *Bacopa monnieri*[+] | Mg | 200 | 2.01% |
| *Boswellia serrata*[+1] | Mg | 200 | 2.01% |
| *Camellia sinensis*[+] (Black) | Mg | 200 | 2.01% |
| *Camellia sinensis*[+] (Green) | Mg | 200 | 2.01% |
| *Cinnamomum zeylanicum*[+] | Mg | 200 | 2.01% |
| *Curcuma longa*[+] (Or A Curcuminoids Compound)[1,2,3,4] | Mg | 400 | 4.01% |
| *Emblica officinalis*[+] | Mg | 200 | 2.01% |
| *Mucuna pruriens*[+] | Mg | 200 | 2.01% |
| *Paeoniae alba*[+] | Mg | 200 | 2.05% |
| *Panax quinquefolius*[+] | Mg | 200 | 2.01% |
| *Polygala tenuifolia*[+] | Mg | 200 | 2.01% |
| *Rosmarinus officinalis*[+] | Mg | 200 | 2.01% |
| *Silybum marianum*[+] | Mg | 200 | 2.01% |
| *Vitis vinifera*[+] | Mg | 200 | 2.01% |
| *Withania somnifera*[+] | Mg | 200 | 2.01% |
| Chemical | | | |
| Acetylcholine (Or Choline Or Phosphatidyl Choline) | Mg | 200 | 2.01% |
| Alpha-R-Lipoic Acid | Mg | 20 | 0.20% |
| Aniracetam (Or Piracetam) | Mg | 200 | 2.01% |
| Caffeine | Mg | 20 | 0.20% |
| Citicoline (Or L-Alpha Glycerylphosphorylcholine) | Mg | 200 | 2.01% |
| Coenzyme $Q_{10}$ (Nanoformulated)[1,2] | Mg | 200 | 2.01% |
| DMAE (Dimethyl Amino Ethanol) | Mg | 200 | 2.01% |
| Epigallocatechin gallate | Mg | 200 | 2.01% |
| Fisetin | Mg | 200 | 2.01% |
| Huperzine A | Mg | 200 | 2.01% |
| L-Arginine | Mg | 200 | 2.01% |
| L-Carnosine | Mg | 200 | 2.01% |
| L-Dopa | Mg | 100 | 1.00% |
| L-Glutathione (Or Ebselen Or N-Acetyl-L-Cysteine) | Mg | 200 | 2.01% |
| L-Theanine | Mg | 200 | 2.01% |
| L-Tyrosine (Or M-Tyrosine Or N-Acetyl Tyrosine) | Mg | 200 | 2.01% |
| Melatonin (Extended Release) | Mg | 3 | 0.03% |
| N-Acetyl-L-Carnitine | Mg | 400 | 4.01% |
| Omega 3-6-9 Acid (Including Decosahexanoic Acid) (Nanoformulated)[1] | Mg | 200 | 2.01% |
| Picamilon | Mg | 200 | 2.01% |
| Phosphatidylserine | Mg | 200 | 2.01% |
| Pyrroloquinoline Quinone (PQQ)[1,2] | Mg | 20 | 0.20% |
| Quercetin[1,2] | Mg | 200 | 2.01% |
| Resveratrol[1,2] | Mg | 200 | 2.01% |
| Tetramethylpyrazine (TMP) | Mg | 200 | 2.01% |
| Trehalose | Mg | 200 | 2.01% |
| Ubiquinol (Nanoformulated)[1,2] | Mg | 1000 | 10.03% |
| Uridine | Mg | 200 | 2.01% |
| Vinpocetine | Mg | 200 | 2.01% |
| Withaferin A (Or Chemical Derivative Or Structural Analog Of Withaferin A) (Nanoformulated)[1,2] | Mg | 400 | 4.01% |
| Mineral | | | |
| Magnesium L-Threonate | Mg | 400 | 4.01% |
| Vitamin | | | |
| Vitamin $B_{12}$ (Methylcobalamin) | Mg | 1 | 0.01% |
| Vitamin $D_3$ | Mg | 0.25 | 0.00% |
| Vitamin $K_2$ | Mg | 2.0 | 0.02% |
| Total Weight | G | 9.97 | 100.00% |

TABLE 8B

Additional Composition Of A Mixture For Lowering The Risks Of Alzheimer's Disease - May Also Include Some Bioactive Compounds From Tables Before & After This Table

|  | Unit | +/−50% | WT % |
|---|---|---|---|
| Botanical | | | |
| *Bacopa monnieri*[+] | Mg | 200 | 2.16% |
| *Boswellia serrata*[+1] | Mg | 200 | 2.16% |
| *Chamomilla recutita* | Mg | 200 | 2.16% |
| *Cinnamomum zeylanicum*[+] | Mg | 200 | 2.16% |
| *Curcuma longa*[+] (Or A Curcuminoids Compound)[1,2,3,4] | Mg | 400 | 4.33% |
| *Humulus lupulus* | Mg | 200 | 2.16% |
| *Melissa officinalis* | Mg | 200 | 2.16% |
| *Passiflora incarnate* | Mg | 200 | 2.16% |
| *Silybum marianum*[+] | Mg | 200 | 2.16% |
| *Valeriana officinalis* | Mg | 200 | 2.16% |
| *Withania somnifera*[+] | Mg | 200 | 2.16% |
| Chemical | | | |
| Acetylcholine (Or Choline Or Phosphatidyl Choline) | Mg | 200 | 2.16% |
| Caffeine | Mg | 20 | 0.22% |
| Citicoline (Or L-Alpha Glycerylphosphorylcholine) | Mg | 200 | 2.16% |
| Coenzyme $Q_{10}$ (Nanoformulated)[1,2] | Mg | 200 | 2.16% |
| L-Glutathione (Or Ebselen Or N-Acetyl-L-Cysteine) | Mg | 200 | 2.16% |
| L-Theanine | Mg | 200 | 2.16% |
| L-Tyrosine (Or M-Tyrosine Or N-Acetyl Tyrosine) | Mg | 200 | 2.16% |
| Melatonin (Extended Release) | Mg | 3 | 0.03% |
| N-Acetyl-L-Carnitine | Mg | 400 | 4.33% |
| Omega 3-6-9 Acid (Including Decosahexanoic Acid) (Nanoformulated)[1] | Mg | 200 | 2.16% |
| Phosphatidylserine | Mg | 200 | 2.16% |
| Pyrroloquinoline Quinone (PQQ)[1,2] | Mg | 20 | 0.22% |
| Quercetin[1,2] | Mg | 200 | 2.16% |
| Resveratrol[1,2] | Mg | 200 | 2.16% |
| Tetramethylpyrazine (TMP) | Mg | 200 | 2.16% |
| Trehalose | Mg | 200 | 2.16% |
| Ubiquinol (Nanoformulated)[1,2] | Mg | 1000 | 10.82% |
| Uridine | Mg | 200 | 2.16% |
| Withaferin A (Or Chemical Derivative Or Structural Analog Of Withaferin A) (Nanoformulated)[1,2] | Mg | 400 | 4.33% |
| Mineral | | | |
| Magnesium L-Threonate | Mg | 400 | 4.33% |
| Vitamin | | | |
| Vitamin $B_{12}$ (Methylcobalamin) | Mg | 1 | 0.01% |
| Vitamin $D_3$ | Mg | 0.25 | 0.00% |
| Vitamin $K_2$ | Mg | 2.0 | 0.02% |

TABLE 8B-continued

Additional Composition Of A Mixture For Lowering The Risks Of Alzheimer's Disease - May Also Include Some Bioactive Compounds From Tables Before & After This Table

| | Unit | +/−50% | WT % |
|---|---|---|---|
| Other | | | |
| Lactoferrin | Mg | 2000 | 21.63% |
| Total Weight | G | 9.25 | 100.00% |

[+1]*Boswellia serrata* can suppress/inhibit 5-lipoxygenase. A bioactive compound (e.g., 3-O-acetyl-11-keto-β-boswellic acid) of *Boswellia serrata*'s can be nanoformulated to improve its bioavailability.

TABLE 8C

Additional Composition Of A Mixture For Lowering The Risks Of Alzheimer's Disease - May Also Include Some Bioactive Compounds From Tables Before & After This Table

| | Unit | +/−50% | WT % |
|---|---|---|---|
| Botanical | | | |
| *Tinospora cordifolia*[+] | Mg | 200 | 5.20% |
| *Withania somnifera*[+] | Mg | 200 | 5.20% |
| Chemical | | | |
| Caffeine | Mg | 20 | 0.52% |
| Citicoline (Or L-Alpha Glycerylphosphorylcholine) | Mg | 400 | 10.40% |
| Curcumin (Nanoformulated)[1,2,3,4] | Mg | 200 | 5.20% |
| Decosahexanoic Acid | Mg | 400 | 10.40% |
| L-Glutathione (Or Ebselen Or N-Acetyl-L-Cysteine) | Mg | 200 | 5.20% |
| L-Theanine | Mg | 200 | 5.20% |
| Melatonin (Extended Release) | Mg | 3 | 0.03% |
| Pyrroloquinoline Quinone (PQQ)[1,2] | Mg | 20 | 0.52% |
| Quercetin[1,2] | Mg | 200 | 5.20% |
| Ubiquinol | Mg | 1000 | 26.01% |
| Withaferin A (Or Chemical Derivative Or Structural Analog Of Withaferin A) (Nanoformulated)[1,2] | Mg | 400 | 10.40% |
| Mineral | | | |
| Magnesium L-Threonate | Mg | 400 | 10.40% |
| Vitamin | | | |
| Vitamin $D_3$ | Mg | 0.25 | 0.01% |
| Vitamin $K_2$ | Mg | 2.0 | 0.05% |
| Total Weight | G | 3.85 | 100.00% |

L-Theanine & melatonin combination for the night time dose, while L-Theanine and caffeine (or only caffeine) for the day time dose.

TABLE 8D

Additional Composition Of A Mixture For Lowering The Risks Of Alzheimer's Disease - May Also Include Some Bioactive Compounds From Tables Before & After This Table

| | Unit | +/−50% | WT % |
|---|---|---|---|
| Botanical | | | |
| *Bacopa monnieri*[+] | Mg | 200 | 5.46% |
| *Sceletium tortuosum*[+] | Mg | 20 | 0.55% |
| *Withania somnifera*[+] | Mg | 200 | 5.46% |
| Chemical | | | |
| Caffeine | Mg | 20 | 0.55% |
| Citicoline (Or L-Alpha Glycerylphosphorylcholine) | Mg | 400 | 10.91% |
| Curcumin (Nanoformulated)[1,2,3,4] | Mg | 200 | 5.46% |
| Decosahexanoic Acid | Mg | 400 | 10.91% |
| L-Glutathione (Or Ebselen Or N-Acetyl-L-Cysteine) | Mg | 200 | 5.46% |
| Melatonin (Extended Release) | Mg | 3 | 0.08% |
| Oleocanthal (Or A Chemical Derivative Or A Structural Analog Of Oleocanthal) (Nanoformulated)[1,2] | Mg | 200 | 5.46% |
| Pyrroloquinoline Quinone (PQQ)[1,2] | Mg | 20 | 0.55% |
| Ubiquinol | Mg | 1000 | 27.28% |
| Withaferin A (Or Chemical Derivative Or Structural Analog Of Withaferin A) (Nanoformulated)[1,2] | Mg | 400 | 10.91% |
| Mineral | | | |
| Magnesium L-Threonate | Mg | 400 | 10.91% |
| Vitamin | | | |
| Vitamin $D_3$ | Mg | 0.25 | 0.01% |
| Vitamin $K_2$ | Mg | 2.0 | 0.05% |
| Total Weight | G | 3.67 | 100.00% |

TABLE 8E

Additional Composition Of A Mixture For Lowering The Risks Of Alzheimer's Disease - May Also Include Some Bioactive Compounds From Tables Before & After This Table

| Chemical | Unit | +/−50% | WT % |
|---|---|---|---|
| 4,5-Bis-(4-methoxyanilino)phthalimide | Mg | 20 | 6.78% |
| 6-Bromoindirubin-3'-oxime[2] | Mg | 10 | 3.39% |
| 6-Bromo-N-2-propenyl-4-quinazolinamine (SMER-28) | Mg | 10 | 3.39% |
| 3,6-Dibromo-α-[(phenylamino)methyl]-9H-carbazole-9-ethanol | Mg | 20 | 6.78% |
| Lithium (Lithium Orotate Or Lithium Chloride) | Mg | 5 | 1.69% |
| Sodium Phenylbutyrate[2] | Mg | 10 | 3.39% |
| Uric Acid (From Inosine: Hypoxanthine Ribose) | Mg | 20 | 6.78% |
| (+/−)-1-(1-Benzo[b]thien-2-ylethyl)-1-hydroxyurea | Mg | 200 | 67.80% |
| Total Weight | G | 0.29 | 100.00% |

TABLE 9

Composition Of A Mixture For Lowering The Risks Of Cardiovascular Disease - May Also Include Some Bioactive Compounds From Tables Before & After This Table

| | Unit | +/−50% | WT % |
|---|---|---|---|
| Botanical | | | |
| *Allium sativum*[+] | Mg | 200 | 1.44% |
| *Crataegus oxyacantha*[+] | Mg | 200 | 1.44% |
| *Inula racemosa*[+] | Mg | 200 | 1.44% |
| *Olea europaea*[+] | Mg | 200 | 1.44% |
| *Rauwolfia serpentina*[+] | Mg | 200 | 1.44% |
| *Terminalia arjuna*[+] | Mg | 200 | 1.44% |
| Chemical | | | |
| Capsaicin (Or Capsinoid) | Mg | 200 | 1.44% |
| Chromium Polynicotinate | Mg | 0.2 | 0.00% |
| Cocoa Flavanols | Mg | 400 | 2.88% |
| Coenzyme $Q_{10}$ (Nanoformulated)[1,2] | Mg | 1000 | 7.19% |

TABLE 9-continued

Composition Of A Mixture For Lowering The Risks Of Cardiovascular Disease - May Also Include Some Bioactive Compounds From Tables Before & After This Table

|  | Unit | +/−50% | WT % |
|---|---|---|---|
| L-Arginine (Nanoformulated)[1,2] | Mg | 1000 | 7.19% |
| L-Glutathione (Or Ebselen Or N-Acetyl-L-Cysteine) | Mg | 200 | 1.44% |
| Plant Sterols (Nanoformulated)[1] | Mg | 5000 | 35.97% |
| Red Yeast Rice Extract | Mg | 2500 | 17.99% |
| Ubiquinol (Nanoformulated)[1,2] | Mg | 1000 | 7.19% |
| Mineral | | | |
| Magnesium | Mg | 400 | 2.88% |
| Other | | | |
| Coconut Oil | Mg | 1000 | 7.19% |
| *Lactobacillus reuteri* | Billion | 10 | 0.00% |
| Total Weight | G | 13.90 | 100.00% |

Table-9 can include 200 mg of *Commiphora mukul* extract.

TABLE 10A

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanical | | | |
| *Andrographis paniculata*[+] | Mg | 200 | 4.00% |
| *Artemisia princeps*[+] | Mg | 200 | 4.00% |
| *Camellia sinensis*[+] (Black) | Mg | 200 | 4.00% |
| *Camellia sinensis*[+] (Green) | Mg | 200 | 4.00% |
| *Caralluma fimbriata*[+] | Mg | 200 | 4.00% |
| *Cinnamomum zeylanicum*[+] | Mg | 200 | 4.00% |
| *Coccinia indica*[+] | Mg | 800 | 16.00% |
| *Irvingia gabonensis*[+] | Mg | 200 | 4.00% |
| *Lagerstroemia speciosa*[+] (Leaf Extract) | Mg | 50 | 1.00% |
| *Litchi chinensis*[+] | Mg | 200 | 4.00% |
| *Momordica charantia*[+] | Mg | 200 | 4.00% |
| *Salacia oblonga*[+] | Mg | 800 | 16.00% |
| Chemical | | | |
| Beta Glucan | Mg | 200 | 4.00% |
| Chromium Polynicotinate | Mg | 0.2 | 0.00% |
| Chlorogenic Acid | Mg | 200 | 4.00% |
| Nobiletin (Or 2000 Mg Naringenin) | Mg | 200 | 4.00% |
| Touchi | Mg | 1000 | 20.00% |
| Total Weight | G | 5.00 | 100.00% |

Chlorogenic acid (CHA) is an activator of calcineurin.

TABLE 10B

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanical | | | |
| *Andrographis paniculata*[+] | Mg | 200 | 2.63% |
| *Artemisia princeps*[+] | Mg | 200 | 2.63% |
| *Coccinia cordifolia*[+] | Mg | 200 | 2.63% |
| *Cordyceps sinensis*[+] | Mg | 200 | 2.63% |
| Green Coffee Bean Extract | Mg | 1200 | 15.79% |
| Lamon Variety Borlotto Bean Extract | Mg | 200 | 2.63% |
| *Paecilomyces hepiali* (providing 70 mg of cordycepic acid) | Mg | 1000 | 13.16% |
| *Momordica charantia*[+] | Mg | 200 | 2.63% |
| *Salacia oblonga*[+] | Mg | 800 | 10.53% |
| *Sorghum bicolor*[+] | Mg | 1000 | 13.16% |
| White Mulberry (providing 1-deoxynojirinmycin 15 (DNJ) mg) Extract | Mg | 400 | 5.26% |
| Chemical | | | |
| Beta Glucan | Mg | 200 | 2.63% |
| Chlorogenic Acid | Mg | 200 | 2.63% |
| Cyanidin 3-glucoside (Nanoformulated)[1,2] | Mg | 400 | 5.26% |
| Phloridzin | Mg | 200 | 2.63% |
| Touchi | Mg | 1000 | 13.16% |
| Total Weight | G | 7.60 | 100.00% |

TABLE 10C

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanical | | | |
| *Coccinia cordifolia*[+] | Mg | 200 | 3.03% |
| *Cordyceps sinensis*[+] | Mg | 200 | 3.03% |
| Green Coffee Bean Extract | Mg | 1200 | 18.18% |
| Lamon Variety Borlotto Bean Extract | Mg | 200 | 3.03% |
| *Momordica charantia*[+] | Mg | 200 | 3.03% |
| *Salacia oblonga*[+] | Mg | 800 | 12.12% |
| *Sorghum bicolor*[+] | Mg | 1000 | 15.15% |
| White Mulberry (providing 1-deoxynojirinmycin 15 (DNJ) mg) Extract | Mg | 400 | 6.06% |
| Chemical | | | |
| 4-(4-Hydroxyphenyl)butan-2-one (Nanoformulated)[1,2] | Mg | 400 | 6.06% |
| Beta Glucan | Mg | 200 | 3.03% |
| Chlorogenic Acid | Mg | 200 | 3.03% |
| Cyanidin 3-glucoside (Nanoformulated)[1,2] | Mg | 400 | 6.06% |
| Phloridzin | Mg | 200 | 3.03% |
| Touchi | Mg | 1000 | 15.15% |
| Total Weight | G | 6.60 | 100.00% |

TABLE 10D

Composition Of A Mixture For Lowering The Risks Of Type-2 Diabetes Disease - May Also Include Some Bioactive Compounds From Tables Before & After This Table

|  | Unit | +/−50% | WT % |
|---|---|---|---|
| Botanical | | | |
| *Coccinia cordifolia*[+] | Mg | 200 | 7.02% |
| *Emblica officinalis*[+] | Mg | 200 | 7.02% |
| Green Coffee Bean Extract | Mg | 1200 | 42.11% |
| *Lagerstroemia speciosa*[+] | Mg | 50 | 1.75% |
| *Punica granatum* | Mg | 200 | 7.02% |
| *Syzygium cumini*[+] | Mg | 200 | 7.02% |
| Chemical | | | |
| 4-(4-Hydroxyphenyl)butan-2-one (Nanoformulated)[1,2] | Mg | 400 | 14.04% |

TABLE 10D-continued

Composition Of A Mixture For Lowering The Risks Of Type-2 Diabetes Disease - May Also Include Some Bioactive Compounds From Tables Before & After This Table

| | Unit | +/−50% | WT % |
|---|---|---|---|
| Cyanidin 3-glucoside (Nanoformulated)[1,2] | Mg | 400 | 14.04% |
| Total Weight | G | 2.85 | 100.00% |

4-(4-Hydroxyphenyl)butan-2-one is raspberry ketone.
Green coffee bean extract has chlorogenic acid (CHA).
Explanation of Notations {+, *, 1, 2, 3 and 4}

| | |
|---|---|
| + | A component (meaning an extract or a powder or a bioactive compound or a bioactive molecule from any part of the specific plant) |
| * | Found in *Citrullus vulgaris*[+] |
| 1 | Nanoformulated means nanoemulsion/nanodispersion/nanosuspension or nanoencapsulation |
| 2 | Chemically coupled with Triphenylphosphonium (TPP) or a chemical derivative of Triphenylphosphonium (TPP) or a structural analog of Triphenylphosphonium (TPP) |
| 3 | Higher bioavailability with black pepper (*Piper nigrum*) and/or vitamin $D_3$ |
| 4 | FLLL-11 or FLLL-12 or GO-Y030 or GO-Y031 can replace curcumin |

TABLE 11

Composition Of A Mixture Of Sugar Free Sweetener

| | Unit | +/−50% | WT % |
|---|---|---|---|
| Botanical | | | |
| *Stevia rebaudiana*[+] Chemical | Mg | 20 | 0.42% |
| Erythritol | Mg | 4500 | 95.34% |
| Trehalose | Mg | 200 | 4.24% |
| Total Weight | G | 4.72 | 100.00% |

TABLE 12A

Composition Of A Mixture Of Sugar Free Super-Sweetener

| | Unit | +/−50% | WT % |
|---|---|---|---|
| Botanical | | | |
| *Capparis masaikai*[+] (Mabinlins Protein) | Mg | 5 | 0.11% |
| *Stevia rebaudiana*[+] Chemical | Mg | 20 | 0.42% |
| Erythritol | Mg | 4500 | 95.24% |
| Trehalose | Mg | 200 | 4.23% |
| Total Weight | G | 4.72 | 100.00% |

TABLE 12B

Composition Of A Mixture Of Sugar Free Super-Sweetener

| | Unit | +/−50% | WT % |
|---|---|---|---|
| Botanical | | | |
| *Curculigo latifolia*[+] (Curculin Protein) | Mg | 5 | 0.11% |
| *Stevia rebaudiana*[+] Chemical | Mg | 20 | 0.42% |
| Erythritol | Mg | 4500 | 95.24% |
| Trehalose | Mg | 200 | 4.23% |
| Total Weight | G | 4.72 | 100.00% |

TABLE 12C

Composition Of A Mixture Of Sugar Free Super-Sweetener

| | Unit | +/−50% | WT % |
|---|---|---|---|
| Botanical | | | |
| *Dioscoreophyllum cumminsii*[+] (Monellin Protein) | Mg | 2 | 0.04% |
| *Stevia rebaudiana*[+] Chemical | Mg | 20 | 0.42% |
| Erythritol | Mg | 4500 | 95.30% |
| Trehalose | Mg | 200 | 4.24% |
| Total Weight | G | 4.72 | 100.00% |

TABLE 12D

Composition Of A Mixture Of Sugar Free Super-Sweetener

| | Unit | +/−50% | WT % |
|---|---|---|---|
| Botanical | | | |
| *Momordica grosvenorii*/ *Siraitia grosvenorii*[+] | Mg | 5 | 0.11% |
| *Stevia rebaudiana*[+] Chemical | Mg | 20 | 0.42% |
| Erythritol | Mg | 4500 | 95.24% |
| Trehalose | Mg | 200 | 4.23% |
| Total Weight | G | 4.72 | 100.00% |

TABLE 12E

Composition Of A Mixture Of Sugar Free Super-Sweetener

| | Unit | +/−50% | WT % |
|---|---|---|---|
| Botanical | | | |
| *Pentadiplandra brazzeana*[+] (Brazzein Protein) | Mg | 5 | 0.11% |
| *Pentadiplandra brazzeana*[+] (Pentadin Protein) | Mg | 5 | 0.11% |
| *Stevia rebaudiana*[+] Chemical | Mg | 20 | 0.42% |
| Erythritol | Mg | 4500 | 95.14% |
| Trehalose | Mg | 200 | 4.23% |
| Total Weight | G | 4.73 | 100.00% |

TABLE 12F

Composition Of A Mixture Of Sugar Free Super-Sweetener

|  | Unit | +/−50% | WT % |
|---|---|---|---|
| Botanical | | | |
| *Stevia rebaudiana*⁺ | Mg | 20 | 0.42% |
| *Synsepalum dulcificum*⁺ (Miraculin Protein) | Mg | 5 | 0.11% |
| Chemical | | | |
| Erythritol | Mg | 4500 | 95.24% |
| Trehalose | Mg | 200 | 4.23% |
| Total Weight | G | 4.72 | 100.00% |

TABLE 12G

Composition Of A Mixture Of Sugar Free Super-Sweetener

|  | Unit | +/−50% | WT % |
|---|---|---|---|
| Botanical | | | |
| *Stevia rebaudiana*⁺ | Mg | 20 | 0.42% |
| *Thaumatococcus daniellii*⁺ (Thaumatin Protein) | Mg | 1 | 0.02% |
| Chemical | | | |
| Erythritol | Mg | 4500 | 95.32% |
| Trehalose | Mg | 200 | 4.24% |
| Total Weight | G | 4.72 | 100.00% |

TABLE 12H

Composition Of A Mixture Of Sugar Free Super-Sweetener

|  | Unit | +/−50% | WT % |
|---|---|---|---|
| Botanical | | | |
| *Dioscoreophyllum cumminsii*⁺ (Monellin Protein) | Mg | 2 | 0.04% |
| *Pentadiplandra brazzeana*⁺ (Brazzein Protein) | Mg | 5 | 0.11% |
| *Pentadiplandra brazzeana*⁺ (Pentadin Protein) | Mg | 5 | 0.11% |
| *Stevia rebaudiana*⁺ | Mg | 20 | 0.42% |
| Chemical | | | |
| Erythritol | Mg | 4500 | 95.10% |
| Trehalose | Mg | 200 | 4.23% |
| Total Weight | G | 4.73 | 100.00% |

TABLE 12I

Composition Of A Mixture Of Sugar Free Super-Sweetener

|  | Unit | +/−50% | WT % |
|---|---|---|---|
| Botanical | | | |
| *Dioscoreophyllum cumminsii*⁺ (Monellin Protein) | Mg | 2 | 0.04% |
| *Pentadiplandra brazzeana*⁺ (Brazzein Protein) | Mg | 5 | 0.11% |
| *Pentadiplandra brazzeana*⁺ (Pentadin Protein) | Mg | 5 | 0.11% |
| *Stevia rebaudiana*⁺ | Mg | 20 | 0.42% |
| *Synsepalum dulcificum*⁺ (Miraculin Protein) | Mg | 5 | 0.11% |
| Chemical | | | |
| Erythritol | Mg | 4500 | 95.00% |
| Trehalose | Mg | 200 | 4.22% |
| Total Weight | G | 4.73 | 100.00% |

TABLE 12J

Composition Of A Mixture Of Sugar Free Super-Sweetener

|  | Unit | +/−50% | WT % |
|---|---|---|---|
| Botanical | | | |
| *Capparis masaikai*⁺ (Mabinlins Protein) | Mg | 5 | 0.11% |
| *Dioscoreophyllum cumminsii*⁺ (Monellin Protein) | Mg | 2 | 0.04% |
| *Pentadiplandra brazzeana*⁺ (Brazzein Protein) | Mg | 5 | 0.11% |
| *Pentadiplandra brazzeana*⁺ (Pentadin Protein) | Mg | 5 | 0.11% |
| *Stevia rebaudiana*⁺ | Mg | 20 | 0.42% |
| *Synsepalum dulcificum*⁺ (Miraculin Protein) | Mg | 5 | 0.11% |
| Chemical | | | |
| Erythritol | Mg | 4500 | 94.90% |
| Trehalose | Mg | 200 | 4.22% |
| Total Weight | G | 4.74 | 100.00% |

TABLE 12K

Composition Of A Mixture Of Sugar Free Super-Sweetener

|  | Unit | +/−50% | WT % |
|---|---|---|---|
| Botanical | | | |
| *Curculigo latifolia*⁺ (Curculin Protein) | Mg | 5 | 0.11% |
| *Dioscoreophyllum cumminsii*⁺ (Monellin Protein) | Mg | 2 | 0.04% |
| *Pentadiplandra brazzeana*⁺ (Brazzein Protein) | Mg | 5 | 0.11% |
| *Pentadiplandra brazzeana*⁺ (Pentadin Protein) | Mg | 5 | 0.11% |
| *Stevia rebaudiana*⁺ | Mg | 20 | 0.42% |
| *Synsepalum dulcificum*⁺ (Miraculin Protein) | Mg | 5 | 0.11% |
| Chemical | | | |
| Erythritol | Mg | 4500 | 94.90% |
| Trehalose | Mg | 200 | 4.22% |
| Total Weight | G | 4.74 | 100.00% |

TABLE 12L

Composition Of A Mixture Of Sugar Free Super-Sweetener

|  | Unit | +/−50% | WT % |
|---|---|---|---|
| Botanical | | | |
| *Capparis masaikai*⁺ (Mabinlins Protein) | Mg | 1 | 0.02% |
| *Curculigo latifolia*⁺ (Curculin Protein) | Mg | 1 | 0.02% |

TABLE 12L-continued

Composition Of A Mixture Of Sugar Free Super-Sweetener

| | Unit | +/−50% | WT % |
|---|---|---|---|
| *Dioscoreophyllum cumminsii*+ (Monellin Protein) | Mg | 2 | 0.04% |
| *Pentadiplandra brazzeana*+ (Brazzein Protein) | Mg | 5 | 0.11% |
| *Pentadiplandra brazzeana*+ (Pentadin Protein) | Mg | 5 | 0.11% |
| *Stevia rebaudiana*+ | Mg | 20 | 0.42% |
| *Synsepalum dulcificum*+ (Miraculin Protein) | Mg | 5 | 0.11% |
| Chemical | | | |
| Erythritol | Mg | 4500 | 94.96% |
| Trehalose | Mg | 200 | 4.22% |
| Total Weight | G | 4.74 | 100.00% |

TABLE 12M

Composition Of A Mixture Of Sugar Free Super-Sweetener

| | Unit | +/−50% | WT % |
|---|---|---|---|
| Botanical | | | |
| *Capparis masaikai*+ (Mabinlins Protein) | Mg | 1 | 0.02% |
| *Curculigo latifolia*+ (Curculin Protein) | Mg | 1 | 0.02% |
| *Dioscoreophyllum cumminsii*+ (Monellin Protein) | Mg | 5 | 0.04% |
| *Pentadiplandra brazzeana*+ (Brazzein Protein) | Mg | 5 | 0.11% |
| *Pentadiplandra brazzeana*+ (Pentadin Protein) | Mg | 5 | 0.11% |
| *Stevia rebaudiana*+ | Mg | 20 | 0.42% |
| *Synsepalum dulcificum*+ (Miraculin Protein) | Mg | 5 | 0.11% |
| Chemical | | | |
| Erythritol | Mg | 4500 | 94.90% |
| Trehalose | Mg | 200 | 4.22% |
| Total Weight | G | 4.74 | 100.00% |

+ Means a component (meaning an extract or a powder or a bioactive compound or a bioactive molecule from any part of the specific plant).

TABLE 13A

Composition Of A Mixture Of A Chewable/Soluble Strip For Health

| | Unit | +/−50% | WT % |
|---|---|---|---|
| Chemical | | | |
| Anhydrous Caffeine/Caffeine | Mg | 50 | 0.92% |
| Curcumin/Nanoformulated Curcumin | Mg | 50 | 0.92% |
| Epigallocatechin Gallate | Mg | 50 | 0.92% |
| Inositol | Mg | 12.5 | 0.23% |
| L-Arginine | Mg | 4000 | 73.89% |
| Licoricidin | Mg | 50 | 0.92% |
| Licorisoflavan A | Mg | 50 | 0.92% |
| Resveratrol | Mg | 50 | 0.92% |
| Taurine | Mg | 50 | 0.92% |
| Optional Botanical | | | |
| *Astragalus* Root[5] | Mg | 200 | 3.69% |
| Licorice Root Extract-Deglycyrrhizinated | Mg | 200 | 3.69% |
| *Magnolia* Bark Extract | Mg | 50 | 0.92% |
| Tea Leaf (Green) Extract | Mg | 50 | 0.92% |
| Vitamin | | | |
| Biotin | Mg | 0.5 | 0.1% |
| Folate | Mg | 0.5 | 0.1% |
| Niacinimide | Mg | 200 | 3.69% |
| Vitamin $B_1$ | Mg | 25 | 0.46% |
| Vitamin $B_2$ | Mg | 25 | 0.46% |
| Vitamin $B_3$ | Mg | 25 | 0.46% |
| Vitamin $B_5$ | Mg | 50 | 0.92% |
| Vitamin $B_6$ | Mg | 25 | 0.46% |
| Vitamin $B_{12}$ | Mg | 0.01 | 0.00% |
| Vitamin C | Mg | 200 | 3.69% |
| Vitamin D | Mg | 0.1 | 0.00 |
| Other | | | |
| *Streptococcus salivarius* K12 | Billion | 10 | 0.00% |
| Total Weight | G | 5.41 | 100.00% |

TABLE 13B

Composition Of A Mixture Of A Chewable/Soluble Strip For Health

| | Unit | +/−50% | WT % |
|---|---|---|---|
| Chemical | | | |
| Anhydrous Caffeine/Caffeine | Mg | 50 | 0.93% |
| Epigallocatechin Gallate | Mg | 50 | 0.93% |
| Inositol | Mg | 12.5 | 0.23% |
| L-Arginine | Mg | 4000 | 74.58% |
| Licoricidin | Mg | 50 | 0.93% |
| Licorisoflavan A | Mg | 50 | 0.93% |
| Resveratrol | Mg | 50 | 0.93% |
| Taurine | Mg | 50 | 0.93% |
| Optional Botanical | | | |
| *Astragalus* Root[5] | Mg | 200 | 3.73% |
| Licorice Root Extract-Deglycyrrhizinated | Mg | 200 | 3.73% |
| *Magnolia* Bark Extract | Mg | 50 | 0.93% |
| Tea Leaf (Green) Extract | Mg | 50 | 0.93% |
| Vitamin | | | |
| Biotin | Mg | 0.5 | 0.01% |
| Folate | Mg | 0.5 | 0.01% |
| Niacinimide | Mg | 200 | 3.73% |
| Vitamin $B_1$ | Mg | 25 | 0.47% |
| Vitamin $B_2$ | Mg | 25 | 0.47% |
| Vitamin $B_3$ | Mg | 25 | 0.47% |
| Vitamin $B_5$ | Mg | 50 | 0.93% |
| Vitamin $B_6$ | Mg | 25 | 0.47% |
| Vitamin $B_{12}$ | Mg | 0.01 | 0.00% |
| Vitamin C | Mg | 200 | 3.73% |
| Vitamin D | Mg | 0.1 | 0.00% |
| Other | | | |
| *Streptococcus salivarius* K12 | Billion | 10 | 0.00% |
| Total Weight | G | 5.36 | 100.00% |

TABLE 13C

Composition Of A Mixture Of A Chewable/Soluble Strip For Health

|  | Unit | +/−50% | WT % |
|---|---|---|---|
| Chemical | | | |
| Anhydrous Caffeine/Caffeine | Mg | 50 | 0.94% |
| Inositol | Mg | 12.5 | 0.24% |
| L-Arginine | Mg | 4000 | 75.28% |
| Licoricidin | Mg | 50 | 0.94% |
| Licorisoflavan A | Mg | 50 | 0.94% |
| Resveratrol | Mg | 50 | 0.94% |
| Taurine | Mg | 50 | 0.94% |
| Optional Botanical | | | |
| *Astragalus* Root[5] | Mg | 200 | 3.76% |
| Licorice Root Extract-Deglycyrrhizinated | Mg | 200 | 3.76% |
| *Magnolia* Bark Extract | Mg | 50 | 0.94% |
| Tea Leaf (Green) Extract | Mg | 50 | 0.94% |
| Vitamin | | | |
| Biotin | Mg | 0.5 | 0.01% |
| Folate | Mg | 0.5 | 0.01% |
| Niacinimide | Mg | 200 | 3.76% |
| Vitamin $B_1$ | Mg | 25 | 0.47% |
| Vitamin $B_2$ | Mg | 25 | 0.47% |
| Vitamin $B_3$ | Mg | 25 | 0.47% |
| Vitamin $B_5$ | Mg | 50 | 0.94% |
| Vitamin $B_6$ | Mg | 25 | 0.47% |
| Vitamin $B_{12}$ | Mg | 0.01 | 0.00% |
| Vitamin C | Mg | 200 | 3.76% |
| Vitamin D | Mg | 0.1 | 0.00% |
| Other | | | |
| *Streptococcus salivarius* K12 | Billion | 10 | 0.00% |
| Total Weight | G | 5.31 | 100.00% |

TABLE 13D

Composition Of A Mixture Of A Chewable/Soluble Strip For Health

|  | Unit | +/−50% | WT % |
|---|---|---|---|
| Chemical | | | |
| Anhydrous Caffeine/Caffeine | Mg | 50 | 3.81% |
| Inositol | Mg | 12.5 | 0.95% |
| Licoricidin | Mg | 50 | 3.81% |
| Licorisoflavan A | Mg | 50 | 3.81% |
| Resveratrol | Mg | 50 | 3.81% |
| Taurine | Mg | 50 | 3.81% |
| Optional Botanical | | | |
| *Astragalus* Root[5] | Mg | 200 | 15.23% |
| Licorice Root Extract-Deglycyrrhizinated | Mg | 200 | 15.23% |
| *Magnolia* Bark Extract | Mg | 50 | 3.81% |
| Tea Leaf (Green) Extract | Mg | 50 | 3.81% |
| Vitamin | | | |
| Biotin | Mg | 0.5 | 0.04% |
| Folate | Mg | 0.5 | 0.04% |
| Niacinimide | Mg | 200 | 15.23% |
| Vitamin $B_1$ | Mg | 25 | 1.90% |
| Vitamin $B_2$ | Mg | 25 | 1.90% |
| Vitamin $B_3$ | Mg | 25 | 1.90% |
| Vitamin $B_5$ | Mg | 50 | 3.81% |
| Vitamin $B_6$ | Mg | 25 | 1.90% |
| Vitamin $B_{12}$ | Mg | 0.01 | 0.00% |
| Vitamin C | Mg | 200 | 15.23% |
| Vitamin D | Mg | 0.1 | 0.01% |
| Other | | | |
| *Streptococcus salivarius* K12 | Billion | 10 | 0.00% |
| Total Weight | G | 1.31 | 100.00% |

TABLE 13E

Composition Of A Mixture Of A Chewable/Soluble Strip For Health

|  | Unit | +/−50% | WT % |
|---|---|---|---|
| Chemical | | | |
| Anhydrous Caffeine/Caffeine | Mg | 50 | 3.96% |
| Inositol | Mg | 12.5 | 0.99% |
| Licoricidin | Mg | 50 | 3.96% |
| Licorisoflavan A | Mg | 50 | 3.96% |
| Taurine | Mg | 50 | 3.96% |
| Optional Botanical | | | |
| *Astragalus* Root[5] | Mg | 200 | 15.83% |
| Licorice Root Extract-Deglycyrrhizinated | Mg | 200 | 15.83% |
| *Magnolia* Bark Extract | Mg | 50 | 3.96% |
| Tea Leaf (Green) Extract | Mg | 50 | 3.96% |
| Vitamin | | | |
| Biotin | Mg | 0.5 | 0.04% |
| Folate | Mg | 0.5 | 0.04% |
| Niacinimide | Mg | 200 | 15.83% |
| Vitamin $B_1$ | Mg | 25 | 1.98% |
| Vitamin $B_2$ | Mg | 25 | 1.98% |
| Vitamin $B_3$ | Mg | 25 | 1.98% |
| Vitamin $B_5$ | Mg | 50 | 3.96% |
| Vitamin $B_6$ | Mg | 25 | 1.98% |
| Vitamin $B_{12}$ | Mg | 0.01 | 0.00% |
| Vitamin C | Mg | 200 | 15.83% |
| Vitamin D | Mg | 0.1 | 0.01% |
| Other | | | |
| *Streptococcus salivarius* K12 | Billion | 10 | 0.00% |
| Total Weight | G | 1.26 | 100.00% |

TABLE 13F

Composition Of A Mixture Of A Chewable/Soluble Strip For Health

|  | Unit | +/−50% | WT % |
|---|---|---|---|
| Chemical | | | |
| Anhydrous Caffeine/Caffeine | Mg | 50 | 4.70% |
| Inositol | Mg | 12.5 | 1.18% |
| Licoricidin | Mg | 50 | 4.70% |
| Licorisoflavan A | Mg | 50 | 4.70% |
| Taurine | Mg | 50 | 4.70% |
| Optional Botanical | | | |
| Licorice Root Extract-Deglycyrrhizinated | Mg | 200 | 18.80% |
| *Magnolia* Bark Extract | Mg | 50 | 4.70% |
| Tea Leaf (Green) Extract | Mg | 50 | 4.70% |
| Vitamin | | | |
| Biotin | Mg | 0.5 | 0.05% |
| Folate | Mg | 0.5 | 0.05% |
| Niacinimide | Mg | 200 | 18.80% |
| Vitamin $B_1$ | Mg | 25 | 2.35% |

TABLE 13F-continued

Composition Of A Mixture Of A Chewable/Soluble Strip For Health

|  | Unit | +/−50% | WT % |
|---|---|---|---|
| Vitamin $B_2$ | Mg | 25 | 2.35% |
| Vitamin $B_3$ | Mg | 25 | 2.35% |
| Vitamin $B_5$ | Mg | 50 | 4.70% |
| Vitamin $B_6$ | Mg | 25 | 2.35% |
| Vitamin $B_{12}$ | Mg | 0.01 | 0.00% |
| Vitamin C | Mg | 200 | 18.80% |
| Vitamin D | Mg | 0.1 | 0.01% |
| Other |  |  |  |
| *Streptococcus salivarius* K12 | Billion | 10 | 0.00% |
| Total Weight | G | 1.06 | 100.00% |

TABLE 13G

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 5.79% |
| Inositol | Mg | 12.5 | 1.45% |
| Licoricidin | Mg | 50 | 5.79% |
| Licorisoflavan A | Mg | 50 | 5.79% |
| Taurine | Mg | 50 | 5.79% |
| Optional Botanical |  |  |  |
| *Magnolia* Bark Extract | Mg | 50 | 5.79% |
| Tea Leaf (Green) Extract | Mg | 50 | 5.79% |
| Vitamin |  |  |  |
| Biotin | Mg | 0.5 | 0.06% |
| Folate | Mg | 0.5 | 0.06% |
| Niacinimide | Mg | 200 | 23.16% |
| Vitamin $B_1$ | Mg | 25 | 2.89% |
| Vitamin $B_2$ | Mg | 25 | 2.89% |
| Vitamin $B_3$ | Mg | 25 | 2.89% |
| Vitamin $B_5$ | Mg | 50 | 5.79% |
| Vitamin $B_6$ | Mg | 25 | 2.89% |
| Vitamin $B_{12}$ | Mg | 0.01 | 0.00% |
| Vitamin C | Mg | 200 | 23.16% |
| Vitamin D | Mg | 0.1 | 0.01% |
| Other |  |  |  |
| *Streptococcus salivarius* K12 | Billion | 10 | 0.00% |
| Total Weight | G | 0.86 | 100.00% |

TABLE 13H

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 6.15% |
| Inositol | Mg | 12.5 | 1.54% |
| Licoricidin | Mg | 50 | 6.15% |
| Licorisoflavan A | Mg | 50 | 6.15% |
| Taurine | Mg | 50 | 6.15% |
| Optional Botanical |  |  |  |
| Tea Leaf (Green) Extract | Mg | 50 | 6.15% |

TABLE 13H-continued

Composition Of A Mixture Of A Chewable/Soluble Strip For Health

|  | Unit | +/−50% | WT % |
|---|---|---|---|
| Vitamin |  |  |  |
| Biotin | Mg | 0.5 | 0.06% |
| Folate | Mg | 0.5 | 0.06% |
| Niacinimide | Mg | 200 | 24.58% |
| Vitamin $B_1$ | Mg | 25 | 3.07% |
| Vitamin $B_2$ | Mg | 25 | 3.07% |
| Vitamin $B_3$ | Mg | 25 | 3.07% |
| Vitamin $B_5$ | Mg | 50 | 6.15% |
| Vitamin $B_6$ | Mg | 25 | 3.07% |
| Vitamin $B_{12}$ | Mg | 0.01 | 0.00% |
| Vitamin C | Mg | 200 | 24.58% |
| Vitamin D | Mg | 0.1 | 0.01% |
| Other |  |  |  |
| *Streptococcus salivarius* K12 | Billion | 10 | 0.00% |
| Total Weight | G | 0.81 | 100.00% |

TABLE 13I

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 6.55% |
| Inositol | Mg | 12.5 | 1.64% |
| Licoricidin | Mg | 50 | 6.55% |
| Licorisoflavan A | Mg | 50 | 6.55% |
| Taurine | Mg | 50 | 6.55% |
| Vitamin |  |  |  |
| Biotin | Mg | 0.5 | 0.07% |
| Folate | Mg | 0.5 | 0.07% |
| Niacinimide | Mg | 200 | 26.19% |
| Vitamin $B_1$ | Mg | 25 | 3.27% |
| Vitamin $B_2$ | Mg | 25 | 3.27% |
| Vitamin $B_3$ | Mg | 25 | 3.27% |
| Vitamin $B_5$ | Mg | 50 | 6.55% |
| Vitamin $B_6$ | Mg | 25 | 3.27% |
| Vitamin $B_{12}$ | Mg | 0.01 | 0.00% |
| Vitamin C | Mg | 200 | 26.19% |
| Vitamin D | Mg | 0.1 | 0.01% |
| Other |  |  |  |
| *Streptococcus salivarius* K12 | Billion | 10 | 0.00% |
| Total Weight | G | 0.76 | 100.00% |

TABLE 13J

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 6.55% |
| Inositol | Mg | 12.5 | 1.64% |
| Licoricidin | Mg | 50 | 6.55% |
| Licorisoflavan A | Mg | 50 | 6.55% |
| Taurine | Mg | 50 | 6.55% |
| Vitamin |  |  |  |
| Folate | Mg | 0.5 | 0.07% |
| Niacinimide | Mg | 200 | 26.21% |

TABLE 13J-continued

Composition Of A Mixture Of A Chewable/Soluble Strip For Health

|  | Unit | +/−50% | WT % |
|---|---|---|---|
| Vitamin $B_1$ | Mg | 25 | 3.28% |
| Vitamin $B_2$ | Mg | 25 | 3.28% |
| Vitamin $B_3$ | Mg | 25 | 3.28% |
| Vitamin $B_5$ | Mg | 50 | 6.55% |
| Vitamin $B_6$ | Mg | 25 | 3.28% |
| Vitamin $B_{12}$ | Mg | 0.01 | 0.00% |
| Vitamin C | Mg | 200 | 26.21% |
| Vitamin D | Mg | 0.1 | 0.01% |
| Other |  |  |  |
| Streptococcus salivarius K12 | Billion | 10 | 0.00% |
| Total Weight | G | 0.76 | 100.00% |

TABLE 13K

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 6.56% |
| Inositol | Mg | 12.5 | 1.64% |
| Licoricidin | Mg | 50 | 6.56% |
| Licorisoflavan A | Mg | 50 | 6.56% |
| Taurine | Mg | 50 | 6.56% |
| Vitamin |  |  |  |
| Niacinimide | Mg | 200 | 26.23% |
| Vitamin $B_1$ | Mg | 25 | 3.28% |
| Vitamin $B_2$ | Mg | 25 | 3.28% |
| Vitamin $B_3$ | Mg | 25 | 3.28% |
| Vitamin $B_5$ | Mg | 50 | 6.56% |
| Vitamin $B_6$ | Mg | 25 | 3.28% |
| Vitamin $B_{12}$ | Mg | 0.01 | 0.00% |
| Vitamin C | Mg | 200 | 26.23% |
| Vitamin D | Mg | 0.1 | 0.01% |
| Other |  |  |  |
| Streptococcus salivarius K12 | Billion | 10 | 0.00% |
| Total Weight | G | 0.76 | 100.00% |

TABLE 13L

Composition Of A Mixture Of A Chewable/Soluble Step For Health

|  | Unit | +/−50% | WT % |
|---|---|---|---|
| Chemical |  |  |  |
| Anhydrous Caffeine/Caffeine | Mg | 50 | 8.89% |
| Inositol | Mg | 12.5 | 2.22% |
| Licoricidin | Mg | 50 | 8.89% |
| Licorisoflavan A | Mg | 50 | 8.89% |
| Taurine | Mg | 50 | 8.89% |
| Vitamin |  |  |  |
| Vitamin $B_1$ | Mg | 25 | 4.44% |
| Vitamin $B_2$ | Mg | 25 | 4.44% |
| Vitamin $B_3$ | Mg | 25 | 4.44% |
| Vitamin $B_5$ | Mg | 50 | 8.89% |
| Vitamin $B_6$ | Mg | 25 | 4.44% |
| Vitamin $B_{12}$ | Mg | 0.01 | 0.00% |

TABLE 13L-continued

Composition Of A Mixture Of A Chewable/Soluble Step For Health

|  | Unit | +/−50% | WT % |
|---|---|---|---|
| Vitamin C | Mg | 200 | 35.55% |
| Vitamin D | Mg | 0.1 | 0.02% |
| Other |  |  |  |
| Streptococcus salivarius K12 | Billion | 10 | 0.00% |
| Total Weight | G | 0.56 | 100.00% |

TABLE 13M

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 9.30% |
| Inositol | Mg | 12.5 | 2.33% |
| Licoricidin | Mg | 50 | 9.30% |
| Licorisoflavan A | Mg | 50 | 9.30% |
| Taurine | Mg | 50 | 9.30% |
| Vitamin |  |  |  |
| Vitamin $B_2$ | Mg | 25 | 4.65% |
| Vitamin $B_3$ | Mg | 25 | 4.65% |
| Vitamin $B_5$ | Mg | 50 | 9.30% |
| Vitamin $B_6$ | Mg | 25 | 4.65% |
| Vitamin $B_{12}$ | Mg | 0.01 | 0.00% |
| Vitamin C | Mg | 200 | 37.20% |
| Vitamin D | Mg | 0.1 | 0.02% |
| Other |  |  |  |
| Streptococcus salivarius K12 | Billion | 10 | 0.00% |
| Total Weight | G | 0.54 | 100.00% |

TABLE 13N

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 9.75% |
| Inositol | Mg | 12.5 | 2.44% |
| Licoricidin | Mg | 50 | 9.75% |
| Licorisoflavan A | Mg | 50 | 2.44% |
| Taurine | Mg | 50 | 2.44% |
| Vitamin |  |  |  |
| Vitamin $B_3$ | Mg | 25 | 4.88% |
| Vitamin $B_5$ | Mg | 50 | 9.75% |
| Vitamin $B_6$ | Mg | 25 | 4.88% |
| Vitamin $B_{12}$ | Mg | 0.01 | 0.00% |
| Vitamin C | Mg | 200 | 39.02% |
| Vitamin D | Mg | 0.1 | 0.02% |

TABLE 13N-continued

Composition Of A Mixture Of A Chewable/Soluble Strip For Health

|  | Unit | +/−50% | WT % |
|---|---|---|---|
| Other |  |  |  |
| *Streptococcus salivarius* K12 | Billion | 10 | 0.00% |
| Total Weight | G | 0.51 | 100.00% |

TABLE 13O

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 10.25% |
| Inositol | Mg | 12.5 | 2.56% |
| Licoricidin | Mg | 50 | 10.25% |
| Licorisoflavan A | Mg | 50 | 10.25% |
| Taurine | Mg | 50 | 10.25% |
| Vitamin |  |  |  |
| Vitamin $B_5$ | Mg | 50 | 10.25% |
| Vitamin $B_6$ | Mg | 25 | 5.13% |
| Vitamin $B_{12}$ | Mg | 0.01 | 0.00% |
| Vitamin C | Mg | 200 | 41.02% |
| Vitamin D | Mg | 0.1 | 0.02% |
| Other |  |  |  |
| *Streptococcus salivarius* K12 | Billion | 10 | 0.00% |
| Total Weight | G | 0.49 | 100.00% |

TABLE 13P

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 11.43% |
| Inositol | Mg | 12.5 | 2.86% |
| Licoricidin | Mg | 50 | 11.43% |
| Licorisoflavan A | Mg | 50 | 11.43% |
| Taurine | Mg | 50 | 11.43% |
| Vitamin |  |  |  |
| Vitamin $B_6$ | Mg | 25 | 5.71% |
| Vitamin $B_{12}$ | Mg | 0.01 | 0.00% |
| Vitamin C | Mg | 200 | 45.70% |
| Vitamin D | Mg | 0.1 | 0.02% |
| Other |  |  |  |
| *Streptococcus salivarius* K12 | Billion | 10 | 0.00% |
| Total Weight | G | 0.44 | 100.00% |

TABLE 13Q

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 12.12% |
| Inositol | Mg | 12.5 | 3.03% |
| Licoricidin | Mg | 50 | 12.12% |
| Licorisoflavan A | Mg | 50 | 12.12% |
| Taurine | Mg | 50 | 12.12% |
| Vitamin |  |  |  |
| Vitamin $B_{12}$ | Mg | 0.01 | 0.00% |
| Vitamin C | Mg | 200 | 48.47% |
| Vitamin D | Mg | 0.1 | 0.02% |
| Other |  |  |  |
| *Streptococcus salivarius* K12 | Billion | 10 | 0.00% |
| Total Weight | G | 0.41 | 100.00% |

TABLE 13R

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 12.12% |
| Inositol | Mg | 12.5 | 3.03% |
| Licoricidin | Mg | 50 | 12.12% |
| Licorisoflavan A | Mg | 50 | 12.12% |
| Taurine | Mg | 50 | 12.12% |
| Vitamin |  |  |  |
| Vitamin C | Mg | 200 | 48.47% |
| Vitamin D | Mg | 0.1 | 0.02% |
| Other |  |  |  |
| *Streptococcus salivarius* K12 | Billion | 10 | 0.00% |
| Total Weight | G | 0.41 | 100.00% |

TABLE 13S

Composition Of A Mixture Of A Chewable/Soluble Strip For Health

|  | Unit | +/−50% | WT % |
|---|---|---|---|
| Chemical |  |  |  |
| Anhydrous Caffeine/Caffeine | Mg | 50 | 23.52% |
| Inositol | Mg | 12.5 | 5.88% |
| Licoricidin | Mg | 50 | 23.52% |
| Licorisoflavan A | Mg | 50 | 23.52% |
| Taurine | Mg | 50 | 23.52% |
| Vitamin |  |  |  |
| Vitamin D | Mg | 0.1 | 0.05% |
| Other |  |  |  |
| *Streptococcus salivarius* K12 | Billion | 10 | 0.00% |
| Total Weight | G | 0.21 | 100.00% |

TABLE 13T

Composition Of A Mixture Of A Chewable/Soluble Strip For Health

|  | Unit | +/−50% | WT % |
|---|---|---|---|
| Chemical | | | |
| Anhydrous Caffeine/Caffeine | Mg | 50 | 23.53% |
| Inositol | Mg | 12.5 | 5.88% |
| Licoricidin | Mg | 50 | 23.53% |
| Licorisoflavan A | Mg | 50 | 23.53% |
| Taurine | Mg | 50 | 23.53% |
| Other | | | |
| *Streptococcus salivarius* K12 | Billion | 10 | 0.00% |
| Total Weight | G | 0.21 | 100.00% |

TABLE 13U

Composition Of A Mixture Of A Chewable/Soluble Strip For Health

|  | Unit | +/−50% | WT % |
|---|---|---|---|
| Chemical | | | |
| Inositol | Mg | 12.5 | 7.69% |
| Licoricidin | Mg | 50 | 30.77% |
| Licorisoflavan A | Mg | 50 | 30.77% |
| Taurine | Mg | 50 | 30.77% |
| Other | | | |
| *Streptococcus salivarius* K12 | Billion | 10 | 0.00% |
| Total Weight | G | 0.16 | 100.00% |

TABLE 13V

Composition Of A Mixture Of A Chewable/Soluble Strip For Health

|  | Unit | +/−50% | WT % |
|---|---|---|---|
| Chemical | | | |
| Licoricidin | Mg | 50 | 33.33% |
| Licorisoflavan A | Mg | 50 | 33.33% |
| Taurine | Mg | 50 | 33.33% |
| Other | | | |
| *Streptococcus salivarius* K12 | Billion | 10 | 0.00% |
| Total Weight | G | 0.15 | 100.00% |

TABLE 13W

Composition Of A Mixture Of A Chewable/Soluble Strip For Health

|  | Unit | +/−50% | WT % |
|---|---|---|---|
| Chemical | | | |
| Licoricidin | Mg | 50 | 50.00% |
| Licorisoflavan A | Mg | 50 | 50.00% |
| Other | | | |
| *Streptococcus salivarius* K12 | Billion | 10 | 0.00% |
| Total Weight | G | 0.10 | 100.00% |

In formulations described in Table-13A through Table-13W, Licoricidin and Licorisoflavan A can prevent gum diseases.

In formulations described in Table-13A through Table-13W, propolis extract of about 100 mg can be added.

In formulations described in Table-13A through Table-13W, coffee and D-Ribose can be added in about 1:1 weight ratio.

In formulations described in Table-13A through Table-13W, L-Arginine Alpha Keto-Glutarate (AAKG) (about 4 grams+/−50%) can be added instead of L-Arginine. L-Arginine or L-Arginine Alpha Keto-Glutarate can be encapsulated in methocel, a micro-polymer hydrophilic ether matrix to control the release rate of L-Arginine or L-Arginine Alpha Keto-Glutarate.

In formulations described in Table-13A through Table-13W, Astragalus root[5] can be mixed with about 200 mg extract of *Agaricus subrufescens*, about 200 mg extract of *Cordyceps sinensis*, about 200 mg extract of *Ganoderma lucidum*, about 200 mg extract of *Grifola frondosa*, about 200 mg extract of *Hericium erinaceus*, about 200 mg extract of *Phallus indusiatus* and about 200 mg extract of *Phellinus linteus*.

In formulations described in Table-13A through Table-13W, about 200 mg of *Commiphora myrrha* powder can be added.

In formulations described in Table-13A through Table-13W, about 200 mg of folic acid can be added.

In formulations described in Table-13A through Table-13W, about 200 mg of catalase, about 200 mg of glutathione peroxidase, about 1000 mg of L-Methionine, about 200 mcg of selenium amino acid complex (sodium selenite, L-selenomethionin and selenium-methyl L-selenocysteine) and about 200 mg superoxide dismutase can be added.

In formulations described in Table-13A through Table-13W, about 200 mg of *Emblica officinalis* extract can be added.

In formulations described in Table-13A through Table-13W, about 1000 mg of D-Aspartic acid, 100 mg of 3-Beta-Hydroxy-Urs-12-En-28-Oic acid, about 100 mg of 2-Phenyl-Di-Benzyl-Benzopyran-4 One, about 200 mg of extract of *Cordyceps sinensis*, about 400 mg of extract of *Trigonella foenum-graecum* with about 50% testofen and about 200 mg of *Panax ginseng* can be added.

In formulations described in Table-13A through Table-13W, inactive ingredients (malitol, sorbitol, gumbase, isomalt, calcium stearate, calcium pantothenate, flavor, gum Arabic, menthol, maltodextrin, acesulfame potassium, titanium dioxide, citric acid, malic acid, aspartame and glycerine) can be added.

Nanoemulsion/Nanodispersion/Nanosuspension

An oil dissolved bioactive compound 100 (e.g., curcumin in coconut oil) and an anti-solvent (e.g., water) are individually pressurized to collide head on at an extremely high velocity to form nanoemulsion/nanodispersion/nanosuspension of the (oil dissolved) bioactive compound 100 (in the anti-solvent).

Furthermore, nanoparticles of the bioactive compound 100 can be realized after evaporating the anti-solvent of nanoemulsion/nanodispersion/nanosuspension.

Furthermore, nanoemulsion/nanodispersion/nanosuspension/nanoparticle can enhance the efficacy and/or bioavailability of the bioactive compound 100 at a lower concentration.

Targeted Delivery: Nanoencapsulation

Figure 6A:
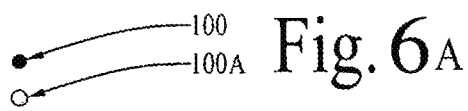
FIGS. 6A, 6B, 6C, 6D and 6E illustrate targeted delivery of bioactive compounds and/or bioactive molecules, utilizing a nanocarrier and/or a nanoshell.

FIG. 6A illustrates a bioactive compound 100 and a bioactive molecule 100A respectively.

Figure 6B:
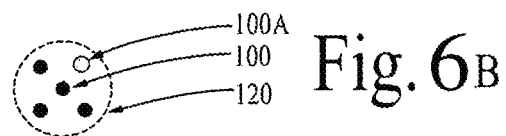

FIG. 6B illustrates the bioactive compound 100 and bioactive molecule 100A, which are encapsulated/caged in a nanoshell 120.

The size of the nanoshell 120 is about 25 nanometers to 115 nanometers in diameter and generally spherical in shape.

The nanoshell 120 can be biodegradable and less toxic.

By way of an example and not by way of any limitation, the nanoshell 120 can be a boron nitride nanotube, carbon nanotube, Cornell-dot, cubisome, dendrimer (including plant based dendrimer), deoxyribonucleic acid (DNA) origami nanostructure, exosome, fullerene $C_{60}$ (e.g., malonic acid derivative of $C_{60}$), gold nanoparticles (suitably coated), grapefruit-derived nanovector (GNV), hollow magnetic cage molecule (e.g., $Co_{12}C_6$, $Mn_{12}C_6$ and $Mn_{24}C_{18}$), lipidoid, liposome, mesoporous silica, micelle, nanocrystal, niosome, polysebacic acid (PSA), polysilsesquioxane (PSQ), porous silicon photonic crystal, quantum dot, quantum dot capped with glutathione, ribonucleic acid (RNA) origami nanostructure, self-assembling peptide (or self-assembling protein), solid-lipid nanoparticle, spherical nucleic acid (SNA), synthasome, tubular/tetrahedral structure fabricated/constructed, utilizing DNA/RNA origami process, virus, zein-plant protein and zeolite-1-nanocrystal.

A Cornell-dot consists of dye molecules encased in a chemically inert silica shell of about 5 nanometers in diameter.

Exosome contains RNAs. Cells communicate with each other by sending and receiving exosomes-thus an exosome can be viewed as a unit for cell-to-cell biological communication directly by surface expressed ligands or transferring molecules from the originating cells. For example, exosomes can carry material from the originating cancer cells to suppress the immune system and stimulate angiogenesis for the growth of cancer cells. Recipient cells act utilizing RNAs—for example, protein manufacturing in the case of mRNA or repression of the expression of some genes in the case of microRNAs. Thus, exosomes (in their specific pathways) can be utilized as the nanoshell 120 to deliver RNA (e.g., a specific small interfering RNA (siRNA)) for therapeutic purposes.

Monolayer coatings applied on the surface of the gold nanoparticles consists of a mix of hydrophobic and hydrophilic layers. Furthermore, additional coatings can be applied to target a selective cell type. A mechanism allows gold nanoparticles to pass through a cell membrane and then seals the opening of the cell membrane, as soon as the gold nanoparticles enter into the selective cells. Harnessing of the cell-penetrating mechanism of the suitably coated gold nanoparticles can be utilized as a way of delivering the bioactive compounds 100 and/or bioactive molecules 100A and/or biosensing molecules to the selective cell's interior, by binding the bioactive compounds 100 and/or bioactive molecules 100A and/or biosensing molecules with the monolayer of coatings and/or additional coatings. The biosensing molecules can detect/monitor a biomarker(s) to indicate the onset/decline of a disease. Furthermore, the biosensing molecules can be embedded within a dissolvable electronic circuit, which is fabricated/constructed by silicon nanowires and silk nanowires.

By way of an example and not by way of any limitation, the nanoshell 120 can be a combination of an artificial material and a biological material.

By way of an example and not by way of any limitation, the nanoshell 120, as a combination of an artificial inorganic/organic material and a natural biological material can be printed by three-dimensional (3-D) self-assembly/nano-printing or four-dimensional (4-D) self-assembly/nano-printing, wherein an extra dimension of time in four-dimensional self-assembly/nano-printing may allow the nanoshell 120 to adapt/evolve/transform over time by an internal/external condition (e.g., pH and light)

Furthermore, a micelle can be fabricated/constructed, utilizing an aptamer, casein protein, epigallocatechin-3-O-gallate derivative (with vitamin E at the center of epigallocatechin-3-O-gallate derivative) and polymer.

By way of an example and not by way of any limitation, the nanocrystal can be a nanodiamond or nanohydroxyapatite. Hydroxyapatite is a form of calcium phosphate $Ca_{10}(PO_4)_6(OH)_2$.

Spherical nucleic acids are configured as three-dimensional superlattice assembly on an inorganic nanoparticle (typically gold or silver). These three-dimensional superlattices can consist of functionalized and oriented nucleic acids-attached to the inorganic nanoparticle. Spherical nucleic acids can be core-filled with the above inorganic nanoparticle or core-less without the above inorganic nanoparticle. The strength/length of the programmable DNA bonds within the three-dimensional superlattice assembly can be adjusted by varying DNA sequence and length. The properties of SNAs can be adjusted by varying nanoparticle size, shape and composition.

Linear nucleic acids cannot enter into cells, but spherical nucleic acids (SNAs) can enter into cell. Core-less spherical nucleic acids do not trigger an immune response. Thus, resulting in longer lifetime in a human body. Spherical nucleic acids can also cross a human body's blood-brain barrier and skin. SNAs can enable nucleic acid-based and small interfering RNA (siRNA) based therapeutics. DNA sequence can be matched to target genes for a different disease.

Synthasome is a spherical hollow nanoshell and it contains an aqueous solution for protecting the bioactive compounds 100 and/or bioactive molecules 100A. The synthasome has a nano-scaled channel(s) (e.g., a transmembrane protein channel) to permit or deny transport of the bioactive compounds 100 and/or bioactive molecules 100A across the synthasome membrane.

Furthermore, an appropriate synthetic polymer material can be utilized to customize the characteristics (e.g., control permeability, release rate and stability) of the synthasome membrane.

Furthermore, a specialized biodegradable and non-toxic theranostic (e.g., perfluorocarbon based polymer) based on as the nanoshell 120 can spontaneously form itself out of tailored polymers macromolecules.

The formation requires a balance between the particle's hydrophilic (capable of dissolving in water) and hydrophobic (not dissolvable in water) parts. The hydrophobic portion makes it possible to fill the particle with the bioactive compound 100 and/or bioactive molecule 100A.

A relatively high concentration of the natural isotope 19F (fluorine) can make the theranostic nanoshell 120 clearly visible on high resolution images taken by magnetic resonance imaging. It is possible to obtain information about how the bioactive compound 100 and/or bioactive molecule 100A is taken up by the cell and whether the treatment utilizing the bioactive compound 100 and/or bioactive molecule 100A is working or not.

Virus (e.g., Influenza A virus-IAV)-configured as harmless/non-infectious can act as a nanoshell 120. For example, Influenza A virus-IAV has eight (8) viral segments, encoding ten (10) major proteins. By eliminating two (2) viral segments, Influenza A virus-IAV can be made harmless/non-infectious. Thus, Influenza A virus-IAV as a nanoshell 120 can deliver the bioactive compound 100 and/or bioactive molecule 100A.

Furthermore, Influenza A virus-IAV can also deliver either coding RNAs or noncoding RNAs or micro RNAs to treat a specific disease.

The interior surface of the nanoshell 120 can be electrically charged (e.g., an opposite electrical charge polarity with respect to the electrical charge polarity of the bioactive compounds 100 and/or bioactive molecules 100A to be encapsulated/caged in the nanoshell 120) to increase the encapsulation efficiency of the bioactive compounds 100 and/or bioactive molecules 100A.

The exterior surface of the nanoshell 120 can be electrically charged to increase the delivery efficiency of the bioactive compounds 100 and/or bioactive molecules 100A.

Figure 6C:
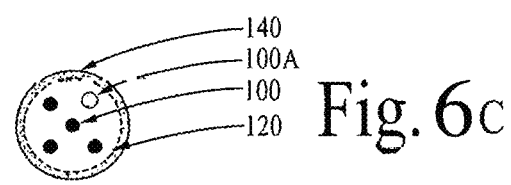

FIG. 6C illustrates the surface of the nanoshell 120, which can be coated with an optional protective (to protect from a human body's blood/biological fluid) functional surface 140.

The optional protective functional surface 140 can be fabricated/constructed, utilizing a casein protein.

Optionally, the nanoshell 120 can be coated with an immune shielding (to protect from a human body's inherent immune surveillance) functional surface 180.

The nanoshell 120 can be coated with galactosamine sugar molecules.

The nanoshell 120 can be coated with mannose sugar molecules.

The nanoshell 120 can be coated with folic acid molecules.

Both galactosamine sugar and mannose sugar can accumulate selectively in the liver.

Figure 6D:
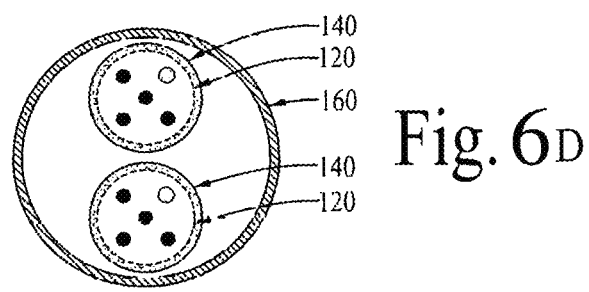

FIG. 6D illustrates the nanoshell 120, which can be further encapsulated/caged in a nanocarrier (e.g., an artificial cell, capsosome, DNA/RNA origami nanostructure, natural biopolymer chitosan and polyethylene glycol (PEG)) 160.

In addition to its well-known DNA's structural properties—A only binds T, G only binds C, one can predict the atomic-level structure of virtually any DNA origami nanostructure with remarkable accuracy.

A DNA origami structure with a lid that can stay locked until exposed to a DNA-based key.

Furthermore, because complementary DNA sequences recognize each other, a short DNA strand can act as an accurate address label to direct a DNA origami structure to a specified cell location.

Furthermore, a DNA-based sensor within a nanoshell 120 can recognize an RNA message produced because of a certain biological event-thus can trigger a release of RNA or DNA strands with therapeutic properties.

The size of the nanocarrier 160 is about 200 nanometers to 300 nanometers in diameter and generally spherical in shape.

The nanocarrier 160 can be biodegradable and less toxic.

To construct a capsosome, a polymer film (containing building blocks modified with cholesterol) is deposited onto small silica spheres. Liposomes (with an immune shielding functional surface 180) are anchored to the cholesterol. Subsequently, more polymer films are added and cross-linked by disulfide bridges. Finally, the small silica spheres are etched away.

Figure 6E:
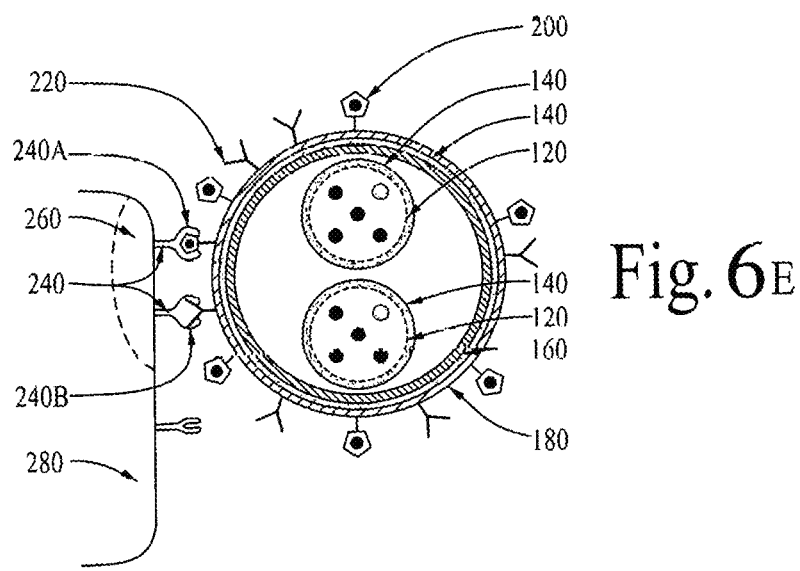

FIG. 6E illustrates the nanocarrier 160, which can be coated with the optional protective (to protect from a human body's blood/biological fluid) functional surface 140.

The nanocarrier 160 can be coated with an immune shielding (to protect from a human body's inherent immune surveillance) functional surface 180.

A human body's natural red blood/artificial red blood cell membrane can be utilized as an immune shielding functional surface 180.

A polymer membrane (e.g., polyethylene glycol polymer/water-like polymer) can also be utilized as an immune shielding functional surface 180 instead of a human body's red blood cell membrane.

Polyethylene glycol membrane is a low-toxicity polymer and it can shield against hydrophobic and/or electrostatic interactions.

However, a human body's natural red blood/artificial red blood can be utilized as an immune shielding functional surface 180, along with polyethylene glycol membrane, wherein polyethylene glycol membrane is configured to shield against hydrophobic and/or electrostatic interactions.

The extracellular space of a human brain is viscous and the viscosity can impede propagation of the nanoshell 120 in a human brain.

Considering the passage through a human body's blood-brain barrier and viscosity in the extracellular space of a human brain, a suitable diameter for propagation is estimated between 65 nanometers to 115 nanometers.

Thus, only the nanoshell 120 (without the nanocarrier 160) can be suitable for the passage through a human body's blood-brain barrier and extracellular space of a human brain.

Biological receptors 240 are located on cell 260 of tissue 280.

A first targeting ligand 200 (e.g., cobalamin/vitamin) can recognize/match/bind with specific biological receptors 240A of 240, located on cell 260 of tissue 280.

A second targeting ligand 220 (e.g., a specific antibody/aptamer) can recognize/match/bind with specific biological receptors 240B of 240, located on cell 260 of tissue 280.

Both targeting ligands 200 and 220 can be utilized as dual navigators toward the biological receptors 240A and 240B respectively.

Both the nanocarrier 160 and nanoshell 120 can break, when (a) the first targeting ligand 200 recognizes/matches/binds with the specific biological receptors 240A and (b) the second targeting ligand 220 recognizes/matches/binds with the specific biological receptors 240B.

Alternatively, both the nanocarrier 160 and nanoshell 120 can break under an external condition/response (e.g., pH and light).

Thus, the bioactive compounds 100 and/or bioactive molecules 100A can be delivered from the nanoshell 120 to the cell 260.

Example Applications of a Nanoshell (can be Decorated with a Human Body's Red Blood Cell Membrane & Polyethylene Glycol Membrane) with a Nanocarrier (can be Decorated with a Human Body's Red Blood Cell Membrane & Polyethylene Glycol Membrane)

Molecular Coupling/Reprogramming

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B (e.g., a messenger RNA (mRNA) aptamer). Upon passing through the nuclear pore, utilizing the second targeting ligand 220A that recognizes/matches/ binds with the nuclear pore, the nanoshell 120 can be uncapped in the nucleus of the cell 260 itself, when the third targeting ligand 220B recognizes/matches/binds with a specific RNA (e.g., a messenger RNA).

The bioactive compounds 100 and/or bioactive molecules 100A can be delivered from the nanoshell 120 specifically to couple and/or edit and/or modulate the specific RNA (e.g., a messenger RNA)-thus enabling a molecular coupling/reprogramming for specific disease prevention.

However, for a specific application of molecular coupling/reprogramming, only the nanoshell 120 (without the nanocarrier 160) can also be utilized.

Gene Text Editing by Zinc Fingers, a Class Of DNA-Binding Proteins

A human genome has about 3 billion pairs of the chemical letters A, C, G, and T (adenine, cytosine, guanine, and thymine). Now to 3 billion letters for a single appearance of the word "CAT," and then replace a "C" with "T" to make the word "TAT." To enable this, one needs an enzyme that is both capable of precise recognition of a specific DNA sequence and outfitted with a scissor and paste to modify the chemical letters. One big unknown of the copy-paste editing strategy is any off-target effects that during fixing a defective or target gene, one must not damage another gene.

Most gene therapy techniques use a virus to carry new genes into a cell, but cannot direct the virus to insert genes into a specific site.

But zinc fingers are a class of engineered DNA-binding proteins used by living cells to turn genes on and off. Each zinc finger recognizes a set of three letters, or bases, on the DNA molecule. Because the zinc fingers recognize specific sequences of DNA, they guide the control proteins to a specific site wherein the target gene begins. Thus, the zinc fingers can be utilized as a word processing system for cutting and pasting into a genetic text.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

The zinc fingers (with desired DNA template) can be delivered from the nanoshell 120 specifically to edit a specific gene for specific disease prevention.

Furthermore, the zinc fingers (with a desired DNA template) can be delivered from the nanoshell 120 specifically to genetically correct stem cells, prior to any use. This strategy can be used to generate genetically corrected, patient derived cells that could be transplanted without fear of a human body's immune-rejection.

However, for a specific application of genetic text editing, only the nanoshell 120 (without the nanocarrier 160) can also be utilized.

Gene Text Editing by Transcription Activator Like Effector Nucleases (TALENs)

The zinc fingers can snip away from a target site—thus, it may be a potentially serious safety problem.

Unlike the zinc fingers that bind to a group of three base pair, transcription activator like effector nucleases can bind to individual nucleotides.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

Transcription activator like effector nucleases (with desired DNA template) can be delivered from the nanoshell 120 specifically to edit a specific gene for specific disease prevention.

Furthermore, transcription activator like effector nucleases (with a desired DNA template) can be delivered from the nanoshell 120 specifically to genetically correct stem cells, prior to any use. This strategy can be used to generate genetically corrected, patient derived cells that could be transplanted without fear of a human body's immune-rejection.

However, for a specific application of genetic text editing, only the nanoshell 120 (without the nanocarrier 160) can also be utilized.

Gene Text Editing by a Synthetic RNA

Challenges of zinc finger or transcription activator like effector nucleases are getting a high level of expression and persistence of the introduced DNA construct.

A synthetic RNA that encodes a gene-editing protein (e.g., TALENs) can be targeted to a specific gene.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

A synthetic RNA to encode a gene-editing protein (e.g., transcription activator like effector nucleases) (with desired DNA template) can be delivered from the nanoshell 120 specifically to edit a specific gene for specific disease prevention.

Furthermore, a synthetic RNA to encode a gene-editing protein (e.g., transcription activator like effector nucleases) (with a desired DNA template) can be delivered from the nanoshell 120 specifically to genetically correct stem cells, prior to any use. This strategy can be used to generate genetically corrected, patient derived stem cells that could be transplanted without fear of a human body's immune-rejection.

However, for a specific application of genetic text editing, only the nanoshell 120 (without the nanocarrier 160) can also be utilized.

Gene Text Editing by Cas9 Complexes with RNA

A DNA-cutting enzyme namely Cas9 complexed with a short 20-nucleotide segment of RNA (matching the target DNA segment) can be programmed to target a DNA sequence. Rather using a protein to target the desired DNA sequence, it uses RNA to guide the DNA-cutting enzyme namely Cas9 to the targeted DNA sequence. This takes advantage of the natural pairing of RNA and DNA sequences. In order to recognize the target DNA, Cas9 requires the short sequence of "GG" in the target DNA adjacent to the site bound by the targeting RNA. The DNA-cutting enzyme namely Cas9 does not have to change for every DNA sequence to be targeted—one simply has to reprogram it with a different RNA transcript, which is easy to design and implement.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

A DNA-cutting enzyme namely Cas9 complexed with a short 20-nucleotide segment of RNA (matching the target DNA segment) can be programmed to target a DNA sequence. The DNA-cutting enzyme namely Cas9 complexed with a short 20-nucleotide segment of RNA can be delivered from the nanoshell 120 specifically to edit a specific gene for specific disease prevention.

Furthermore, the DNA-cutting enzyme namely Cas9 complexed with a short 20-nucleotide segment of RNA can be delivered from the nanoshell 120 specifically to genetically correct stem cells, prior to any use. This strategy can be used to generate genetically corrected, patient derived cells that could be transplanted without fear of a human body's immune-rejection.

However, for a specific application of genetic text editing, only the nanoshell 120 (without the nanocarrier 160) can also be utilized.

Example Applications of Gene Text Editing

HIV needs to latch onto a human body's white blood cell's CCR5 receptor to invade cells. However, a genetic mutation in a human body's white blood-cell's CCR5 receptor can prevent a transmission of HIV virus. Thus, gene editing can be utilized to disable the specific genes responsible for the production of CCR5 receptors.

Transcription Factor Control by Engineered CRISPR-Cas9 System with RNA

Transcription factors proteins can bind with specific DNA sequences in the gene's promoter region for either recruiting or blocking the enzymes needed to copy that gene into mRNA.

An engineered CRISPR-Cas9 system with RNA can act as a transcription factor, wherein Cas9 complexed with a short 20-nucleotide segment of RNA (matching the target DNA segment) can be programmed to target a DNA sequence; wherein Cas9 is disabled with a first protein to cut DNA after binding with DNA. Furthermore, the engineered CRISPR-Cas9 is embedded with a second protein (e.g., programmable oligomers), wherein the second protein can activate or repress gene expression by modulating the transcription.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on the cell 260 to allow the nanoshell 120 to the cell 260.

The nanoshell 120 can be decorated with a second targeting ligand 220A for recognition of a nuclear pore and a third targeting ligand 220B. Upon passing through the nuclear pore utilizing the second targeting ligand 220A that recognizes/matches/binds with the nuclear pore, the nanoshell 120 can be uncapped in the nucleus of the cell 260, when the third targeting ligand 220B recognizes/matches/binds with a specific DNA.

The engineered CRISPR-Cas9 system with RNA can be delivered from the nanoshell 120 specifically to activate or repress gene expression by modulating the transcription for specific disease prevention.

Cas9 does not have to change for every DNA sequence to be targeted one simply has to reprogram it with a different RNA transcript, which is easy to design and implement.

Molecular Coupling to a Virus/Programmed Suicide of a Virus Infected Cell to Inhibit Virus Multiplication/Propagation The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cell to allow the nanoshell 120 to the cell infected with a virus.

The nanoshell 120 can be decorated with the second targeting ligand 220 (e.g., an aptamer/protein kinase R (PKR) protein) which can recognize/match/bind with a single-stranded RNA/double-stranded RNA/double-stranded DNA of a virus). The nanoshell 120 can be uncapped in the cell infected with the virus, when the second targeting ligand 220 recognizes/matches/binds with a single-stranded RNA/double-stranded RNA/double-stranded DNA of the virus in the cell.

The bioactive compounds 100 and/or bioactive molecules 100A can be delivered from the nanoshell 120 to induce the cell infected with the virus for a programmed cell suicide (e.g., via apoptotic protease activating factor 1) to inhibit the multiplication/propagation of the virus.

However, for a specific application of molecular coupling to a virus/programmed suicide of a virus infected cell to inhibit virus multiplication/propagation, only the nanoshell 120 (without the nanocarrier 160) can be utilized.

Molecular Coupling to a Cancer Cell/Programmed Suicide of a Cancer Cell to Inhibit Cancer Multiplication/Propagation The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cancer cell to allow the nanoshell 120 to the cancer cell.

The nanoshell 120 can be decorated with the second targeting ligand 220 (e.g., a specific aptamer is designed to be complementary to an RNA sequence unique to the cancer cell). The nanoshell 120 can be uncapped in the cancer cell, when the second targeting ligand 220 recognizes/matches/binds with an RNA sequence unique to the cancer cell.

The bioactive compounds 100 and/or bioactive molecules 100A can be delivered from the nanoshell 120 to induce the cancer cell 260 for a programmed cell suicide (e.g., via p53 pathway) to stop cancer multiplication/propagation.

For example, 2-(4-morpholinoanilino)-6-cyclohexylaminopurine, a small bioactive molecule can induce selectively cell death of a cancer cell.

For example, a Bax activator compound can bind directly and selectively to Bax for Bax activation. When activated, Bax damages the cell's mitochondria, releasing signals to self-destruct the cell and digest its pieces.

However, for a specific application of molecular coupling to a cancer cell/programmed suicide of a cancer cell to inhibit cancer multiplication/propagation, only the nanoshell 120 (without the nanocarrier 160) can be utilized.

Molecular Coupling to Inhibit Insulin Degrading Enzyme

Normally about 50% of the insulin produced by the pancreas is immediately destroyed by the liver; but there may be a mechanism to regulate how much insulin enters into a human body's bloodstream. The insulin degrading enzyme is a protease, an enzyme that chops proteins or peptides into smaller pieces. If the insulin degrading enzyme is inhibited, insulin can remain in a human body's blood stream longer. Insulin is involved in a surprisingly wide range of important processes, including memory and cognition. Thus, the insulin degrading enzyme inhibitors may have multiple therapeutic applications. The insulin degrading enzyme is a thiol-sensitive zinc-metallopeptidase.

A short-lived insulin degrading enzyme inhibitor, taken before a meal can be beneficial to manage Type-2 Diabetes disease.

By way of an example and not by way of any limitation, a bioactive compound $C_{21}H_{22}FN_3O_5S_2$ with the structural formula (as described below) can inhabit the insulin degrading enzyme.

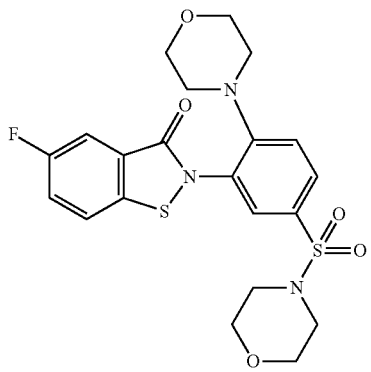

Structural Formula Of $C_{21}H_{22}FN_3O_5S_2$

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cell to allow the nanoshell 120 to the cell.

The nanoshell 120 can be decorated with the second targeting ligand 220 (e.g., a specific aptamer is designed to bind with a specific target on the insulin degrading enzyme). The nanoshell 120 can be uncapped in the cell, when the second targeting ligand 220 recognizes/matches/binds with the specific target of the insulin degrading enzyme to deliver the bioactive compound such as, $C_{21}H_{22}FN_3O_5S_2$ to inhibit the insulin degrading enzyme.

Molecular Coupling to Inhibit Insulin Degrading Enzyme Integrated with In-Vivo Gene Regulation by a Riboswitch Just as natural riboswitches can regulate gene expression in response to small-molecule ligands during transcription or translation, synthetic riboswitches can be engineered to repress or activate gene expression in a ligand-dependent fashion. A riboswitch can be turned on or off by a small molecule. Such riboswitch biosensors would provide spatial as well as temporal information regarding the levels of specific ligands in disease and the input information can be used to regulate cellular behavior for achieving therapeutic goals.

The nanoshell 120 can be encapsulated/caged in the nanocarrier 160. The nanocarrier 160 can be decorated with the first targeting ligand 200. The first targeting ligand 200 can recognize/match/bind with specific biological receptors 240A on a cell to allow the nanoshell 120 to the cell. The nanoshell 120 can be decorated with the second targeting ligand 220 (e.g., a specific aptamer is designed to bind with a specific target on the insulin degrading enzyme). The nanoshell 120 can be uncapped in the cell, when the second targeting ligand 220 recognizes/matches/binds with the specific target of the insulin degrading enzyme to deliver the bioactive compound such as, $C_{21}H_{22}FN_3O_5S_2$ to inhibit the insulin degrading enzyme and a riboswitch engineered to recognize glucose as its ligand and in response, the riboswitch engineered to recognize glucose as its ligand and in response, regulates the expression of the insulin degrading enzyme gene in-vivo.

Example Applications of a Nanoshell (can be Decorated with a Human Body's Red Blood Cell Membrane & Polyethylene Glycol Membrane) without a Nanocarrier Collective Intelligence from Quorum Sensing of a Large Array of Smart Nanoshells DNA structure can assemble into a two dimensional and/or a three-dimensional nanomechanical device. This two dimensional and/or a three-dimensional nanomechanical device can be further integrated with (a) a targeting ligand (e.g., a specific aptamer/RNA) and a biocompatible nanosensor (e.g., an exosome) to act as a smart nanoshell 120. The smart nanoshell 120 can be activated by using a targeting ligand to deliver bioactive compounds 100 and/or bioactive molecules 100A.

Collective intelligence (e.g., swarm intelligence acquired from the quorum sensing of the biocompatible nanosensors) of a large array of smart nanoshells 120 can be derived/utilized to predict the efficacy of the bioactive compounds 100 and/or bioactive molecules 100A for a treatment or to diagnose a disease and/or an array of diseases.

In many size constrained applications, the nanoshell 120 (without the nanocarrier 160) coated with an immune shielding functional surface 180 can be utilized.

The nanoshell 120 (coated with a light sensitive layer) can be activated by a suitable wavelength from an external light source (e.g., an ultraviolet/visible/infrared light source) to deliver the bioactive compounds 100 and/or bioactive molecules 100A from the nanoshell 120 to the cell 260.

Alternatively, the nanoshell 120 (alternatively configured with a magnetic nanoparticle) can be activated by a suitable external magnetic field to deliver the bioactive compounds 100 and/or bioactive molecules 100A from the nanoshell 120 to the cell 260.

A specific small interfering RNA can be designed to suppress/inhibit unwanted protein manufacturing in the cell 260. The specific small interfering RNA can be encapsulated/caged in the nanoshell 120. The nanoshell 120 decorated with a targeting ligand can deliver the specific siRNA to suppress/inhibit specific unwanted protein manufacturing to the cell 260.

Molecular Coupling to a Virus/Programmed Death of a Virus Infected Cell to Inhibit Virus Multiplication/Propagation To sense an invading virus, a cell can use a pattern recognition receptor. The pattern recognition receptor can recognize/match/bind to a molecular signature, specific to the virus. This binding causes the pattern recognition receptors to change its structural shape. Thus, initiating a chain-reaction of a signal (regarding the virus) to the surrounding cells.

For example, one of these pattern recognition receptors is RIG-1, which can practically target all RNA viruses. In an absence of a virus, a molecular virus sensor of RIG-1 receptor is exposed, while the domain responsible for cell signaling is hidden out of reach of the signaling machinery.

But when RIG-1 receptor detects a virus it changes its shape—waking up the cell signaling domains and triggering interferon production in the cell.

The changing shape of RIG-1 receptor can be detected upon binding of the molecular virus sensor of RIG-1 receptor with a molecular probe targeting ligand (e.g., a molecular beacon) wherein the molecular probe is configured with a suitable fluorophore.

The molecular probe (configured with the suitable fluorophore) targeting ligand can be decorated on the nanoshell 120.

Furthermore, the bioactive compound 100 and/or bioactive molecule 100A for programmed cell suicide can be encapsulated/caged in/with an ultra-sensitive photolabile protecting group (PPG). The photolabile protecting group can be encapsulated/caged in the nanoshell 120.

Thus, in vivo fluorescence can trigger a release of the bioactive compound 100 and/or bioactive molecule 100A from the photolabile protecting group for programmed cell suicide (e.g., via apoptotic protease activating factor 1) of the virus infected cell to inhibit virus multiplication/propagation.

However, instead of RIG-1 receptor, the nanoshell 120 can be decorated with a specific targeting ligand. The specific targeting ligand can recognize/match/bind with a single-stranded RNA/double-stranded RNA/double-stranded DNA of a virus.

Molecular Coupling to a Virus/Programmed Death of a Virus Infected Cell to Inhibit Virus Multiplication/Propagation Utilizing DNA/RNA Origami Structure Smart Nanoshell The (DNA/RNA origami structure based) nanoshell 120 can be fabricated/constructed, inputting a list of DNA/RNA strands that can be mixed together, by utilizing DNA/RNA modeling software.

DNA/RNA modeling software can predict how DNA/RNA base pairs can bind/match together to create a particular DNA/RNA origami structure.

The (DNA/RNA origami structure based) nanoshell 120 can be decorated with a targeting ligand (e.g., a specific aptamer) to recognize/match/bind a target molecule in the signaling domain of RIG-1 receptor, when RIG-1 receptor changes its shape in the presence of a virus.

When the targeting ligand and target molecule recognize/match/bind in the signaling domain of RIG-1 receptor, when RIG-1 receptor changes its shape in the presence of a virus, the DNA strand can be configured to unzip, unlocking the (DNA/RNA origami structure based) nanoshell 120 and releasing the bioactive compound 100 and/or bioactive molecule 100A for programmed cell suicide (e.g., via apoptotic protease activating factor 1) of a virus infected cell to inhibit virus multiplication/propagation.

However, instead of RIG-1 receptor, the (DNA/RNA origami structure based) nanoshell 120 can be decorated with a specific targeting ligand. The specific targeting ligand can recognize/match/bind with a single-stranded RNA/double-stranded RNA/double-stranded DNA of a virus.

To enhance specificity, two targeting ligands can be utilized, instead of one targeting ligand.

Thus, it would require two different matching signals in order to unzip the (DNA/RNA origami structure based) nanoshell 120.

Synthesis of Protein on-Demand

An amino acid, a DNA/modified DNA (wherein the DNA/modified DNA encapsulated/caged in/with a photolabile protecting group) and a ribosome can be encapsulated/caged in the nanoshell 120.

For example, a nanosized hole in DNA can be drilled by an atomic beam to insert/delete a suitable atom or a molecule in order to fabricate/construct the modified DNA.

An incident light can activate the photolabile protecting group to synthesize a desired protein on-demand in-vitro and in-vivo. The nanoshell 120 can then deliver the desired protein directly to the cell 260. The desired protein can be utilized as a treatment against a disease.

Synthesis of Protein on-Demand by Synthetic Nucleotides to DNA

Natural genetic alphabet of DNA, the As, Cs, Gs, and Is that write the stories/book of life can be integrated (chemically bonded) with new compatible synthetic letters (e.g., $\alpha$ and $\beta$) to create a hybrid DNA (to write expanded stories/book of life). Furthermore, the hybrid DNA can be integrated (chemically bonded) with an importin protein(s). Importin is a type of protein that can transport its cargo hybrid DNA into the nucleus by binding to a specific recognition sequence, called the nuclear localization signal (NLS). Importin protein can bind with its cargo hybrid DNA in the cytoplasm, after which they are able to interact with the nuclear pore complex and pass through its channel. Once inside the nucleus, interaction with Ran-GTP causes a conformational change in the importin protein that causes it to dissociate from its cargo hybrid DNA. The nanoshell 120 decorated with a targeting ligand, wherein the targeting ligand can recognize/match/bind with specific receptors of a cell-thus allowing the cell membrane to be opened for the passage of the nanoshell 120 to deliver hybrid DNA integrated (chemically bonded) with an importin protein in cytoplasm and then ultimately into the nucleus.

Utilizing an artificial mRNA, hybrid DNA can manufacture useful protein(s)/protein(s)-on Demand, unknown to exist in nature, leading to a large number of amino acids and a vast array of proteins. For example, adding just two (2) synthetic alphabets of DNA, one can manufacture one hundred seventy-two (172) amino acids with three (3) base pairs such as $\alpha\beta$A or TG$\alpha$.

Furthermore, a hybrid DNA code can be used to build hybrid biological circuits (in cells) which may/may not interfere with the natural biological circuits.

Alzheimer's Disease

Shape and/or electrical polarity of the nanoshell 120 can be important parameters to suppress/inhibit Alzheimer's disease.

A tubular shaped nanoshell 120 can enhance/promote amyloid beta protein, increasing rate of decline in cognitive abilities in a human brain.

A negative electrical charged and tetrahedral shaped nanoshell 120 can distort and suppress/inhibit amyloid beta protein, significantly decreasing rate of decline in cognitive abilities in a human brain.

A specific small interfering RNA can be designed to suppress/inhibit unwanted protein manufacturing in the cell 260. The specific siRNA can be encapsulated/caged in the nanoshell 120. The nanoshell 120 decorated with a targeting ligand, wherein the targeting ligand can recognize/match/bind with adenosine receptors-thus allowing a human body blood-brain barrier to be opened for the passage of the nanoshell 120 to deliver a specific siRNA to suppress/inhibit unwanted protein manufacturing in a human brain.

Increased CD33 protein activity in microglia can impair amyloid beta protein. More CD33 protein is on the cell surface of microglia, then more amyloid beta protein, toxic amyloid beta plaques and damaging debris are in a human brain. Thus, reducing or silencing CD33 protein may be beneficial against Alzheimer's disease. The nanoshell 120 decorated with a targeting ligand, wherein the targeting ligand can recognize/match/bind with adenosine receptors-thus allowing a human body's blood-brain barrier to be opened for the passage of the nanoshell 120 to deliver a specific siRNA to suppress/inhibit CD33 protein manufacturing in a human brain. However, it should be noted that a certain version of the CD33 gene may decrease CD33 protein activity in microglia.

Alzheimer's disease can be caused by a loss of synapses (between neurons) due to disintegration of tau protein, wherein tau protein can interact with amyloid beta protein.

Aging and/or poor autophagy can upregulate amyloid precursor protein cleaving enzyme: Bace1 (β-secretase-a molecular scissor).

Bace1 can cut amyloid precursor protein to produce amyloid beta (Aβ) protein and another small fragment called AICD. Both amyloid beta protein and AICD can be linked to Alzheimer's disease. If Bace1 is acetylated via activation of ATase1 enzyme and ATase2 enzyme, then Bace1 can travel through the cell in a series of steps to produce amyloid precursor protein. If Bace1 is not acetylated, then Bace1 takes a different pathway toward degradation.

RanBP9 protein can push amyloid precursor protein at the cell (neuron cell) edge, wherein both Bace1 and presenilin complex (γ-secretase-α molecular scissor) can cut amyloid precursor protein to generate amyloid beta protein.

A potential prevention and/or treatment of Alzheimer's disease can be achieved by suppressing/inhibiting RanBP9 protein manufacturing. RanBP9 protein is encoded by RanBP9 gene.

Curcumin (e.g., a nanoformulated curcumin) can suppress/inhibit RanBP9 protein manufacturing in a human brain.

Cucurbitacin (e.g., Cucurbitacin E) can suppress/inhibit RanBP9 protein manufacturing in a human brain. Nanoformulated cucurbitacin can enhance the efficacy and/or bioavailability at a lower concentration.

Metformin (N,N-dimethylimidodicarbonimidic diamide) can suppress/inhibit RanBP9 protein manufacturing in a human brain.

An anticancer compound imatinib mesylate can suppress/inhibit RanBP9 protein manufacturing in a human brain. But imatinib mesylate cannot pass through a human body's blood-brain barrier Imatinib mesylate is 4-[(4-Methyl 1-piperazinyl)methyl]-N-[4-methyl-3-[[4-(3-pyridinyl)-2-pyrimidinyl]amino]-phenyl]benzamide methanesulfonate and its structural formula is shown below:

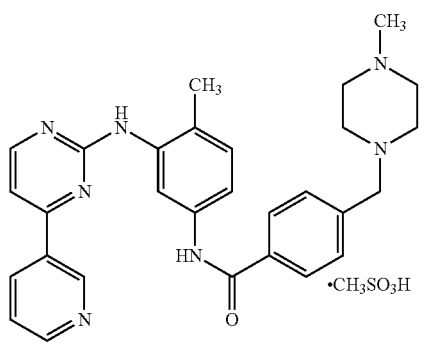

Structural Formula Of Imatinib mesylate

The molecular formula of Imatinib mesylate is $C_{29}H_{31}N_7O.CH_4SO_3$ and its molecular weight is 589.7.

Imatinib mesylate can be encapsulated/caged in the nanoshell 120. The nanoshell 120 decorated with a targeting ligand, wherein the targeting ligand can recognize/match/bind with adenosine receptors-thus allowing a human body's blood-brain barrier to be opened for the passage of the nanoshell 120 to deliver imatinib mesylate to suppress/inhibit RanBP9 protein manufacturing in a human brain.

Nanoformulated imatinib mesylate can enhance the efficacy and/or bioavailability at a lower concentration.

Sodium phenylbutyrate can suppress/inhibit RanBP9 protein manufacturing in a human brain.

An anticancer compound dasatinib can suppress/inhibit RanBP9 protein manufacturing in a human brain.

The dasatinib is N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate and its structural formula is shown below:

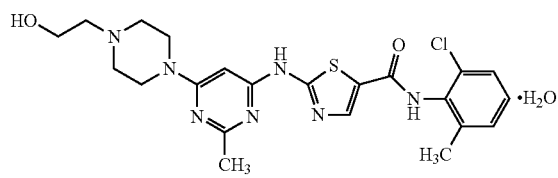

Structural Formula Of Dasatinib

The molecular formula of dasatinib is $C_{22}H_{26}ClN_7O_2S.H_2O$ and its molecular weight is 506.02 (monohydrate).

Nanoformulated dasatinib can enhance the efficacy and/or bioavailability at a lower concentration.

Dasatinib can be encapsulated/caged in the nanoshell 120. The nanoshell 120 decorated with a targeting ligand, wherein the targeting ligand can recognize/match/bind with adenosine receptors-thus allowing a human body's blood-brain barrier to be opened for the passage of the nanoshell 120 to deliver dasatinib to suppress/inhibit RanBP9 protein manufacturing in a human brain.

Affibody molecule (an engineered protein) can be encapsulated/caged in the nanoshell 120. The nanoshell 120 decorated with a targeting ligand, wherein the targeting ligand can recognize/match/bind with adenosine receptors-thus allowing a human body's blood-brain barrier to be opened for the passage of the nanoshell 120 to deliver affibody molecule to suppress/inhibit formation of amyloid beta protein in a human brain.

PARK7 gene (known as DJ-1) can protect cells (neurons) against oxidative damage. Sodium phenylbutyrate and/or a short protein fragment of non-mutated PARK7 can turn on PARK7 gene to protect against oxidative damage.

Sodium phenylbutyrate and/or a short protein fragment of non-mutated PARK7 can be encapsulated/caged in the nanoshell 120. The nanoshell 120 decorated with a targeting ligand, wherein the targeting ligand can recognize/match/bind with adenosine receptors-thus allowing a human body's blood-brain barrier to be opened for the passage of the nanoshell 120 to deliver sodium phenylbutyrate and/or a short protein fragment of non-mutated PARK7 to protect against oxidative damage.

Glial cell line-derived neurotrophic factor (GDNF) protein can nourish dopamine neurons by activating survival and growth-promoting pathways inside the neurons of a human brain. But glial cell line-derived neurotrophic factor protein is limited in its ability to cross a human body's blood-brain barrier. The nanoshell 120 decorated with a targeting ligand, wherein the targeting ligand can recognize/match/bind with adenosine receptors-thus allowing a human body's blood-brain barrier to be opened for the passage of the nanoshell 120 to deliver glial cell line-derived neurotrophic factor protein to protect against damage of dopamine neurons.

Oleocanthal (its structural formula is shown below), a phenolic component of extra-virgin olive oil can reduce the risk of Alzheimer's disease by clearing toxic amyloid beta protein from a human brain via up regulation of (a) P-glycoprotein (P-gp) and (b) low-density lipoprotein receptor-related protein 1 (LRP1). P-glycoprotein and low density lipoprotein receptor-related protein 1 are major amyloid beta transport proteins at a human body's blood-brain barrier. However, the bioavailability of oleocanthal is unknown.

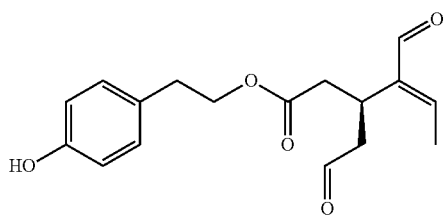

Structural Formula Of Oleocanthal

The nanoshell 120 decorated with a targeting ligand, wherein the targeting ligand can recognize/match/bind with adenosine receptors-thus allowing a human body's blood-brain barrier to be opened for the passage of the nanoshell 120 to deliver oleocanthal to protect against Alzheimer's disease.

The receptor for advanced glycation end products (RAGE) is a transporter of amyloid beta (Aβ) protein across a human body's blood-brain barrier into a human brain from the systemic circulation, while the low-density lipoprotein receptor-related protein 1 (LRP1) mediates transport of amyloid beta protein out of the brain. Accumulation of amyloid beta protein leading to Alzheimer's disease can be due to a relative distribution/ratio of the receptor for advanced glycation end products protein and low-density lipoprotein receptor-related protein 1 . However, the nanoshell 120 decorated with a targeting ligand, wherein the targeting ligand can recognize/match/bind with adenosine receptors-thus allowing a human body's blood-brain barrier to be opened for the passage of the nanoshell 120 to deliver bioactive compounds 100 and/or bioactive molecules 100A and/or small interfering RNA to suppress/inhibit the receptor for advanced glycation end products protein manufacturing to protect against Alzheimer's disease.

Stress/corticosteroid can cause the 5-lipoxygenase to overexpress and increase its levels which in turn increases the levels of the amyloid beta protein and tau protein. The nanoshell 120 decorated with a targeting ligand, wherein the targeting ligand can recognize/match/bind with adenosine receptors-thus allowing a human body's blood-brain barrier to be opened for the passage of the nanoshell 120 to deliver bioactive compounds 100 and/or bioactive molecules 100A and/or small interfering RNA to suppress/inhibit 5-lipoxygenase protein manufacturing to protect against Alzheimer's disease.

Amyloid beta protein can injure synapses directly by inducing the release of excessive amounts of neurotransmitter glutamate from brain cells named astrocytes, located near neurons. Normal level of glutamate can promote memory and learning, but excessive levels are very harmful. Excessive glutamate activates extrasynaptic receptors, designated as eNMDA receptors (N-methyl-D-aspartate). These eNMDA receptors can be hyperactivated-thus leading to synaptic loss. Memantine, a positively charged molecule can be easily repelled by positively diseased neurons; minimizing memantine's effectiveness, as it chemically binds with eNMDA receptors. Nitroglycerin can also bind eNMDA receptors. Nitroglycerin, isosorbide dinitrate and isosorbide mononitrate can convert into nitric oxide by mitochondrial aldehyde dehydrogenase and nitric oxide (NO) is a potent natural vasodilator. A combination of memantine and nitroglycerin (or isosorbide dinitrate or isosorbide mononitrate) can reduce excessive glutamate-thus protecting against Alzheimer's disease. Such a combination can include a chemical derivative or a structural analog of nitroglycerin (or isosorbide dinitrate or isosorbide mononitrate). Furthermore, the nanoshell 120 decorated with a targeting ligand, wherein the targeting ligand can recognize/match/bind with adenosine receptors-thus allowing the human body's blood-brain barrier to be opened for the passage of the nanoshell 120 to deliver bioactive compounds: memantine and nitroglycerin (or isosorbide dinitrate or isosorbide mononitrate) to protect against Alzheimer's disease.

GLYX-13 (a small molecule) mimics an antibody and targets NMDA (N-methyl-Daspartate) receptors on neurons' surface. These NMDA receptors help control synaptic plasticity and neuro-chemical basis of learning, memory and depression. The nanoshell 120 decorated with a targeting ligand, wherein the targeting ligand can recognize/match/bind with adenosine receptors-thus allowing a human body's blood-brain barrier to be opened for the passage of the nanoshell 120 to deliver bioactive compounds: GLYX-13 to protect against Alzheimer's disease.

Amyloid beta protein can bind with LilrB2 on neuron-cell surfaces-thus upregulating cofilin activity to destroy synapses' structural integrity. Furthermore, the nanoshell 120 decorated with a targeting ligand, wherein the targeting ligand can recognize/match/bind with adenosine receptors-thus allowing a human body's blood-brain barrier to be opened for the passage of the nanoshell 120 to deliver bioactive compounds 100 and/or bioactive molecules 100A to protect against binding of amyloid beta protein binding with LilrB2.

Angiotensin-converting enzyme (ACE) is a naturally occurring enzyme that can have either detrimental or beneficial effects, depending on how and where it is active. Angiotensin-converting enzyme contributes to production of angiotensin II, a hormone that often causes blood vessels to narrow and blood pressure to rise; inhibiting the enzyme relaxes vessels and reduces pressure. But in the brain, high levels of angiotensin-converting enzyme quickly and efficiently lead an immune system response against beta-amyloid protein. Furthermore, the nanoshell 120 decorated with a targeting ligand, wherein the targeting ligand can recognize/match/bind with adenosine receptors-thus allowing a human body's blood-brain barrier to be opened for the passage of the nanoshell 120 to deliver bioactive compounds 100 and/or bioactive molecules 100A for overexpressing angiotensin-converting enzyme to protect against Alzheimer's disease Long acting insulin derivative [2-sulfo-9fluroenyl-methoxycarbonyl]-3insulin can be encapsulated/caged in a nanoshell 120. The nanoshell 120 can be delivered for inhale via intranasal administration to protect against Alzheimer's disease.

Furthermore, intranasal administration can include stem cells to protect against Alzheimer's disease or other neurological diseases. Furthermore, intranasal administration can include nanoengineered (nanoengineered to express certain genes) stem cells to protect against Alzheimer's disease or other neurological diseases.

Cancer Disease

Bee venom contains a potent toxin called melittin that can poke holes in a cancer cell. However, large amounts of free melittin can also cause a lot of damage to healthy cells.

An assassin protein perforin can be a cancer's weapon of mass destruction. Perforin is encoded by the PRF1 gene. Perforin is expressed in T cells and natural killer (NK) cells. Interestingly, perforin resembles a cellular weapon employed by a bacterium (e.g., anthrax). Perforin has an ability to embed itself to form a pore in a cell-membrane. The pore by itself may be damaging to a cell and it enables an entry of a toxic enzyme granzyme B, which induces an apoptosis (a programmed suicide process) of a cancer cell.

The nanoshell 120 with melittin (its structural formula is shown below) can attack a cancer cell.

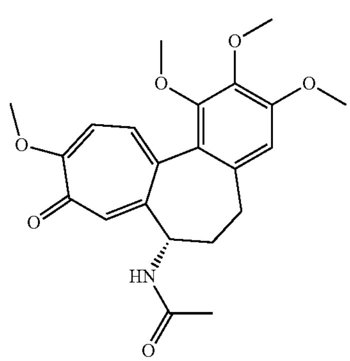

Structural Formula Of Melittin

The nanoshell 120 with both melittin and/or perforin can attack a cancer cell.

Cancer cells have a significantly increased rate of mitosis-thus cancer cells are significantly more vulnerable to toxic poisoning than are normal cells.

Colchicine is a toxic natural product and secondary metabolite, originally extracted from plants of the genus *Colchicum*. Colchicine only becomes active and detonates when in contact with an enzyme found in solid tumors sparing healthy tissue. The nanoshell 120 with colchicine can attack a cancer cell at a low dose.

The nanoshell 120 can be integrated with a targeting ligand (e.g., a specific antibody/aptamer) to bind specifically with a specific cancer cell.

The nanoshell 120 can be integrated with a fluorescent probe molecule to illuminate cancer cells for locating purposes.

Alternatively, the fluorescent probe molecule can be chemically integrated with the targeting ligand.

The nanoshell 120 can be integrated with a photodynamic sensitizer molecule for detecting a specific cancer cell.

Alternatively, the nanoshell 120 can be integrated with a magnetic nanoparticle to guide the nanoshell 120 to a specific cancer cell by a magnetic field.

The nanoshell 120 can deliver the bioactive compounds 100 and/or bioactive molecules 100A to cancer cells (for therapy/treatment) under an external stimulus (e.g., pH).

Diabetes Disease

Long acting insulin derivative [2-sulfo-9fluroenyl-methoxycarbonyl]-3insulin and leptin (or a chemical derivative/structural analog of leptin) can be encapsulated/caged in a pH responsive nanoshell 120. The pH responsive nanoshell 120 can be delivered for oral intake/inhale.

Long acting insulin derivative [2-sulfo-9fluroenyl-methoxycarbonyl]-3insulin and oleoylethanolamide (OEA) (or a chemical derivative/structural analog of oleoylethanolamide) can be encapsulated/caged in a pH responsive nanoshell 120. The pH responsive nanoshell 120 can be delivered for oral intake/inhale.

Oleoylethanolamide (or a chemical derivative/structural analog of oleoylethanolamide) can be encapsulated/caged in a pH responsive nanoshell 120. The pH responsive nanoshell 120 can be delivered for oral intake/inhale.

A specific small interfering RNA can be designed to suppress/inhibit cryptochrome protein manufacturing. The specific small interfering RNA can be encapsulated/caged in the nanoshell 120. The nanoshell 120 can deliver the specific small interfering RNA to suppress/inhibit cryptochrome protein manufacturing.

Hearing Loss Disease

Free radicals can induce manufacturing of Bak, a protein. Bak protein can trigger suicide of cells (these cells do not regenerate like other cells in a human body) in the auditory portion of the inner ear.

The level of Bak protein can also increase with aging.

A specific small interfering RNA can be designed to suppress/inhibit Bak protein manufacturing. The specific small interfering RNA can be encapsulated/caged in the nanoshell 120. The nanoshell 120 can deliver the specific siRNA (locally through the round window membrane (RWM) of the inner ear) to suppress/inhibit Bak protein manufacturing in a human ear.

Cochlear hair cell apoptosis (cell death)-a key factor in several forms of acute hearing loss, can be induced by p53 protein. However, an inhibition of p53 protein can be achieved by specific small interfering RNA. The specific small interfering RNA can be encapsulated/caged in the nanoshell 120. The nanoshell 120 can deliver the specific small interfering RNA (locally through the round window membrane of the inner ear) to suppress/inhibit p53 protein manufacturing in a human ear.

The administration of the bioactive compound 100 and/or bioactive molecule 100A to treat hearing loss disease is through the permeation of the round window membrane. The ultra-fine structures of the round window membrane are not well known, but there are vesicles in the round window membrane, wherein clathrin and caveolin pathways may be involved in the transportation of the nanoshell 120 through round window membrane.

Mammalian hearing loss due to damage to auditory hair cells is normally irreversible. The Notch signaling pathway represents a critical component in the molecular circuits that control cell fate and plays a regulatory role in oxidative stress. But a partial recovery of auditory hair cells can be possible by inhibiting the Notch signaling pathway utilizing (a) curcumin, (b) niclosamide (5-chloro-N-2-chloro-4-nitrophenyl)-2-hydroxybenzamide) and (c) a γ-secretase inhibitor.

Furthermore, the nanoshell 120 can be decorated with targeting ligands, which can bind to specific receptors on spiral ganglion cells (Trk-B receptors) and on the vasculature (the matrix metalloproteins, MMP2).

Brain-derived neurotrophic factor (BDNF) can also interact with Trk-B receptors.

Furthermore, cell entry of the nanoshell 120 can be facilitated by a viral-TAT peptide (e.g., TAT-Influenza-HA), binding of the nanoshell 120 with Trk-B receptors can be facilitated by brain-derived neurotrophic factor ligand and the nuclear pore complex entry of the nanoshell 120 can be facilitated by a nuclear targeting peptide.

Furthermore, brain-derived neurotrophic factor, Atoh1/Math1 gene (for growth of hair cells), small interfering RNA (designed to suppress/inhibit Bak protein manufacturing in a human ear), MRI contrast agent and molecular tags can be encapsulated/caged in the nanoshell 120-thus realizing a multifunctional nanoshell.

Reactive oxygen species are involved in cisplatin-induced hearing loss. It depresses significantly the levels of antioxidant enzymes, superoxide dismutase, glutathione peroxidase, glutathione reductase, glutathione transferase and catalase—all antioxidants that protect cells from free radicals. Similarly, free radicals elevate the levels of products of lipid peroxidation, a process in which free radicals degrade the cell membrane. It also depletes the level of glutathione, another important antioxidant. When hair cells become damaged, glutamate (an excitatory neurotransmitter responsible for converting vibrational sounds into electrical signal) is produced in excessive amounts. Excessive amounts of glutamate can be toxic to neurons.

Coenzyme $Q_{10}$ (ubiquinol) can delay progression of hearing loss in patients with a genetic defect (7445A G mitochondrial mutation). Although, supplementation with a single antioxidant may produce some beneficial effects in improving hearing disorders. However, a single antioxidant in a high oxidative environment can even act as a pro-oxidant.

The nanoshell 120 can deliver a synergistic combination of acetyl-L-carnitine, alpha-lipoic acid, glutathione, magnesium, n-acetylcysteine (NAC), 4-Hydroxyphenyl N-tert-butyl nitrone/4-OHPBN nitrone and ubiquinol (coenzyme $Q_{10}$) to reduce hearing loss.

Some photochemicals protect cells by disrupting established pathways by blocking activation of pro-inflammatory genes. Different photochemicals have different ways of interfering with toll-like receptors and nucleotide binding oligomerization domain containing proteins.

Furthermore, the nanoshell 120 can deliver a synergistic combination of curcumin and resveratrol and selenium (selenomethionine) to reduce hearing loss. Curcumin can undermine certain toll-like receptors when a specific part of curcumin's chemical structure-known as a beta unsaturated carboxyl group reacts with so-called sulfhydryl groups in toll-like receptors. Resveratrol can also interfere with molecules called TBK1 and RIP1. TBK1 and RIP1 convey signals to and from toll-like receptors. But when resveratrol interacts with TBK1 and RIP1, however, the effect is somewhat like a traffic light, which controls the flow of vehicles on a busy street.

Furthermore, the nanoshell 120 can deliver neurotrophin to reduce hearing loss.

Exposure to a high intensity noise can cause a decrease in total antioxidant capacity and an increase in nitric oxide. Increased nitric oxide can cause formation of peroxynitrite, which is very damaging to hair cells. The nanoshell 120 can deliver a combination of anticonvulsant zonisamide and glucocorticoid (e.g., methylprednisolone or betamethasone phosphate (BP)) to cochleae (cochleae is a Hopf oscillator acting as a nonlinear power amplifier, boosting weak signals much more than strong ones) over a sustained period of time to reduce hearing loss due to a high intensity noise.

Hepatitis B, Hepatitis C, HIV & Other Deadly Virus Based Diseases

Bee venom contains a potent toxin called melittin that can poke holes in the double-layered membranes indiscriminately of a virus (e.g., hepatitis B, hepatitis C and HIV). However, large amounts of free melittin can also cause a lot of damage to healthy cells.

In contrast, most anti-HIV drugs inhibit the virus's ability to replicate. But this anti-replication strategy does nothing to stop initial infection and some mutated strains of the virus have found ways around these drugs and reproduce anyway.

An assassin protein perforin can be a virus's weapon of mass destruction. Perforin is encoded by the PRF1 gene. Perforin is expressed in T cells and natural killer (NK) cells. Interestingly, perforin resembles a cellular weapon employed by a bacterium (e.g., anthrax). Perforin has an ability to embed itself to form a pore in a cell-membrane. The pore by itself may be damaging to a cell and it enables an entry of a toxic enzyme granzyme B, which induces an apoptosis (a programmed suicide process) of a diseased cell.

The nanoshell 120 with melittin can attack an essential part of the virus' (e.g., hepatitis B, hepatitis C and HIV) structure to destroy the virus.

The nanoshell 120 with melittin and perforin in combination can attack an essential part of the virus' (e.g., hepatitis B, hepatitis C and HIV) structure to destroy the virus.

The nanoshell 120 with a targeted small interfering RNA can attack an essential part of the virus' (e.g., hepatitis B, hepatitis C and HIV) structure to destroy the virus.

The nanoshell 120 a targeted small interfering RNA in combination with melittin can attack an essential part of the virus' (e.g., hepatitis B, hepatitis C and HIV) structure to destroy the virus.

The nanoshell 120 a targeted small interfering RNA in combination with perforin can attack an essential part of the virus' (e.g., hepatitis B, hepatitis C and HIV) structure to destroy the virus.

The nanoshell 120 a targeted small interfering RNA in combination with melittin and perforin can attack an essential part of the virus' (e.g., hepatitis B, hepatitis C and HIV) structure to destroy the virus.

Furthermore, the virus destroying strategy as cited in the previous paragraphs can be utilized to destroy other deadly virus strains (e.g., Ebola). In the case of Ebola, a specific small interfering RNA is needed to silence the gene responsible for replication-polymerase L.

The nanoshell 120 can be decorated with a targeting ligand (e.g., a specific aptamer) to recognize/match/bind a target molecule in the signaling domain of a receptor (e.g., TIM-1) of Ebola virus.

When the targeting ligand and target molecule recognize/match/bind in the signaling domain of the receptor of Ebola virus, the nanoshell 120 can release the specific small interfering RNA to inhibit replication of polymerase L.

However, instead of the receptor, the nanoshell 120 can be decorated with a specific targeting ligand to recognize/match/bind with a negative-stranded RNA based Ebola virus (which means the genome consists of one or more molecules of single-stranded "antisense" RNA).

To enhance specificity, two targeting ligands can be utilized instead of one targeting ligand.

Thus, it would require two different matching signals in order to unzip the nanoshell 120.

Immune

An antigen/antibody generator can evoke the production of one or more antibodies. Each antibody binds to a specific antigen by way of an interaction similar to the fit between a lock and a key. The antigen can originate from within a human body or external environment. The immune system can destroy or neutralize any antigen that is recognized as a foreign/potentially harmful invader.

The nanoshell 120 with specific antigen or an array of antigens can prevent immune-mediated diseases (e.g., Type-1 Diabetes disease). Insulin is destroyed in Type-1 Diabetes disease, because the autoimmune disease kills the beta cells producing that antigen. The nanoshell 120 with insulin can delay the onset or prevent Type-1 Diabetes disease.

The nanoshell 120 with myelin antigens can be engulfed by macrophages, a type of immune cell. Macrophages can then display the antigens on their cell surface. The immune system can view the nanoshell 120 as ordinary dying blood cells without any concern. Thus, the nanoshell 120 with myelin antigens can inhibit the activity of myelin responsive T cells.

Inflammation

Reactive oxygen species can cause an inflammation in cardiovascular, hearing loss, infection and neurological diseases. An accumulation of reactive oxygen species can result in manifestation hydrogen peroxide or hypochlorous acid. Furthermore, an onset of reactive oxygen species related inflammation in cardiovascular, hearing loss, infection and neurological diseases can be approximately correlated with massive oxidative stress (thus, accumulation of hydrogen peroxide in the hair follicle), decreased antioxidant capacities including catalase, thioredoxin reductase and the repair mechanisms methionine sulfoxide reductases.

A synergistic combination of about 200 mg of catalase (or a chemical derivate or a structural analog of catalase or a pseudocatalase activated via sunlight), about 200 mg of glutathione peroxidase, about 1000 mg of L-methionine, about 100 mg of methionine sulfoxide reductase (MSR), about 200 mcg of selenium amino acid complex (sodium selenite, L-selenomethionin and selenium-methyl L-selenocysteine), about 200 mg superoxide dismutase and about 200 mg of *Emblica officinalis* extract can reduce damages due to free radicals and hydrogen peroxide in the hair follicle.

Hydrogen peroxide or hypochlorous acid sensitive nanoshell 120 can degrade in the presence of a minute amount of hydrogen peroxide or hypochlorous acid in order to deliver the bioactive compounds 100 and/or bioactive molecules 100A to reduce the inflammation in cardiovascular, hearing loss, infection and neurological diseases.

Inflammation in a human is an earlier indicator of Alzheimer's disease. A pathway involving TYROBP (an inflammatory gene) can interact with TREM2, a gene involved in Alzheimer's disease. TREM2-TYROBP pathway can play an initial role in driving Alzheimer's disease. Targeting TREM2-TYROBP pathway early on may delay/decrease the risk of developing Alzheimer's disease.

TL1A protein takes part in driving the inflammation. The nanoshell 120 with siRNA can be utilized to block TL1A protein production.

Premature Ageing (Progeria) Disease

A cellular instability leading to premature aging (Progeria) disease can be caused by toxic Lamin A protein. Toxic Lamin A protein is manufactured due to a mutation in the LMNA gene. A specific small interfering RNA can be designed to suppress/inhibit toxic Lamin A protein manufacturing. The nanoshell 120 can deliver the specific siRNA to suppress/inhibit toxic Lamin A protein manufacturing.

Furthermore, Lamin A protein interacts with SUN 1 protein. The nanoshell 120 can deliver the specific small interfering RNA to suppress/inhibit SUN 1 protein manufacturing.

Protein Misfolding Disease

The complexity and dynamics of unfolded proteins can play a crucial role in aggregation, misfolding and subsequent diseases (e.g., Alzheimer's and Diabetes diseases).

Fragments of misfolded proteins can seed and then coerce/recruit normal protein to misfold and propagate various neurological diseases (e.g., Alzheimer's and Prion diseases) relentlessly. In the case of Alzheimer's disease, the proteins' individual amino acids can be assembled into strands, which stack into sheets that run the length of the entire structure. Those sheets can then group with increasing rigidity into protofilaments, filaments and finally mature and tough fibrils. Besides the intricate structure, many of the packing interactions are derived from the amyloid self-assembly process.

The reconfiguration dynamics of unfolded proteins may be governed by the physics of thermodynamics. The reconfiguration dynamics can be measured by the rate of intramolecular diffusion (the diffusion rate of one part of a protein sequence with respect to another part).

The nanoshell 120 decorated with a first targeting ligand, wherein the first targeting ligand can recognize/match/bind with adenosine receptors-thus allowing a human body's blood-brain barrier to be opened for the passage of the nanoshell 120 to deliver the bioactive compounds 100 and/or bioactive molecules 100A for prevention of aggregation/misfolding (e.g., bioactive compound nanocurcumin can prevent aggregation/misfolding on alpha-synuclein) by shifting intramolecular diffusion rate out of the danger range.

Furthermore, the nanoshell 120 can be decorated with a second targeting ligand, wherein the second targeting ligand can recognize/match/bind with a suitable part of an aggregation-prone protein sequences. The nanoshell 120 can then deliver the bioactive compounds 100 and/or bioactive molecules 100A for prevention of protein aggregation/misfolding.

It is critical to prevent protein aggregation/misfolding at a very early stage of a neurological disease, so that the rogue protein may not be able to seed and then coerce/recruit normal protein to misfold and propagate a neurological disease.

Protozoan Infection

Natural artemisinin (from sweet wormwood plant/*Artemesia annua L*) can be an effective treatment against protozoan infection-*P. falciparum* malaria. When artemisinin comes in contact with high concentrations of iron (ferrous compounds generally found in protozoan infection-*P. falciparum* malaria), a chemical reaction is produced to create free radicals that attack cell membranes, breaking them apart and killing protozoan infection-*P. falciparum* malaria. Genes (e.g., encoding dehydrogenase enzymes) from *Artemesia annua L* can be inserted into suitable genes (with more rare words (codons) near the start of the genes) of bacterium/yeast to produce artemisinic acid, a precursor of synthetic artemisini. Artemisinic acid can be photochemically converted to artemisini. Similarly, bacterium/yeast can produce the anticancer compound taxol and the anti-HIV compound prostratin. It should be noted that synthetic OZ439 bioactive compound can be an alternative to artemisini.

Furthermore, the nanoshell 120 can be decorated with a targeting ligand, wherein the targeting ligand can recognize/match/bind with a suitable part of protozoan infection-*P. falciparum* malaria. The nanoshell 120 can then deliver the bioactive compounds (e.g., artemisini or OZ439) to treat against protozoan infection-*P. falciparum* malaria.

Superbug Infection

An antibiotic is a bioactive compound that kills/slows down the growth of bacteria by a mechanism like: (a) inhibiting the cell wall synthesis, (b) blocking DNA/RNA expression, (c) stopping the folic acid synthesis, (d) disrupting cell membrane permeability and arresting the central dogma of bacteria (DNA, RNA and protein synthesis) and (e) inhibiting the protein synthesis.

But superbugs embody a group of bacteria which contains several resistance genes which when expressed leads to development of antibiotic resistance by a mechanism like: (a) coding for specific enzymes which devastate antibiotics, (b) modifying the efflux pump which causes trans-shipment of antibiotic out of the bacterial cell, (c) modifying the configuration of target site so that antibiotics cannot bind with the bacterial cell and (d) production of alternative target (enzyme) to bind the antibiotics. In short, bacterial resistance is due to either transformation or transduction or conjugation.

For example: New Delhi metallo-beta-lactamase-1 (NDM-1) is a gene carried by bacteria, which is responsible for producing an enzyme, carbapenemase within the bacteria making them resistant to (almost all) the present antibiotics.

The nanoshell 120 can be coated with positively charged dimethyldecylammonium chitosan methacrylate. The interaction of positively charged dimethyldecylammonium chitosan methacrylate with the negatively charged bacterial cell wall can result in the disintegration of bacterial cell wall.

The nanoshell 120 can be decorated with enzyme Lysostaphin, a natural enzyme and/or a compound configured for releasing nitric oxide and/or a compound configured for releasing reactive oxygen species and/or a compound configured for releasing reactive nitrogen species. Lysostaphin attacks the bacterial cell wall causing its slicing and disintegration. The reactive oxygen species and/or reactive nitrogen species can modify the essential protein in bacteria causing bacterial cell death.

With more and more antibacterials and antibiotics, strains of bacteria can evolve or mutate into superbugs, which are resistant to antibacterial drug(s). These drug resistant superbugs include CRE bacteria, *Clostridum difficile* and methicillin-resistant *staphylococcus aureus* (MRSA). Methicillin-resistant *staphylococcus aureus* cells can grow to about 1 million cells in a day.

The nanoshell 120 can be decorated with a biomarker binder (e.g., an apatmer), which is very specific to a superbug. The nanoshell 120 (containing melittin from bee venom and/or an assassin protein perforin inside the nanoshell 120) with negatively charged electrical surface can be drawn to the positively charged cell surface of a superbug (e.g., methicillin-resistant *staphylococcus aureus*).

Melittin and/or perforin can pierce through the cell membrane of the superbug. Thus, only the contents of the cell of the superbug are spilled out and the superbug is destroyed without harming any healthy cells. Additionally, the nanoshell 120 can be decorated with a targeting ligand (e.g., a specific aptamer) to specifically bind with the particular superbug.

An immune system called the CRISPR-Cas system is present in many bacteria. The CRISPR-Cas system protects a bacterium from an invader (e.g., a virus) by creating small strands of RNA called CRISPR-RNAs—matching the specific DNA sequences of the invader. When CRISPR RNAs find a match, the bacterium unleashes Cas proteins to cut the DNA of the invader. Conversely, a designer CRISPER RNAs can target DNA sequences in the bacterium, as a bacterium's CRISPR-Cas system attacks its own DNA, causing bacterium to suicide. The nanoshell 120 (containing a designer CRISPER RNAs-targeting DNA sequences in the bacterium, inside the nanoshell 120) can cause a superbug to suicide, without harming any healthy cells. Additionally, the nanoshell 120 can be decorated with a targeting ligand (e.g., a specific aptamer) to specifically bind with the particular superbug.

Diseases of Mind—Depression

Ketamine (with its structural formula is shown below) binds to and blocks a receptor in a human brain called NMDA receptor. Ketamine triggers both anesthetic and antidepressant effects.

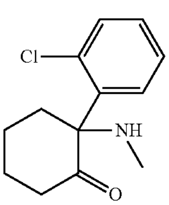

Structural Formula Of Ketamine

Like an electroshock therapy, ketamine eases depression by blocking a neurotransmitter called glutamate from binding to the NMDA receptor on neurons.

Too much glutamate on the NMDA receptor, can lead to the opening of a calcium ion channel-thus releasing too much calcium downstream-thus affecting a brain chemical brain derived neurotrophic factor protein.

Ketamine causes neurons to make more brain derived neurotrophic factor, protein, which increases connections between neurons in the brain. These connections can help the brain regulate emotions better and reset the background activity of a human brain.

Ketamine (used in the easing depression) can be delivered at an extremely low dose and over a longer period.

The nanoshell 120 decorated with a targeting ligand, wherein the targeting ligand can recognize/match/bind with adenosine receptors-thus allowing a human body's blood-brain barrier to be opened for the passage of the nanoshell 120 to deliver ketamine at an extremely low dose.

However, instead of NMDA receptor, the bioactive compounds 100 and/or bioactive molecules 100A can activate eEF2 protein to treat depression.

Psilocybin, a prodrug of psilocin (4-hydroxy-dimethyltryptamine) can also ease depression. Psilocybin can decrease cerebral blood flow (CBF) after its use.

The nanoshell 120 decorated with a targeting ligand, wherein the targeting ligand can recognize/match/bind with adenosine receptors-thus allowing a human body's blood-brain barrier to be opened for the passage of the nanoshell 120 to deliver psilocybin at an extremely low dose.

Alternatively, the nanoshell 120 decorated with a targeting ligand, wherein the targeting ligand can recognize/match/bind with adenosine receptors-thus allowing a human body's blood-brain barrier to be opened for the passage of the nanoshell 120 to deliver ibogain (derived from *Tabermanthe iboga*) at an extremely low dose.

Furthermore, there are about 100 trillion microbes in the gut. Leaky gut/displaced bacteria can activate inflammation and autoimmune response(s), which are responsible for onset of depression and fatigue.

Glutamine, N-accetylcysteine and zinc (L-Opti) or a combination of glutamine, N-accetylcysteine and zinc (L-Opti) can be encapsulated/caged in a nanoshell 120. The nanoshell 120 can deliver appropriate amounts of glutamine, N-accetylcysteine and zinc (L-Opti) or combination(s) of glutamine, N-accetylcysteine and zinc (L-Opti) to reduce inflammation and autoimmune response(s) for the leaky gut—thereby delaying the onset of depression and fatigue.

Reprogramming of an Epigenetic Marker

Changes in the epigenome do not change a gene's sequence, but rather its activity level. The environment (e.g., diet and exercise) can alter the epigenome, changing the activity level of genes to raise or lower the risk for developing a disease, but also appear to influence the epigenome of future generations. Epigenetic modifications can influence disease susceptibility, potentially lasting through several generations. Due to a phenomenon of genomic imprinting, maternal and paternal genomes are differentially marked and must be properly reprogrammed every time they pass through the germline. Many genes may be coated with methyl groups. When a cell divides, this cellular memory is passed on from one generation to the next generation.

Reprogramming refers to an erasure and/or a remodeling of epigenetic marks (e.g., DNA methylation) accumulated from previous generations.

Trichostatin A ($C_{17}H_{22}N_2O_3$) (with its structural formula is shown below) into a human brain can remove the methyl groups and behavioral deficits.

Structural Formula Of Trichostatin A

Trichostatin A has low-toxicity. To reduce toxicity of trichostatin A, the nanoshell 120 decorated with a targeting ligand, wherein the targeting ligand can recognize/match/bind with adenosine receptors-thus allowing a human body's blood-brain barrier to be opened for the passage of the nanoshell 120 to deliver trichostatin A at an extremely low dose.

Delivery of Bioactive Compounds &/or Bioactive Molecules from a Nanoshell: A Nanoshell Configured with a Bacterium/Microbe/Genetically Engineered Microbe The nanoshell 120 can be configured with a harmless bacterium (e.g., lactobacillus)/microbe/genetically engineered microbe to deliver the bioactive compounds 100 and/or bioactive molecules 100A.

Delivery of Bioactive Compounds &/or Bioactive Molecules from a Nanoshell Configured with a Nanopump.

Prestin is a motor protein enabling direct voltage-to-force converter.

An engineered bacteria battery: M13 bacteriophage can translate mechanical energy into electrical energy. To improve the piezoelectric property of M13 bacteriophage, the outer protein layer of M13 bacteriophage can be engineered by adding appropriate molecules.

Furthermore, to amplify piezoelectric effect, multi-layers of engineered M13 bacteriophage can be utilized. Multi-layers of engineered M13 bacteriophage can then be sandwiched between two biocompatible electrodes to act as a battery, when stressed mechanically.

A thin-film battery/thin-film printed battery/biofuel battery/engineered bacteria battery coupled with prestin-motor protein can be fabricated/constructed, as a nanopump (or as an array of nanopumps with networks of prestin-motor proteins).

Alternatively, a thin-film battery/thin-film printed battery/biofuel battery/engineered bacteria battery coupled with phi29 DNA polymerase enzyme can be fabricated/constructed, as a nanopump (or as an array of nanopumps with an array of phi29 DNA polymerase enzymes).

A nanopump can generate a sustained mechanical wave in the nanoshell 120 to release/eject the bioactive compounds 100 and/or bioactive molecules 100A from the nanoshell 120.

Delivery of Bioactive Compounds &/or Bioactive Molecules from a Nanotube/Nanotube Configured with a Nanopump A nanotube (e.g., a boron nitride/carbon nanotube or a tubular/tetrahedral structure, fabricated/constructed, utilizing DNA/RNA origami process) can cross a cell membrane and enter the nuclei of the cell, while the cell may not recognize the nanotube as an unfriendly intruder. The nanotube can be biodegradable and less toxic.

The uptake of the bioactive compounds 100 and/or bioactive molecules 100A from a solution into the nanotube can be achieved by van der Waals attraction between the nanotube and the bioactive compounds 100 and/or bioactive molecules 100A.

The nanotube's exterior surface can be coated with (a) an optional protective (to protect from a human body's blood/biological fluid) functional surface and (b) an immune shielding (to protect from a human body's inherent immune surveillance) functional surface.

Furthermore, the nanotube's exterior surface can be decorated with a targeting ligand to recognize/match/bind with specific biological receptors on the cell to allow entry of the nanotube to the cell.

Therefore, the bioactive compounds 100 and/or bioactive molecules 100A can be delivered to the cell with unprecedented accuracy and efficiency.

Prestin is a motor protein enabling direct voltage-to-force converter. A thin-film battery/thin-film printed battery/biofuel battery/engineered bacteria battery coupled with prestin-motor protein can be fabricated/constructed, as a nanopump (or as an array of nanopumps with networks of prestin-motor proteins).

Alternatively, a thin-film battery/thin-film printed battery/biofuel battery/engineered bacteria battery coupled with phi29 DNA polymerase enzyme can be fabricated/constructed, as a nanopump (or as an array of nanopumps with an array of phi29 DNA polymerase enzymes).

A nanopump can generate a sustained mechanical wave in the nanotube to release/eject the bioactive compounds 100 and/or bioactive molecules 100A from the nanotube.

Targeted Delivery to Mitochondria

The mitochondria are the power plants of cells. Mitochondria generate most of the cell's supply of adenosine triphosphate (ATP). Adenosine triphosphate is used as a source of chemical energy.

While mitochondria are present in all cells, in some cells, because of their size and purpose—it is necessary to transport mitochondria at proper positions within the cell to maintain proper function of the cell.

For example, neurons have a complex cellular structure of a main cell body and enormous arms of axons and dendrites that fan out from the cell core and transmit signals to adjoining cells via synapses at their termini.

Thus, the supply chain to mitochondria is very long. Mitochondria are also constantly cycling throughout the neuron. Neurons can transport mitochondria (some mitochondria are stationary/fixed, while other mitochondria are mobile) down the enormous arms of axons and dendrites at proper positions to provide other parts of the cell with energy, help with the transmission of signals and maintenance of the cellular health.

Additionally, at any given time about half of the mobile mitochondria in the neurons are returning to the cell—to be recycled/replenished.

One interesting property of mitochondria is that they have their own DNA. Mitochondrial DNA is different from chromosomal/nuclear DNA. First, it exists as a simple plasmid (a DNA loop) than the chromosomal/nuclear DNA. Second, most repair mechanisms to correct chromosomal/nuclear DNA are missing from mitochondrial DNA. Thus, relatively unprotected/unrepairable mitochondrial DNA can suffer about 10 times more damage than chromosomal/nuclear DNA.

Mitochondrial electron transport is not perfect. Even under ideal mitochondrial conditions, some electrons can leak from the electron transport chain. These leaking electrons can interact with oxygen to produce superoxide radicals.

Furthermore, with mitochondrial dysfunction, leakage of electrons can increase significantly.

The close proximity of mitochondrial DNA to the flux of superoxide radicals (or hydroxyl radicals) and the lack of mitochondrial protection/repair mechanism can lead to mitochondrial dysfunction.

Many diseases can be related to mitochondrial dysfunction-thus an ability to transport the bioactive compounds 100 and/or bioactive molecules 100A to mitochondria specifically can be beneficial.

Furthermore, the disruptive changes to mitochondria can occur, when both amyloid beta protein and tau protein (rather truncated version of tau protein, not regular version of tau protein) are present together and the disruptive changes are: (a) about 30% remaining electrical potential (but 100% electrical potential is needed to produce energy efficiently), (b) abnormal mitochondria clumping, (c) fragmentation of mitochondria, (d) incorrect control of calcium level and (e) release of (toxic) free radicals.

Triphenylphosphonium (TPP) can pass through and accumulate several hundred folds in the mitochondrial matrix.

The bioactive compounds 100 and/or bioactive molecules 100A can be chemically coupled with triphenylphosphonium/chemical derivative of triphenyl phosphonium/structural analog of triphenylphosphonium to enhance an uptake of the bioactive compounds 100 and/or bioactive molecules 100A in mitochondria.

Passive Micropatch

Figure 7A:
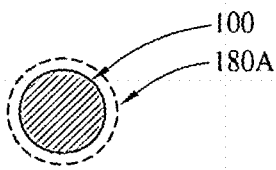
FIGS. 7A, 7B, 7C, 7D, 7E, 7F, 7G, 7H, 7I, 7J, 7K, 7L and 7M illustrate a passive (via a micropatch) delivery of bioactive compounds and/or bioactive molecules, utilizing thin-films, nanocrystals and microelectro-mechanical-system (MEMS) reservoirs.

FIG. 7A illustrates an expanded view of a negative electrical charged surface 180A on the bioactive compound 100.

Figure 7B:
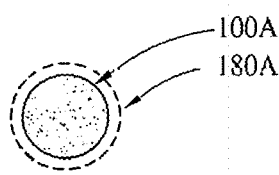

FIG. 7B illustrates an expanded view of a negative electrical charged surface 180A on the bioactive molecule 100A.

Figure 7C:
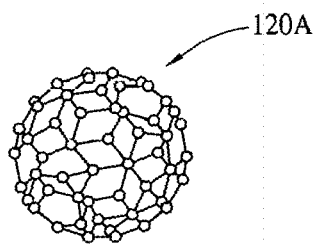

FIG. 7C illustrates an expanded view of a nanocrystal 120A.

Figure 7D:
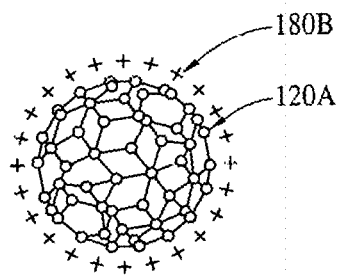

FIG. 7D illustrates an expanded view of a positive electrical charged surface 180B on the nanocrystal 120A.

The charge conjugation can increase the encapsulation efficiency and/or delivery efficiency of the bioactive compounds 100 and/or bioactive molecules 100A.

Figure 7E:
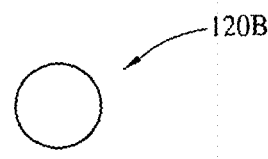

FIG. 7E illustrates an expanded view of a fluorophore (e.g., a quantum dot fluorophore) 120B.

With a quantum dot fluorophore, the size of the bandgap can be controlled by varying the diameter of the quantum dot. Larger diameter (e.g., 10 nanometers in diameter) quantum dot fluorophore will have a smaller bandgap-thus the larger diameter quantum dot fluorophore will fluoresce in the red part of the optical spectrum. Conversely, smaller diameter (e.g., 5 nanometers in diameter) quantum dot fluorophore will have a larger bandgap-thus the smaller diameter quantum dot fluorophore will fluoresce in the blue part of the optical spectrum.

Figure 7F:
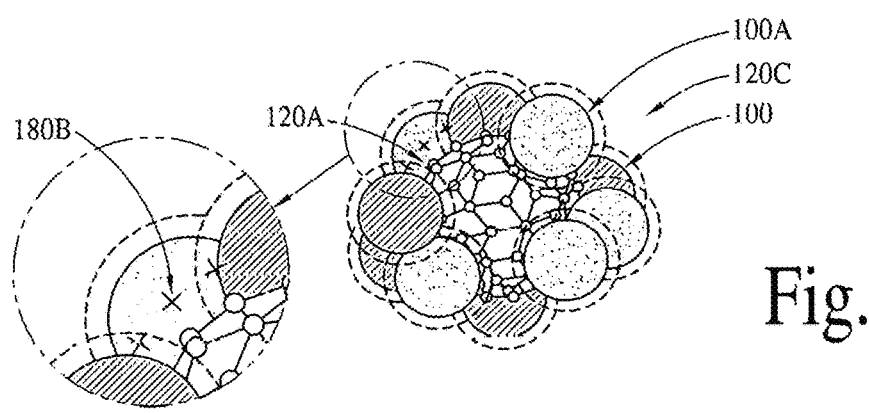

FIG. 7F illustrates 120C, wherein the negative electrical charged bioactive compounds 100 and/or bioactive molecules 100A are surrounded by a cluster of the positive electrical charged nanocrystals 120A.

Figure 7G:
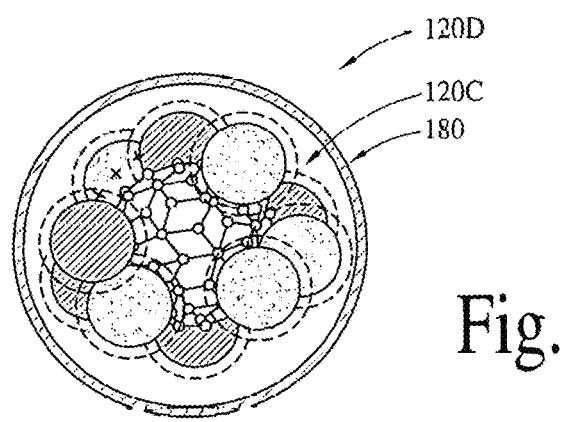

FIG. 7G illustrates 120D, wherein 120C is chemically bonded with the immune shielding functional surface 180.

Figure 7H:
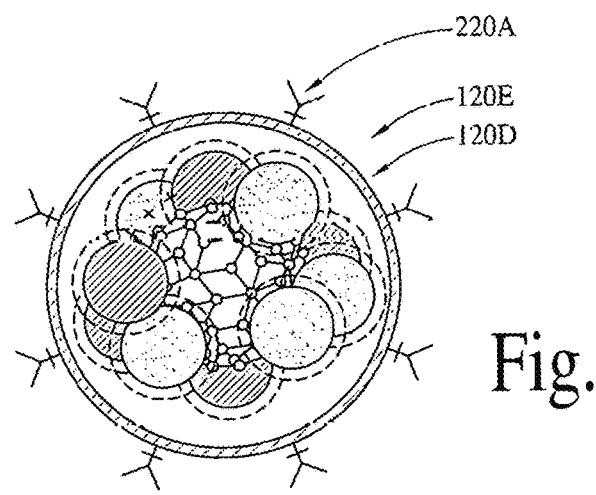
Figure 7:
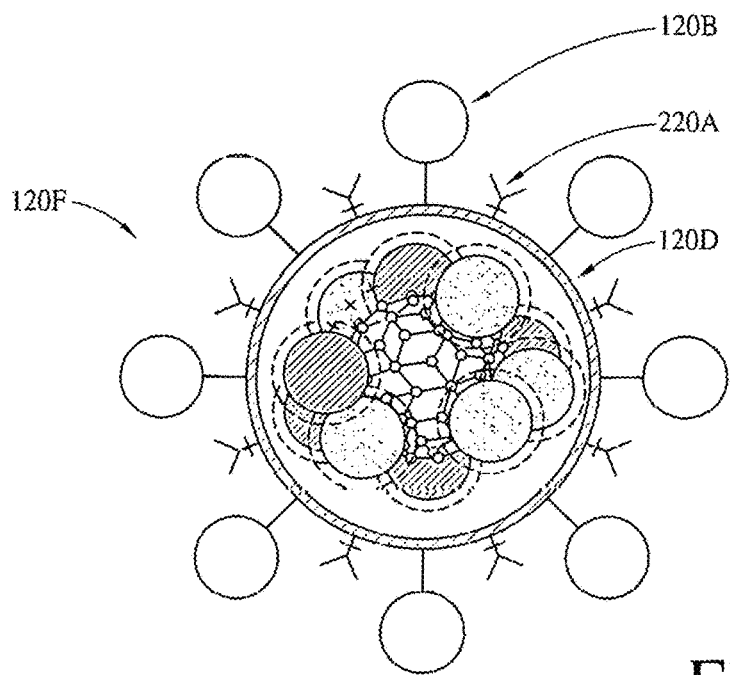
FIG. 7N illustrates a programmable/active (via a micropatch and microelectro-mechanical-system reservoir(s) integrated with needles) delivery of bioactive compounds and/or bioactive molecules, utilizing thin-films, nanocrystals, hydrogel, microelectro-mechanical-system reservoirs and micropumps.
FIG. 7O illustrates a programmable/active (via a micropatch and microelectro-mechanical-system reservoir(s) integrated with nanotubes) delivery of bioactive compounds and/or bioactive molecules, utilizing thin-films, nanocrystals, hydrogel, microelectro-mechanical-system reservoirs and micropumps.
Figure 7:
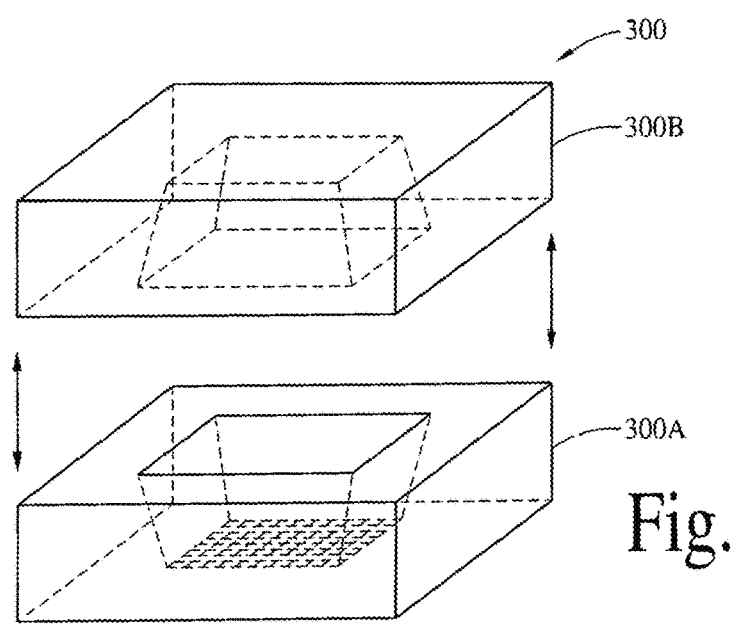

FIG. 7H illustrates 120E, wherein 120D can be chemically bonded with a specific targeting ligand 220A.

FIG. 7I illustrates 120F, wherein 120E is optionally chemically bonded with the fluorophore 120B.

The above nanoassembly 7I can be utilized for targeted delivery of the bioactive compounds 100 and/or bioactive molecules 100A.

FIG. 7J illustrates a microelectro-mechanical systems (MEMS) reservoir 300.

The microelectro-mechanical-system reservoir 300 can be fabricated/constructed, utilizing liquid crystal polymers/polyimide/silicon/silk/SU-8 resin/other suitable material.

Figure 7K:
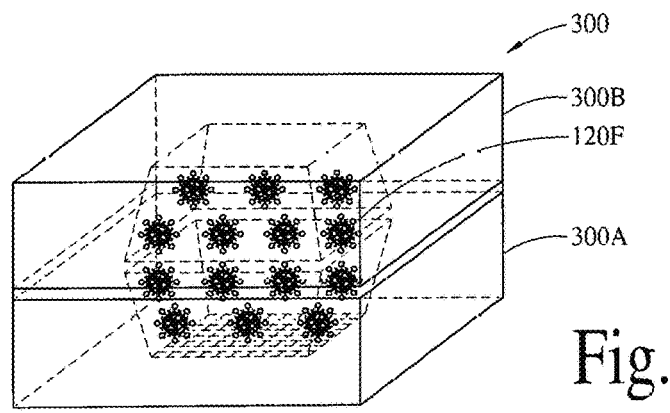

FIG. 7K illustrates 120Fs. 120Fs are inserted/caged in the microelectro-mechanical-system reservoir 300.

Figure 7L:
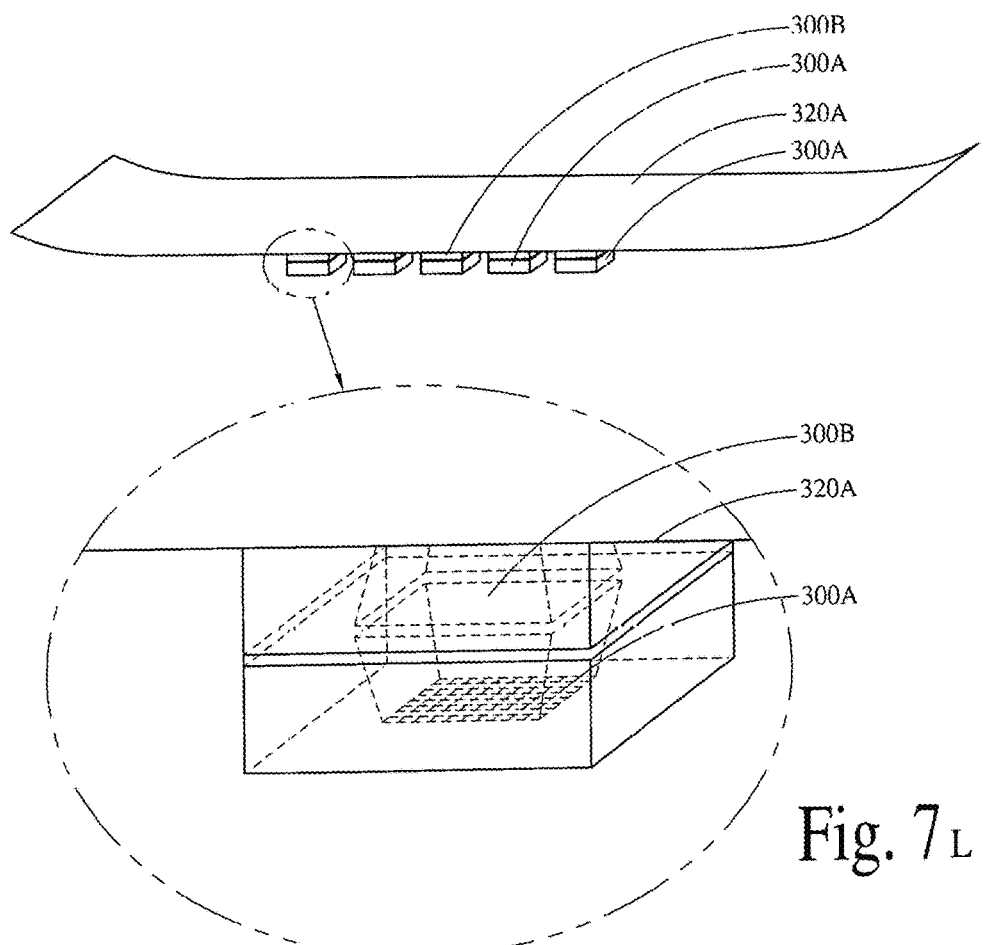

FIG. 7L illustrates the top surface 300B of the microelectro-mechanical-system reservoir 300. 300B can be attached onto a non-porous adhesive top thin-film 320A.

The porous bottom surface of the microelectro-mechanical-system reservoir 300 is 300A. 300A can be attached onto a biological transport medium (e.g., skin) for delivery of the bioactive compounds 100 and/or bioactive molecules 100A.

Thus, a long-term passive micropatch (about 15 millimeters$^2$ in area) (with the porous bottom surface of the microelectro-mechanical-system reservoir) can be fabricated/constructed for the delivery of the bioactive compounds 100 and/or bioactive molecules 100A.

The porous bottom surface of the microelectro-mechanical-system reservoir 300 is 300A. The porous bottom surface of (the microelectro-mechanical-system reservoir 300) 300A can be attached onto a nanoporous membrane (e.g., a nanoporous membrane of titanium dioxide nanotubes or a carbon nanomembrane), then onto a biological transport medium for delivery of the bioactive compounds 100 and/or bioactive molecules 100A.

Thus, a long-term passive micropatch (about 15 millimeters$^2$ in area) (with the porous bottom surface of the microelectro-mechanical-system reservoir and nanoporous membrane) can be fabricated/constructed for the delivery of the bioactive compounds 100 and/or bioactive molecules 100A.

Figure 7M:
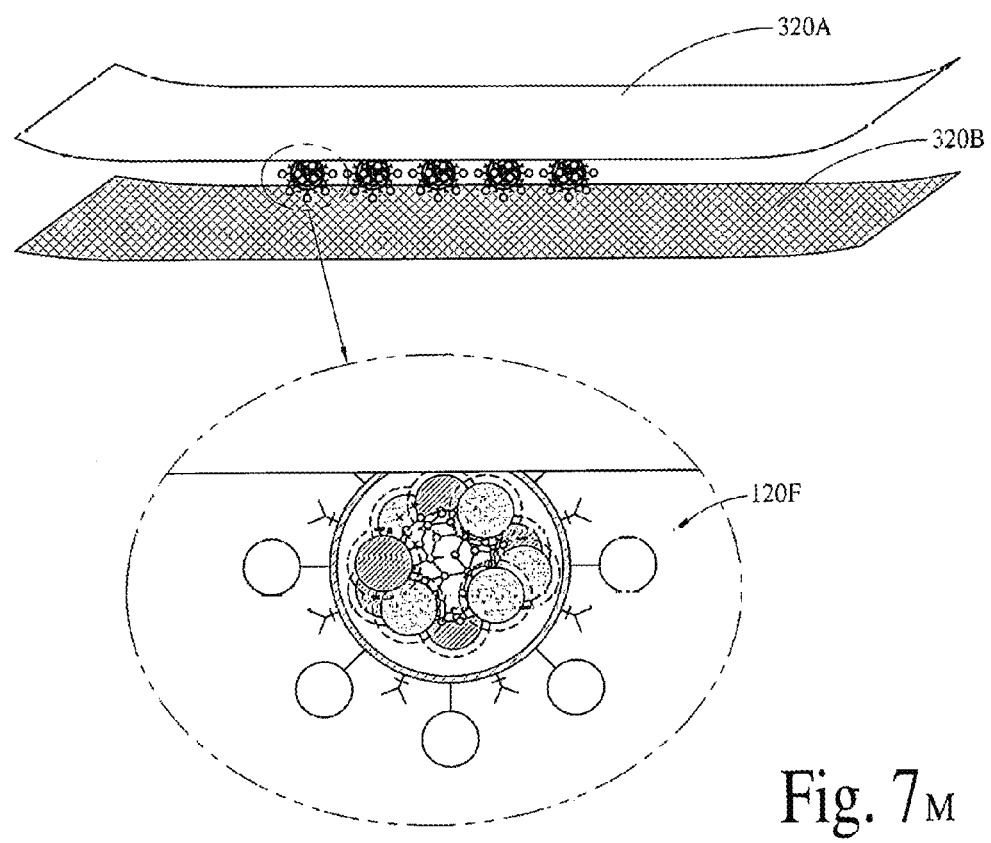

FIG. 7M illustrates 120F bonded directly between a non-porous top (adhesive) thin-film 320A and a porous bottom (adhesive) thin-film 320B. The porous bottom (adhesive) thin-film 320B can be attached onto a biological transport medium.

The non-porous top (adhesive) thin-film 320A can utilize chitin (a biopolymer based on the N-acetyl-glucosamine monomer) and/or chitin's variant deacetylated counterpart chitosan and/or fibroin (a protein derived from silk) as a base material/protective coating material for the non-porous top (adhesive) thin-film 320A.

Thus, a short-term passive micropatch (about 15 millimeters$^2$ in area) with the porous bottom (adhesive) thin-film 320B can be fabricated/constructed for the delivery of the bioactive compounds 100 and/or bioactive molecules 100A.

Furthermore, a specific vaccine can be preserved by drying in sugar. Then the sugar-dried vaccine can be fabricated/constructed, as an array of dissolvable microneedles. Such an array of dissolvable microneedles can be embedded with the porous bottom (adhesive) thin-film 320B, for the instant delivery of the vaccine.

Passive Micropatch of Porous Nanofiber Mesh

Electrospinning uses an electric field to catapult a charged fluid jet through air to create very fine nanometer-scale fibers (e.g., biocompatible material/material mixtures of alginate and/or chitin and/or fibroin) and it can be manipulated to control the material's solubility, strength and geometry.

A nanofiber mesh can be stretchy to physically block a human body's blood/biological fluid and/or deliver the bioactive compounds 100 and/or bioactive molecules 100 through the nanofiber mesh.

The nanofiber mesh can incorporate many fibers with variable properties to deliver the bioactive compounds 100 and/or bioactive molecules 100 through the nanofiber mesh at different delivery rates to increase the potency. The nanofiber mesh can be used on or in a human body.

Two-Dimensional Array of Nanosized Wells of a Porous Material, as an Alternative to a MEMS Reservoir Alternatively, a two-dimensional array of nanosized wells of a suitable porous material (e.g., porous hydrogel/porous silicon/silicate based polymer nanocomposite) containing the bioactive compounds 100 and/or bioactive molecules 100A (or indirectly utilizing nanocrystals, wherein the nanocrystals encapsulate/cage the bioactive compounds 100 and/or bioactive molecules 100A) can replace the above microelectro-mechanical-system reservoir 300 in both the long-term/short-term passive micropatch.

The two-dimensional array of nanosized wells of the suitable porous material thin-film can be fabricated/constructed, utilizing lithography (e.g., phase mask/electron-beam lithography) and inductively-coupled plasma (ICP) etching/focused ion beam etching.

The two-dimensional array of nanosized wells of the suitable porous material thin-film can be functionalized with peptide nucleic acid (PNA) probes to target distinguishing different bacterial strains (e.g., *S. aureus* and *E. coli*).

Furthermore, the two-dimensional array of nanosized wells of the suitable porous material thin-film can be functionalized with peptide nucleic acid probes to target simultaneous identification of resistant and non-resistant *E. coli*, causing urinary tract infections.

Smart Porous Thin-Film, as an Alternative to a MEMS Reservoir

A smart thin-film (e.g., a composite-gel) can regulate permeability in response to an external stimulus.

The smart thin-film can contain an ordered array of nanochannels. Furthermore, the ordered array of nanochannels can contain an ordered array of magnetic polystyrene latex particles.

The magnetic polystyrene latex particle can change its size in response to an external stimulus (e.g., temperature). Expansion/contraction of the magnetic polystyrene latex particles can affect the permeability of the smart porous thin-film from on state to off state.

Thus, a controlled transport and/or a tunable transport of the bioactive compounds 100 and/or bioactive molecules 100A can be achieved, by utilizing the suitable smart porous material thin-film.

Thus, in addition to delivering the bioactive compounds 100 and/or bioactive molecules 100A, utilizing the long-term/short-term passive micropatch, other bio/health sensors to monitor vital health parameters (e.g., blood sugar and heart rate) can be integrated with the long-term/short-term passive micropatch.

An example of a bio/health sensor integrated with the long-term/short-term passive micropatch is in situ blood sugar measurement. Blood sugar measurement can involve an electrochemical reaction activated by an enzyme. Glucose oxidase can convert glucose into hydrogen peroxide ($H_2O_2$) and other chemicals-thus their concentrations can be measured with a miniature potentiostat or nanosized potentiostat as a biosensor for calculating the glucose level in sweat. Furthermore, the bio/health sensor can be integrated with an analog signal to a digital signal converter (ADC) circuit.

Furthermore, Wibree, Bluetooth, WiFi and near field communication can be integrated with the long-term/short-term passive micropatch.

Thus, the bio/health sensor integrated with the long-term/short-term passive micropatch can deliver the bioactive compounds 100 and/or bioactive molecules 100A utilizing the long-term/short-term passive micropatch.

Example Applications of a Passive Micropatch

7M can be utilized as a passive micropatch to deliver a compound, drug, molecule (e.g., a micro RNA (miRNA) and small interfering RNA)) and protein.

7M can be utilized as a passive micropatch to deliver an antibiotic bioactive compound.

Furthermore, an antibiotic bioactive compound can be integrated with magnesium oxide nanoparticles, self-assembling peptides (e.g., RADA16-I) and silver nanoparticles.

7M can be utilized as a passive micropatch to deliver the preprogrammed release of an array of growth factors for wound healing. Furthermore, the growth factors for wound healing can be photo activated/modulated (by a small quantity of reactive molecular species), utilizing a laser/an array of lasers of suitable wavelength and intensity. Furthermore, after a wound, epidermal cells can replicate and move into the area of a wound to close it up and start the healing process. This causes ionic/free radical concentrations to shift, a change that generates subtle but characteristic electrical fields. The fields can be detected by sensor arrays-printed onto the passive micropatch itself, wherein the passive micropatch can be fabricated/constructed on a flexible/stretchable substrate (e.g., manufactured by MC10 company).

7M can be utilized as a passive micropatch to deliver sildenafil.

7M can be utilized as a passive micropatch to deliver testosterone.

7M can be utilized as a passive micropatch to deliver luric acid and/or an isolated active protein from the *propionibacterium acnes* phages for treatment against acne.

*Propionibacterium acnes* phages, (a family of harmless viruses that live on human skin) are naturally programmed to kill the *propionibacterium acnes*, a bacterium that triggers acne.

Furthermore, 7M can be utilized as a passive micropatch to deliver a mixture of suitable oils and/or luric acid and/or an isolated active protein from the *propionibacterium acnes* phages for treatment against acne.

7M can be utilized as a passive micropatch to deliver rivastigmine for treatment against Alzheimer's disease.

7M can be utilized as a passive micropatch to deliver rotigotine for treatment against Parkinson's disease.

7M can be utilized as a passive micropatch (as a transplant passive micropatch) to deliver insulin-producing stem cells (by manipulating both the Wnt and Notch signals. Wnt enhances self-renewal of adult pancreatic stem cells and inhibiting Notch signaling increases production of insulin) or cells against Type 1 Diabetes disease. The passive micropatch may also contain protein and immune suppressing bioactive compound to allow the insulin-producing cells/stem cells to successfully graft, survive and function within a human body.

β-cell replication is difficult to control in a human body. A decrease in the function of β-cells late in life is the main cause of Type 2 Diabetes disease. Betatrophin, a liver hormone stimulates β-cell replication with remarkable efficiency. 7M can be utilized as a passive micropatch to deliver betatrophin.

7M can be utilized as a passive micropatch to deliver a nanoshell 120 decorated with a targeting ligand, wherein the targeting ligand can recognize/match/bind with adenosine receptors-thus allowing a human body's blood-brain barrier to be opened for the passage of the nanoshell 120 to deliver oxytocin ("the love hormone). The oxytocin hormone may help build a long-lasting love.

A constant and low dose of psilocybin can calm the psychological turbulence of people afflicted with a number of conditions, including depression and/or alcohol addiction. 7M can be utilized as a passive micropatch to deliver a nanoshell 120 decorated with a targeting ligand, wherein the targeting ligand can recognize/match/bind with adenosine receptors-thus allowing a human body's blood-brain barrier to be opened for the passage of the nanoshell 120 to deliver psilocybin.

Bacteria outnumber human cells about ten to one. A human body has a complex network of bacteria.

Bacteria possess genes that can encode beneficial compounds and/or molecules for a human body.

Furthermore, bacteria communicate/socialize (within similar and/or dissimilar species) via chemical molecular quorum sensing (also known as diffusion/efficiency sensing).

The quorum sensing is like census-taking. Quorum sensing allows bacteria to communicate using secreted chemical signaling molecules called autoinducers.

The quorum sensing can collectively regulate gene expressions of bacteria.

The quorum sensing can collectively regulate good/bad behaviors of bacteria.

7M can be utilized as a passive micropatch to deliver a pro-quorum sensing compound.

7M can be utilized as a passive micropatch to deliver an anti-quorum sensing compound. Such anti-quorum compounds are called disaccharide derivatives and they mimic a class of natural molecules known as rhamnolipids, which are produced and secreted by the bacterium itself. Such compounds have the potential to inhibit horizontal gene transfer, the process by which bacteria share genetic information, such as the ability to be drug-resistant.

7M can be utilized as a passive micropatch to deliver melittin and/or perforin to protect against Hepatitis B.

7M can be utilized as a passive micropatch to deliver melittin and/or perforin to protect against Hepatitis C.

7M can be utilized as a passive (vaginal) micropatch to deliver melittin and/or perforin to protect against HIV. However, the passive (vaginal) micropatch (to deliver melittin and/or perforin) can be coated with super hydrophilic nanoparticle to prevent breakage.

7M can be utilized to deliver granulocyte macrophage colony-simulating factor (GMC-SF), which can reprogram a human body's immune system to attack cancer cells.

7M can be utilized with an integrated bio/health sensor.

7M can be placed (attached and/or implanted) on or in (meaning within) a human body.

Active Micropatch Integrated with an Electrically Controlled Layer

The porous bottom thin-film 320B can be composed of electrically charged (an opposite electrical charge polarity with respect to the electrical charge polarity of nanocrystals 120A) pigmented layers. Electrically charged pigmented layers can hold (an opposite electrical charge polarity) electrically charged nanocrystals 120A by an electrostatic field.

By applying a voltage (about a few millivolts from a thin-film printed battery), the electrically charged pigmented layers can disintegrate.

Thus, the bioactive compounds 100 and/or bioactive molecules 100A can be delivered in a variable quantity from the electrically charged nanocrystals 120A.

Active Micropatch Integrated with an Electrically Controlled Layer & a Smart Porous Thin-Film The porous bottom thin-film 320B can be composed of a smart thin-film. A smart thin-film (e.g., a composite-gel) can regulate permeability in response to an external stimulus. The smart thin-film can contain an ordered array of nanochannels. Furthermore, the ordered array of nanochannels can contain an ordered array of magnetic polystyrene latex particles. The magnetic polystyrene latex particle can change its size in response to an external stimulus (e.g., temperature). Expansion/contraction of the magnetic polystyrene latex particles can affect the permeability of the smart porous thin-film from an on state to an off state.

Thus, a controlled transport and/or a tunable transport of the bioactive compounds 100 and/or bioactive molecules 100A can be achieved, by utilizing the smart porous material thin-film.

Thus, in addition to delivering the bioactive compounds 100 and/or bioactive molecules 100A utilizing the active micropatch, other bio/health sensors to monitor vital health parameters (e.g., blood sugar and heart rate) can be integrated with the active micropatch.

An example of a bio/health sensor integrated with the active micropatch is in situ blood sugar measurement. Blood sugar measurement can involve an electrochemical reaction activated by an enzyme. Glucose oxidase can convert glucose into hydrogen peroxide and other chemicals-thus their concentrations can be measured with a miniature potentiostat or nanosized potentiostat as a biosensor for calculating the glucose level in sweat. Furthermore, the bio/health sensor can be integrated with an analog signal to digital signal converter circuit.

Furthermore, Wibree, Bluetooth, WiFi and near field communication can be integrated with the active micropatch. Furthermore, thin-film digital/source-gated transistor based circuits as an artificial skin can be integrated with the active micropatch for on-demand delivery of the bioactive compounds 100 and/or bioactive molecules 100A.

Thus, the bio/health sensor integrated with the active micropatch can enable active (actively controlled via closed loop measurement) delivery of the bioactive compounds 100 and/or bioactive molecules 100A utilizing the active micropatch.

Example Applications of an Active Micropatch Integrated with Electrically Controlled Layer NAD is a key molecule that coordinates activities between the cell's nuclear genome and the mitochondrial genome. With aging, levels of NAD decline. Without sufficient NAD, SIRT1 can not keep tabs on HIF-1. Levels of HIF-1 can escalate and begin wreaking havoc on the cross-genome communication. Over time, this loss of communication reduces the cell's ability to make energy and signs of aging related diseases become apparent. By administering an endogenous compound (that cells can transform into NAD) such as, plasma NAD metabolites-nicotinamide mononucleotide (NMN), one could restore cross-genome communication, if the endogenous compound was administered early enough, prior to excessive mutation accumulation. An active micropatch can be utilized to deliver an endogenous compound (that cells can transform into NAD) to delay onset of aging related diseases.

An active micropatch can be utilized to deliver a compound, drug and molecule (e.g., a micro RNA and small interfering RNA).

An active micropatch can be utilized to deliver an antibiotic bioactive compound.

Furthermore, an antibiotic bioactive compound can be integrated with magnesium oxide nanoparticles, self-assembling peptides (e.g., RADA16-I) and silver nanoparticles.

An active micropatch can be utilized to deliver the preprogrammed release of an array of growth factors for wound healing. Furthermore, the growth factors for wound healing can be photo activated/modulated (by a small quantity of reactive molecular species), utilizing a laser/an array of lasers of suitable wavelength and intensity. Furthermore, after a wound, epidermal cells can replicate and move into the area of a wound to close it up and start the healing process. This causes ionic/free radical concentrations to shift, a change that generates subtle but characteristic electrical fields. The fields can be detected by sensor arrays-printed onto the active micropatch itself, wherein the active micropatch can be fabricated/constructed on a flexible/stretchable substrate (e.g., manufactured by MC10 company).

An active micropatch can be utilized to deliver sildenafil.

An active micropatch can be utilized to deliver testosterone.

An active micropatch can be utilized to deliver luric acid and/or an isolated active protein from the *propionibacterium acnes* phages for treatment against acne.

An active micropatch can be utilized to deliver rivastigmine for treatment against Alzheimer's disease.

An active micropatch can be utilized to deliver rotigotine for treatment against Parkinson's disease.

An active micropatch (as a transplant active micropatch) can be utilized to deliver insulin-producing stem cells (by manipulating both the Wnt and Notch signals. Wnt enhances self-renewal of adult pancreatic stem cells and inhibiting Notch signaling increases production of insulin) or cells against Type 1 Diabetes disease. The active micropatch may also contain protein and immune suppressing bioactive compound to allow the insulin-producing cells/stem cells to successfully graft, survive and function within a human body.

$\beta$-cell replication is difficult to control in a human body. A decrease in the function of $\beta$-cells late in life is the main cause of Type 2 Diabetes disease. Betatrophin, a liver hormone stimulates $\beta$-cell replication with remarkable efficiency. An active micropatch can be utilized to deliver betatrophin.

An active micropatch can be utilized to deliver a nanoshell 120 decorated with a targeting ligand, wherein the targeting ligand can recognize/match/bind with adenosine receptors-thus allowing a human body's blood-brain barrier to be opened for the passage of the nanoshell 120 to deliver oxytocin ("the love hormone"). The oxytocin hormone may help build a long lasting love.

A constant and low dose of psilocybin can calm the psychological turbulence of people afflicted with a number of conditions, including depression and alcohol addiction. An active micropatch can be utilized to deliver a nanoshell 120 decorated with a targeting ligand, wherein the targeting ligand can recognize/match/bind with adenosine receptors-thus allowing a human body's blood-brain barrier to be opened for the passage of the nanoshell 120 to deliver psilocybin.

Bacteria outnumber human cells ten to one. A human body has a complex molecular network of bacteria.

Bacteria possess genes that can encode beneficial compounds and/or molecules for a human body.

Furthermore, bacteria communicate/socialize (within similar and/or dissimilar species) via chemical molecular quorum sensing (also known as diffusion/efficiency sensing).

The quorum sensing is like census-taking. Quorum sensing allows bacteria to communicate using secreted chemical signaling molecules called autoinducers.

The quorum sensing can collectively regulate gene expressions of bacteria.

The quorum sensing can collectively regulate good/bad behaviors of bacteria.

An active micropatch can be utilized to deliver a pro-quorum sensing compound.

An active micropatch can be utilized to deliver an anti-quorum sensing compound. Such anti-quorum compounds are called disaccharide derivatives and they mimic a class of natural molecules known as rhamnolipids, which are produced and secreted by the bacterium itself. Such compounds have the potential to inhibit horizontal gene transfer, the process by which bacteria share genetic information, such as the ability to be drug-resistant.

An active micropatch can be utilized to deliver granulocyte macrophage colony-simulating factor (GMC-SF), which can reprogram a human body's immune system to attack cancer cells.

An active micropatch can be utilized with an integrated bio/health sensor.

An active micropatch can be placed (attached and/or implanted) on or in (meaning within) a human body.

Active Micropatch of Three-Dimensional Porous Graphene Scaffold/Foam

A three-Dimensional porous graphene scaffold/foam can be synthesized by chemical vapor deposition (CVD) using a Ni foam template. The three-dimensional porous graphene scaffold/foam can serve as a biocompatible container, when it is coated with laminin/matrix proteins.

The three-dimensional porous graphene scaffold/foam, as an active micropatch (e.g., a transdermal patch) can be electrically controlled by polyaniline (PAni) hydrogel electrodes and a thin-film battery/thin-film printed battery/biofuel battery/DNA solar cell.

A biofuel battery has a paste with two carbon nanotubes, wherein one carbon nanotube is mixed with glucose oxidase and the other carbon nanotube is mixed with glucose and polyphenol oxidase. Current is delivered to the biofuel battery's circuit via a platinum wire inserted into the paste. The biofuel battery is wrapped in a biocompatible material to prevent any leaking.

A DNA solar cell incorporates metal atoms and other chemicals to mimic the efficient mechanisms bacteria used to derive energy from the sunlight.

Silicon/polymer nanowires (about 50 nanometers to 100 nanometers in diameter) for stable electronic sensors are more electrically sensitive than metal electrodes. These stable electronic sensors can be embedded in the three-dimensional porous graphene scaffold/foam to monitor electrical activity-thus enabling how living cells and/or stem cells would respond to specific bioactive compounds 100 and/or bioactive molecules 100A.

Example Applications of an Active Micropatch of Three-Dimensional Porous Graphene Scaffold/Foam Nitric mono oxide is a short-lived, gaseous signaling free radical molecule, produced in cells. Once released into a human body's bloodstream, it signals a human body to perform certain functions such as vasodilatation opening up the blood vessels and capillaries to increase blood flow and deliver oxygen and critical nutrients throughout the human body at the time it needs them most.

Controlled amount of nitric mono oxide (NO) gas can be beneficial for health. Nitric mono oxide can remain stable and trapped within the three-dimensional porous graphene scaffold/foam.

The three-dimensional porous graphene scaffold/foam utilizing graphene/polyaniline hydrogel electrodes and a thin-film battery/thin-film printed battery/biofuel battery/engineered bacteria battery can act as an active micropatch for nitric mono oxide.

Trapped nitric mono oxide can be released in a controlled manner utilizing graphene/polyaniline hydrogel electrodes and a thin-film battery/thin-film printed battery/biofuel battery/engineered bacteria battery.

Furthermore, chitosan can be added to the three-dimensional porous graphene scaffold/foam for increasing an antimicrobial killing action. Controlled amounts of nitric mono oxide gas can be beneficial for wound healing.

The three-dimensional porous graphene scaffold/foam utilizing graphene/polyaniline hydrogel electrodes and a thin-film battery/thin-film printed battery/biofuel battery/engineered bacteria battery, as an active micropatch can deliver adipose-derived stem cells (ADSC) for wound healing.

Furthermore, the three-dimensional porous graphene foam utilizing graphene/polyaniline hydrogel electrodes and a thin-film battery/thin-film printed battery/biofuel battery/engineered bacteria battery, as an active micropatch can deliver neural stem cells.

Furthermore, the three-dimensional porous graphene foam utilizing graphene/polyaniline hydrogel electrodes and a thin-film battery/thin-film printed battery/biofuel battery/engineered bacteria battery and silicon nanowire sensors, as an active micropatch can deliver neural stem cells with embedded silicon nanowire sensors (configured to monitor specific biochemical functions) and specific bioactive compounds 100 and/or bioactive molecules 100A.

Active Micropatch of Three-Dimensional Porous Graphene Scaffold/Foam Coupled with a Porous Nanomembrane & Nanopump The three-dimensional porous graphene scaffold/foam can be integrated with an atomically thick (about 1 nanometer thick) porous nanomembrane (e.g., a carbon nanomembrane), wherein the atomically thick porous nanomembrane is attached on the human body.

The three-dimensional porous graphene scaffold/foam integrated with the atomically thick porous nanomembrane can be activated by a thin-film battery/thin-film printed battery/biofuel battery/engineered bacteria battery coupled with phi29 DNA polymerase enzyme as a nanopump (or as an array of nanopumps with an array of phi29 DNA polymerase enzymes) to deliver the bioactive compounds 100 and/or bioactive molecules 100A across the porous nanomembrane, wherein the atomically thick porous carbon nanomembrane is attached on a human body.

Active Micropatch of Three-Dimensional Porous Epoxy Scaffold/Foam

A three-dimensional porous epoxy scaffold/foam (e.g., hydrogel scaffold/foam), as an active (implantable) micropatch can serve as a biocompatible container for living cells and/or stem cells and/or bioactive compounds 100 and/or bioactive molecules 100A. The three-dimensional porous epoxy scaffold/foam, as an active (implantable) micropatch can be electrically controlled with boron-doped diamond electrodes and a thin-film battery/thin-film printed battery/biofuel battery/engineered bacteria battery.

Boron-doped conducting diamond like material can be grown on a silicon dioxide ($SiO_2$) substrate by chemical vapor deposition at about 900 degree centigrade. Boron-doped conducting diamond like material can be bonded on a polymer substrate and then lifted off from the silicon dioxide substrate by hydrofluoric (HF) acid. Thus, a boron-doped conducting diamond-like material can act as an interface electrode for any biological application.

Silicon/polymer nanowires (about 50 nanometers to 100 nanometers in diameter) for stable electronic sensors are more electrically sensitive than metal electrodes. These stable electronic sensors can be embedded in the three-dimensional porous epoxy scaffold/foam to monitor electrical activity-thus enabling how living cells and/or stem cells would respond to specific bioactive compounds 100 and/or bioactive molecules 100A.

Example Applications of an Active Micropatch of Three-Dimensional Porous Epoxy Scaffold/Foam Nitric mono oxide is a short-lived, gaseous signaling free radical molecule, produced in cells. Once released into a human body's bloodstream, it signals a human body to perform certain functions such as vasodilatation opening up the blood vessels and capillaries to increase blood flow and deliver oxygen and critical nutrients throughout the human body at the time it needs them most.

Controlled amount of nitric mono oxide gas can be beneficial for health. Nitric mono oxide can remain stable and trapped within the three-dimensional porous epoxy scaffold/foam.

The three-dimensional porous epoxy scaffold/foam utilizing boron-doped diamond electrodes and a thin-film battery/thin-film printed battery/biofuel battery/engineered bacteria battery can act as an active micropatch. Trapped nitric mono oxide can be released in a controlled manner utilizing boron-doped diamond electrodes and thin-film battery/thin-film printed battery/biofuel battery/engineered bacteria battery.

Chitosan can be added to the three-dimensional porous epoxy scaffold/foam for increasing an antimicrobial killing action. Controlled amount of nitric mono oxide gas can be beneficial for wound healing.

Furthermore, the three-dimensional porous epoxy scaffold/foam utilizing boron-doped diamond electrodes and a thin-film battery/thin-film printed battery/biofuel battery/engineered bacteria battery, as an active micropatch can deliver adipose-derived stem cells for wound healing.

Furthermore, the three-dimensional porous epoxy foam utilizing boron-doped diamond electrodes and a thin-film battery/thin-film printed battery/biofuel battery/engineered bacteria battery, as an active micropatch can deliver neural stem cells.

Furthermore, the three-dimensional porous epoxy foam utilizing boron-doped diamond electrodes, a thin-film battery/thin-film printed battery/biofuel battery/engineered bacteria battery and silicon nanowire sensors, as an active micropatch can deliver neural stem cells with embedded silicon nanowire sensors (configured to monitor specific biochemical functions) and specific bioactive compounds 100 and/or bioactive molecules 100A.

Active Micropatch of Three-Dimensional Porous Epoxy Scaffold/Foam Coupled with a Porous Nanomembrane & Nanopump The three-dimensional porous epoxy scaffold/foam can be integrated with an atomically thick (about 1 nanometer thick) porous nanomembrane (e.g., a carbon nanomembrane), wherein the atomically thick porous nanomembrane is attached on a human body.

The three-dimensional porous epoxy scaffold/foam integrated with the atomically thick porous nanomembrane can be activated by a thin-film battery/thin-film printed battery/biofuel battery/engineered bacteria battery coupled with phi29 DNA polymerase enzyme as a nanopump (or an array of nanopumps of phi29 DNA polymerase enzymes) to deliver the bioactive compounds 100 and/or bioactive molecules 100A across the porous nanomembrane, wherein the atomically thick porous nanomembrane is attached on a human body.

Active Micropatch of Three-Dimensional Porous Scaffold/Foam of Other Material Matrix

TABLE 14A

Compositions Of A Scaffold

| Composition | Wt % Material A | Wt % Material B | Wt % Material C | Wt % Material D |
|---|---|---|---|---|
| 1 | 80% Hydrogel | 20% Chitin | | |
| 2 | 80% Hydrogel | 20% Chitosan | | |
| 3 | 80% Hydrogel | 20% Fibroin | | |
| 4 | 80% Hydrogel | 10% Chitin | 10% Chitosan | |
| 5 | 80% Hydrogel | 10% Chitin | 10% Fibroin | |
| 6 | 80% Hydrogel | 10% Chitosan | 10% Fibroin | |
| 7 | 80% Hydrogel | 10% Chitin | 10% PGLA | |
| 8 | 80% Hydrogel | 10% Chitosan | 10% PGLA | |
| 9 | 80% Hydrogel | 10% Fibroin | 10% PGLA | |
| 10 | 70% Hydrogel | 10% Chitin | 10% Fibroin | 10% PGLA |
| 11 | 70% Hydrogel | 10% Chitosan | 10% Fibroin | 10% PGLA |

TABLE 14B

Compositions Of A Scaffold Integrated With Various Nanowire Field Effect Transistors (FETs)

| Compositions From Table-14A | Integrated With An Array Of Nanowire FETs |
|---|---|
| 1 | Nanowire$^{P1}$/Nanowire$^{P2}$/Nanowire$^{P3}$/Nanowire$^{z}$/Nanowire$^{c}$ |
| 2 | Nanowire$^{P1}$/Nanowire$^{P2}$/Nanowire$^{P3}$/Nanowire$^{z}$/Nanowire$^{c}$ |
| 3 | Nanowire$^{P1}$/Nanowire$^{P2}$/Nanowire$^{P3}$/Nanowire$^{z}$/Nanowire$^{c}$ |
| 4 | Nanowire$^{P1}$/Nanowire$^{P2}$/Nanowire$^{P3}$/Nanowire$^{z}$/Nanowire$^{c}$ |
| 5 | Nanowire$^{P1}$/Nanowire$^{P2}$/Nanowire$^{P3}$/Nanowire$^{z}$/Nanowire$^{c}$ |
| 6 | Nanowire$^{P1}$/Nanowire$^{P2}$/Nanowire$^{P3}$/Nanowire$^{z}$/Nanowire$^{c}$ |
| 7 | Nanowire$^{P1}$/Nanowire$^{P2}$/Nanowire$^{P3}$/Nanowire$^{z}$/Nanowire$^{c}$ |
| 8 | Nanowire$^{P1}$/Nanowire$^{P2}$/Nanowire$^{P3}$/Nanowire$^{z}$/Nanowire$^{c}$ |
| 9 | Nanowire$^{P1}$/Nanowire$^{P2}$/Nanowire$^{P3}$/Nanowire$^{z}$/Nanowire$^{c}$ |
| 10 | Nanowire$^{P1}$/Nanowire$^{P2}$/Nanowire$^{P3}$/Nanowire$^{z}$/Nanowire$^{c}$ |
| 11 | Nanowire$^{P1}$/Nanowire$^{P2}$/Nanowire$^{P3}$/Nanowire$^{z}$/Nanowire$^{c}$ |

Nanowire$^{P1}$ FET is a polymer nanowire FET (optionally coated with a lipid layer).
Nanowire$^{P2}$ FET is an engineered protein nanowire FET (optionally coated with a lipid layer). An engineered protein based field effect transistor (FET) can be fabricated/constructed, utilizing a suitable material decorated on engineered protein (e.g., a three dimensional (3-D) ball and spike engineered protein-synthesized by a fusion of both Dps and gp5c genes).
Nanowire$^{P3}$ FET is a proton nanowire H+ FET (optionally coated with a lipid layer). A natural biopolymer chitosan/melanin based proton field effect transistor (H$^{+}$ FET) and it incorporates a polymer substrate as a gate, a gate oxide insulator film, a source metal thin-film and a drain metal thin-film for proton current.
Nanowire$^{z}$ FET is zinc oxide wire nanowire FET (optionally coated with a lipid layer).
Nanowire$^{c}$ FET is carbon nanotube nanofiber FET (optionally coated with a lipid layer).

Compositions as described in Table-14B can enable merging biology and electronics to monitor a biological function/parameter of a cell/stem cell.

A three-dimensional porous scaffold/foam of various mixtures as illustrated by Table-14A and Table-14B can be fabricated/constructed, utilizing electrospinning/three-dimensional printing process.

Active Micropatch of Porous Nanofiber Mesh Electrically Connected with Nanofiber Field Effect Transistors A porous nanofiber mesh can be electrically connected with nanofiber field effect transistor (e.g., polymer field effect transistor/zinc oxide field effect transistor) to monitor electrical activity-thus enabling how living cells and/or stem cells would respond to specific bioactive compounds 100 and/or bioactive molecules 100A. Furthermore, the nanofiber field effect transistor can be coated/integrated with a lipid layer.

Active Micropatch Integrated with Microelectro-Mechanical-System Reservoirs & Microneedles A passive delivery of the bioactive compounds 100 and/or bioactive molecules 100A is generally limited by low permeability (of the bioactive compounds 100 and/or bioactive molecules 100A) in a biological transport medium.

Figure 7N:
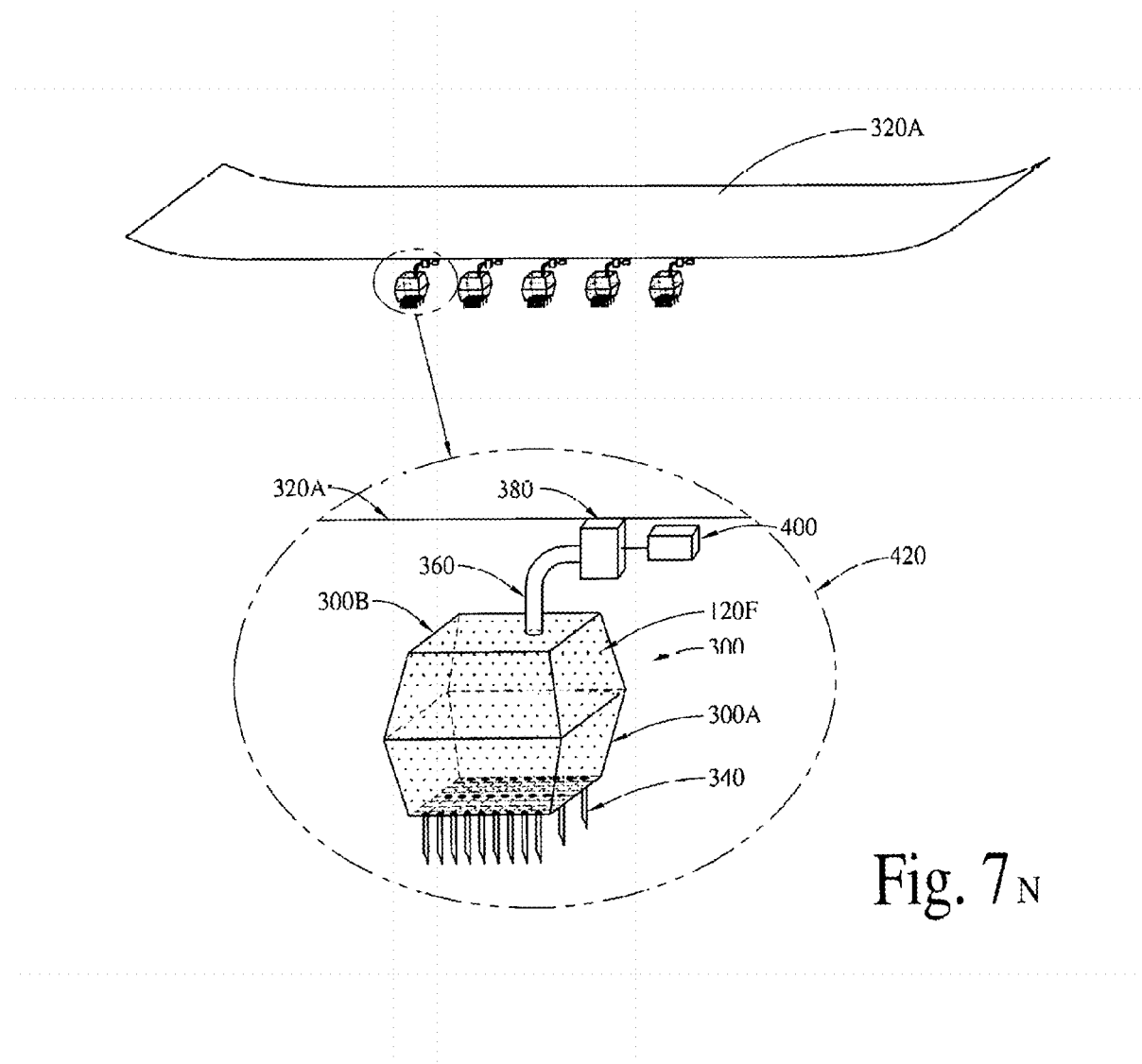

FIG. 7N illustrates a thin-film 320A attached with a microelectro-mechanical-system microassembly as 420.

The microelectro-mechanical-system microassembly 420 illustrates microelectro-mechanical-system reservoirs 300 with monolithically integrated microneedles 340, utilizing a microflow tube 360.

The microflow tube 360 can be connected to a micropump 380.

The micropump 380 can be powered by an electrical power providing component 400. The electrical power providing component 400 can be a thin-film battery/thin-film printed battery/biofuel battery/engineered bacteria battery.

The microelectro-mechanical-system reservoir 300 can be fabricated/constructed, utilizing liquid-crystal polymers/polyimide/silicon/silk/SU-8 resin/other suitable material.

The microelectro-mechanical-system reservoir 300 can be monolithically integrated with microneedles 340.

The microneedle 340 is biocompatible and about 450 micron long with an internal hole-diameter of about 45 micron.

The microneedle 340 can be fabricated/constructed, utilizing liquid-crystal polymers/polyimide/silicon/silk/SU-8 resin/other suitable material.

The microneedle 340 can be coated with carbon nanotubes, wherein the carbon nanotubes are integrated with the enzyme Lysostaphin. Lysostaphin is a natural enzyme, which attacks the bacterial cell wall causing its slicing and disintegration.

The microneedle 340 can be coated with positively charged dimethyldecylammonium chitosan methacrylate. The interaction of positively charged dimethyldecylammonium chitosan methacrylate with the negatively charged bacterial cell wall can result in the disintegration of bacterial cell wall.

Furthermore, the microneedle 340 can be coated with polyvinyl alcohol integrated with nitric oxide releasing nanoparticle and/or reactive oxygen species releasing nanoparticle and/or reactive nitrogen species releasing nanoparticle and/or silver oxide nanoparticle and/or titanium oxide nanoparticle and/or zinc oxide nanoparticle to combact bacterial infection.

Furthermore, the microneedle 340 can be coated with poly(ethylene glycol)-poly(lactic acid) (PEG-PLA) nanoparticle with silver carbene complexes (SCCs) to act as a controlled release system against bacterial infection.

The microelectro-mechanical-system microassembly is indicated as 420.

Thus, a long-term active micropatch (about 15 millimeters$^2$ in area) can be fabricated/constructed for the delivery of the bioactive compounds 100 and/or bioactive molecules 100A from the nanoassembly 120F in the microelectro-mechanical-system reservoirs 300.

Alternatively, a hydrogel contains up to 99.7% water and 0.3% cellulose polymers by weight, wherein the polymers are held by cucurbiturils. Cucurbiturils are methylene-linked macrocyclic molecules made of glycoluril [=C4H2N4O2=] monomers. The oxygen atoms are located along the edges of the band and are tilted inwards, forming a partly enclosed cavity.

The hydrogel can protect the bioactive compounds 100 and/or bioactive molecules 100A for about six (6) months.

The hydrogel (embedded with the bioactive compounds 100 and/or bioactive molecules 100A) can be utilized in the microelectro-mechanical-system reservoirs 300 with the nanoassembly 120F.

The hydrogel (embedded with the bioactive compounds 100 and/or bioactive molecules 100A) can be utilized in the microelectro-mechanical-system reservoirs 300 without the nanoassembly 120F.

Bee venom contains a potent toxin called melittin that can indiscriminately poke holes in the double-layered membranes of a virus (e.g., hepatitis B, hepatitis C and HIV). However, large amounts of free melittin can cause a lot of damage to healthy cells. The nanoshell 120 can attack an essential part of the virus' structure. Furthermore, melittin-loaded nanoshell 120 can be also effective in killing cancer cells.

The hydrogel embedded with melittin can be utilized in the microelectro-mechanical-system reservoirs 300 without the nanoassembly 120F.

Alternatively, a long-term active micropatch (about 15 millimeters$^2$ in area) can be fabricated/constructed for the delivery of the bioactive compounds 100 and/or bioactive molecules 100A from the hydrogel (embedded with the bioactive compounds 100 and/or bioactive molecules 100A e.g., melitin) in the microelectro-mechanical-system reservoirs 300.

Furthermore, the bioactive compounds 100 and/or bioactive molecules 100A can be utilized directly in the microelectro-mechanical-system reservoirs 300 without the nanoassembly 120F for a long-term active micropatch.

Thus, in addition to delivering the bioactive compounds 100 and/or bioactive molecules 100A utilizing the long-term active micropatch, other bio/health sensors to monitor vital health parameters (e.g., blood sugar and heart rate) can be integrated with the long-term active micropatch.

An example of a bio/health sensor integrated with the long-term active micropatch is in situ blood sugar measurement. Blood sugar measurement can involve an electrochemical reaction activated by an enzyme. Glucose oxidase can convert glucose into hydrogen peroxide and other chemicals-thus their concentrations can be measured with a miniature potentiostat or nanosized potentiostat as a biosensor for calculating the glucose level in sweat. Furthermore, the bio/health sensor can be integrated with an analog signal to a digital signal converter circuit.

Furthermore, Wibree, Bluetooth, WiFi and near field communication can be integrated with the long-term active micropatch.

Thus, the bio/health sensor integrated with the long-term active micropatch can enable active (actively controlled via closed loop measurement) delivery of the bioactive compounds 100 and/or bioactive molecules 100A utilizing the long-term active micropatch.

Example Applications of an Active Micropatch Integrated with Microelectro-Mechanical-System Reservoirs & Microneedles NAD is a key molecule that coordinates activities between the cell's nuclear genome and the mitochondrial genome. With aging, levels of NAD decline. Without sufficient NAD, SIRT1 can not keep tabs on HIF-1. Levels of HIF-1 can escalate and begin wreaking havoc on the cross-genome communication. Over time, this loss of communication reduces the cell's ability to make energy and signs of aging related diseases become apparent. By administering an endogenous compound (that cells can transform into NAD) such as, plasma NAD metabolites-nicotinamide mononucleotide (NMN), one could restore cross-genome communication, if the endogenous compound was administered early enough, prior to excessive mutation accumulation. 7N can be utilized to deliver an endogenous compound (that cells can transform into NAD) to delay onset of aging related diseases.

7N can be utilized as an active micropatch to deliver a liquid drug (e.g., immunoglobul in).

7N can be utilized as an active micropatch to deliver a liquid nanoemulsified drug.

7N can be utilized as an active micropatch to deliver insulin.

7N can be utilized as an active micropatch to deliver insulin with leptin.

7N can be utilized as an active micropatch to deliver exenatide.

7N can be utilized as an active micropatch to deliver specific micro RNA (miRNA).

7N can be utilized as an active micropatch to deliver specific small interfering RNA (siRNA).

7N can be utilized to deliver granulocyte macrophage colony-simulating factor, which can reprogram a human body's immune system to attack cancer cells.

7N can be utilized with an integrated bio/health sensor.

7N can be placed (attached and/or implanted) on or in (meaning within) a human body.

Figure 7O:
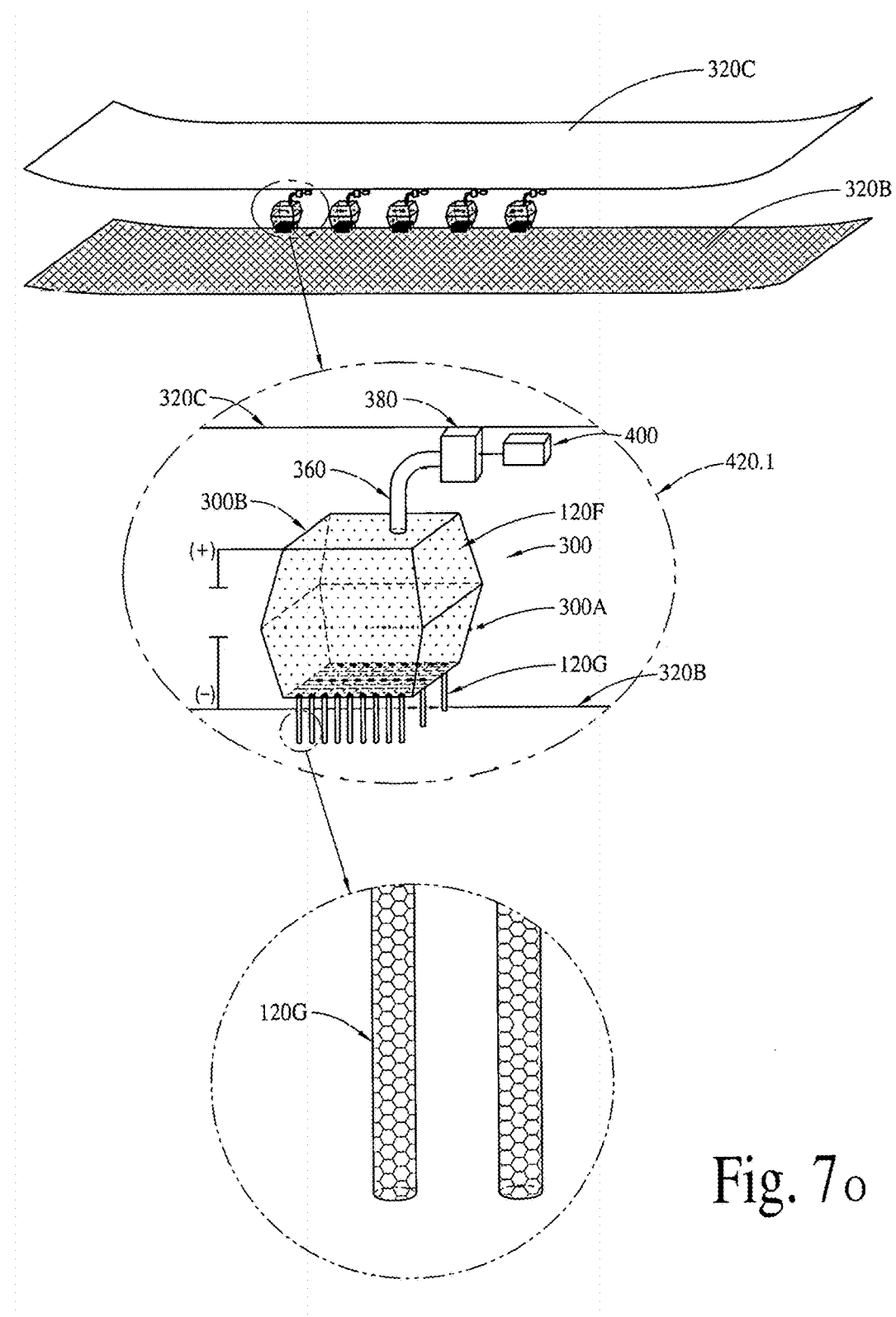

Active Micropatch Integrated with Microelectro-Mechanical-System Reservoirs & Nanotubes FIG. 7O illustrates a conducting thin-film 320C attached with the microelectro-mechanical-system reservoirs 300.

Furthermore, the microelectro-mechanical-system reservoirs 300, with integrated/bonded nanotubes (e.g., a boron nitride/carbon nanotube or a tubular structure fabricated/constructed, utilizing DNA/RNA origami process) 120G, utilizing a microflow tube 360, which can be connected to a micropump 380. The microelectro-mechanical-system microassembly is indicated as 420.1.

The micropump 380 can be powered by an electrical power providing component 400. The electrical power providing component 400 can be a thin-film battery/thin-film printed battery/biofuel battery/engineered bacteria battery.

Thus, a long-term active micropatch (about 15 millimeters$^2$ in area) can be fabricated/constructed for the delivery of the bioactive compounds 100 and/or bioactive molecules 100A from the nanoassembly 120F.

Alternatively, a long-term active micropatch (about 15 millimeters$^2$ in area) can be fabricated/constructed for the delivery of the bioactive compounds 100 and/or bioactive molecules 100A from the hydrogel (embedded with the bioactive compounds 100 and/or bioactive molecules 100A) in the microelectro-mechanical-system reservoirs 300.

Furthermore, the bioactive compounds 100 and/or bioactive molecules 100A can be utilized directly within the microelectro-mechanical-system reservoirs 300 without the nanoassembly 120F.

The nanotubes 120G can be further integrated/bonded with the porous bottom thin-film 320B.

By applying a voltage (about millivolts from a thin-film battery/thin-film printed battery/biofuel battery/engineered bacteria battery) between 320C and the nanostructure membrane 120G, the bioactive compounds 100 and/or bioactive molecules 100A can be delivered in a variable quantity according to the required dose/need.

Example Applications of an Active Micropatch Integrated with Microelectro-Mechanical-System Reservoirs & Nanotubes NAD is a key molecule that coordinates activities between the cell's nuclear genome and the mitochondrial genome. With aging, levels of NAD decline. Without sufficient NAD, SIRT1 can not keep tabs on HIF-1. Levels of HIF-1 can escalate and begin wreaking havoc on cross-genome communication. Over time, this loss of communication reduces the cell's ability to make energy and signs of aging related diseases become apparent. By administering an endogenous compound (that cells can transform into NAD) such as, plasma NAD metabolites-nicotinamide mononucleotide, one could restore cross-genome communication, if the endogenous compound was administered early enough, prior to excessive mutation accumulation. 7O can be utilized to deliver an endogenous compound (that cells can transform into NAD) to delay onset of ageing related diseases.

7O can be utilized as an active micropatch to deliver a liquid drug (e.g., immunoglobulin).

7O can be utilized as an active micropatch to deliver a nanoformulated liquid drug.

7O can be utilized as an active micropatch to deliver insulin.

7O can be utilized as an active micropatch to deliver exenatide.

7O can be utilized as an active micropatch to deliver specific micro RNA (miRNA).

7O can be utilized as an active micropatch to deliver specific small interfering RNA (siRNA).

7O can be placed (attached and/or implanted) on or in (meaning within) a human body.

Figure 8:
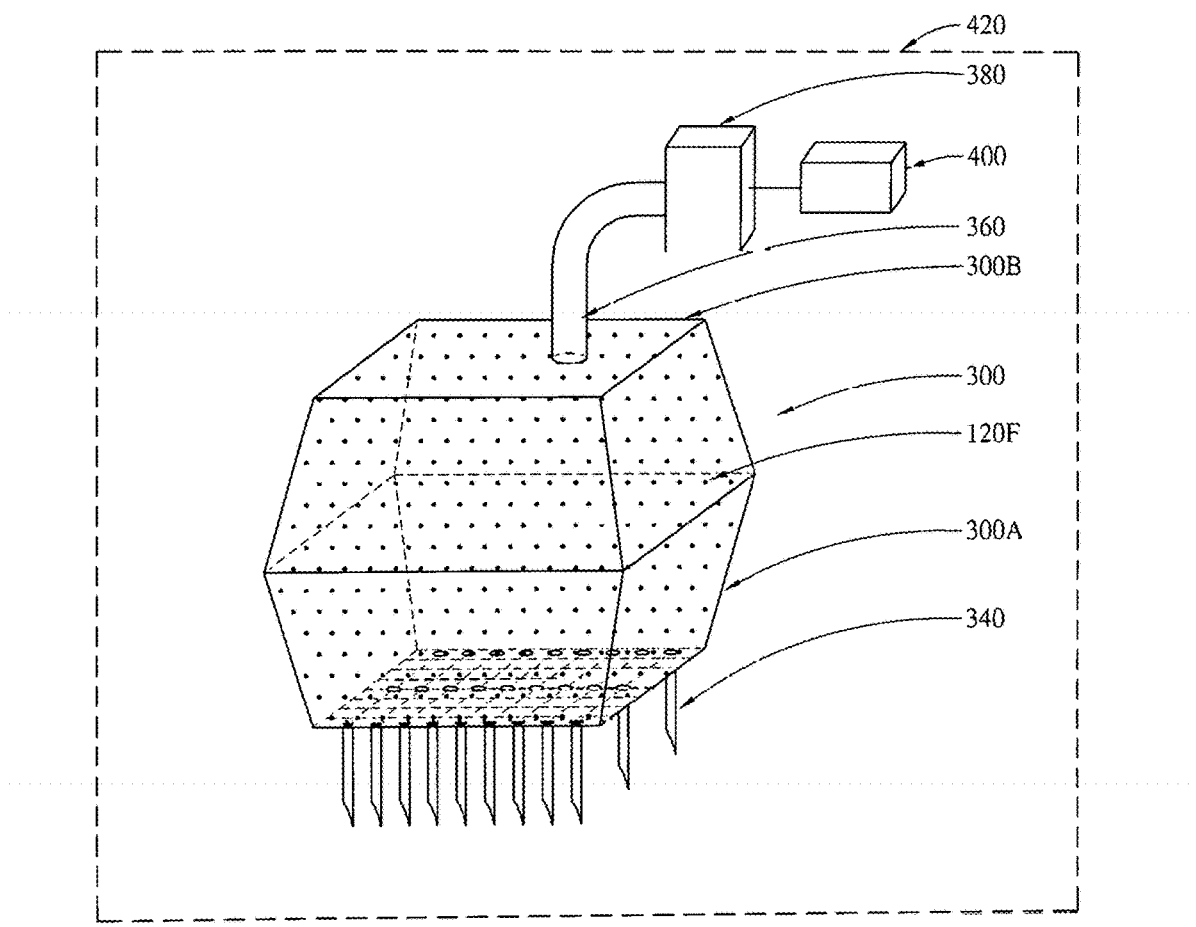
FIG. 8 illustrates a programmable/active (via a micropatch and microelectro-mechanical-system reservoir(s) integrated with needles) delivery of bioactive compounds and/or bioactive molecules, utilizing a microelectro-mechanical-system reservoir and a micropump.

FIG. 8 illustrates the microelectro-mechanical-system reservoir 300 with 120Fs dispersed in a liquid medium. 120Fs can encapsulate/cage the bioactive compounds 100 and/or bioactive molecules 100A.

However, the bioactive compounds 100 and/or bioactive molecules 100A can be dispersed directly (via a liquid medium) in the microelectro-mechanical-system reservoir 300, without the need for 120F.

The microelectro-mechanical-system reservoir 300 is about 1 millimeter in total thickness.

The microelectro-mechanical-system reservoir 300 can be monolithically integrated with microneedles 340 at the bottom surface 300A of the MEMS reservoir 300.

The microneedle 340 is biocompatible and about 450 micron long with an internal hole-diameter of about 45 micron.

The microneedle 340 can be fabricated/constructed, utilizing liquid crystal polymers/polyimide/silicon/silk/SU-8 resin/other suitable material.

The microelectro-mechanical-system reservoir 300 can be connected to a microflow tube 360, which is connected to a micropump 380.

The micropump 380 can be powered by an electrical power providing component 400. The electrical power providing component 400 can be a thin-film battery/thin-film printed battery/biofuel battery/engineered bacteria battery.

Such a microelectro-mechanical-system biomodule 420 can be utilized to achieve a higher permeability (of the bioactive compounds 100 and/or bioactive molecules 100A) through a biological transport medium for long-term programmable/active delivery of the bioactive compounds 100 and/or bioactive molecules 100A.

Alternatively, a microelectro-mechanical-system biomodule 420 can be utilized to achieve a higher permeability (of the bioactive compounds 100 and/or bioactive molecules 100A) through a biological transport medium for long-term programmable/active delivery of the bioactive compounds 100 and/or bioactive molecules 100A, utilizing a hydrogel.

The hydrogel embedded with the bioactive compounds 100 and/or bioactive molecules 100A can be utilized in the microelectro-mechanical-system reservoirs 300.

The microelectro-mechanical-system biomodule 420 can be placed (attached and/or implanted) on or in (meaning within) a human body.

Figure 9A:
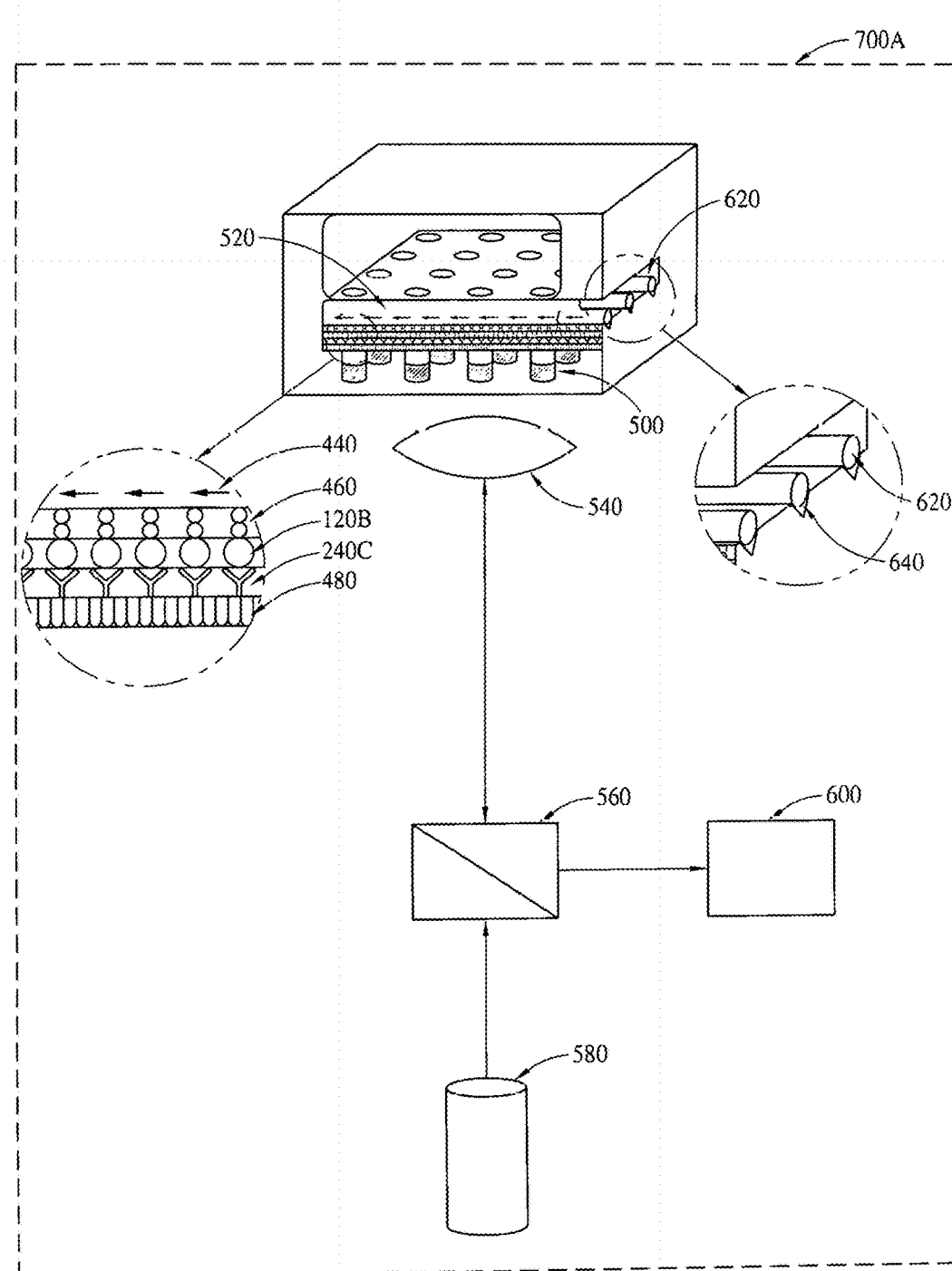
FIGS. 9A, 9B, 9C and 9D illustrate an array of photonic crystal cavities based integrated optical diagnostics biomodule to detect a disease specific biomarker/an array of disease specific biomarkers.

Array of Photonic Crystal Cavities Based Optical Diagnostics Biomodule for Detection of a Disease Specific Biomarker/an Array of Disease Specific Biomarkers FIG. 9A illustrates an array of photonic crystal cavities 500 based optical diagnostics biomodule 700A for detection of a disease specific biomarker 460 (in a patient's blood 440 which can be propagated through a microfluidic channel 620 to a microfluidic cavity 520).

The disease specific biomarker 460 can chemically bind with a disease specific biomarker binder 240C, wherein the disease specific biomarker binder 240C can chemically bind with a fluorophore 120B on an optional biomolecular interface layer 480, within the array of photonic crystal cavities (fabricated/constructed, utilizing both low index materials and high index materials) 500.

By way of an example and not by way of any limitation, a disease specific biomarker 460 can be a disease predicting biomarker (e.g., higher concentration of fetuin-A protein in a human body's blood can indicate an increased risk of Diabetes disease or higher level of C-reactive protein (CRP) protein or lactate dehydrogenase (LDH) protein in a human body's blood can indicate an increased risk of heart attack).

Incident light from a microelectro-mechanical-system enabled wavelength tunable surface emitting vertical cavity laser 580 can be split through an optical beam splitter 560, collimated by a lens 540, absorbed by the fluorophore 120B.

Reference incident emission from the microelectro-mechanical-system enabled wavelength tunable surface emitting vertical cavity laser 580 and the fluorescence emission wavelength can be measured by a spectrophotometer 600.

By way of an example and not by way of any limitation, the spectrophotometer 600 can be a charged-coupled detector array/echelle gratings based demultiplexer/microspectrophotometer-on-a-chip/photonic crystal/planar lightwave circuit based demultiplexer/silicon nanowire waveguide based demultiplexer spectrophotometer.

700A can be scaled to an array of disease specific biomarkers 460, an array of disease specific biomarker binders 240C and an array of fluorophores 120B with distinct fluorescence emission wavelengths. A direct correlation exists between the fluorescence emission wavelength and the diameter of a quantum dot fluorophore.

Microspectrophotometer-on-A-Chip

The penetration depth of photons in silicon depends upon the wavelength of the photons. The shorter wavelength photons can be absorbed in top thin-films, while the longer wavelength photons travel some distance, before they can be absorbed in bottom thin-films.

A pixel of a microspectrophotometer-on-a-chip has vertically stacked detection material thin-film (e.g., silicon) and wavelength tunable optical filters (utilizing a combination of non-absorbing dielectric thin-films and resistor thin-films configured with thermo-optic semiconductor thin-films).

A two-dimensional array of the pixels can constitute a microspectrophotometer-on-a-chip.

Alternatively, a spectrophotometer can be based on a cascaded configuration of a coarse arrayed waveguide gratings coupler (AWG), fine arrayed waveguide gratings coupler and an array of photodetectors. However, an ultra-compact spectrophotometer can be realized by utilizing a configuration of a coarse arrayed waveguide gratings coupler/photonic crystal (PC) based coarse arrayed waveguide gratings coupler and fine arrayed waveguide gratings coupler/photonic crystal based fine arrayed waveguide gratings coupler.

Alternatively, a spectrophotometer can be based on a cascaded configuration of a coarse arrayed waveguide gratings coupler, fine arrayed waveguide gratings coupler, an array of ring-resonators and an array of photodetectors.

Microelectro-Mechanical-System Biomodule to Draw/Propagate Blood

Figure 9B:
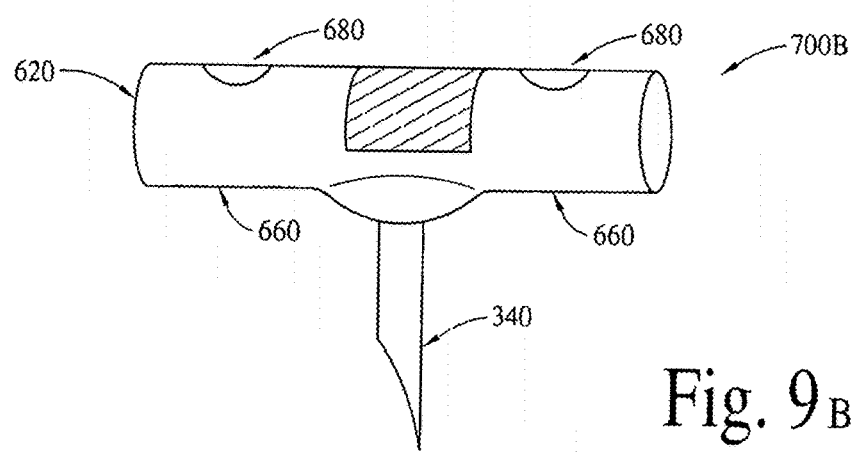

FIG. 9B illustrates a microelectro-mechanical-system biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the microelectro-mechanical-system biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in FIG. 9B).

The precisely machined connector can be attached precisely/detached from the microelectro-mechanical-system biomodule for drawing/propagating the patient's blood.

Figure 9C:
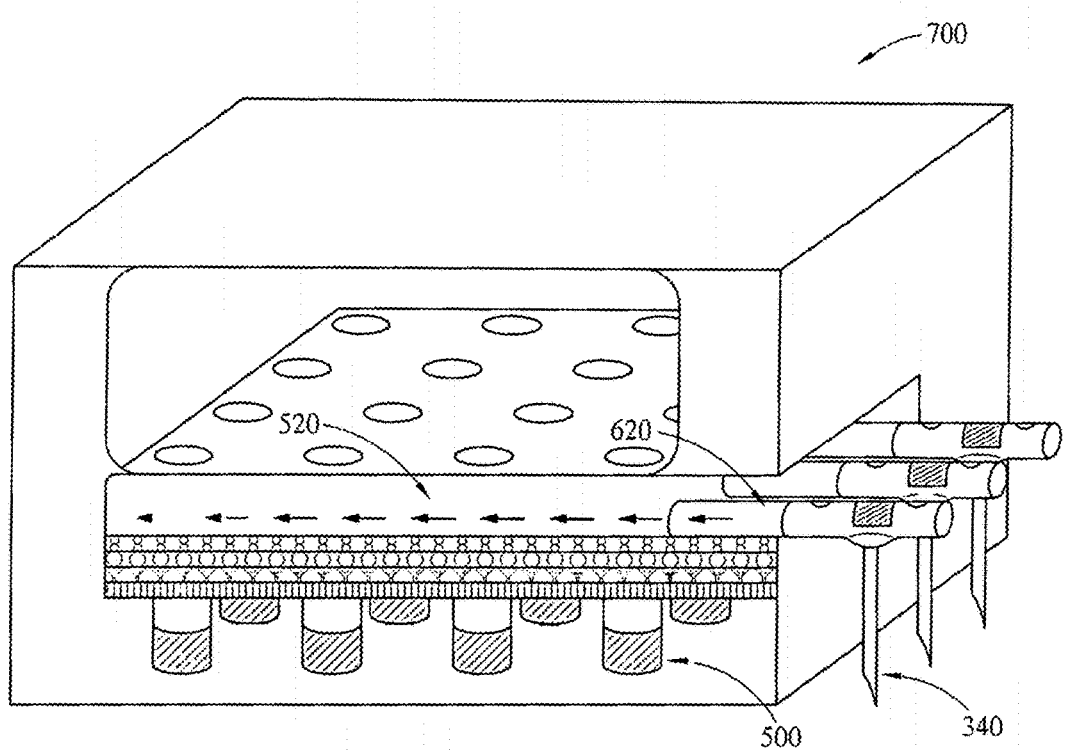

Array of Photonic Crystal Cavities Based Integrated Optical Diagnostics Biomodule for Detection of a Disease Specific Biomarker/an Array of Disease Specific Biomarkers FIG. 9C illustrates an array of photonic crystal cavities based integrated optical diagnostics biomodule 700.

Stokes Shift to Detect a Disease Specific Biomarker/an Array of Disease Specific Biomarkers The Stokes Shift is the difference between the absorption wavelength and fluorescence emission wavelength.

Figure 9D:
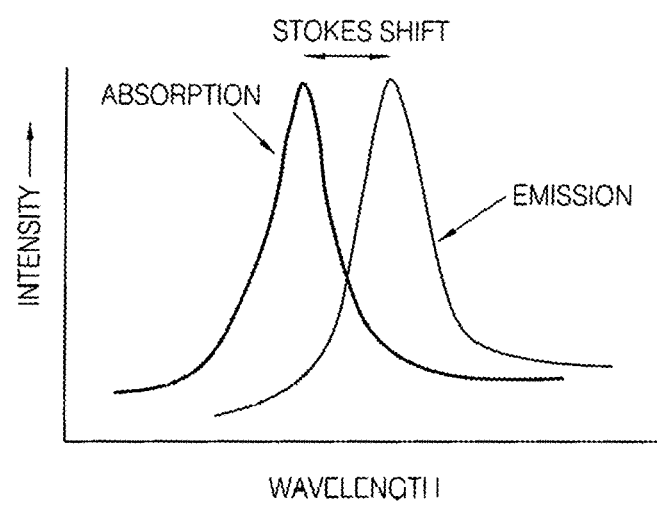

FIG. 9D illustrates the Stokes Shift due to binding of a disease specific biomarker 460 with a disease specific biomarker binder 240C.

The Stokes Shift can be utilized to detect the presence of a disease specific biomarker/an array of disease specific biomarkers.

Figure 10A:
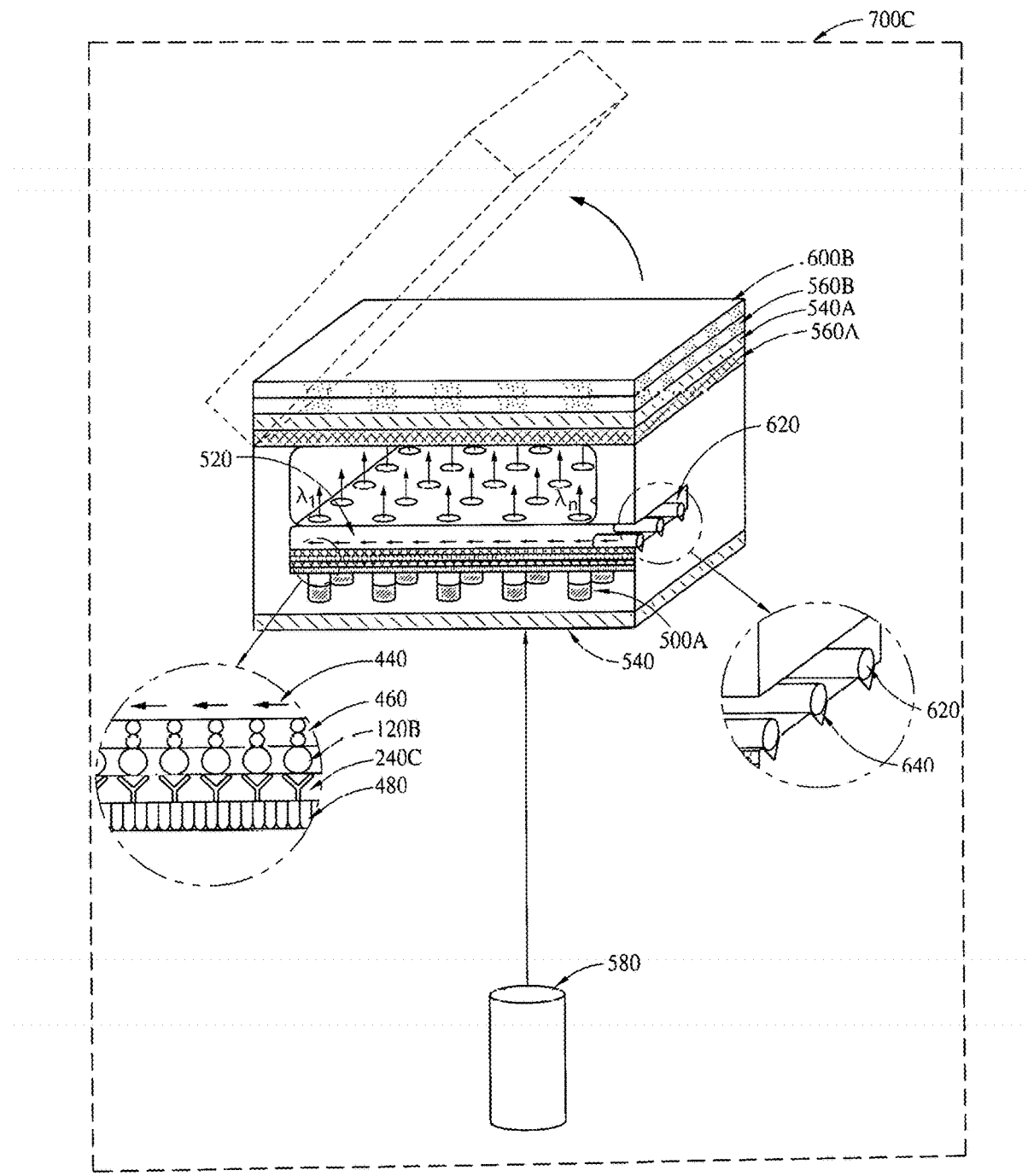
FIGS. 10A, 10B, 10C and 10D illustrate (an array of microcapillaries based) integrated optical diagnostics biomodules (various embodiments) to detect a disease specific biomarker/an array of disease specific biomarkers.

Array of Microcapillaries Based Optical Diagnostics Biomodule for Detection of a Disease Specific Biomarker/an Array of Disease Specific Biomarkers FIG. 10A illustrates an array of microcapillaries 500A based optical diagnostics biomodule 700C for detection of a disease specific biomarker 460 (in a patient's blood 440, which can be propagated through a microfluidic channel 620 to a microfluidic cavity 520). Furthermore, the array of microcapillaries 500A can be an array of fluidic containers, micro sized fluidic containers/micro sized test tubes/nano sized test tubes.

The disease specific biomarker 460 can chemically bind with a disease specific biomarker binder 240C, wherein the disease specific biomarker binder 240C can chemically bind with a fluorophore 120B, on an optional biomolecular interface layer 480, within the array of microcapillaries 500A.

The array of microcapillaries 500A can be fabricated/constructed, utilizing fused silica/glass/paper/plastic/quartz/other suitable material.

Furthermore, the top optical assembly can be removed to allow a direct access to fill the array of microcapillaries 500A with a human body's blood/biological fluid.

Furthermore, a particular biological fluid can be considered as gold nanoparticles chemically bonded with DNAzyme (DNAzyme, a synthetic DNA enzyme that can cleave a nucleic acid molecule) in liquid form. When a disease gene is introduced, the DNA can be cleaved from the gold nanoparticles, turning the liquid red in color The array of microcapillaries 500A is optically transparent to the incident light. Incident light from a microelectro-mechanical-system enabled wavelength tunable surface emitting vertical cavity laser 580 can be collimated by a lens 540, absorbed by the fluorophore 120B.

A fluorophore 120B can exist within one well of the array of microcapillaries 500A.

700C can be scaled to an array of disease specific biomarkers 460, an array of disease specific biomarker binders 240C and an array of fluorophores 120B with distinct fluorescence emission wavelengths.

Fluorescence emission can propagate through a first optical filter (not to transmit the incident wavelength from the microelectro-mechanical-system enabled wavelength tunable surface emitting vertical cavity laser 580) 560A, an array of lenses 540A and an array of second optical filters 560B, then finally be detected by an array of light detectors 600B.

By way of an example and not by way of any limitation, the light detector 600B can be a charge-coupled detector/intensified charge-coupled detector (ICCD)/color-complementary metal-oxide-semiconductor (CMOS) detector, wherein a complementary metal-oxide-semiconductor pixel can be integrated with a transparent polyimide light collecting lens and a color (blue, green and red) selective optical filter.

A color selective optical filter can be a wavelength tunable optical filter (utilizing a combination of non-absorbing dielectric thin-films and resistor thin-films configured with thermo-optic semiconductor thin-films).

Microelectro-Mechanical-System Biomodule to Draw/Propagate Blood

Figure 10B:
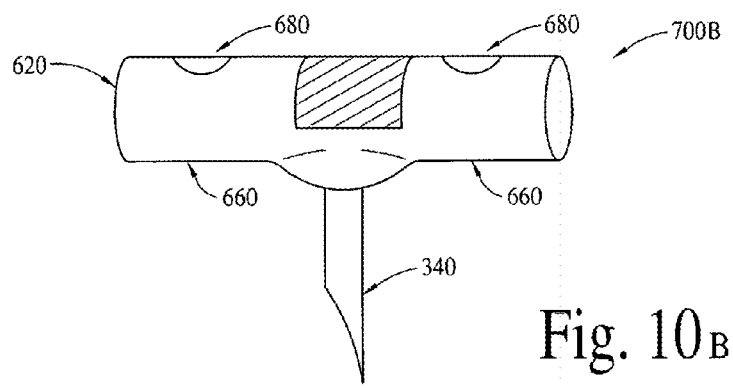

FIG. 10B illustrates a microelectro-mechanical-system biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the microelectro-mechanical-system biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in FIG. 10B).

The precisely machined connector can be attached precisely/detached from the MEMS biomodule for drawing/propagating the patient's blood.

Figure 10C:
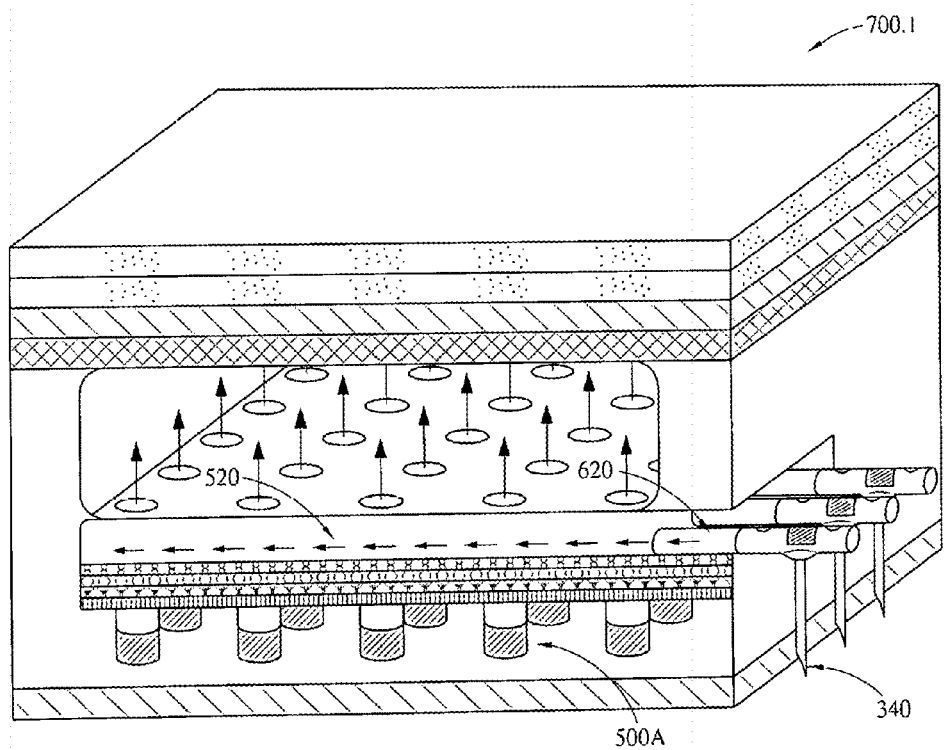

Array of Microcapillaries Based Optical Integrated Diagnostics Biomodule for Detection of a Disease Specific Biomarker/an Array of Disease Specific Biomarkers FIG. 10C illustrates an array of microcapillaries based integrated optical diagnostics biomodule 700.1.

Stokes Shift to Detect a Disease Specific Biomarker/an Array of Disease Specific Biomarkers The Stokes Shift is the difference between the absorption wavelength and fluorescence emission wavelength.

Figure 10D:
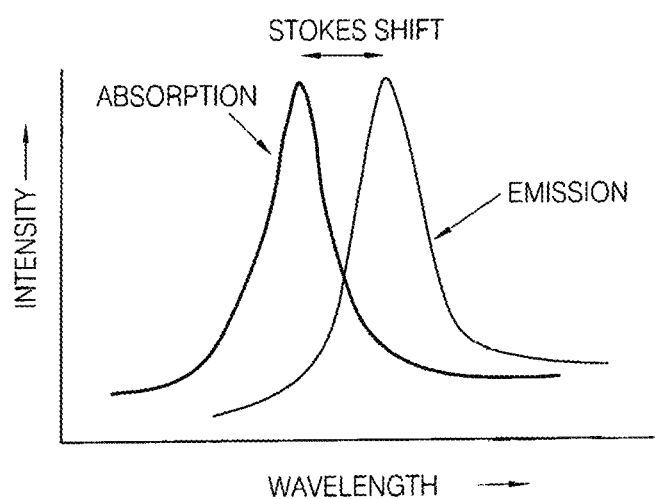

FIG. 10D illustrates the Stokes Shift due to binding of a disease specific biomarker 460 with a disease specific biomarker binder 240C.

The Stokes Shift can be utilized to detect the presence of a disease specific biomarker/an array of disease specific biomarkers.

Figure 11A:
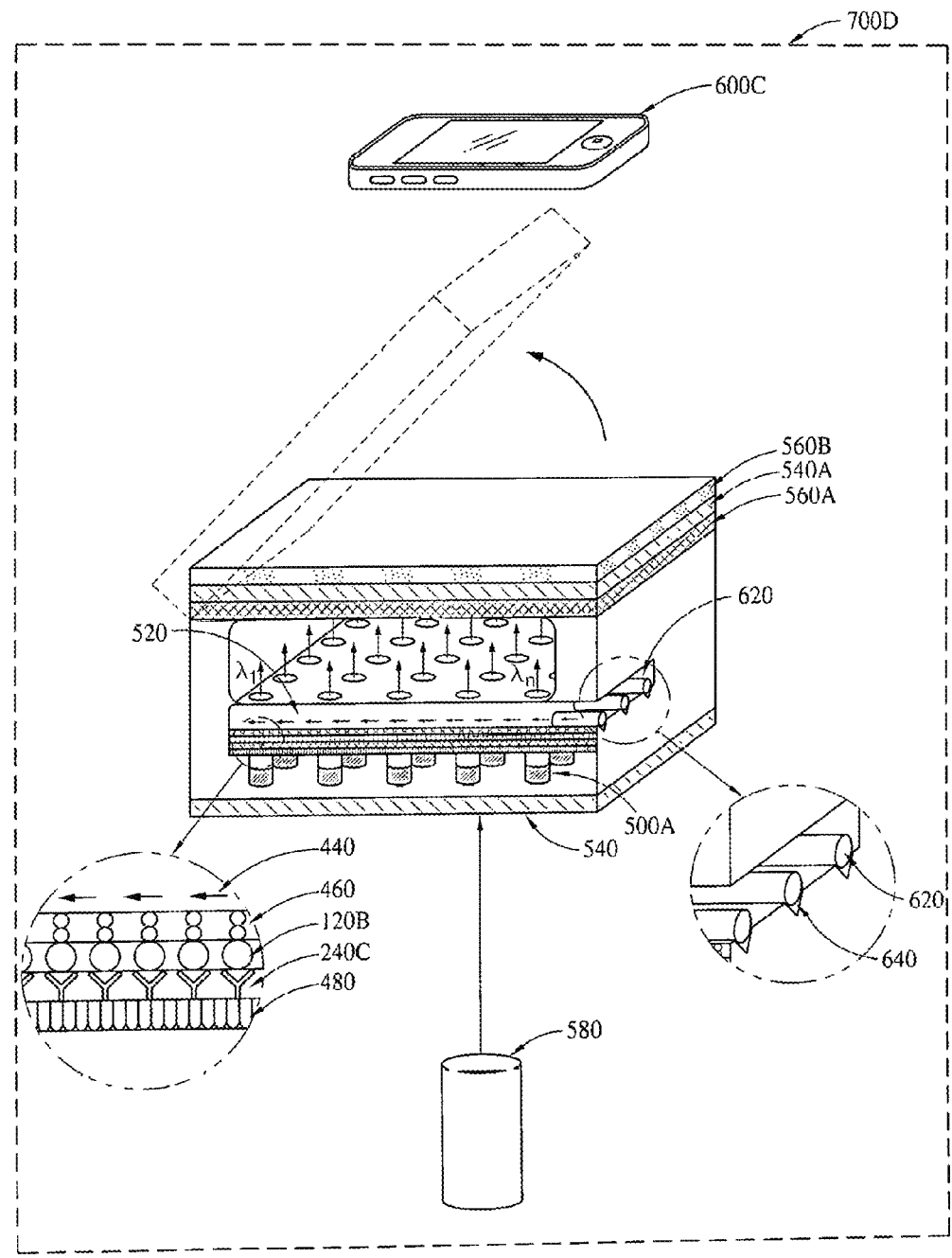
FIGS. 11A, 11B, 11C and 11D (an array of microcapillaries based) illustrate integrated optical diagnostics biomodules (various other embodiments) to detect a disease specific biomarker/an array of disease specific biomarkers.

Array of Microcapillaries Based Optical Diagnostics Biomodule (Configured by a Camera of a Portable Internet Appliance) for Detection of a Disease Specific Biomarker/an Array of Disease Specific Biomarkers FIG. 11A illustrates an array of microcapillaries 500A based optical diagnostics biomodule 700D, configured by a camera (optionally integrated with a color image processing algorithm) 600C of the portable internet appliance. This configuration can replace an array of light detectors 600B. The camera (of the portable internet appliance) can enable quantitative fluorescence based measurement for a real-time application, utilizing the camera as a photodetector and the portable internet appliance's microprocessor.

Furthermore, the top optical assembly can be removed to allow direct access to fill the array of microcapillaries 500A with a human body's blood/biological fluid.

700D can be scaled to an array of disease specific biomarkers 460, an array of disease specific biomarker binders 240C and an array of fluorophores 120B with distinct fluorescence emission wavelengths.

Microelectro-Mechanical-System Biomodule to Draw/Propagate Blood

Figure 11B:
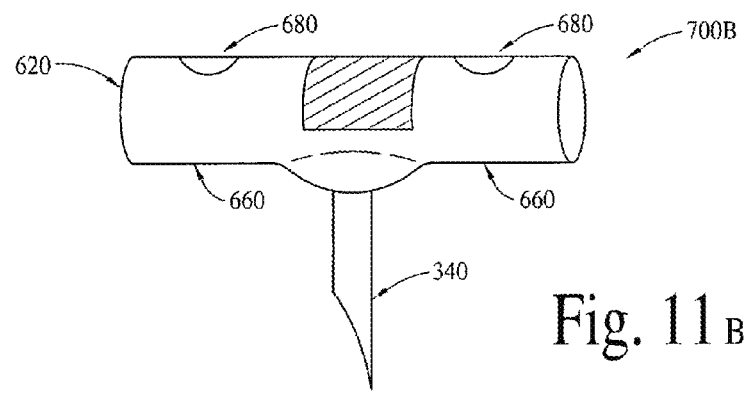

FIG. 11B illustrates a microelectro-mechanical-system biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the microelectro-mechanical-system biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in the FIG. 11B).

The precisely machined connector can be attached precisely/detached from the MEMS biomodule for drawing/propagating the patient's blood.

Figure 11C:
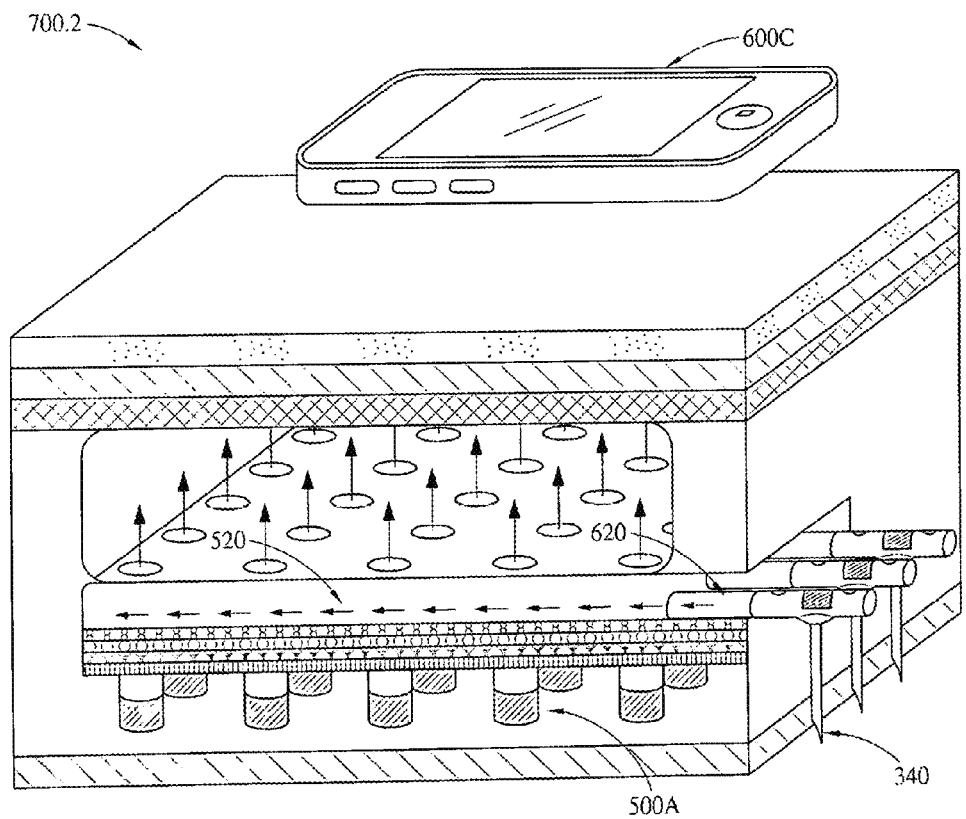

Array of Microcapillaries Based Optical Integrated Diagnostics Biomodule (Configured by a Camera of a Portable Internet Appliance) for Detection of a Disease Specific Biomarker/an Array of Disease Specific Biomarkers FIG. 11C illustrates an array of microcapillaries based integrated optical diagnostics biomodule (configured by a camera of the portable internet appliance) 700.2.

Stokes Shift to Detect a Disease Specific Biomarker/an Array of Disease Specific Biomarkers The Stokes Shift is the difference between the absorption wavelength and fluorescence emission wavelength.

Figure 11D:
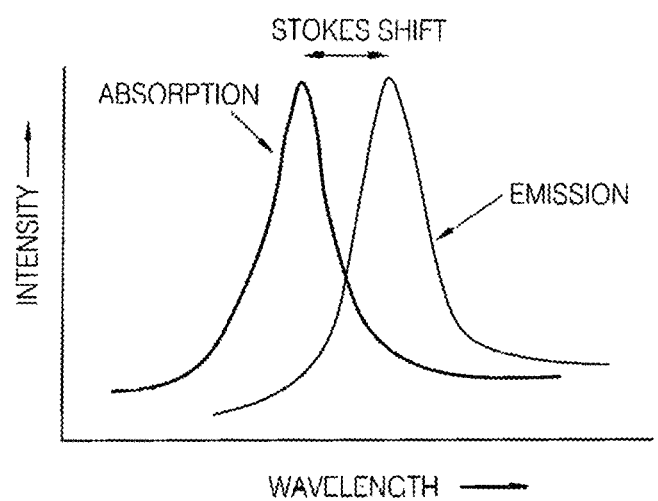

FIG. 11D illustrates the Stokes Shift due to binding of a disease specific biomarker 460 with a disease specific biomarker binder 240C.

The Stokes Shift can be utilized to detect the presence of a disease specific biomarker/an array of disease specific biomarkers.

Figure 12A:
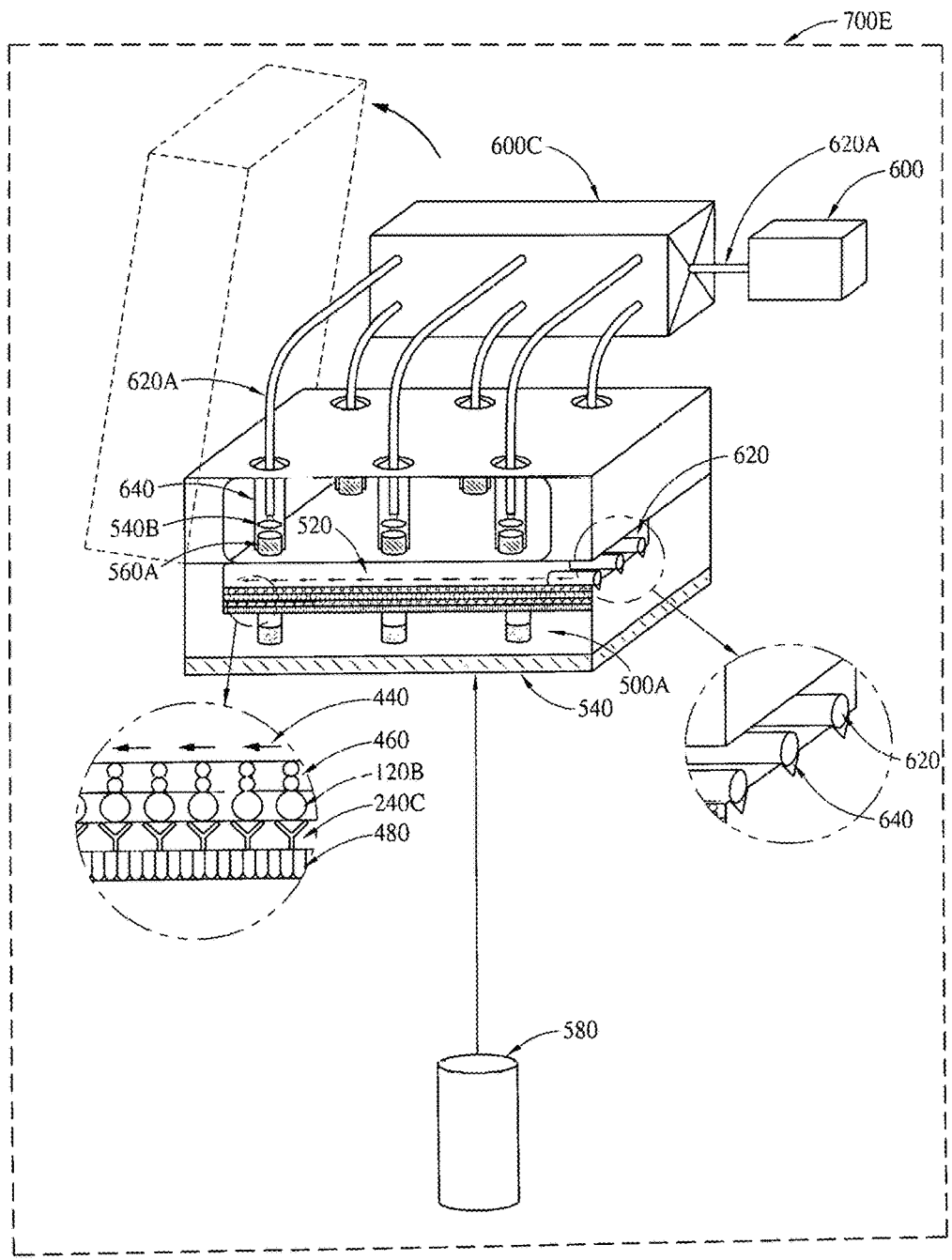
FIGS. 12A, 12B and 12C illustrate (an array of microcapillaries based) illustrate integrated optical diagnostics biomodules (various other embodiments) to detect a disease specific biomarker/an array of disease specific biomarkers.

Array of Microcapillaries Based Optical Diagnostics Biomodule (Configured by an Array of Optical Fibers & a N×1 Optical Switch) for Detection of a Disease Specific Biomarker/an Array of Disease Specific Biomarkers FIG. 12A illustrates an array of microcapillaries 500A based optical diagnostics biomodule 700E, configured by an array of optical fibers 620A and a N×1 optical switch 600C.

FIG. 12A illustrates a microcapillary optical diagnostics biomodule 700E for detection of a disease specific biomarker (in a patient's blood 440, which can be propagated through a microfluidic channel 620 to a microfluidic cavity 520).

The disease specific biomarker 460 can chemically bind with a disease specific biomarker binder 240C, wherein the disease specific biomarker binder 240C can chemically bind with a fluorophore 120B, on an optional biomolecular interface layer 480 within the array of microcapillaries 500A.

Furthermore, the top optical assembly can be removed to allow direct access to fill the array of microcapillaries 500A with a human body's blood/biological fluid.

Incident light from a microelectro-mechanical-system enabled wavelength tunable surface emitting vertical cavity laser 580 can be collimated by a lens 540, absorbed by the fluorophore 120B.

Fluorescence emission can propagate through an array of optical filters (not to transmit the incident wavelength from the laser 580) 560A, an array of focusing lenses 540B and an array of multi-mode/single-mode optical fibers 620A to the N×1 multi-mode/single-mode optical switch 600C and a spectrophotometer 600.

Furthermore, the array of optical fibers 620A can be attached onto an array of precise silicon/ceramic v-grooves 640.

The array of optical fibers 620A can be replaced by an array of optical waveguides (not shown in FIG. 12A).

N×1 multi-mode/single-mode optical switch 600C can be replaced by an ultra-fast N×1 optical switch based on metamaterial (not shown in FIG. 12A) to detect a presence of a disease specific biomarker/an array of disease specific biomarkers rapidly.

N×1 multi-mode/single-mode optical switch 600C can be replaced by an ultra-fast N×1 optical switch based on (Pb,La)(Zr,Ti)O$_3$ or LiNbO$_3$ waveguide, when the ultra-fast optical switch is composed of an (a) input-output 3-dB coupler and (b) a Mach-Zehnder (MZ) modulator.

Alternatively, N×1 multi-mode/single-mode optical switch 600C can be replaced by an ultra-fast N×1 optical switch based on vanadium dioxide (VO$_2$). A directional coupler (e.g., silicon-on-insulator (SOI) waveguide directional coupler) with vanadium dioxide thin-film can be utilized as a fast optical switch, when the vanadium dioxide thin-film is excited by a mode locked laser (e.g., a mode locked microelectro-mechanical-system tunable vertical cavity surface emitting semiconductor laser at 1550 nanometers excitation wavelength) with a light intensity of about 2 mJ/cm$^2$ to 4 mJ/cm$^2$ and a light pulse width of about 2 picoseconds to 4 picoseconds) with an integrated focusing lens to focus the excitation light beam to a spot size of 4.5 microns by 4.5 microns. Instead of a focusing lens, curved second order gratings can be utilized for vertically coupling/focusing onto the vanadium dioxide thin-film. Furthermore, instead of a classical focusing lens, surface plasmon polariton based nanofocussing waveguide (as illustrated in FIG. 19O) can be utilized for vertically coupling/focusing onto the vanadium dioxide thin-film. Upon excitation by the mode locked laser onto the vanadium dioxide thin-film, the vanadium dioxide thin-film undergoes a semiconductor to metal phase transition/switching and the optical properties of the directional coupler can be rapidly changed, such that the optical signal (as the input) at the upper branch of the directional coupler is shifted (as the output) to the lower branch of the directional coupler. The vanadium dioxide thin-film is about 4 microns to 10 microns on one side by 4 microns to 10 microns on the other side-or an area of about 16 microns$^2$ to 100 microns$^2$ with thickness in the range of 25 nanometers to 50 nanometers. The vanadium dioxide thin-film is formed about 25 nanometers to 100 nanometers away from the straight middle section of the directional coupler. The vanadium dioxide thin-film can be fabricated by electron beam evaporation or laser assisted electron beam evaporation or RF magnetron sputtering or molecular beam epitaxy or atomic layer deposition. Alternatively, a metamaterial of vanadium dioxide-nanoparticles (with diameter in the range of 25 nanometers to 50 nanometers) can be utilized, instead of the vanadium dioxide thin-film. Furthermore, vanadium(III) oxide (V$_2$O$_3$) thin-film/nanoparticles can also be utilized, instead of the vanadium dioxide thin-film/nanoparticles respectively.

In another embodiment, a fast optical switch-fabricated/constructed as: integrated (a) 3-dB input-output coupler and (b) a Mach-Zehnder type device (with electrodes on vanadium dioxide/vanadium(III) oxide thin-film, in intimate proximity to two arms of Mach-Zehnder type device) can be activated electrically for a semiconductor to metal phase transition/switching, without any optical excitation.

The semiconductor to metal phase transition/switching in the vanadium dioxide/vanadium(III) oxide can be realized below 0.2 picosecond time, under optical excitation or electrical activation. Thus, the silicon-on-insulator-vanadium dioxide/vanadium(III) oxide silicon photonics platform can enable a new class of ultrafast silicon photonic devices (e.g., optical limiters, optical logic gates and optical memories).

With the combination of an electrical activation (preferably voltage) and an optical excitation to the vanadium dioxide/vanadium(III) oxide thin-film, a high density optical memory can be realized, wherein optical excitation is based on an array of vertically aligned nanolasers (as described in the later paragraphs) and surface plasmon polaritons nanofocusing lens. Alternatively, vanadium dioxide/vanadium (III) oxide nanoparticles (50 nanometers in diameter) deposited on an array of nanowires lasers/light emitting diodes can be utilized. For example, vanadium dioxide/vanadium(III) oxide nanoparticles deposited on an array of gallium nitride nanowires light emitting diodes can be utilized. Furthermore, gallium nitride nanowires light emitting diodes can be electrically powered by zinc oxide nanowires. Complementary metal-oxide semiconductor processing element can be integrated with zinc oxide nanowires nanogenerator/nanobattery. However, any material with both semiconducting and piezoelectric properties can replace gallium nitride-zinc oxide combination.

A nano-scaled waveguide (rectangular tapered to a point) of an insulating material, wherein the nano-scaled waveguide is coated/deposited with ultra thin-film of gold can focus a light beam onto an approximate size of 25 nanometers by 100 nanometers, due to the surface plasmon polaritons (SPPs) effect.

Flip-chip bonding packaging was developed as an alternative to wire-bonding. In flip-chip bonding, components are flipped upside-down and placed on an array of solder bumps that form the connection between circuitry and package. The optical switch can be packaged, utilizing flip-chip bonding on a precise silicon optical bench substrate.

Fiber can be aligned passively with precise metal alignment pins seated into v-grooves on the precise silicon optical bench substrate. The precise metal alignment pins are mated with a pluggable optical fiber connector integrated with a molded plastic lens.

In another embodiment, an ultra-fast N×1 optical switch based on metamaterial can be fabricated/constructed, utilizing an array of nanostructured elements, wherein each nanostructured element can be actuated by electrostatic forces on pairs of parallel flexible strings of nanoscale membrane. Electrically reconfigurable metamaterial element changes the transmission and reflection spectra of the metamaterial.

In another embodiment, an ultra-fast N×1 Bose-Einstein condensate based optical switch can be realized utilizing an array of single-mode/multi-mode waveguides on the left-hand side and a single-mode/multi-mode waveguide on the right hand side, wherein both the array of single-mode/multi-mode waveguides on the left hand side and the single-mode/multi-mode waveguide on the right-hand side are optically coupled with polariton Bose-Einstein condensate.

Short-lived room temperature polariton Bose-Einstein condensate can be created through the interaction of a laser light (bouncing back and forth within multiple dielectric thin-films) and a luminescent polymeric thin-film of about 30 nanometers in thickness. The luminescent polymeric thin-film is embedded within multiple dielectric thin-films, wherein the multiple dielectric thin-films is then illuminated from the bottom (of the multiple dielectric thin-films, each dielectric thin-film is about 40 nanometers in thickness) by a vertical surface emitting laser or an in-plane laser integrated with a suitable mirror and a focusing lens.

Furthermore, an ultra-fast N×N Bose-Einstein condensate based optical switch can be realized by utilizing an array of single-mode/multi-mode waveguides on the right-hand side instead of just one single-mode/multi-mode waveguide on the right-hand side.

700E can be scaled to an array of disease specific biomarkers 460, an array of disease specific biomarker binders 240C and an array of fluorophores 120B with distinct fluorescence emission wavelengths.

Microelectro-Mechanical-System Biomodule to Draw/Propagate Blood

Figure 12B:
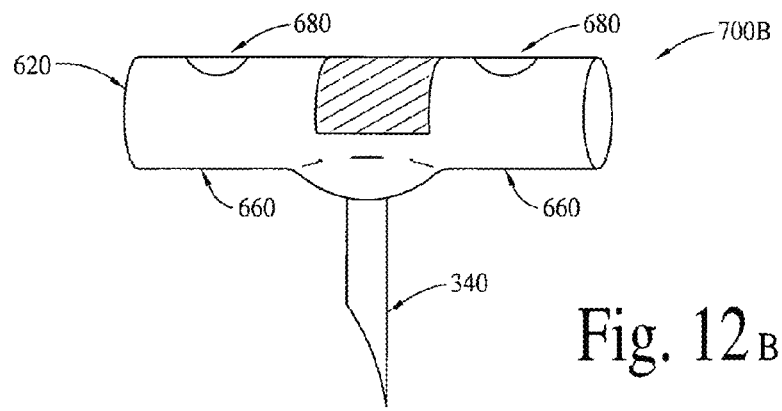

FIG. 12B illustrates a microelectro-mechanical-system biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the microelectronic-mechanical-system biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in the FIG. 12B).

The precisely machined connector can be attached precisely/detached from the microelectro-mechanical-system biomodule for drawing/propagating the patient's blood.

Light Incident at Side of an Array of Microcapillaries

In FIGS. 10A, 11A and 12A light from the microelectro-mechanical-system enabled wavelength tunable surface emitting vertical cavity laser 580 can be incident at the side of the array of microcapillaries 500A.

Light Source Integrated with a Plasmonic Optical Nanoantenna

A plasmonic optical nanoantenna consists of two triangular shaped gold configurations, wherein each triangular shaped gold configuration is about 75 nanometers long and facing directly across from each other in the shape of a miniature bowtie.

The plasmonic optical nanoantenna can squeeze an incident light from the microelectro-mechanical-system enabled wavelength tunable surface emitting vertical cavity laser 580 into a 20 nanometers gap, separating the two gold triangular configurations-thus resulting in an intense (about thousand times more intense than the light from the microelectro-mechanical-system enabled wavelength tunable surface emitting vertical cavity laser 580) speck of light.

Nanolaser, as a Light Source

For miniaturization, in conjunction with a nanocapillary/an array of nanocapillaries, a nanolaser/an array of nanolasers can be utilized, instead of a microelectro-mechanical-system enabled wavelength tunable surface emitting vertical cavity laser/an array of microelectro-mechanical-system enabled wavelength tunable surface emitting vertical cavity lasers 580.

By way of an example and not by way of any limitation, a structure of a metal-insulator-semiconductor-insulator-metal (MISIM) semiconductor nanolaser (operating at a room temperature) with a rectangular cross-section cavity can consist of a metal organic chemical vapor deposited (MOCVD) rectangular pillar of InP/InGaAs/InP protected on all four sides of the rectangular pillar with a thin silicon nitride insulating layer.

The InP/InGaAs/InP layer stack can form a waveguide, largely confining the optical field in a vertical direction. The above rectangular pillar is then encapsulated in silver metal from all four sides as well as from the top forming a rectangular cavity in horizontal directions.

The n-contact is silver metal and the p-side contact is connected to an external electric source via p-type InGaAsP contact layer underneath the rectangular pillar.

Focusing Light onto a Nanosized Spot

A nano-scaled waveguide (rectangular tapered to a point) of an insulating material, wherein the nano-scaled waveguide is coated/deposited with an ultra thin-film of gold can focus a light beam onto an approximate size of 25 nanometers by 100 nanometers, due to the surface plasmon polaritons effect.

Fluorescent or Raman signal light can also propagate in a reverse direction from the point of the nano-scaled tapered device for further analysis.

Light Source Coupled with an Array of Micromirrors

A programmable microelectro-mechanical-system mirror chip can be utilized to divert light of varying wavelengths of the incident light from a microelectro-mechanical-system enabled wavelength tunable surface emitting vertical cavity laser 580 at ultra-high speed and with micrometer-accuracy to the bottom of each microcapillary (for example in FIG. 12A) from a single light source-thus it will eliminate the need for an array of microelectro-mechanical-system enabled wavelength tunable surface emitting vertical cavity lasers 580.

A programmable microelectro-mechanical-system mirror chip can consist of a large array of individual miniature micromirrors which can each be tilted separately and virtually in a continuous way. By controlling the deflection of all mirrors to distribute the angle of incidence and the intensity of the light with up to 1,000 changes per second over the entire area can be realized.

This particular configuration can enable one to analyze one microcapillary at a time-thus reducing any optical cross-talk.

Figure 12C:
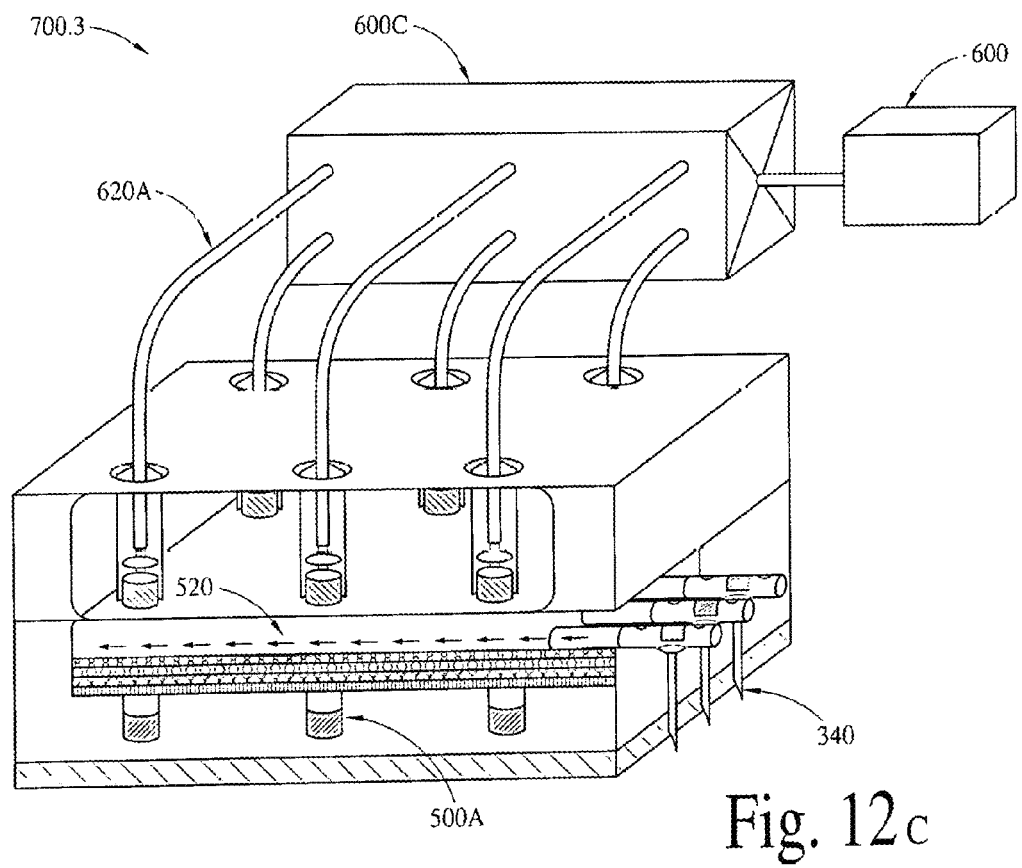

Array of Microcapillaries Based Optical Integrated Diagnostics Biomodule (Configured by an Array of Optical Fibers & a N×1 Optical Switch) for Detection of a Disease Specific Biomarker/an Array of Disease Specific Biomarkers FIG. 12C illustrates an array of microcapillaries based integrated optical diagnostics biomodule 700.3 (configured by an array of optical fibers 620A and a N×1 optical switch 600C).

Figure 12D:
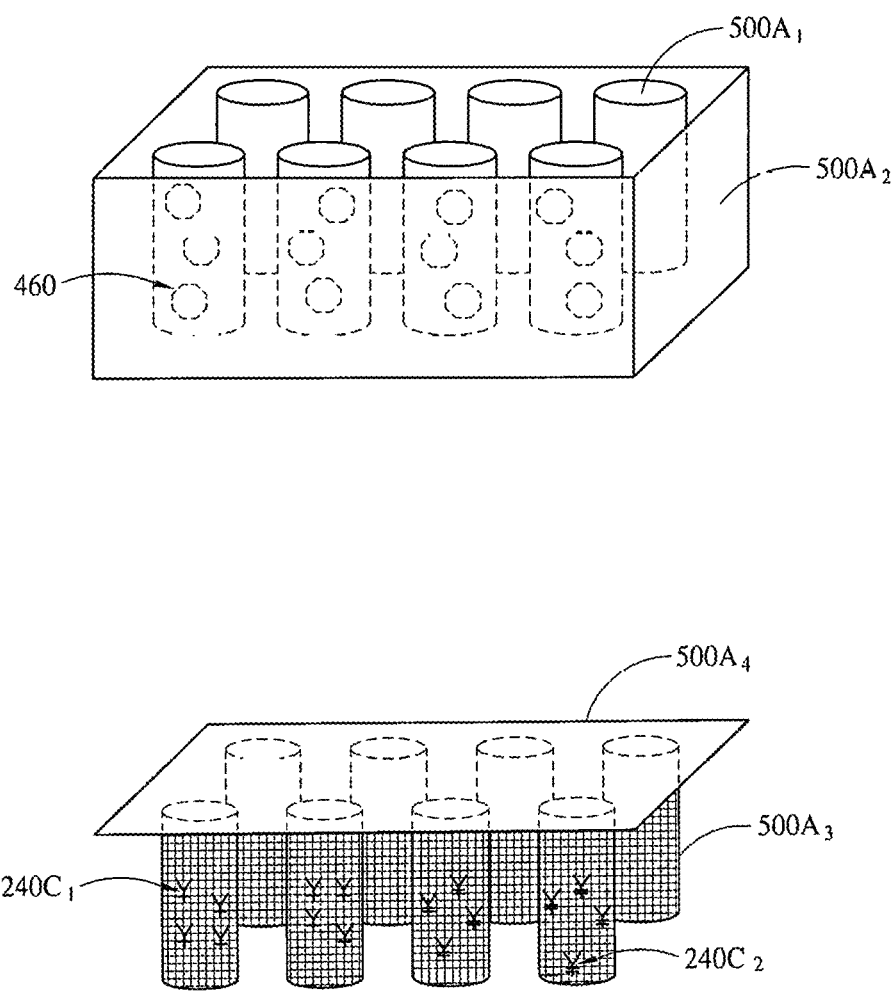

Array of Microcapillaries Based Optical Integrated Diagnostics Biomodule (Configured by an Array of Optical Fibers, a N×1 Optical Switch & Multiplexing of Biomarker Binders) for Detection of a Disease Specific Biomarker/an Array of Disease Specific Biomarkers FIG. 12D illustrates an array of microwells $500A_1$, containing a human body's blood/biological fluid with an array of disease specific biomarkers 460.

$500A_2$ is an enclosure for the array of microwells $500A_1$. $500A_3$ is an array of microsized/nanosized mesh tubes $500A_4$ is a removable holder.

The array of microsized/nanosized mesh tubes $500A_3$ can contain a biomarker binder assembly 240C, and biomarker binder assembly $240C_2$.

Figure 12E:
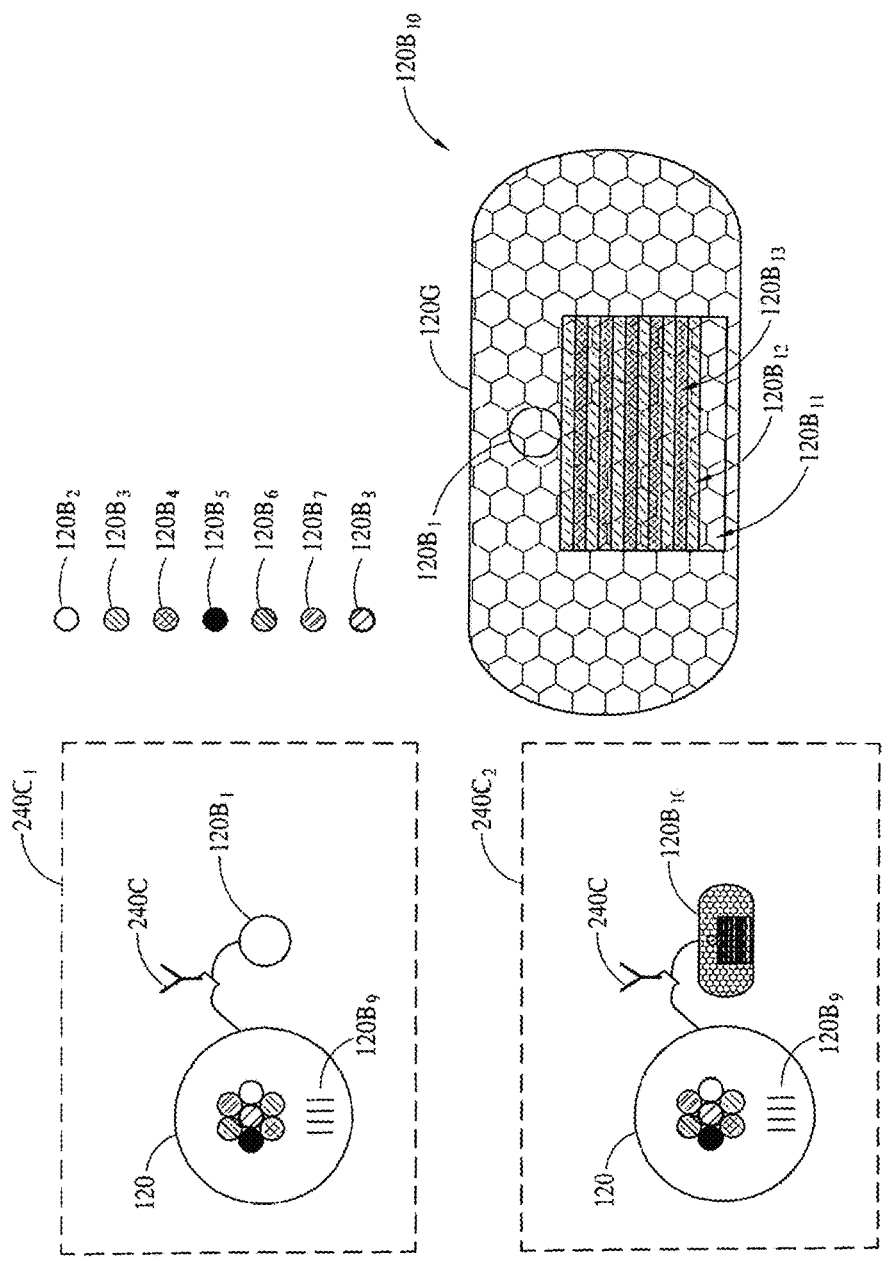

FIG. 12E illustrates the biomarker binder assembly $240C_1$. $240C_1$ can integrate a biomarker binder 240C, a nanoshell 120 and a fluorophore $120B_1$.

The nanoshell 120 can have a printed (by electroplating/laser induced direct printing/soft lithography) metal barcode patterns of alternating reflective gold/silver/nickel/platinum metal $120B_9$ on it.

The stripe width of the metal barcode patterns can be controlled by an amount of current passed during the electroplating process.

The nanoshell 120 can also encapsulate/cage six (6) quantum dot fluorophores $120B_2$, $120B_3$, $120B_4$, $120B_5$, $120B_6$ and $120B_7$, wherein each quantum dot fluorophore has a unique fluorescence color based on the diameter of the quantum dot fluorophore.

Furthermore, the intensity of each fluorophore's unique florescence emission colors can be varied.

The nanoshell 120 can encapsulate/cage a paramagnetic nanoparticle (e.g., an iron oxide nanoparticle) $120B_8$.

FIG. 12E also illustrates the biomarker binder assembly $240C_2$. $240C_2$ can integrate a biomarker binder 240C, a nanoshell 120 and a nanotube assembly $120B_{11}$.

The nanotube assembly $120B_{11}$ can consist of a nanotube (e.g., a boron nitride/carbon nanotube or a tubular structure fabricated/constructed, utilizing DNA/RNA origami process) 120G. The nanotube 120G can encapsulate/cage at least one quantum dot fluorophore 120B, on alternating thin-films of titanium dioxide dielectric (about 15-30 nanometers in thickness) $120B_2$ and metal silver $120B_{13}$ (about 5-10 nanometers in thickness) on a biochemically functional glass/plastic substrate $120B_{11}$.

Figure 12F:
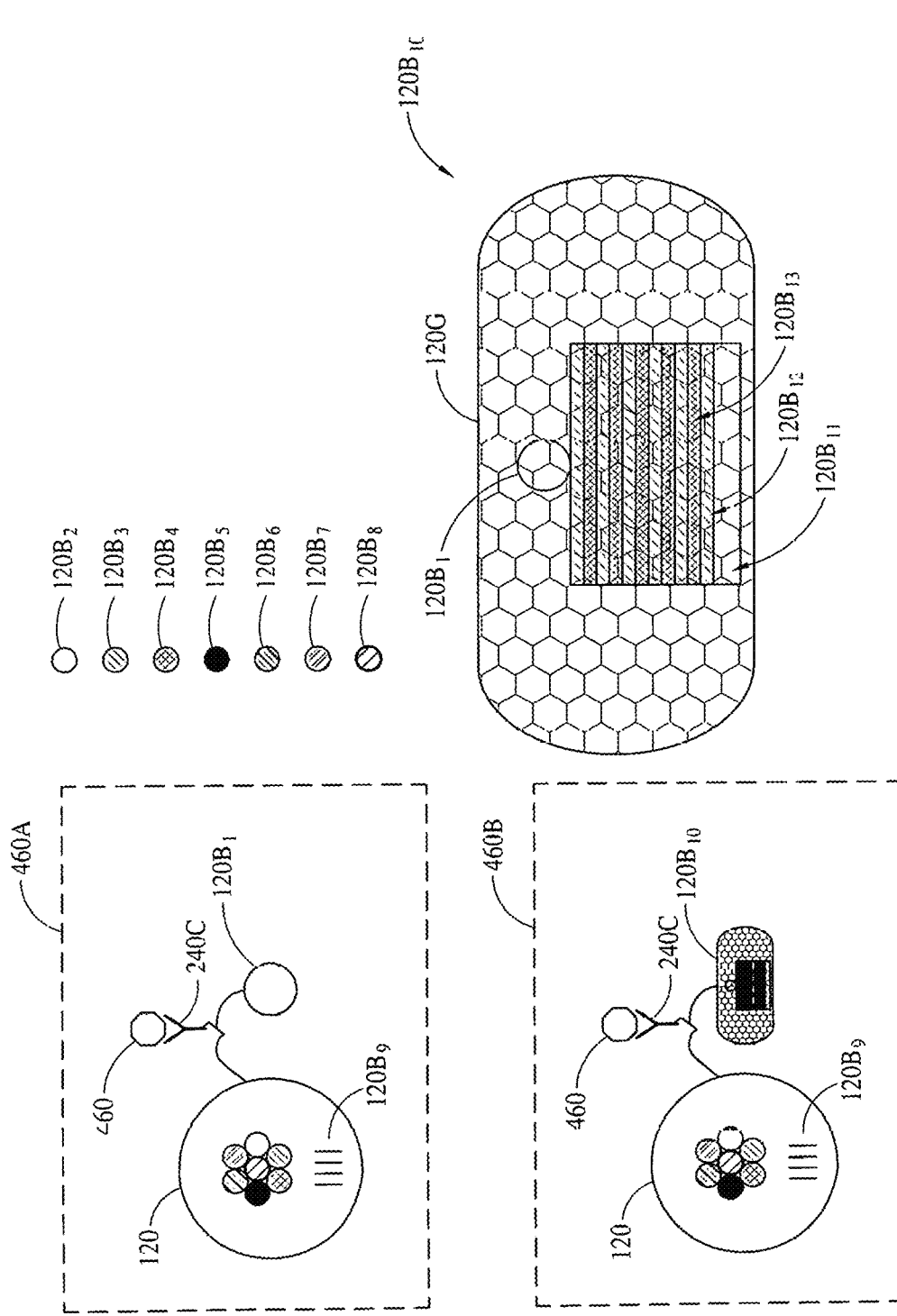

FIG. 12F illustrates the biomarker binder assembly $240C_1$, chemically bonded with the biomarker 460 and an entire biomarker binder assembly-biomarker combination is represented as 460A.

FIG. 12F illustrates the biomarker binder assembly $240C_2$, chemically bonded with the biomarker 460 and an entire biomarker binder assembly-biomarker combination is represented as 460B.

FIG. 12G illustrates an optical diagnostics biomodule 700.4 to determine fluorescence of 460A and 460B upon being magnetically pulled down by an optically transparent magnetic substrate $120B_{14}$ and then excited by an array of microelectro-mechanical-system enabled wavelength tunable surface emitting vertical cavity lasers 580 and collimated by an array of lenses 540.

An assembly 640A integrates suitable optical filters, suitable lenses and two (2) optical fibers 620A on precise silicon/ceramic v-grooves.

At one instance utilizing wavelength $\lambda=\lambda_1$ from the microelectro-mechanical-system enabled wavelength tunable surface emitting vertical cavity laser 580, transmission of wavelength $\lambda=\lambda_1$ through a metal barcode pattern, further propagated through a suitable optical filter, suitable lens and optical fiber 620A is then multiplexed by the N×1 multimode/single-mode optical switch 600C and analyzed by the spectrophotometer 600.

Any suitable image processing software can be utilized to resolve any misorientated metal barcode pattern.

At another instance, utilizing wavelength from the microelectro-mechanical-system enabled wavelength tunable surface emitting vertical cavity laser 580, a fluorescence spectrum of the entire biomarker binder assembly-biomarker combination 460A/460B, is propagated through a suitable optical filter, suitable lens and optical fiber 620A, then multiplexed by the N×1 multi-mode/single-mode optical switch 600C and analyzed by the spectrophotometer 600.

The array of optical fibers 620A can be replaced by an array of optical waveguides (not shown in FIG. 12G).

Furthermore, an array of optical waveguides and lenses can be integrated (by a monolithic and/or a hybrid process) on silica on silicon substrate.

One million optical barcodes can be realized utilizing six (6) unique fluorescent emission colors and ten (10) intensity levels for each unique fluorescent emission color.

Furthermore, one million optical barcodes can be further enhanced in conjunction with reflective metal barcode patterns.

Up to 2 million or more disease specific biomarkers 460 per microwells $500A_1$ can be identified utilizing a combination of optical barcode multiplexing and metal barcode multiplexing. Data from 2 million or more disease specific biomarkers 460 can be a Big Data.

For example, consider 19,599 genes in a human body can, in turn produce about 200,000 types of RNA. Each RNA strand can encode up to 200,000 proteins-resulting in 40 billion proteins in a human body. Furthermore, there are millions of patients worldwide-thus mathematical/statistical analysis tools of a Big Data are needed.

Analysis of a Big Data Related to Biology

Big Data can be converted into a smaller data set utilizing linear simplification and/or signal clustering, as the underlying data has geometrical structures and patterns (repeated over time). Furthermore, signal clustering can be categorized and weighted for importance.

Alternatively, topological data analysis or Bayesian analysis coupled with Markov chain Monte Carlo methods can be utilized for analysis of Big Data.

Analysis of Big Data can be coupled with an augmented intelligence modeling algorithm and/or predictive modeling for a disease/an array of diseases.

Furthermore, analysis of Big Data in an unstructured format can also be realized by a cloud based machine learning/relearning interactive expert cognitive computer (e.g., IBM Watson) utilizing natural language.

Furthermore, analysis of Big Data can be coupled with an intelligent learning set of instructions. An intelligent learning set of instructions can include: artificial intelligence, data mining, fuzzy/neuro-fuzzy logic, machine vision, natural language processing, neural networks, pattern recognition, reasoning modeling and self-learning.

Enhancement of Fluorescent Signal

Light is a wave. Thus, an optical antenna can amplify light waves in the same way as a television and/or a mobile phone captures radio waves.

Two gold particles (about 40 nanometers in diameter) and a fluorophore (e.g., a quantum dot fluorophore) bonded to a synthetic DNA strand (about 15 nanometers in length) can act as an optical nanoantenna.

The fluorophore can act as a quantum source, supplying the optical nanoantenna with photons.

Generation of Raman Signal

In FIGS. 12A and 12G, the function of the disease specific biomarker binder 240C can be enhanced by a dielectric (e.g., silica) sphere (about 50 nanometers in diameter).

The dielectric sphere can be encapsulated/caged in a thin metal (e.g., gold), wherein the thin metal is coupled with the biomarker binder (e.g., a specific antibody/aptamer) 240C to bind with the disease specific biomarker 460.

When light from the microelectro-mechanical-system enabled wavelength tunable surface emitting vertical cavity laser 580 is incident on the above silica sphere, it can shift a characteristic Raman signal (Raman Shift) upon chemically binding with the disease specific biomarker 460.

Measurement of Raman Shift

Measurements of Raman Shift can require a high-performance laser module. But a Raman sensor can utilize the microelectro-mechanical-system enabled wavelength tunable surface emitting vertical cavity laser 580 to scan over a narrow band of Raman Shift via a suitable wavelength tunable optical filter.

Surface-Enhanced Raman Scattering/Spectroscopy (SERS) Surface-Enhanced Resonance Raman Scattering/Spectroscopy (SERRS)

If the bottom of the microsized/nanosized mesh tubes $500A_3$ (FIG. 12D) is atomically rough, then the disease specific biomarker 240C can be identified by surface-enhanced Raman scattering/spectroscopy or alternatively by surface-enhanced Resonance Raman scattering/spectroscopy.

Electron-beam lithographically patterned and ion beam etched (about) 25 nanometers pitch surface gratings of metal thin-film (about 2 to 5 nanometers in thickness deposited by a low-temperature atomic layer deposition process on porous silicon substrate can be utilized as a reproducible atomically rough surface.

Surface-enhanced Raman scattering/spectroscopy is a surface-sensitive analytical technique that can enhance Raman scattering by a factor of $10^{10}$.

One disadvantage of surface-enhanced Raman scattering/spectroscopy is spectral interpretation. The signal enhancement is so dramatic that even weak Raman bands (unnoticeable in conventional Raman scattering/spectroscopy) can appear in surface-enhanced Raman scattering/spectroscopy.

Some trace contaminants can contribute unwanted peaks in surface-enhanced Raman scattering/spectroscopy. Furthermore, chemical interactions with metal surfaces, certain strong peaks (noticeable in conventional Raman scattering/spectroscopy) might not appear in surface-enhanced Raman scattering/spectroscopy.

Because of above complications in surface-enhanced Raman scattering/spectroscopy, surface-enhanced resonance Raman scattering/spectroscopy can integrate both the surface-enhancement and the Raman resonance-thus the Raman signal intensity can be as high as $10^{14}$ and the Raman spectra can be easier to interpret.

Enhancement of Fluorescent or Raman Signal by a Plasmonic Optical Nanoantenna

A nano-scaled metamaterial (whose properties owe more to its micro-structure than to the constituent materials) based optical receiver/optical plasmonic optical nanoantenna attached to a fluorophore 120B can be utilized to enhance the fluorescence or Raman signal from the array of microcapillaries 500A.

Alternatively, a nano-scaled metamaterial (whose properties owe more to its micro-structure than to the constituent materials) based optical receiver/optical plasmonic optical nanoantenna attached to a disease specific biomarker binder 240C can be utilized to enhance the fluorescence or Raman signal from the array of microcapillaries 500A.

Alternatively, a nano-scaled metamaterial (whose properties owed more to its micro-structure than to the constituent materials) based optical receiver/optical plasmonic optical nanoantenna attached to a disease specific biomarker 460 can be utilized to enhance the fluorescence or Raman signal from the array of microcapillaries 500A.

With a colloidal lithography, a self-assembling hexagonal monolayer of polymer spheres can be fabricated/constructed, as a shadow mask on a membrane substrate (e.g., a bilayer of lipid molecules) for subsequent deposition of gold nanoparticles.

When the polymer spheres are removed, what remains is an arrays of gold nanoparticles and triangles over which the membrane is fabricated/constructed.

By way of an example and not by way of any limitation, a plasmonic optical nanoantenna can consists of two triangular pieces of gold, each about 75 nanometers long, whose tips face directly across from each other in the shape of a miniature bowtie.

The membrane with an array of large number (e.g., billions) plasmonic optical nanoantennas can significantly enhance fluorescent or Raman signal.

Furthermore, the membrane (with an array of large number (e.g., billions) of plasmonic optical nanoantennas) and a fluorophore (e.g., a quantum dot fluorophore) can be bonded via a synthetic DNA strand (about 15 nanometers long).

Addition of Nanostructures to Enhance Fluorescence Signal or Raman Signal from an Array of Microcapillaries To enhance the fluorescence signal or Raman signal from the array of microcapillaries 500A, a two-dimensional array of nanometer sized linear gratings can be fabricated/constructed/bonded at the bottom of each microcapillary on the array of microcapillaries 500A.

To enhance the fluorescence signal or Raman signal from the array of microcapillaries 500A, alternatively a two-dimensional array of nanometer sized curved gratings can be fabricated/constructed/bonded at the bottom of each microcapillary on the array of microcapillaries 500A.

To enhance the fluorescence signal or Raman signal from the array of microcapillaries 500A, alternatively a two-dimensional array of nanometer sized photonic crystal gratings can be fabricated/constructed/bonded at the bottom of each microcapillary on the array of microcapillaries 500A.

To enhance the fluorescence signal or Raman signal from the array of microcapillaries 500A, alternatively a two-dimensional array of nanometer sized three-dimensional structures can be fabricated/constructed/bonded at the bottom of each microcapillary on the array of microcapillaries 500A.

The shape, diameter, height and pitch of the nanometer sized three-dimensional structures can be varied for maximum enhancement of the fluorescence or Raman emission.

Furthermore, the above linear gratings, curved gratings, photonic crystal gratings and nanometer sized three-dimensional structures can be decorated with a thin-film metal (e.g., gold/silver).

By Way of an Example and not by Way of any Limitation, an Exosome as a Disease Specific Biomarker A disease specific biomarker 460 can indicate a progression of a disease. Exosome (40 nanometers to 100 nanometers in diameter) and microvesicle (>100 nanometers to 1000 nanometers in diameter) are small vesicles that are shed by cells periodically. On an average, each exosome contains only 1 to 10 RNA molecules, wherein each RNA molecule has an average of 100 nucleotides. However, taking into account that exosomes are present in very high numbers in body fluids (typically>$10^9$ per mL), as a population they are capable of inducing significant biological effects.

An exosome and/or a microvesicle carry messenger RNAs, micro-RNAs and signaling proteins. An exosome contains RNAs. Cells communicate with each other by sending and receiving exosomes-thus an exosome can be viewed as a unit for cell-to-cell biological communication directly by surface expressed ligands or transferring molecules from the originating cells. For example, exosomes can carry material from the originating cancer cells to suppress the immune system and stimulate angiogenesis for the growth of cancer cells.

An exosome and/or a microvesicle can be isolated from a human body's blood/biological fluid by ultracentrifugation and filtration. An exosome can contain many types of small RNAs, including miRNA, Y-RNA, piwi-RNA and tRNA. The circulating level, origination and message transported by an exosome and/or a microvesicle can be utilized as a disease specific biomarker 460. A specific microRNA in an exosome and/or a microvesicle isolated from a disease specific blood can be elevated compared to an exosome and/or a microvesicle isolated from non-disease specific blood. Thus, microRNA analysis within an exosome and/or a microvesicle can be utilized to predict a patient-specific disease, before any clinical symptoms occur.

Relevant properties of an exosome and/or a microvesicle are size, size distribution, density, morphology, composition and zeta potential. Furthermore, an exosome and/or a microvesicle as a disease specific biomarker can be selectively qualified and/or quantified by a disease specific biomarker binder, wherein the disease specific biomarker binder is coupled with a fluorophore (e.g., a quantum dot fluorophore).

By Way of an Example and not by Way of any Limitation, an Antibody or Aptamer or Molecular Beacon as a Disease Specific Biomarker Binder A disease specific biomarker binder 240C can be a specific antibody/aptamer/molecular beacon.

There are DNA aptamers or RNA aptamers or XNA aptamers or peptide aptamers. DNA/RNA/XNA aptamers generally consist of short strands of oligonucleotides. Peptide aptamers generally consist of a short variable peptide domain, attached at both ends to a protein scaffold.

Furthermore, an aptamer can be a (fluorescence) wavelength-shifting aptamer, wherein upon binding a (fluorescence) wavelength-shifting aptamer switches fluorescence wavelength from one wavelength to another wavelength. Thus, a (fluorescence) wavelength-shifting aptamer can reduce background signal in a human body's blood/biological fluid.

A molecular beacon is looped like a hairpin. The loop like hairpin can contain a molecular probe sequence, which is complementary to a disease specific nucleic acid molecule. The molecular beacon can be chemically coupled with a fluorophore at one end and a non-fluorescent quencher at the other end.

Furthermore, in addition to molecular quenchers, many nanomaterials (e.g., graphene oxide (GO)) also possess excellent quenching efficiency.

Upon binding to the disease specific nucleic acid molecule, the molecular probe sequence undergoes a spontaneous conformational reorganization, which removes the fluorophore from the vicinity of the quencher and restores its fluorescence.

Optionally, the molecular beacon can be chemically coupled with two (2) or more quantum dot fluorophores, assembled/fabricated/constructed, utilizing the tip of an atomic force microscope.

Furthermore, the molecular beacons chemically coupled with fluorophores (each fluorophore has a distinct fluorescence emission) can be utilized as an array of disease specific biomarkers.

Array of Microcapillaries-Planar Sudden Constricted Microchannels Based Optical Integrated Diagnostics Biomodule (Configured by an Array of Optical Fibers, a N×1 Optical Switch & Multiplexing of Biomarker Binders) for Detection of a Disease Specific Biomarker/an Array of Disease Specific Biomarkers A way to inject a large molecule, nanoshell 120, protein/viral protein and RNA (from a microreservoir/microelectromechanical-system reservoir) into a cell/stem cell is by squeezing the cell/stem cell through a planar sudden constricted microchannel. During such a passage through the sudden constricted (about 25% to 75% smaller than the diameter of cell/stem cell) microchannel at a high speed, a temporary tiny opening in the cell/stem cell membrane is formed, without any permanent damage to the cell/stem cell.

The above configuration can be utilized to inject a bioactive compound 100 and/or a bioactive molecule 100A into cancer cells to analyze the effectiveness of the bioactive compound 100 and/or the bioactive molecule 100A.

The above configuration can be utilized to inject a viral protein into immune cells to analyze the effectiveness of the viral protein.

The above configuration can be utilized to inject a protein to differentiate stem cells (into specialized tissues) to analyze the effectiveness of the protein.

For injecting and/or analyzing an array of large molecules, nanoshells 120, proteins/viral proteins and RNAs into a diversity of different cells/stem cells, a cascaded configuration of an array of planar sudden constricted microchannels can be utilized.

An array of microcapillaries based integrated optical diagnostics biomodule 700.3/700.4 can be further integrated by an array of planar sudden constricted microchannels, wherein the planar sudden constricted microchannel in a horizontal plane is connected/coupled with the vertical microcapillary.

Array of Liquid Core Ring Resonators-Planar Sudden Constricted Microchannels Based Optical Integrated Diagnostics Biomodule for Detection of a Disease Specific Biomarker/an Array of Disease Specific Biomarkers Optionally a cascaded configuration (for injecting an array of large molecules, nanoshells 120, proteins/viral proteins and RNAs one after another in a cascaded manner into a diversity of different cells/stem cells) of an array of planar sudden constricted microchannels can be integrated with an array of liquid core optical ring resonators.

Each liquid core optical ring resonator has a microcapillary, whose circular cross section forms a ring resonator. A human body's blood/biological fluid can be passed through the liquid core optical ring resonator capillary, while a waveguide arranged perpendicularly to the microcapillary configured to deliver/couple light into a human body's blood/biological fluid core optical ring resonator wall evanescently via a presence of the evanescent field of the whispering gallery mode.

The liquid core optical ring resonator and the whispering gallery mode derive its sensitivity from monitoring frequency shift, induced by binding (of a biomarker with a biomarker binder) at the sites of highly confined field intensities.

Furthermore, the field intensity can be amplified by excitation of plasmon resonances in a nanoparticle layer/layer of an array of plasmonic optical nanoantennas attached to a fluorophore.

By way of an example and not by way of any limitation, a plasmonic optical nanoantenna can consist of two triangular pieces of gold, each about 75 nanometers long, whose tips face directly across from each other in the shape of a miniature bowtie.

One method to increase the sensitivity is to implement a reference measurement in a proximate liquid core optical ring resonator capillary.

Another method to increase the sensitivity is by pushing more light for more light-matter interaction or by reducing the wall thickness and/or fabricating concentric rings.

In-Situ DNA Microarray Chip with Dual Array of Micromirrors to Determine Suitability of Bioactive Compounds &/or Bioactive Molecules for Treating a Disease As before, an array of miniature mirrors pattern/deflect light via a combination of a shutter and a lens to the bottom of each microcapillary (for example in FIG. 12A) from a single light source. This particular configuration can enable one to analyze one microcapillary at a time.

Furthermore, each microcapillary (of an array of microcapillaries, for example in FIG. 12A) with a flat rectangular bottom can be coupled to an optical fiber (and a DNA synthesizer as well).

The array of micromirrors (as virtual masks) can reflect/focus the desired pattern of light (e.g., ultra-violet light/nitrogen laser beam onto the flat rectangular bottom via a combination of a shutter and lens-including a metamaterial negative refractive index optical superlens) with individually addressable mirrors controlled by a computer. Each micromirror is individually controlled and it can rock on its angle about 2 milliseconds time scale.

A metamaterial negative refractive index optical superlens can be fabricated/constructed, utilizing nanoscale patterns (e.g., photonic crystals).

However, a metamaterial negative refractive index optical superlens for ultra-violet light can be fabricated/constructed, utilizing alternating nanometer-thick layers of silver (Ag) and titanium dioxide ($TiO_2$). This type of design has a stack of strongly coupled waveguides sustaining backward waves, the metamaterial exhibits a negative index of refraction to incoming light, regardless of its angle of propagation.

Furthermore, the computer also controls the delivery of chemicals. The light can cleave a photo-labile protecting group at the precise location wherein the next nucleotide is to be coupled. The desired pattern of light can be coordinated with the DNA synthesizer, such that there are 385,000 to 4.2 million unique probes on a DNA microarray chip.

Such a DNA microarray chip in the microcapillary can enable a suitability measurement of bioactive compounds 100 and/or bioactive molecules 100A in treating a disease.

Electrical Diagnostics Biomodule for Detection of a Disease Specific Biomarker/an Array of Disease Specific Biomarkers Graphene is a two-dimensional crystal with a high carrier mobility and low noise. It has the ideal properties to be an excellent component of electrical circuits. Graphene epitaxially grown on silicon carbide (SiC) substrate can be suitable for production of electrical circuits.

Graphene is a graphene variant wherein hydrogen atoms are attached to the carbon lattice in insulating layers.

Graphyne is one-atom-thick sheet of carbon that resembles graphene, except that its two-dimensional framework (of atomic bonds) contains triple bonds in addition of double bonds.

Graphyne has a graphene-like electronic structure resulting in effectively massless electrons due to Dirac Cones. All electrons are travelling at roughly the same speed (about 0.3 percent of the speed of light). This uniformity leads to conductivity greater than copper.

Graphyne can be utilized as a semiconductor practically as-is, rather than requiring noncarbon dopant atoms to be added as a source of electrons, as noncarbon dopants are required for graphene. Furthermore, structures of graphyne crystal allow electrons to flow in one direction.

Molybdenite ($MoS_2$) is also a two-dimensional crystal with a natural bandgap. It can be suitable for production of electrical circuits.

Figure 13A:
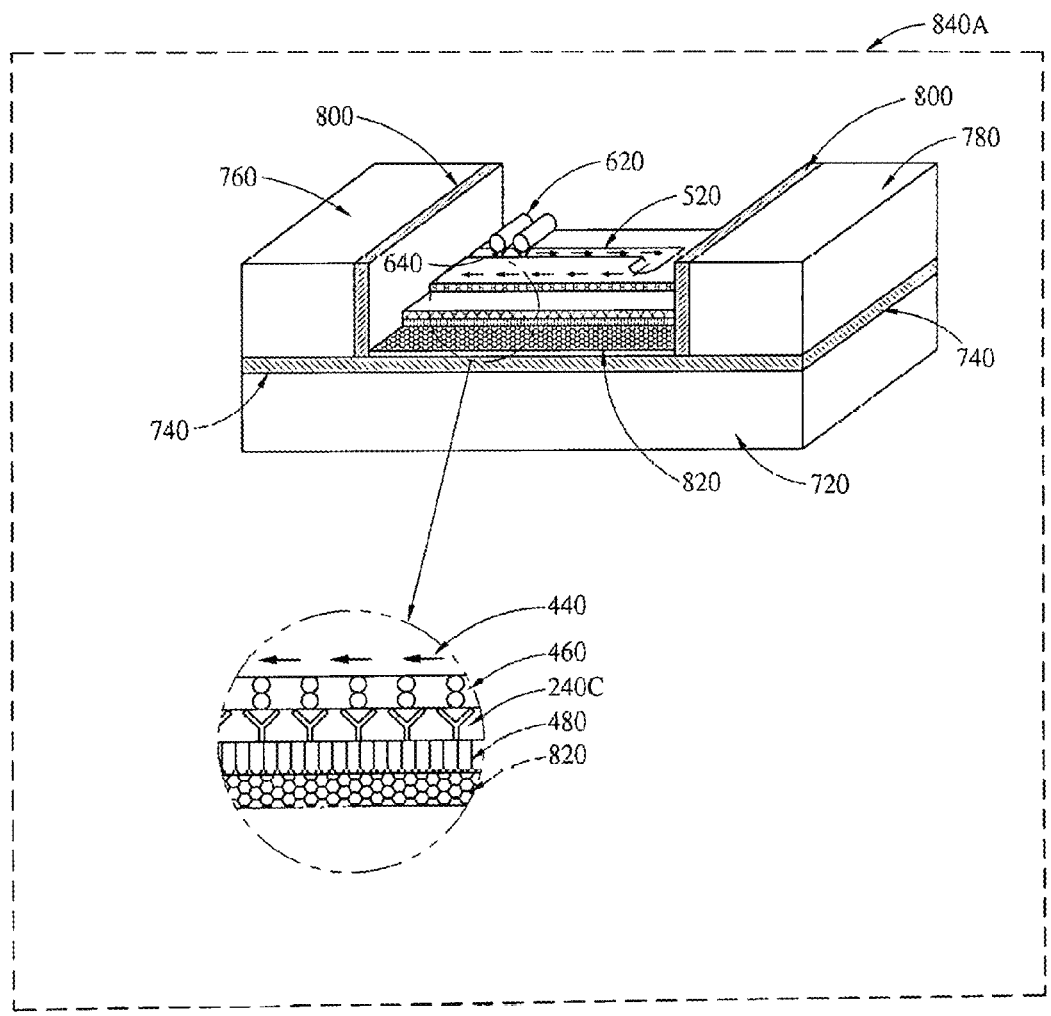
FIGS. 13A, 13B and 13C illustrate (a two-dimensional (2-D) crystal based field effect transistor based) integrated electrical diagnostics biomodules (various embodiments) to detect a disease specific biomarker/an array of disease specific biomarkers.

FIG. 13A illustrates an electrical diagnostics biomodule 840A based on change in electrical characteristics of a two-dimensional crystal based field effect transistor (e.g., graphene or molybdenite) due to a disease specific biomarker 460 (in a patient's blood 440) which can be propagated through a microfluidic channel 620 to a microfluidic cavity 520).

The disease specific biomarker 460 can chemically bind with a disease specific biomarker binder 240C on the optional biomolecular interface layer 480 on a single layer of the two-dimensional crystal substrate 820.

The field effect transistor can integrate: a semiconductor substrate as a gate 720, a gate oxide insulator thin-film 740, a source metal thin-film 760, a drain metal thin-film 780, a polymeric insulator thin-film 800 and a two-dimensional crystal substrate 820.

Furthermore, graphene's ability to form chemical bonds can be turned on or turned off based on what is underneath graphene. When silicon dioxide is underneath graphene, it is reactive when exposed to certain biomarkers/chemicals. But when boron nitride is underneath graphene, it is not reactive when exposed to certain biomarkers/chemicals. An array of materials (e.g., an array of boron nitride and silicon dioxide) underneath graphene can be utilized with an array of sensors to detect a trace amount of biomarkers/chemicals.

Microelectro-mechanical-System Biomodule to Draw/Propagate Blood

Figure 13B:
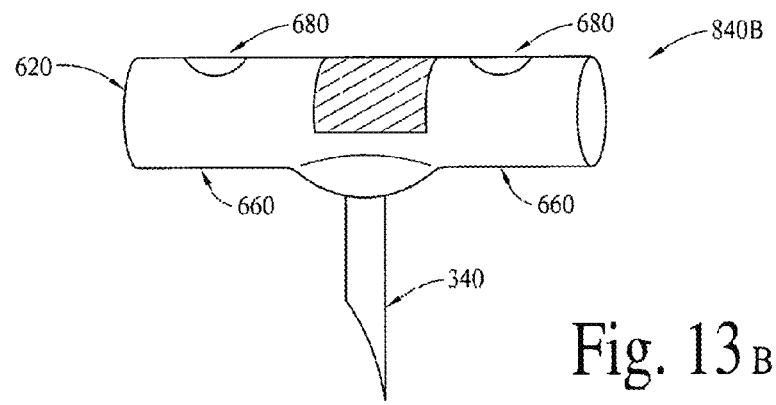

FIG. 13B illustrates a microelectro-mechanical-system biomodule 700B to draw blood from a patient, utilizing the microneedle 340, which can be monolithically integrated with a micromachined (voltage deflectable) membrane 660, a membrane sensor 680 and a microfluidic channel 620.

The microneedle 340 can be electrically powered and programmed to draw the patient's blood at a periodic interval of time.

Furthermore, the microelectro-mechanical-system biomodule 700B can include an array of microneedles 340, an array of micromachined membranes 660, an array of membrane sensors 680 and an array of microfludic channels 620.

Furthermore, an array of microfluidic channels 620 can be placed onto an array of precise silicon/ceramic v-grooves 640.

The array of precise silicon/ceramic v-grooves 640 can be enclosed within a precisely machined connector (not shown in the FIG. 13B).

The precisely machined connector can be attached precisely/detached from the microelectro-mechanical-system biomodule for drawing/propagating the patient's blood.

Figure 13C:
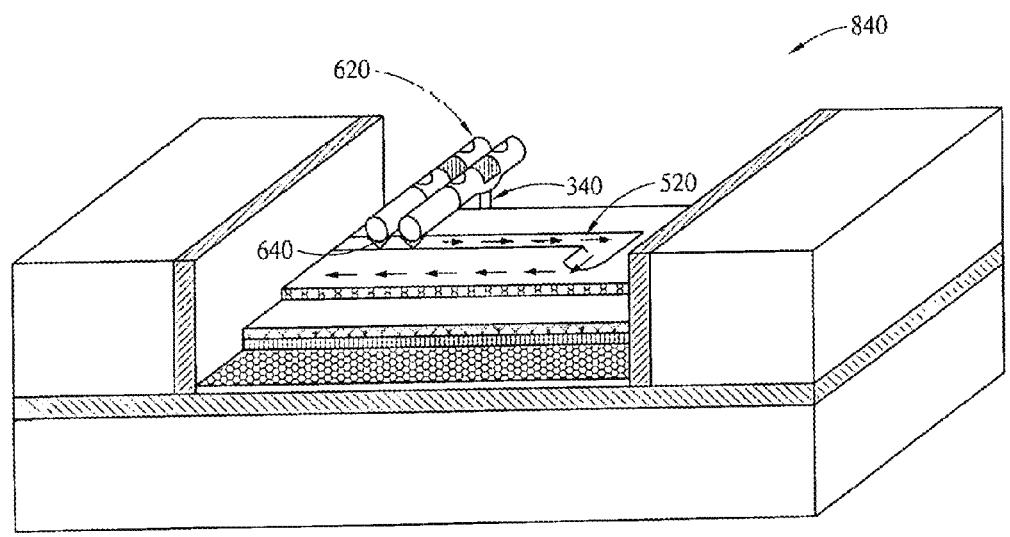

Integrated Two-Dimensional Crystal Field Effect Transistor Based Electrical Diagnostics Module for Detection of a Disease Specific Biomarker/an Array of Disease Specific Biomarkers FIG. 13C illustrates an integrated two-dimensional crystal field effect transistor based electrical diagnostics biomodule 840.

Engineered Protein Based Field Effect Transistor (FET) to Replace a Two-Dimensional Crystal Field Effect Transistor Furthermore, the two-dimensional crystal field effect transistor can be replaced by an engineered protein based field effect transistor.

The engineered protein based field effect transistor can be fabricated/constructed, utilizing a suitable material decorated on engineered protein (e.g., a three-dimensional ball and spike engineered protein-synthesized by a fusion of both Dps and gp5c genes).

Figure 13D:
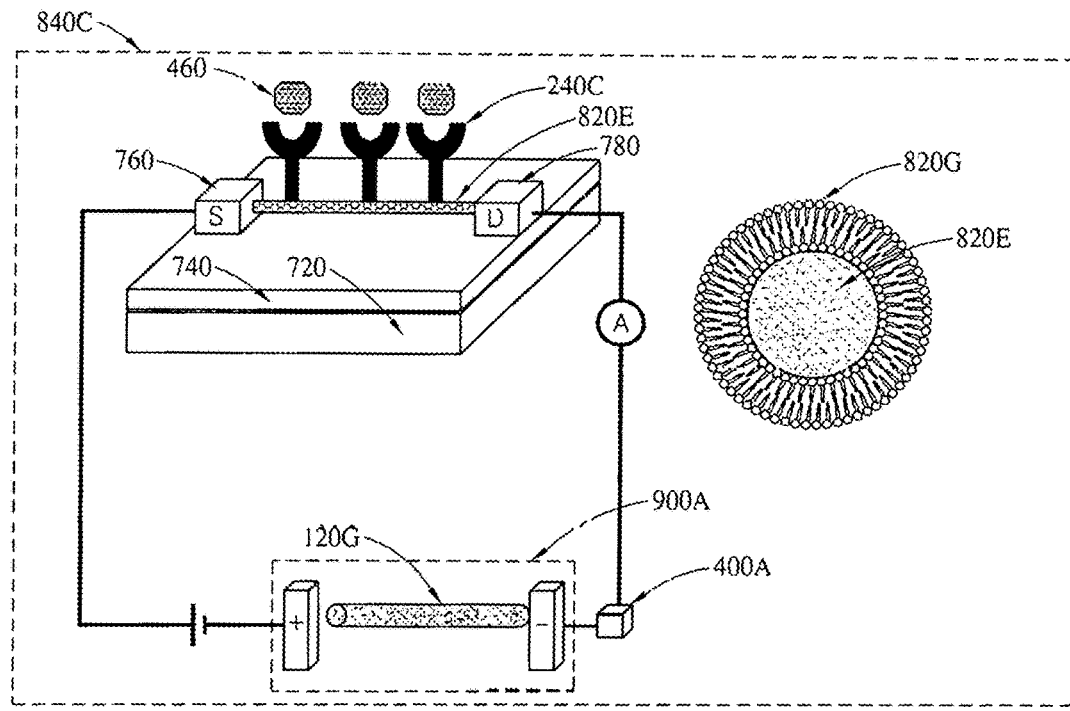
FIG. 13D illustrates chitosan/melanin based proton field effect transistor ($H^+$ FET) integrated with a lipid layer and a nanotransmitter to detect a disease specific biomarker/an array of disease specific biomarkers.

Proton Based Field Effect Transistor Decorated with a Lipid Layer to Replace a Two-Dimensional Crystal Field Effect Transistor FIG. 13D illustrates a natural biopolymer chitosan/melanin based proton field effect transistor 820E and it incorporates a semiconductor substrate as a gate 720, a gate oxide insulator thin-film 740, a source metal thin-film 760 and a drain metal thin-film 780 for proton current.

Furthermore, palladium hydride contacts can replace a traditional source metal thin-film 760 and/or a drain metal thin-film 780.

Furthermore, the proton field effect transistor 820E can be decorated with a lipid layer (a double wall of oil molecules, that biological cell utilizes to separate its inside from its outside environment) 820G.

The lipid layer 820G can be decorated with a disease specific biomarker binder 240C.

The disease specific biomarker binder 240C can chemically bind with a disease specific biomarker 460-thus it can change the electrical characteristics of the proton field effect transistor 820E.

Furthermore, the proton field effect transistor 820E can be integrated with a nanotube (e.g., a boron nitride/carbon/tubular structure nanotube, a nanotube fabricated/constructed, utilizing DNA/RNA origami process) 120G based nanoradio transmitter with a nanoantenna 900A.

The nanotube 120G based nanoradio transmitter with the nanoantenna 900A can be electrically powered by a nanobattery 400A.

A miniaturized non-rechargeable lithium battery/glucose fuel cell battery can replace the nanobattery 400A.

A glucose cell fabricated/constructed on a silicon substrate with integrated platinum catalyst to strip electrons from glucose can act as a glucose fuel cell and an array of glucose fuel cells can act as a battery.

Furthermore, in melanin based electrical circuits both electron and proton can be utilized. A chitosan/melanin based proton field effect transistor 820E integrated with the nanoradio transmitter with a nanoantenna 900A and the nanobattery 400A can be indicated as 840C.

Figure 13E:
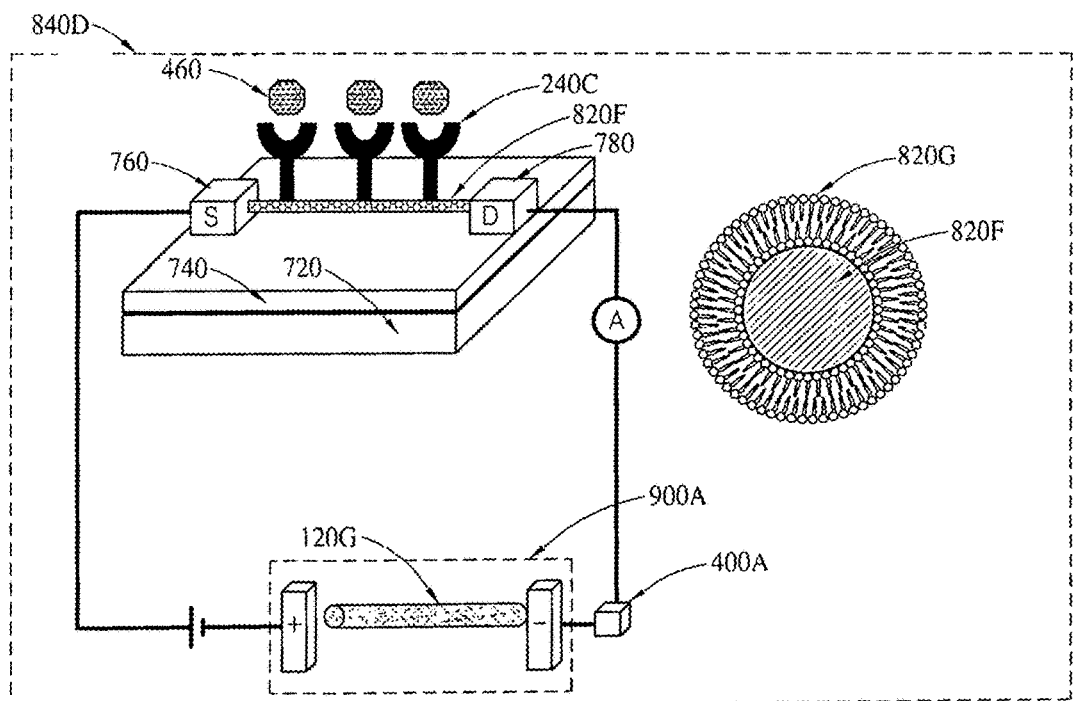
FIG. 13E illustrates a silicon nanowire based field effect transistor integrated with a lipid layer and a nanotransmitter to detect a disease specific biomarker/an array of disease specific biomarkers.

Silicon Nanowire Based Field Effect Transistor Decorated with a Lipid Layer to Replace a Two-Dimensional Crystal Field Effect Transistor FIG. 13E illustrates a similar configuration as 13D except that a silicon nanowire to replace chitosan/melanin.

A silicon nanowire field effect transistor 820F integrated with the nanotube 120G based nanoradio transmitter, the nanoantenna 900A and the nanobattery 400A can be indicated as 840D.

Furthermore, the silicon substrate of silicon nanowire field effect transistor 820F can also be replaced by melanin.

Furthermore, a conducting polymer nanowire can replace a silicon nanowire.

A nanoantenna printed on a biocompatible material (e.g., silk) can be placed in (within) a human body such that any change in current flow in the nanoantenna can induce a change in the radio transmitter placed on a human body.

Furthermore, device configurations, as illustrated in FIG. 13D or 13E can be integrated with an organic semiconductor circuit. A shape memory polymer can be laminated and cured on the organic semiconductor circuit or on the device, as illustrated in FIG. 13D or 13E.

Interface Electrode

Boron-doped conducting diamond like material can be grown on a silicon dioxide substrate by chemical vapor deposition process at about 900 degrees centigrade.

Boron-doped conducting diamond like material can be bonded on a polymer substrate and then lifted off from the silicon dioxide substrate by hydrofluoric acid.

Thus, a boron-doped conducting diamond-like material can act as an interface electrode for any biological application.

It should be noted implantable (within a human body) miniature diagnostic modules 840C and 840D can be rendered nonfunctional due to biofouling, because of a triggered immune response.

A thermoresponsive material can contract and expand in response to changes in temperature. Thus, the implantable (within a human body) miniature diagnostic module can be coated with a biocompatible thermoresponsive material (e.g., hydrogel). By increasing the temperature of the biocompatible thermoresponsive material, the thermoresponsive material contracts, as proteins and cells are dislodged from the coated surface of the thermoresponsive material. When the heat is removed, the thermoresponsive material can return to its normal state. This heating/cooling process can be repeated until the implantable (within a human body) miniature diagnostic module is cleaned from biofouling.

Detection of a Disease Specific Biomarker/an Array of Disease Specific Biomarkers & Programmable/Active Delivery of Bioactive Compounds/Bioactive Molecules in Near Real-Time/Real-Time If 840C/840D detects an abnormal level of a disease specific biomarker 460, then the nanoradio transmitter with the nanoantenna 900A can transmit the information so that a microelectro-mechanical-system reservoir can enable the programmable/active delivery of the bioactive compounds 100 and/or bioactive molecules 100A in near real-time/real-time via a dynamic closed feedback loop.

Furthermore, an array of 840C/840D can be utilized instead of a single 840C/840D.

Nanostructure Based Diagnostics Biomodule for Detection of a Disease Specific DNA/Protein A probe DNA sequence can be attached to the lipid layer on a nanostructure (e.g., carbon nanotube) utilizing an electrochemical functionalization. The detection can be based on a unique impedance measurement technique coupled to a field effect transistor device, when a complementary target DNA binds with the probe DNA. The lipid layer can be replaced by a suitable polymer layer.

Alternatively, DNA can be replaced by a disease specific designer protein. The disease specific designer protein has a leave-one-out configuration, wherein each protein has an omitted segment to create a binding site to fit a protein for a specific disease.

Furthermore, an array of nanostructures can be utilized instead of a single nanostructure for detection of an array of disease specific DNAs and/or proteins.

Nanohole Based Diagnostics Biomodule for Detection of a Disease Specific Biomarker/an Array of Disease Specific Biomarkers Four (4) molecules, when chemically bonded together, that make up the structural units of DNA are: adenine (A), cytosine (C), guanine (G) and thymine (T). A segment of a DNA strand can be a gene.

Four (4) molecules, when chemically bonded together, that make up the structural units of RNA are: adenine (A), cytosine (C), guanine (G) and uracil (U).

Figure 14A:
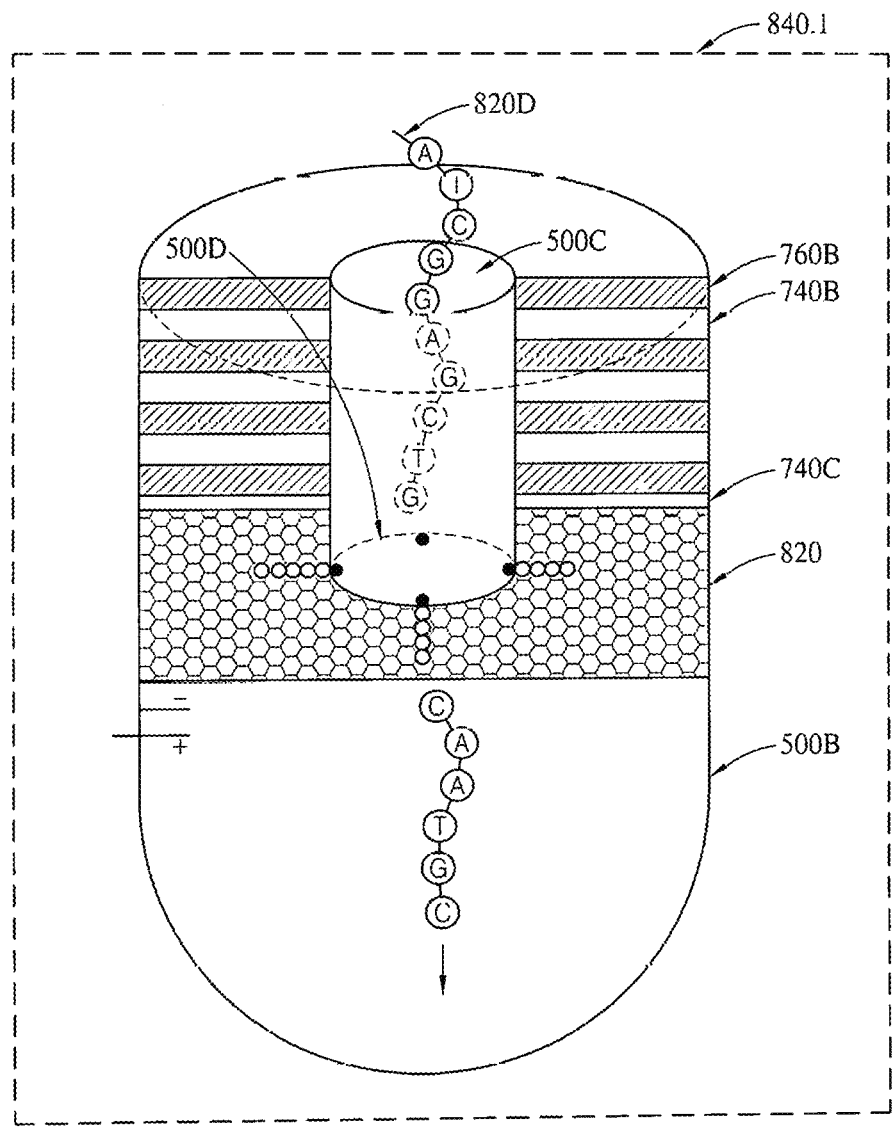
FIGS. 14A and 14B illustrate a nanohole based single molecule DNA/RNA sequencing electrical diagnostics biomodule to detect a disease specific biomarker/an array of disease specific biomarkers (by measuring an alteration/elimination of a single molecule of a single stranded DNA/RNA).

FIG. 14A illustrates a nanotunnel 500C. The nanotunnel 500C can be fabricated/constructed, utilizing a low-temperature atomic layer deposition process on an atomically thick substrate.

Multi-layers of dielectrics 740B and metals 760B are embedded in the nanotunnel 500C.

The nanohole 500D is about 1.5 nanometers in diameter. The nanohole 500D can be fabricated/constructed just below the nanotunnel 500C.

Through an amazing coincidence, the graphene layer's thickness is about 3.35 A° or 0.335 nanometers, which exactly fits the gap between two DNA/RNA molecules. Hence the nanohole 500D can be fabricated/constructed from atomically thick graphene.

Alternatively, the nanohole 500D can also be fabricated/constructed, utilizing two-dimensional material like molybdenum disulfide.

Alternatively, the nanohole 500D can be fabricated/constructed, utilizing a tunable self-assembly material $Ni_3(HITP)_2$, which is a combination of nickel and an organic compound: HITP (2,3,6,7,10,11-hexaiminotriphenylene). $Ni_3(HITP)_2$ has graphene's perfectly hexagonal honeycomb crystal structure. Furthermore, multiple thin-layers of $Ni_3(HITP)_2$ naturally form perfectly aligned stacks, with the openings at the centers of the hexagons of about 2 nanometers. Since, $Ni_3(HITP)_2$ has a natural bandgap-thus electronic circuits can also be fabricated/constructed.

Alternatively, the nanohole 500D can also be fabricated/constructed, utilizing the DNA/RNA origami process on the same atomically thick substrate. The DNA/RNA origami structure can be fabricated/constructed into an accurately controlled size/shape of the nanohole 500D.

The nanohole 500D has four (4) embedded tunneling metal electrodes 820A. The four (4) embedded tunneling electrodes 820A are metal (e.g., gold nanoparticle based) tunneling electrodes. The four (4) embedded tunneling metal electrodes 820A can be fabricated/constructed, utilizing the DNA/RNA origami process.

Optionally, the tips of the tunneling metal electrodes 820A can have ultrasharp apexes with radii of curvatures of less than 1 nanometer. The electromagnetic field is enhanced at the tip of the ultrasharp tunneling metal electrodes 820, when they are irradiated with laser light. The electromagnetic field enhancement can lead to an amplification of Raman signals to enable even single molecule detection. The ultrasharp tunneling metal electrodes 820 can enable field enhancement of $10^{11}$ and lateral resolution less than 0.2 nanometers to identify/distinguish a single molecule of the single stranded DNA/RNA 820D by laser induced Raman spectroscopy. The ultrasharp tunneling metal electrodes 820 can be coated with a monolayer of diamond thin-film for contamination-free operation, stability and reliability.

The DNA origami process is a template for the design and fabrication of nanoscale structures. One can engineer selected staple strands on a DNA origami structure with site-specific attachment of gold nanoparticles to fabricate conducting nanowires from the DNA origami nanostructure.

Similarly, the RNA origami template can replace the DNA origami template.

By way of an example and not by way of any limitation, the DNA/RNA origami structure with site-specific attachment of gold nanoparticles can act as a tunneling metal electrode.

Furthermore, polythiophene, a light emitting diode (LED) polymer molecule can be chemically bonded/attached/integrated with the tunneling metal electrode or chemically bonded/attached/integrated with the tip of the tunneling metal electrode.

Figure 14B:
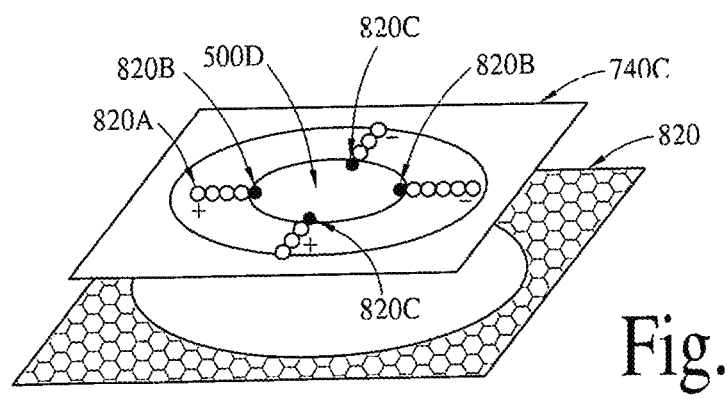

FIG. 14B illustrates a set of two (2) embedded tunneling metal electrodes 820A diametrically positioned as opposite to each other.

FIG. 14B also illustrates another set of two (2) embedded tunneling metal electrodes 820A diametrically positioned as opposite to each other.

The nanohole 500D can be mechanically supported on a larger (about 2 nanometers in diameter) nanohole in an atomically thick dielectric 740C.

The dielectric 740C can be fabricated/constructed, utilizing a low-temperature atomic layer deposition (ALD) process.

The larger (about 2 nanometers in diameter) nanohole in the dielectric 740C can be fabricated/constructed, utilizing electron-beam lithography and focused ion beam etching.

Furthermore, the larger nanohole (about 2 nanometers in diameter) in the dielectric 740C can be mechanically supported or fabricated/constructed on an atomically thick two-dimensional crystal (e.g., graphene, molybdenum sulfide and phosphorene) membrane 820.

It should be noted that molybdenum sulfide is different from other semiconductor materials, because it can be grown in layers of one atom thickness without compromising its properties. In sharp contrast to graphene, which is a semi-metal with no bandgap by nature, molybdenum sulfide monolayers offer an attractive semiconductor option due to a direct bandgap of 1.8 eV. molybdenum sulfide monolayers are a better candidate than graphene for many electronic and photonic devices. Thus, a molybdenum sulfide monolayer deposited on a suitable substrate can be utilized for (a) an electronics circuit (e.g., an electronics circuit to measure transverse tunneling currents preciously), (b) tunneling electrodes and (c) a nanohole (fabricated/constructed, utilizing electron-beam lithography and focused ion beam etching) for identifying molecules in a single stranded DNA/RNA 820D, wherein the substrate in the nanohole area is removed/etched back—further simplifying fabrication/construction of a nanohole based diagnostics biomodule for detection of a disease specific biomarker (e.g., a gene mutation)/an array of disease specific biomarkers.

Unlike graphene, phosphorene is a natural semiconductor. Thus, a phosphorene monolayer deposited on a suitable substrate can be utilized for (a) an electronics circuit (e.g., an electronics circuit to measure transverse tunneling currents preciously), (b) tunneling electrodes and (c) a nanohole (fabricated/constructed, utilizing electron-beam lithography and focused ion beam etching) for identifying molecules in a single stranded DNA/RNA 820D, wherein the substrate in the nanohole area is removed/etched back—further simplifying fabrication/construction of a nanohole based diagnostics biomodule for detection of a disease specific biomarker (e.g., a gene mutation)/an array of disease specific biomarkers.

Furthermore, the nanohole in the atomically thick two-dimensional crystal membrane 820 is about 2 nanometers in diameter, which can be optionally integrated with tunnel junctions.

Furthermore, the nanohole in the atomically thick two-dimensional crystal membrane 820 is about 2 nanometers in diameter, which can be optionally integrated with nanotransistor as described in FIG. 13C, FIG. 13D and FIG. 13E, built on top of the atomically thick two-dimensional crystal membrane 820.

Furthermore, the nanohole in the atomically thick two-dimensional crystal membrane 820 is about 2 nanometers in diameter, which can be optionally integrated with nanotransistor such as graphene nanoribbon transistor, built on top of the atomically thick two-dimensional crystal membrane 820.

The atomically thick two-dimensional crystal membrane 820 can be a metallic graphene nanoribbon with zigzag edges or metallic chiral graphene nanoribbon or wires made of a two-dimensional topological insulator.

The nanohole 500D can be electrically connected to the atomically thick two-dimensional crystal membrane 820 for reliable electrical contact.

Alternatively, the nanohole 500D can be electrically connected to an atomically thick (about 1 nanometer thick) porous carbon nanomembrane/silicon nitride nanomembrane for reliable electrical contact instead of the atomically thick two-dimensional crystal membrane 820.

A single stranded DNA/RNA 820D can be pulled down through the nanotunnel 500C and nanohole 500D by a vertical electrical field, as the DNA/RNA 820D is electrically charged.

A four-point-probe measurement of transverse tunneling currents (of about 3A° long single molecule of the single stranded DNA/RNA 820D) through the nanotunnel 500C and nanohole 500D can electrically identify each single molecule of the single stranded DNA/RNA 820D.

Tunneling is confined to tiny distances such that a tunnel junction can identify about a 3 Å long single molecule (e.g., adenine (A), cytosine (C), guanine (G) and thymine (T) of the single stranded DNA) of the single stranded DNA/RNA 820D at a time without interference from other molecules.

Because of extreme sensitivity requirements in measurement of transverse tunneling currents, tiny vibrations can severely degrade a tunneling signal.

A tiny voltage bias between the tunneling metal electrodes can enable polythiophene, a light emitting diode polymer molecule to emit light (e.g., light of red wavelength), which can be detected by a nano-scaled detector (e.g., a detector based on graphene/molybdenum sulfide heterostructure or a detector based on nano-scaled three-dimensional (3-D) structure or a nanogap detector based on colloidal quantum dot).

Variation in optical intensity detection can also identify the approximately 3A° long single molecule (e.g., adenine (A), cytosine (C), guanine (G) and thymine (T) of the single stranded DNA) of the single stranded DNA/RNA 820D at a time without interference from other molecules.

A large electric field is needed to push the single stranded DNA/RNA 820D through the nanohole 500D, but the same large electric field can also push single stranded DNA/RNA 820D too rapidly through the nanohole 500D-thus reducing the ability of four embedded tunneling metal electrodes 820A to sense/read individual molecule in single stranded DNA/RNA, utilizing the four-point-probe measurement of transverse tunneling currents.

However, the pulling speed of the single stranded DNA/RNA 820D can be reduced by traversing the single stranded DNA/RNA 820D through an alternating electric field generated by multi-layers of dielectrics 740B and metals 760B, embedding/surrounding the nanotunnel 500C.

The single stranded DNA/RNA can be chemically coupled to a magnetic nanoparticle to push the single stranded DNA/RNA by a magnetic field in the opposite upward direction with respect to the downward electric field.

Furthermore, the pulling speed of the single stranded DNA/RNA 820D can be reduced by chemically coupling phi29 DNA polymerase enzyme with the single stranded DNA/RNA or to the magnetic nanoparticle.

The tug-of-war between the electric field and the magnetic field (oppositely orientated with respect to each other) can be optimized to reduce the velocity of the single stranded DNA/RNA-thus allowing four embedded tunneling metal electrodes 820A the ability to sense/read individual molecule in the single stranded DNA/RNA, utilizing the four-point-probe measurement of transverse tunneling currents.

Furthermore, a piezoelectric thin-film (e.g., zinc oxide or gallium nitride thin-film) can be deposited intimately surrounding the nanohole 500D. The piezoelectric thin-film can be deposited by the atomic layer deposition process. The piezoelectric thin-film physically can strain in response to an electric field-thus adjusting approximately the diameter of the nanohole 500D in-situ for reducing the velocity of the single stranded DNA/RNA 820D.

A molecule can either be right handed (D) or left handed (L). This property is called chirality. A chiral molecule can recognize/transfer information that has the same chirality (same handedness, L to L or D to D) and discriminate the molecule of different chirality (L to D and D to L).

The diametrically opposite first set of two (2) embedded tunneling electrodes 820A, wherein each embedded tunneling electrode is chemically configured with a recognition molecule 820B such that, the recognition molecule 820B for adenine (A) can effectively clutch adenine (A) of the single stranded DNA/RNA 820D.

The diametrically opposite second set of two (2) embedded tunneling electrodes 820A, wherein each embedded tunneling electrode is chemically configured with a recognition molecule 820C such that, the recognition molecule 820C for guanine (G) can effectively clutch guanine (G) of the single stranded DNA/RNA 820D.

Furthermore, an additional change in edge conduction current can be measured when the single stranded DNA/RNA 820D is pushed through the nanohole in the atomically thick two-dimensional crystal membrane 820.

The atomically thick two-dimensional crystal membrane 820 can be a metallic graphene nanoribbon with zigzag edges (ZGNR) or metallic chiral graphene nanoribbon or wires made of a two-dimensional topological insulator.

Nanohole Integrated with a Suitable Functional/Fluorescent Molecule & a Nanoantenna for Single Molecule Fluorescence/Single Molecule Raman Spectroscopy Furthermore, the single stranded DNA/RNA 820D can be also configured (at a sub-nanometer precision by dip pen lithography) with suitable functional/fluorescent molecules-thus improving the sensitivity and reliability of the molecular identification of the single stranded DNA/RNA 820D.

The nanohole 500D can be integrated (utilizing dip pen lithography) with a suitable functional fluorescent molecule.

Furthermore, the proximity or vicinity of the nanohole 500D can be integrated with a plasmonic optical nanoantenna, for single molecule fluorescence or single molecule Raman spectroscopy, when the single stranded DNA/RNA 820D is also appropriately decorated with suitable functional molecules.

By way of an example and not by way of any limitation, a plasmonic optical nanoantenna can consists of two triangular pieces of gold, each about 75 nanometers long, whose tips face directly each other in the shape of a miniature bowtie.

Furthermore, the plasmonic optical nanoantenna can be integrated with a lens based on metamaterial.

It may not be necessary to uniquely identify all four (4) molecules for some applications. A binary conversion of molecular sequence (e.g., A or T=0, and G or C/U=1) can be utilized to identify a disease specific biomarker and/disease specific genomic alteration/elimination in the single stranded DNA/RNA 820D.

Furthermore, statistics enhanced repeated four-point-probe measurements of transverse tunneling currents can reliably identify each single molecule of the single stranded DNA/RNA 820D-thus detecting an alteration/elimination of a single molecule in the single stranded DNA/RNA 820D, without need of PCR and Sanger sequencing.

Furthermore, such a two-dimensional array of the nanotunnels 500C and the nanoholes 500D can sequence many single stranded DNA/RNA 820D in parallel.

Sequencing of a DNA/RNA can generate Big Data.

Big Data can be converted into a smaller data set utilizing linear simplification and/or signal clustering, as the underlying data has geometrical structures and patterns (repeated over time). Furthermore, signal clustering can be categorized and weighted for importance.

Alternatively, topological data analysis or Bayesian analysis coupled with Markov chain Monte Carlo methods can be utilized for analysis of Big Data.

Furthermore, analysis of Big Data in an unstructured format can also be realized by a cloud based machine learning/relearning interactive expert cognitive computer (e.g., IBM Watson) utilizing natural language.

Furthermore, analysis of Big Data can be coupled with an intelligent learning set of instructions. An intelligent learning set of instructions can include: artificial intelligence, data mining, fuzzy/neuro-fuzzy logic, machine vision, natural language processing, neural networks, pattern recognition, reasoning modeling and self-learning.

By utilizing biostatistics, data mining algorithm (e.g., a topological data mining algorithm), genomics, proteomics, augmented intelligence modeling algorithm and/or predictive modeling algorithm, one can identify a set of primary predictive genes/proteins for a specific disease.

The nanohole based diagnostics biomodule (including the two-dimensional array of the nanotunnels 500C and two-dimensional array of nanoholes 500D) for detection of a disease specific biomarker/an array of disease specific biomarkers is identified as 840.1.

Furthermore, 840.1 is integrated with a suitable port to input/drop a DNA/RNA sample and 840.1 can connect to the USB port of a personal computer for displaying and analyzing the DNA/RNA sample. The ability to correlate a patient's DNA with a specific disease treatment can be beneficial.

Nanohole Based Diagnostics Biomodule for Application to Personalized Medicine

Most treatments today rely on clinical data taken from average patients. However, the way an individual responds to different drugs can vary remarkably even to the point where an effective dose tolerated by one individual could be completely ineffective or even toxic to another.

In many cases this can be due to the Cytochrome P450 (CYP450) family of proteins which is responsible for the metabolism of most drugs into active forms and/or forms that can be excreted from the body. The CYP450 family of proteins is not large, but different people can express different members of the family and/or express the same members at different levels. Knowing this information is the first step towards delivering personalized medicine-thus drug doses can be tailored to the individual. The sequencing of a human genome, identification of gene families (such as CYP450) and a greater understanding of the genetics behind responses to drugs may allow delivery of personalized medicine.

The nanohole based diagnostics biomodule 840.1 can rapidly and reliably analyze samples from a patient to determine the presence of specific genetic sequences which predisposing them to disease or sensitivity to specific bioactive compounds and/or bioactive molecules and/or drugs and also the levels and types of proteins that they are producing (such as CYP450 family members).

Nanohole Based Diagnostics Biomodule for Application to Epigenetic Factors

If genome/genes are the blueprint of life, the epigenome is life's etch a sketch. Our lives are little more than a checklist of various genes on a genetic scantron sheet that can be turned on or off. The regulation of gene expression is controlled by multiple mechanisms, such as the sequence-specific binding of transcription factors to DNA, epigenetic signals and a dynamic chromatin state. Epigenome is responsible for the determination of cell type and cell activity. Epigenetic regulation of genes acquired during early development is inherited not only during cell division (mitotic inheritance), but it can be passed on from one generation to the next (meiotic inheritance), but how long these changes persist remains unclear. Epigenetic changes, like so many vital biological processes, fall to human bodies to deal with. Genes become epigenetically set to deal with conditions (e.g., diet, lifestyle and stress) and then pass that on to the next generation. Epigenetics holds great promise in the area of personalized medicine. When a human eats, his/her metabolism changes, but food doesn't change a cell's genome, but instead, food modulates the epigenome, the molecular markers on the chromatin that influence gene expression by affecting how tightly DNA is wrapped around its protein scaffolding.

Epigenetic factors (guided by molecular architect piRNAs), traverse the static genome and turn the genes on or off. The staggering number of potential combinations of active and inactive genes explains why a relatively small number of genes can carry out such a wide range of functions. If a cell has ever turned on a gene in the past, the piRNA will recognize it and allow it to be expressed.

But if a gene has not been active in a cell before, the piRNA will set the silencing mechanism into action so it remains off. The silencing or lack of silencing is permanent. If the piRNA doesn't silence a gene the first time it encounters it, it won't ever silence it. And if it silences it once, then every time that gene appears in the future, the system will turn it off.

Several types of cancers can be triggered when the wrong kinds of piRNAs guide epigenetic factors to activate the wrong genes. Blocking the action of these piRNAs should become a new opportunity to treat cancers.

Epigenetic mechanisms involve adding chemical tags to DNA or the proteins it is wrapped around. Changes to the cell's environment cause the chemical tags to be added or removed. These epigenetic markers are passed on to daughter cells when the original cell divides in two. Mapping the epigenome—the chemical modifications to the DNA and its protein scaffolding that are used to switch genes on and off throughout an organism's life is critical and can be achieved by the nanohole based diagnostics biomodule 840.1.

Differences in the epigenetic markers carried on a genome may also explain some of the differences between apparently identical individuals, due to diet, lifestyle and stress.

A connectivity brain scan (measures water diffusion in a human brain) can map the strength of neural connections and how information is routed in a human brain to estimate risk factors for neurological diseases (e.g., Alzheimer's disease).

Furthermore, the above connectivity scan can be correlated with a gene sequencing to determine a genetic error for Alzheimer's disease.

Plasmonic Microhole Based Diagnostics Biomodule for Detection of a Disease Specific Biomarker/an Array of Disease Specific Biomarkers Furthermore, the nanohole based diagnostics biomodule (including the two-dimensional array of the nanotunnels 500C and two-dimensional array of nanoholes 500D) for detection of a disease specific biomarker/an array of disease specific biomarkers identified as 840.1 can be integrated with a plasmonic microhole based diagnostics biomodule for validation.

A plasmonic microhole based diagnostics biomodule can be fabricated/constructed with an array of microholes on a metal foil, wherein the light from the bottom of the metal foil can set plasmons to work on the surface and wherein each microhole is coated with a different disease biomarker binder. Plasmons trap so much energy around the microholes that they can convert more light on the top of metal foil. If a disease biomarker from a human body's blood/biological fluid binds with a respective disease biomarker binder, then it will attenuate the light intensity.

Optionally, each microhole can be decorated with a synthetic DNA strand designed to bind with a specific disease (e.g., a specific cancer) cell from a human body's blood/biological fluid. If the specific disease cell from a human body's blood/biological fluid binds with the respective synthetic DNA strand, then it will attenuate the light intensity. Furthermore, captured disease cells can be separated/squeezed into a petri dish. Then various bioactive compounds and bioactive molecules or drugs can be added to the separated/squeezed disease cells to evaluate the most effective treatment for the specific disease.

Plasmonic Nanohole-Nanolaser Based Diagnostics Biomodule for Detection of a Disease Specific Biomarker/an Array of Disease Specific Biomarkers Furthermore, the nanohole based diagnostics biomodule (including the two-dimensional array of the nanotunnels 500C and two-dimensional array of nanoholes 500D) for detection of a disease specific biomarker/an array of disease specific biomarkers identified as 840.1 can be integrated with a plasmonic nanohole-nanolaser based diagnostics biomodule for further validation.

A plasmonic nanohole-nanolaser based diagnostics biomodule can be fabricated/constructed with an array of nanoholes on a metal foil, wherein the light from an array of nanolasers (configured at the bottom of the metal foil) can set plasmons to work on the surface and wherein each nanohole is coated with a different disease biomarker binder. Plasmons trap so much energy around the nanoholes that they can convert more light on the top of metal foil. If a disease biomarker from a human body's blood/biological fluid binds with a respective disease biomarker binder, then it will attenuate the light intensity of the respective nanolaser.

Optionally, each nanohole can be decorated with a synthetic DNA strand designed to bind with a specific disease (e.g., a specific cancer) cell from a human body's blood/biological fluid. If the specific disease cell from a human body's blood/biological fluid binds with the respective synthetic DNA strand, then it will attenuate the light intensity. Furthermore, captured disease cells can be separated/squeezed into a petri dish. Then various bioactive compounds and bioactive molecules or drugs can be added to the separated/squeezed disease cells to evaluate the most effective treatment for the specific disease.

Figure 15A:
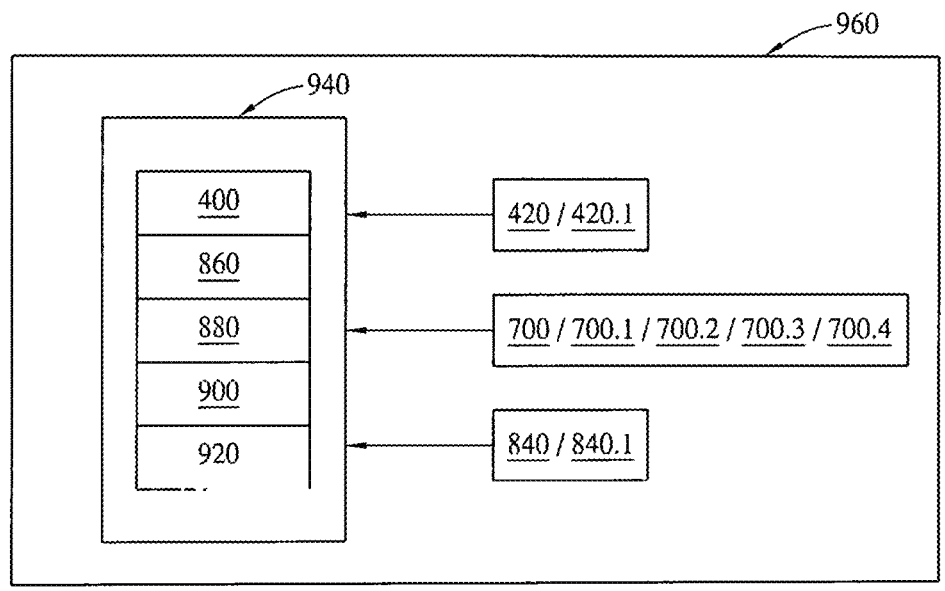
FIG. 15A illustrates integrated bioelectronics subsystems (various embodiments) to detect a disease specific biomarker/an array of disease specific biomarkers and deliver (programmable/active) bioactive compounds and/or bioactive molecules.

Bioelectronics Subsystem for Detection of a Disease Specific Biomarker/an Array of Disease Specific Biomarkers & Programmable/Active Delivery of Bioactive Compounds &/or Bioactive Molecules in Near Real-Time/Real-Time FIG. 15A illustrates an integrated bioelectronics subsystem 960 for detection of a disease specific biomarker/an array of disease specific biomarkers and programmable/active delivery of bioactive compounds 100 and/or bioactive molecules 100A in near real-time/real-time.

The integrated bioelectronics subsystem 960 at least includes (a) a microelectro-mechanical-system biomodule 420/420.1, (b) an integrated optical diagnostics biomodule 700.1/700.2/700.3/700.4, (c) an integrated electrical diagnostics biomodule 840/840.1 and (d) an electronic module 940.

Furthermore, the electronics module 940 can be fabricated/constructed on a flexible/bendable/stretchable substrate by lifting off the electronics circuit layer from a rigid semiconductor substrate and then bonding/connecting the lifted off electronics circuit layer on nanoribbons of wires mounted onto a lightweight and stretchable membrane, wherein the wires can bend, twist and stretch, while maintaining their functionality.

The integrated bioelectronics subsystem 960 can stick to the biological transport medium via the van der Waals force, without the need of an adhesive.

Thus, the integrated bioelectronics subsystem 960 can be removed easily from the biological transport medium (e.g., skin).

The electronics module 940 can integrate: (a) an electrical power providing component 400, (b) a microprocessor component 860, (c) a memory/data storage component 880, (d) a wireless (radio) transceiver component 900 and (e) an embedded operating algorithm 920.

By way of an example and not by way of any limitation, the wireless (radio) transceiver component 900 can be configured with Wibree, Bluetooth, WiFi and near field communication.

Other bio/health sensors to monitor vital health parameters (e.g., blood sugar and heart rate) can be integrated with the electronics module 940 to monitor vital health parameters (e.g., blood sugar and heart rate).

Silicon on Insulator as an Integration Platform Substrate for the Integrated Bioelectronics Subsystem 960

For fabricating/constructing a compact bioelectronics subsystem 960 optical components/electronics circuitry components can be attached (including flip-chip bonding on metalized thermal bumps integrated with thin-film solder) on silicon on insulator as an integration platform substrate. Printed Electronics Over a Three-Dimensional Structure for Miniaturization/Manufacturing of the Integrated Bioelectronics Subsystem 960

Aerosol jet can atomize nanoparticle based print materials into microscopic droplets. These microscopic droplets can be focused utilizing a sheath of gas into a precise jet stream by a nozzle.

The nozzle can be placed about 5 millimeters away from a surface/irregular shaped surface.

Both the nozzle and a container securing the surface/irregular shaped surface can be manipulated through different angles to print (size smaller than 0.01 millimeters wide) on a three-dimensional structure.

Higher level of miniaturization and manufacturing can be realized, utilizing printed electronics (e.g., aerosol nanoparticle jet to print an antenna, electronics circuitry, radio frequency component and sensor).

Furthermore, printed electronics can print a section of the integrated bioelectronics subsystem 960 over a three-dimensional structure, instead of assembling many discrete components.

However, printed electronics can be extended to any substrate of any material of any shape.

For example, resting arms of a wheel chair can be printed with various bio/health sensors to monitor vital health parameters (e.g., blood pressure, blood sugar, heart rate, % oxygen in blood and weight) and low-power wireless sensors (e.g., Wibree, Bluetooth, WiFi and near field communication) to transmit such vital health parameters to a portable Internet appliance for statistical analysis, then eventually to a healthcare professional.

Furthermore, DuPont Kevlar and carbon fiber can be utilized to reduce the weight of the wheel chair.

Alternatively, fiber-reinforced composite (thermoplastic composite) can be utilized to reduce the weight of the wheel chair. Alternatively, a nanocomposite material composed of graphene flakes, carbon nanotubes and a poly vinyl alcohol (PVA) binder matrix, can be utilized to reduce the weight of the wheel chair. Carbon nanotubes and graphene flakes can form an interconnected network within the poly vinyl alcohol binder matrix. Strength of the nanocomposite material can be varied by changing the weight ratio (from 0.1 to 1) of carbon nanotube to graphene flakes. Alternatively, a material matrix (of either carbon fiber or polyacrilonitrile nanofiber) can be added with 1 wt % to 10 wt % graphene (or 1 wt % to 10 wt % graphene like nanostructual material) and/or 1 wt % to 10 wt % nanotubes (e.g., boron nitride/carbon) to form a nanocomposite. Such a nanocomposite can be utilized to reduce the weight of the wheel chair.

The integrated bioelectronics subsystem 960 can communicate with an integrated intelligent expert algorithm (utilizing an artificial intelligence algorithm and/or a neural network algorithm and/or a fuzzy/neuro-fuzzy algorithm) of diseases/treatments (the integrated intelligent expert algorithm can be located at a cloud based data storage unit, wherein the cloud based data storage unit can be configured with an additional hardware and/or software to spill out volumes of wrong data, in an event of memory-access-pattern security breach).

Furthermore, the intelligent expert algorithm can be complimented by a collection of inputs (including identification of images) from healthcare professionals. The inputs from the healthcare professionals can be in near real-time/real-time. These inputs can complement/enhance the intelligent expert algorithm.

Furthermore, the integrated intelligent expert algorithm can include: statistical analysis (e.g., Student t-test, ANOVA (analysis of variance) and Chi-Square), data mining, ANN (artificial neural network), hierarchical cluster analysis, KNN (K-nearest neighbor analysis) and performance analysis (e.g., specificity, sensitivity and accuracy).

Furthermore, the integrated intelligent expert algorithm can be enhanced by a first set of intelligent learning instructions-such as: artificial intelligence, data mining, fuzzy/neuro-fuzzy logic, machine vision, natural language processing, neural networks, pattern recognition, reasoning modeling (including hypothesis based reasoning modeling) and self-learning (including evidence based learning) and a second set of intelligent learning instructions-such as: algorithm-as-a-service, patients' behavior/nutrition modeling, physical search algorithm and software agent.

Figure 15B:
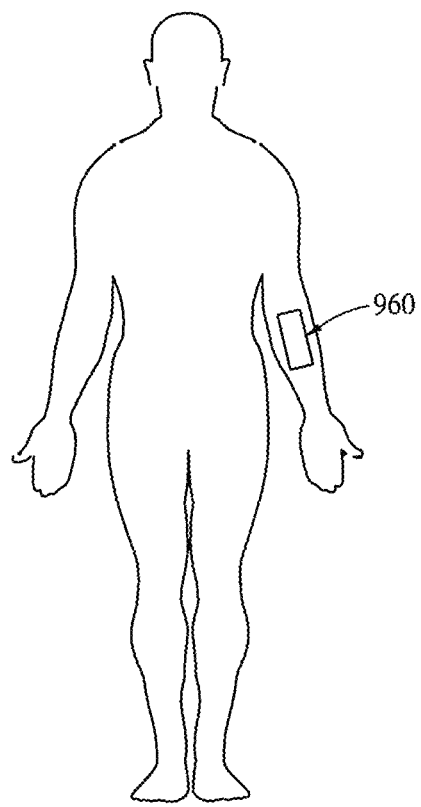
FIG. 15B illustrates a near real-time/real-time application of the wearable integrated bioelectronics subsystem.

FIG. 15B illustrates a near real-time/real-time application of a wearable integrated bioelectronics subsystem of 960.

The above bioelectronics subsystem 960 can enable near real-time/real-time measurement of a disease specific biomarker and instantaneous programmable/active delivery of the bioactive compounds 100 and/or bioactive molecules 100A in near real-time/real-time (via a dynamic closed feedback loop).

The above bioelectronics subsystem 960 can enable near real-time/real-time measurement of a disease specific biomarker and delayed programmable/active delivery of the bioactive compounds 100 and/or bioactive molecules 100A in near real-time/real-time (via a dynamic closed feedback loop) utilizing a remote wireless command from a healthcare professional.

Rapid Point of Care Detection of a Disease/an Array of Diseases by a DNAzyme/an Array of DNAzymes on a Substrate/Membrane with an Array of Plasmonic Optical Nanoantennas Gold nanoparticles absorb light. The wavelength of absorption depends on whether the nanoparticles are separated or aggregated. The difference in color can be seen with the naked eye. A powder of individual particles appears red, but when the powder aggregates, it appears blue-violet in color. The difference in color can be seen with a naked eye.

DNAzyme is a synthetic DNA molecule that can enzymatically split another nucleic acid molecule.

Gold nanoparticles chemically bonded with DNAzyme in a powder/solution form on a membrane/paper/polymer substrate. Furthermore, gold nanoparticles chemically bonded with DNAzyme may be preserved by drying in sugar for an extended period of time.

When a disease specific gene from a human body's blood/biological fluid is introduced, the DNA can be cleaved from the gold nanoparticles, turning the color of the membrane/paper/polymer substrate red in color.

The membrane/paper/polymer substrate can have many strips. Each strip is configured with a disease specific DNAzyme to test a disease specific gene.

Furthermore, each separate strip of the membrane/paper/polymer substrate can be integrated with an array of large numbers (e.g., billions) of plasmonic optical nanoantennas to significantly enhance the change in color.

Rapid Point of Care Detection of a Disease/an Array of Diseases by a Designer Protein/an Array of Designer Proteins on a Substrate/Membrane with an Array of Plasmonic Optical Nanoantennas A membrane/paper/polymer substrate can have many strips. Each strip is configured with a disease specific designer protein to test a specific disease.

A disease specific designer protein has a leave-one-out configuration, wherein each protein has an omitted segment to create a binding site to fit to a disease specific protein.

For example, a synthetic designed-in protein analogous to an abnormal protein (produced by mutated BRCA1 gene or BRCA2 gene) has a leave-one-out configuration to create a binding site to detect the breast cancer disease. The above example can be applied to an array of synthetic designed-in proteins analogous to abnormal proteins (produced by mutated BRCA1 gene or BRCA2 gene). Other mutations as single nucleotide polymorphisms (SNP) in pieces of chromosomes may be linked to higher breast cancer disease risk with an abnormal BRCA1 gene or BRCA2 gene.

The disease specific design protein can be integrated with a fluorescent protein (e.g., Green Fluorescent Protein (GFP)) or a fluorophore (e.g., fluorophore based on quantum dot).

Furthermore, each separate strip of the membrane/paper/polymer substrate can be integrated with an array of large number (e.g., billions) of plasmonic optical nanoantennas to significantly enhance the fluorescence upon binding with the specific disease protein, to fit at the binding site of the designer protein with the specific leave-one-out configuration.

Early Point of Care Detection of a Disease with Exosomes and Plasmonic Optical Nanoantennas Serum can be separated from blood. Serum can be mixed and incubated at 4° C. with System Bio Exoquick and further centrifuged and filtered to isolate exosomes. Furthermore, to obtain embedded proteins and RNAs within the exosomes, a suitable chemical (e.g., System Bio company's Micro SeraMir) can break membrane of exosomes. Isolation of exosomes can be automated by a robotic tool.

A disease specific designer protein (integrated with a fluorescent protein or a fluorophore) has a leave-one-out configuration, wherein each protein has an omitted segment to create a binding site to fit a disease specific protein, which was once caged within the exosomes.

Similarly, a disease specific aptamer (integrated with a fluorescent protein or a fluorophore) can bind with a disease specific mRNA, which was once caged within the exosomes.

Light scattering and/or reflected fluorescence can detect/quantify disease specific proteins and/or messenger RNAs, which were once caged within the exosomes.

Plasmonic optical nanoantennas can be integrated with a fluorescent protein or a fluorophore to enhance fluorescence. Alternatively, fluorescence can be magnified with an array (e.g., billions) of plasmonic optical nanoantennas within the fluid chamber, containing specific proteins and/or messenger RNAs and/or piRNAs which were once caged within the exosomes.

Measurement of fluorescence can be performed by the optical diagnostics biomodule 700A (FIG. 9A), or 700C (FIG. 10A) or 700D (FIG. 11A) or 700E (FIG. 12A).

Early Point of Care Detection of a Disease with Exosomes, Microfluidic-Photonics Circuit and Plasmonic Optical Nanoantennas Alternatively, in the first part, a microfluidic-photonics circuit (MPC) chip can take blood samples at inlets. The microfluidic-photonics circuit chip consists of a set of chambers molded in poly(dimethylsiloxane) (PDMS). The microfluidic-photonics circuit messenger RNAs (MPC) chip is degassed via vacuum prior to its use and the absorption of gas by poly(dimethylsiloxane) provides the mechanism for actuating and metering the flow of fluid in the microfluidic channels and chambers.

In a second part, the microfluidic-photonics circuit chip can use tiny microfluidic channels of 30 microns in diameter underneath the inlets to separate the serum from the blood by utilizing laws of microscale physics. The serum moves through the microfluidic-photonics circuit chip via a process called degas-driven flow.

Superparamagnetic nanoparticles iron oxide ($Fe_3O_4$) can be synthesized with a positive electrical charge to bond onto the membrane surface of exosomes (exosomes are found within a human body's blood/biological fluid) of negative electrical charge due to electrostatic interactions. In a third part, the microfluidic-photonics circuit chip can be integrated with a magnet. Exposure to a magnetic field can separate superparamagnetic nanoparticles iron oxide bonded with exosomes.

Alternatively, a third part of the microfluidic-photonics circuit chip can be integrated with a nanosieve/nanomembrane (e.g., a carbon nanomembrane) of about 100 nanometers pore diameter to filter only exosomes.

Furthermore, a suitable chemical (e.g., System Bio company's Micro SeraMir) can be added in a fourth part of the microfluidic-photonics circuit chip to break the membrane of exosomes to obtain embedded RNAs and proteins within the exosomes.

The fourth part of the microfluidic-photonics circuit has a disease specific aptamer (integrated with a fluorescent protein or a fluorophore) to bind with a disease specific mRNA, which was once caged within the exosomes.

Furthermore, the fourth part of the microfluidic-photonics circuit chip has a disease specific designer protein (integrated with a fluorescent protein or a fluorophore) with a leave-one-out configuration, wherein each protein has an omitted segment to create a binding site to fit a disease specific protein, which was once caged within the exosomes.

Light scattering and/or reflected fluorescence can detect/quantify disease specific mRNAs and/or proteins which were once caged within the exosomes.

Plasmonic optical nanoantennas can be integrated with the fluorescent protein or the fluorophore (e.g., quantum dot fluorophore) to enhance fluorescence.

Alternatively, the fourth part of the microfluidic-photonics circuit has an array (e.g., billions) of plasmonic optical nanoantennas on the floor of the fourth part of the microfluidic-photonics circuit to enhance fluorescence.

In one instance, a modified microfluidic-photonics circuit chip without separating the serum from in a human body's blood can be utilized-thus the serum separation part is not needed. In this instance, the first part of the modified microfluidic-photonics circuit chip can contain a large array of nickel coated superparamagnetic nanoparticles iron oxide/nickel coated magnetic beads to detect malaria, as nickel chemically binds with a protein namely histidine-rich protein 2, produced by malaria in a human body's blood The large array of nickel coated superparamagnetic nanoparticles iron oxide/nickel coated magnetic beads chemically bonded with histidine-rich protein 2 (produced by malaria) can be isolated by a magnet in the second part of the modified microfluidic-photonics circuit chip.

In a third part of the modified microfluidic-photonics circuit chip, contaminants on nickel coated superparamagnetic nanoparticles iron oxide/nickel coated magnetic beads chemically bonded with histidine-rich protein 2 (produced by malaria) can be washed.

In a fourth part, the modified microfluidic-photonics circuit chip contains a suitable salt solution to bind with nickel-thus histidine-rich protein 2 (produced by malaria) can be detached.

In the fifth part, the modified microfluidic-photonics circuit has a disease specific aptamer (integrated with a fluorescent protein or a fluorophore) to bind with histidine-rich protein 2 (produced by malaria).

Alternatively, the fifth part of the modified microfluidic-photonics circuit chip has malaria disease specific designer protein (integrated with a fluorescent protein or a fluorophore) with a leave-one-out configuration, wherein malaria disease specific designer protein has an omitted segment to create a binding site to fit with histidine-rich protein 2 (produced by malaria).

Light scattering and/or reflected fluorescence can detect/quantify histidine-rich protein 2 (produced by the malaria).

Plasmonic optical nanoantennas can be integrated with the fluorescent protein or the fluorophore (e.g., quantum dot fluorophore) to enhance fluorescence.

Alternatively, the fifth part of the modified microfluidic-photonics circuit has an array (e.g., billions) of plasmonic optical nanoantennas on the floor of the fifth part of the modified microfluidic-photonics circuit to enhance fluorescence.

In another instance, a modified microfluidic-photonics circuit chip without separating the serum from in a human body's blood can be utilized-thus the serum separation part is not needed. In this instance, a first part of the modified microfluidic-photonics circuit chip can contain a large array of silica coated superparamagnetic nanoparticles iron oxide/silica coated magnetic beads to detect tuberculosis, as silica chemically binds with the DNA of tuberculosis.

The large array of silica coated superparamagnetic nanoparticles iron oxide/nickel coated magnetic beads chemically bonded with DNA of tuberculosis can be isolated by a magnet in a second part of the modified microfluidic-photonics circuit chip.

In a third part of the modified microfluidic-photonics circuit chip, contaminants on silica coated superparamagnetic nanoparticles iron oxide/nickel coated magnetic beads chemically bonded with the DNA of tuberculosis can be washed.

The fourth part of the modified microfluidic-photonics circuit has the tuberculosis specific aptamer (integrated with a fluorescent protein or a fluorophore) to bind with the DNA of tuberculosis.

Plasmonic optical nanoantennas can be integrated with the fluorescent protein or the fluorophore (e.g., quantum dot fluorophore) to enhance fluorescence.

Light scattering and/or reflected fluorescence can detect/quantify the DNA of tuberculosis.

Alternatively, the fourth part of the modified microfluidic-photonics circuit has an array (e.g., billions) of plasmonic optical nanoantennas to enhance fluorescence.

X-Ray Fluorescence Diagnostics Biomodule Utilizing an Array of Microcapillaries & an Array of Miniature X-Ray Sources An array of microcapillaries containing a biological sample can be excited by an array of miniature x-ray sources (powered by the portable electrical power providing component) to induce x-ray fluorescence in the biological sample for various elemental concentrations related to a disease.

Furthermore, multiple DNAs and/or protein biomarkers can be detected based on characteristic x-ray fluorescence.

The array of sharp tips of a pyroelectric crystal (e.g., lithium niobate/lithium tantalite can be fabricated/constructed on a thin-film resistor. The array of sharp tips can be capped with a metal thin-film. The metal thin-film emits x-rays when bombarded by electrons emitted by the sharp tips.

The x-ray fluorescence can be detected by an array of silicon drift detectors. Due to the unique process/fabrication technology of the silicon drift detectors, the leakage current of the silicon drift detectors is low such that the silicon drift detectors can be operated with a moderate cooling, provided by a single stage thermoelectric cooler (TEC)/microrefrigerator.

Furthermore, a high-efficiency nanostructure 50 A° thick $Sb_2Te_3$/10 A° thick $Bi_2Te_3$ based thin-film superlattices miniature thermoelectric cooler/microrefrigerator (about 1 millimeter×3 millimeters in size) can be utilized to cool the array of silicon drift detectors.

However, significant thermoelectric cooler/microrefrigerator efficiency can be gained by fabricating a quantum wire/quantum dot, transitioning from a two-dimensional superlattice.

Retinal Contact Lens Biomodule Subsystem for Detection of a Disease Specific Biomarker/an Array of Disease Specific Biomarkers & Programmable/Active Delivery of Bioactive Compounds &/or Bioactive Molecules in Near Real-Time/Real-Time Specific proteins (e.g., a protein biomarker of Alzheimer disease) can accumulate in the retina. These specific proteins can be utilized to diagnose disease specific biomarkers/an array of disease specific biomarkers in near real-time/real-time.

Figure 16A:
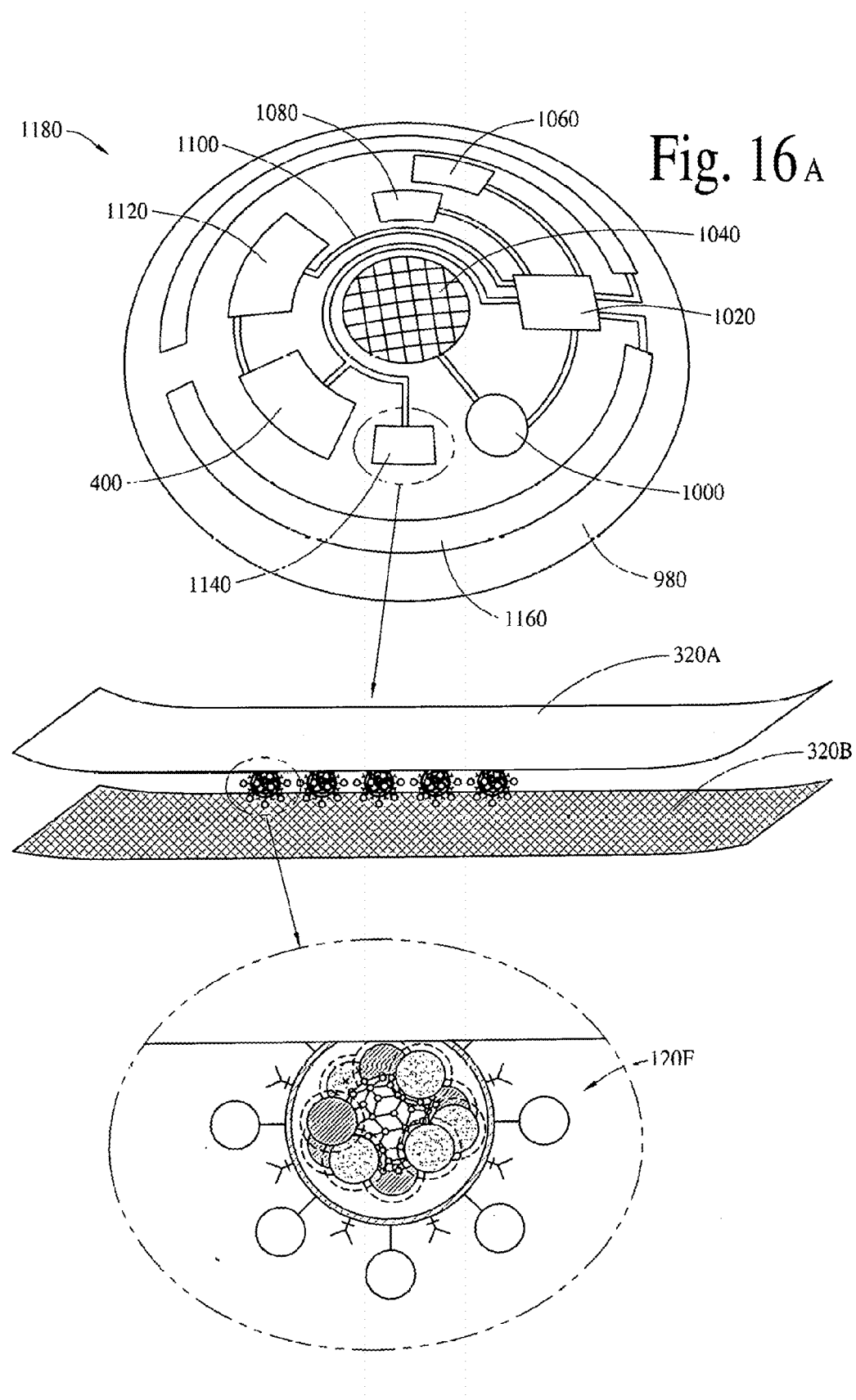
FIG. 16A illustrates a retinal contact lens subsystem to detect a disease specific biomarker/an array of disease specific biomarkers and deliver (programmable/active) bioactive compounds and/or bioactive molecules.

FIG. 16A illustrates a retinal contact lens biomodule subsystem 1180 on a biocompatible frame 980.

The biocompatible frame 980 can be fabricated/constructed, utilizing liquid crystal polymers/polyimide/silica/silicon/silk/SU-8 resin/other suitable material.

Furthermore, if needed, the biocompatible frame 980 can be coated with a fluorinated silicon material to protect against water and/or oil.

The retinal contact lens biomodule subsystem 1180 can integrate: (a) a control circuitry component 1000, (b) an array of display pixels 1020, (c) an array of microlenses 1040, (d) a biosensor component 1060, (e) a biosensor read-out component 1080, (f) a solar cell component 1120, (g) a micropatch component 1140, (h) a low-power wireless (radio) transmitter (with an antenna) component 1160 and (g) an electrical power providing component (e.g., a printed thin-film battery or an array of glucose fuel cells) 400, utilizing a connecting electrical contact layer 1100.

Example of a biosensor component 1060: Blood sugar measurement can involve an electrochemical reaction activated by an enzyme. Glucose oxidase can convert glucose into hydrogen peroxide and other chemicals-thus their concentrations can be measured with a miniature potentiostat or nanosized potentiostat as a biosensor for calculating the glucose level in tears. Furthermore, the biosensor component 1060 can be integrated with an analog signal to digital signal converter circuit.

A glucose fuel cell consists of a platinum catalyst that strips electrons from glucose-mimicking the activity of cellular enzymes that break down glucose to generate ATP.

Multi-layers of positive electrical charged ferritin protein, separated by a layer of nanocrystals, from multi-layers of negative electrical charged ferritin protein—sandwiched between two (2) transparent metal electrodes on a biocompatible substrate (e.g., silk) can act as the solar cell component 1120.

Furthermore, the micropatch component 1140, can consists of porous nanoshells or nanodiamonds to deliver timolol maleate (which is commonly used in eye drops) to manage glaucoma.

Printed Electronics Over a Three-Dimensional Structure for Miniaturization/Manufacturing of the Retinal Contact Lens Biomodule Subsystem Printed electronics can print a section of the retinal contact lens biomodule subsystem 1180 over a three-dimensional structure, instead of assembling many discrete components. Higher levels of miniaturization and manufacturing can be realized, utilizing printed electronics (e.g., aerosol nanoparticle jet to print an antenna, electronics circuitry, radio frequency component and sensor).

The retinal contact lens biomodule subsystem 1180 can be fabricated/constructed by lifting off the electronics circuit layer from a rigid semiconductor substrate and then bonding/connecting, the lifted off electronics layer on nanoribbons of wires mounted onto a lightweight and stretchable membrane, wherein the wires can bend, twist and stretch, while maintaining their functionality.

Furthermore, the micropatch components 1140 can integrate a microelectro-mechanical-system reservoir to store the bioactive compounds 100 and/or bioactive molecules 100A for a sustained delivery. The above retinal contact lens biomodule subsystem 1180 can enable a near real-time/real-time measurement of a disease specific biomarker and programmable/active delivery of the bioactive compounds 100 and/or bioactive molecules 100A in near real-time/real-time (via a dynamic closed feedback loop).

Figure 16B:
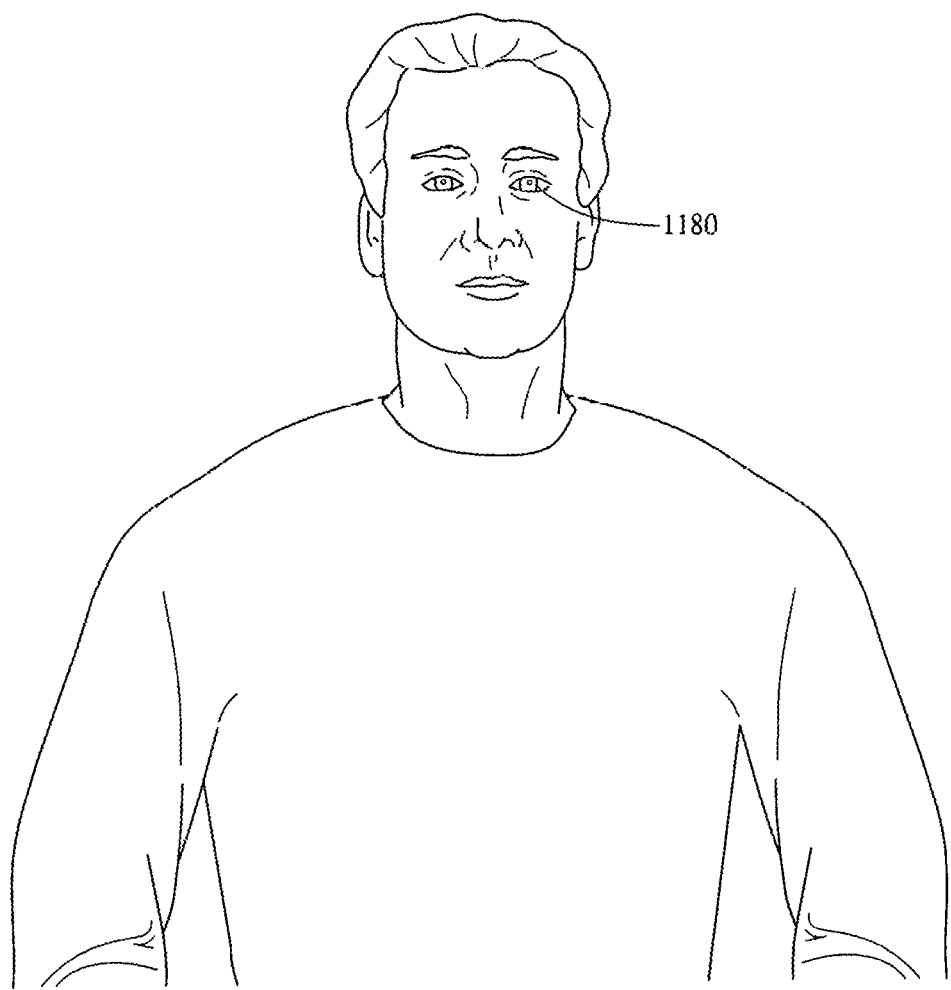
FIG. 16B illustrates a near real-time/real-time application of the wearable retinal contact lens subsystem in FIG. 16A.

FIG. 16B illustrates a near real-time/real-time application of a wearable retinal contact lens biomodule subsystem 1180.

Near Real-Time/Real-Time Wearable Integrated Bioelectronics Subsystem, as an Augmented Reality Personal Assistant FIGS. 17A, 17B, 17C, 17D and 17E illustrate a near real-time/real-time wearable bioelectronics subsystem 1580.

FIG. 17A illustrates a near real-time/real-time wearable subsystem 1540 with a bifocal retinal contact lens 1180A on a biocompatible frame 980.

The bifocal retinal contact lens 1180A on the biocompatible frame 980 has two (2) different focal lengths—one can focus foreground light into the middle of the pupil, while the other can focus the background light onto the edge of the pupil. Furthermore, the bifocal retinal contact lens 1180A can be embedded with optical nanostructures to achieve higher optical performances.

The biocompatible frame 980 can be fabricated/constructed, utilizing liquid crystal polymers/polyimide/silica/silicon/silk/SU-8 resin/other suitable material.

Furthermore, if needed, the biocompatible frame 980 can be coated with a fluorinated silicon material to protect against water and/or oil.

The bifocal retinal contact lens 1180A can be fabricated/constructed, utilizing liquid crystal polymers/polyimide/silica/silicon/silk/SU-8 resin/other suitable material. Furthermore, a photochromic transparent nanoemulsion polymer material can be used, which has an ability to block glare by darkening immediately in strong sunlight and to revert back to transparency in normal sunlight. The photochromic transparent nanoemulsion polymer material also can offer ultraviolet-blocking ability, high water content, oxygen permeability and suitable mechanical properties.

Furthermore, the bifocal retinal contact lens 1180A on a biocompatible frame 980 can optionally integrate (a) a biosensor component 1060, (b) biosensor read-out component 1080 and (c) a micropatch component 1140 to enable a near real-time/real-time measurement of a disease specific biomarker and programmable/active delivery of the bioactive compounds 100 and/or bioactive molecules 100A in near real-time/real-time (via a dynamic closed feedback loop).

A common cause of blindness is when a retina is damaged by diseases that kill the photoreceptors and/or destroy the circuits that create the coded neural pulses. But often these diseases do not damage the output cells. The bifocal retinal contact lens 1180A on a biocompatible frame 980 can integrate (a) an artificial retina system which can consist of an array of thin-film electrodes (in a biocompatible package) for stimulating the retina, a visual processing unit, a miniature video camera and a transmitter mounted on an eye glass frame. The array of the thin-film electrodes should conform to the curvature of the retina. Thus, the array of thin-film electrodes should be fabricated/constructed on flexible polymers.

An artificial retina can require high-density electrical interconnects between the array of the thin-film electrodes and a biocompatible package.

The high-density electrical interconnects can be fabricated/constructed, utilizing an array of carbon fibers (about 10 microns in diameter), wherein each carbon fiber is coated with chemicals to prevent moisture, ionic and biological contamination from causing a failure/damage of the carbon fiber.

The high-density electrical interconnects should be insulated/hermetically sealed in a biocompatible package (e.g., fabricated/constructed, utilizing polycrystalline diamond material) to prevent moisture, ionic and biological contamination from causing a failure of the artificial retina.

A light pattern incident to the artificial retina can be converted into a set of mathematical equations/codes of electrical pattern. An encoder chip can convert a general light pattern (incident on a retina) into a set of mathematical equations/codes of an electrical pattern.

A miniaturized projector-decoder chip can convert the above electrical pattern into a modified coded light pattern to drive the light-sensitive proteins (these light-sensitive proteins can be delivered by the nanoshell 120 and/or by gene therapy in the ganglion cells) to the modified light pattern to a human brain, which understands the stream of coded light pattern to translate into meaningful images.

Furthermore, an encoder circuit, a decoder circuit and a biocircuit (a biocircuit fabricated/constructed, utilizing DNA, RNA and protein to respond to biological signals) can be integrated in the biocompatible package.

Alternatively, a retinal implant microchip can be used below the fovea (area of sharpest vision in the retina). The retinal implant microchip is approximately 3 millimeters×3 millimeters in area and 50 microns in thickness. The retinal implant microchip has about 1500 pixels, wherein each pixel has an area of about 75 microns×75 microns. An array of photocells (e.g., a light dependant resistor/light dependant phototransistor), an amplifying circuit, a stimulation electrode, an encoder circuit and a decoder circuit are integrated with each pixel. The photocells absorb the light entering the eye, transforming the light into electrical signals. The retinal implant microchip can be electrically powered by a subdermal coil behind the ear. The subdermal coil can be electrically powered by a battery via transdermal inductive transmission.

Furthermore, in the case of blindness caused by destroyed photoreceptors, suitable light sensitive proteins can be delivered by the nanoshell 120 and/or by gene therapy, so that sensitive proteins can chemically bind with remaining bipolar cells, wherein the bipolar cells are located below the destroyed photodetectors. These suitable light sensitive proteins can interact with an array of nano-scaled cameras to communicate with the ganglion cells for restoring vision, at least in a limited way. By way of an example and not by way of any limitation, Light Harvesting Complex II proteins of spinach can be utilized as suitable light sensitive protein.

Additionally, interactions of photons (of various wavelengths) with light sensitive protein(s) chemically bonded with cells (e.g., neurons) can be utilized to model treatment (with bioactive compounds and/or bioactive molecules) efficiency for various diseases (e.g., neurological diseases).

FIG. 17B illustrates a power unit 400, a storage/memory component 880, a wireless transceiver (e.g., a radio/millimeter wave (including 60 GHz)/terahertz band) with an antenna 900, a control circuitry component 1000, a microphone 1200, a scrolling audio recording buffer 1220, a camera (e.g., a three-dimensional holographic camera) with a built-in sensor 1240, a location determination component (e.g., an indoor positioning system-IPS component and/or a global positioning system (GPS) component) 1260 and a first PCS component (a PCS is an integration of a projector, a camera and a touch/eye motion/gesture sensor) component 1280 embedded in the eye glass frame.

Furthermore, Broadcom's BCM4752 chipset can support IPS with Bluetooth, WiFi and near field communication.

The powering unit 400 can be a nanobattery or a wireless enabled powering unit.

Figure 17C:
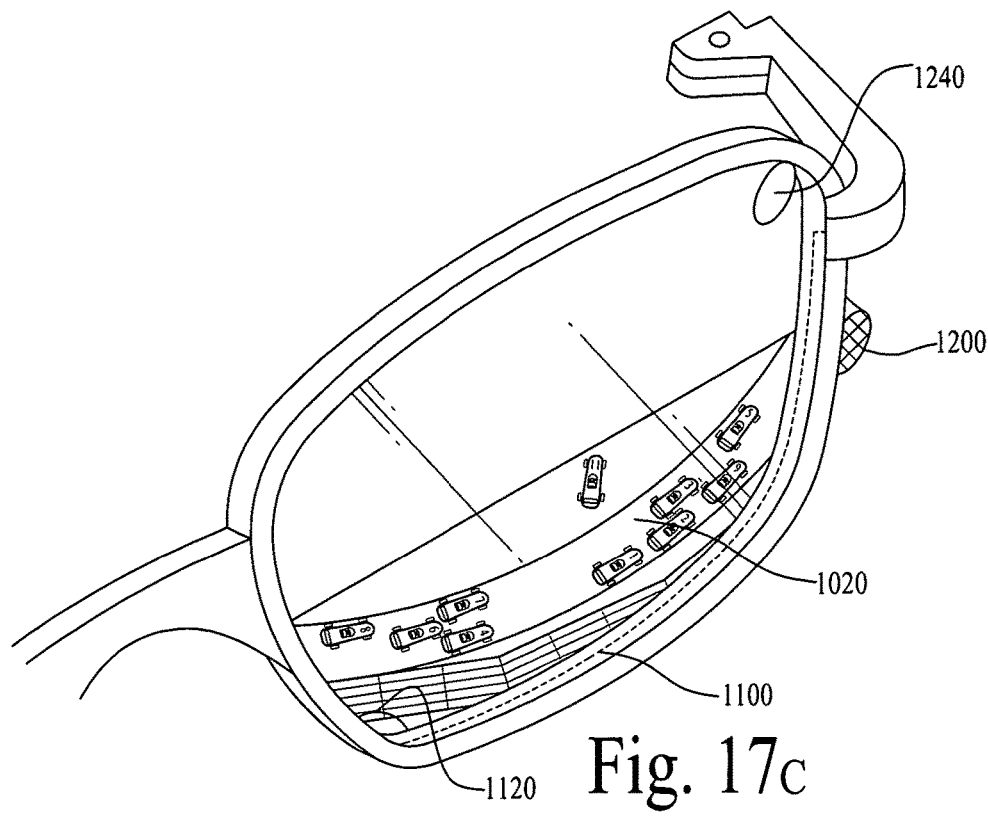

FIG. 17B also illustrates an array of display pixels (e.g., pixels of liquid-crystal display (LCD), light emitting diode (LED) and organic light emitting diode display (OLED)/quantum dots based display) 1020 covering about ½ of the eye glass, displaying an instant live action (e.g., a live surgery or a car race illustrated in FIG. 17C) or a physical environment, an electrical contact layer/thread (e.g., superstrong electrically conducting DuPont Aracon-made of Kevlar clothing fiber) 1100, a solar cell component 1120 on the corners of the eye glasses (optionally the solar cell component 1120 can be located anywhere on the frame, rather than on the corners of the eye glasses) and an integrated eye tracking sensor and decoder 1300, at the enter of the eye glass frame.

Light emitting diode display/organic light emitting diode display/quantum dots based display is limited to a few pixels, but liquid-crystal display based display can permit a larger surface.

A spherical curved liquid-crystal display based array of display pixels 1020 can enable text, images and other visuals on the spherical curved liquid-crystal display based on array of display pixels 1020.

Furthermore, liquid-crystal display-based array of display pixels 1020 can be an array of three-dimensional liquid-crystal display pixels. Details of three-dimensional liquid-crystal display are described in the later paragraphs.

The display can be integrated with an array of sensors, such sensors can be fabricated/constructed (e.g., optically sensing waveguides) by a femtosecond laser. Utilizing a femtosecond laser module, a two-dimensional/three-dimensional optically sensing waveguide(s) can be fabricated/constructed at various depths of the display substrate.

The display can be integrated with (a) a transparent image sensor based on graphene, (b) a transparent microprocessor based on nanowires (e.g., zinc oxide nanowires) and (c) a transparent battery.

The display can be integrated with a transparent solar cell (e.g., $CH_3NH_3PbI_3$-xClx perovskite based solar cell utilizing indium tin oxide (ITO) or fluorine-doped tin oxide (FTO) and gold or graphene electrode). Furthermore, the transparent solar cell can be integrated with vanadium oxide nanoparticles/thin-film for both electricity generation and electricity saving.

Additionally, the transparent microprocessor can be integrated with an array of transparent sensors (e.g., transparent vanadium oxide/bismuth ferrite based sensors). Such transparent sensors integrated with the transparent microprocessor can sense, manipulate and respond quickly, because either feedback or feed forward controls are within one integrated system-on-chip.

The display can be an integrated vanadium oxide thin-film thermochromic device, when it is activated by either voltage or temperature.

Alternatively, the display pixel 1020 can be touch-sensitive.

Alternatively, the glass material for the display pixel 1020 can be replaced by a super-strong, scratch-resistant and bendable (about 0.5 millimeters in thickness) plastic. The plastic has a fingerprint proof material layer at the front and a polymer hardening material layer at the back.

Alternatively, thin-film transistor-organic light emitting diode (TFT-OLED) display pixels 1020 can enable text, images and other visuals on the spherical curved thin-film transistor-organic light emitting diode display pixels 1020.

Furthermore, thin-film transistor can be either organic transistor based or carbon nanotube based. Carbon nanotube based thin-film transistor can be fabricated/constructed by a gravure printing method, where a plastic substrate is mounted onto a cylindrical drum, which rolls it over a flat surface that serves as a patterned mask of holes filled with inks made of the desired materials. The gravure printing method can be processed at a relatively low temperature, making it suitable with a plastic substrate. Furthermore, the gravure printing method can be utilized to fabricate/construct various sensors/micro-scaled sensors/nano-scaled sensors. Thus, a thin-film transistor-organic light emitting diode display pixel 1020 can be integrated or embedded with a sensor/micro-scaled sensor/nano-scaled sensor.

The display pixel related circuits using conventional thin-film transistors are slow for any real-time tasks. But graphene conducts electricity faster than silicon. By chemically flaking graphene, filtering it and using N-Methylpyrrolidone, transparent graphene based display pixel related circuits can be printed through a conventional inkjet printer.

FIG. 17B also illustrates a second PCS component 1280 and the microprocessor/super-processor (including a graphical processing unit) 1320 connected to an operating algorithm 920 on the right frame. Optionally, the operating algorithm 920 can be located at a cloud based data storage unit to interact with the local microprocessor/super-processor (including a graphical processing unit) 1320.

Furthermore, the operating algorithm 920 can be integrated with a voice recognition algorithm 1340, a voice-to-text conversion algorithm 1360, an algorithm to decipher and understand a sound 1380, a gesture (to interpret body movements by embedded sensors in a peripheral device (e.g., a stylus/body wear)) recognition algorithm 1400, a face recognition algorithm 1420, a pattern recognition algorithm 1440, an intelligent learning algorithm 1460 and a software agent 1480.

The intelligence from the intelligent learning algorithm 1460 can be coupled with a data mining algorithm and a predictive modeling algorithm. Both the data mining algorithm and predictive modeling algorithm can reside in a cloud based data storage unit to interact with the intelligent learning algorithm 1460.

Additionally, the voice recognition algorithm 1340, the voice-to-text conversion algorithm 1360, the algorithm to decipher and understand natural language/sound 1380, the algorithm to understand gesture (to interpret body movements by embedded sensors in a peripheral device (e.g., a stylus/body wear)) 1400, the face recognition algorithm 1420, the pattern recognition algorithm 1440, the intelligent learning algorithm 1460 and the software agent 1480 can reside in a cloud based data storage unit to interact with the local microprocessor/super-processor (including a graphical processing unit) 1320 and derive intelligence synthesized from vast amount of data patterns.

Additionally, many components can be integrated within a plastic/polymer layer (e.g., super-strong electrically conducting DuPont Aracon—made of Kevlar clothing fiber).

Figure 17D:
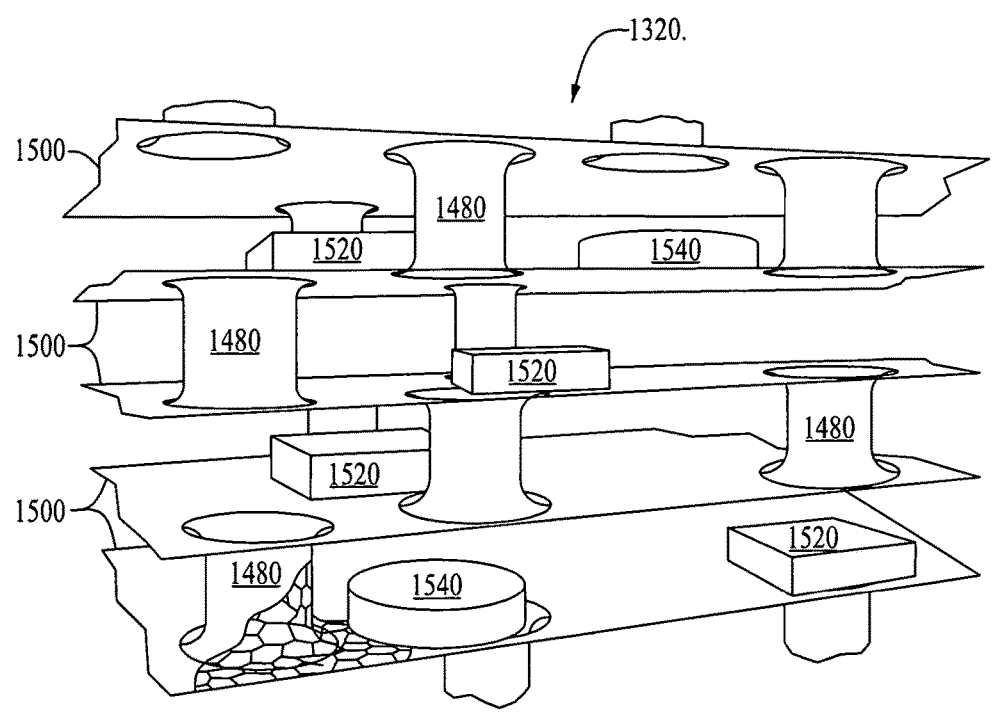

As illustrated in FIG. 17D, stacking circuits of the microprocessor/super-processor (including a graphical processing unit) 1320 in three-dimension can be achieved by utilizing a large array of vertical nanotubes (e.g., a boron nitride/carbon nanotubes) 1480 and a horizontal frame 1500 of a two-dimensional material (e.g., graphene/molybdenum sulfide) or silicene with an electrical circuit 1520 and memristor 1540-thus substantially eliminating interconnect wires. For example, memristor 1540 can be fabricated/constructed, as silver/amorphous-silicon/poly-silicon structure.

Furthermore, a large array of vertical nanotubes (e.g., boron nitride/carbon nanotube) grown on a two-dimensional material-graphene interface chemically bonded on a diamond substrate can act as a chip-to-chip interconnect, as well as a heat sink.

Alternatively, the vanadium dioxide or vanadium(III) oxide based optical switch (as described in the previous paragraphs) can be utilized as a chip-to-chip interconnect. Details of an embodiment of a chip-to-chip interconnect are illustrated in FIG. 21A of U.S. Non-Provisional patent application Ser. No. 13/448,378 entitled "SYSTEM AND METHOD FOR INTELLIGENT SOCIAL COMMERCE", filed on Apr. 16, 2012.

Stacking circuits of the microprocessor/super-processor (including a graphical processing unit) 1320 in three-dimensional can be also achieved by utilizing droplets of nanoparticle-infused liquid-thus substantially eliminating interconnect wires.

Furthermore, stacking circuits of the microprocessor/super-processor (including a graphical processing unit) 1320 in three-dimensional can be also achieved by DNA/RNA template wires for a nano-scaled circuit board-thus substantially eliminating interconnect wires.

The bifocal retinal contact lens 1180A and some components of a device 1560 can be integrated on a common biocompatible substrate. The bifocal retinal contact lens 1180A with the device 1560 is a near real-time/real-time wearable integrated bioelectronics subsystem 1580.

The near real-time/real-time wearable integrated bioelectronics subsystem 1580 can integrate a nano-scaled system. Such a nano-scaled system can include: (a) a nanoprocessor (e.g., $MoS_2$ nanoprocessor), (b) a nanomemory/nanostorage (e.g., a memristor 1540 based nanomemory/nanostorage), (c) a nanoradio transceiver with a nanoantenna (e.g., graphene based nanoantenna) and (d) a nanosensor, wherein the nanoprocessor and nanomemory are wirelessly connected for data bus by the nanoradio transceiver with the nanoantenna. A nanobattery or a wireless enabled powering unit can electrically power the nano-scaled system.

Furthermore, the near real-time/real-time wearable integrated bioelectronics subsystem 1580 can assist in memory recollection for patients with Alzheimers's disease.

FIGS. 17A, 17B, 17C, 17D and 17E illustrate the near real-time/real-time wearable integrated bioelectronics subsystem 1580, which can act as an augmented reality personal assistant to (a) eavesdrop on a user's communication (e.g., an e-mail/text/image/sensing/viewing), (b) search the internet with or without (anonymously) the user's input and (c) then recommend a solution to the user's need (utilizing the intelligent learning algorithm 1460, integrated with a predictive modeling algorithm) in near real-time/real-time.

Furthermore, the camera with a sensor 1240 is configured to track the user's hands for sensing, when the user touches anything, along with the microphone 1200 to capture the user's voice for spoken commands.

The integrated eye tracking sensor and decoder 1300 can be configured to detect a radio frequency identification tag or detect a near field communication tag or recognize an optical identification (e.g., a barcode/quick response code).

Furthermore, the integrated eye tracking sensor and decoder 1300 can be configured to communicate with other sensors (e.g., bio/health sensors) in near real-time/real-time.

For example, the integrated eye tracking sensor and decoder 1300 of the near real-time/real-time integrated bioelectronics wearable subsystem 1580, as an augmented reality personal assistant can detect the user's eye position to pinpoint an item/person that the user is focused on.

The integrated eye tracking sensor and decoder 1300 can then read the item/person and convert/record the reading into a text/image as a location based real-time snapshots of contextual world around the user.

Additionally, an indoor positioning system (IPS) can track/map how and where the user spends time both online and offline and if these are times happy or sad. Furthermore, an indoor positioning system can link location, payment pattern and personal analytics of the user in near real-time/real-time or depicting the user's daily life in near real-time/real-time ("social graph"). It should be noted that social graph is synonymous with personal analytics.

The near real-time/real-time wearable integrated bioelectronics subsystem 1580, as an augmented reality personal assistant (integrated with indoor positioning system) is with the user all the time and it already contains a host of personal information/data/preference and it can manage daily aspects of the user's life, utilizing an intelligent web portal ("social wallet").

Details of a social wallet have been disclosed in U.S. Non-Provisional patent application Ser. No. 13/448,378 entitled "SYSTEM AND METHOD FOR INTELLIGENT SOCIAL COMMERCE", filed on Apr. 16, 2012 and entire contents of this US Non-Provisional patent application are incorporated herein.

For example, by eavesdropping on the user's communication, the near real-time/real-time wearable integrated bioelectronics subsystem 1580, as an augmented reality personal assistant can anticipate the user's need for emergency healthcare and then recommend the fastest route to an emergency section of a nearby hospital by synthesizing data (anonymously searching the internet) regarding traffic, road and weather condition. If the user is about to go to the emergency section of a nearby hospital, but another healthcare facility is cheaper with a special offer. The near real-time/real-time wearable integrated bioelectronics subsystem 1580, as an augmented reality personal assistant can alert the user. Again, this can be achieved passively, without giving away the user's location.

Furthermore, the near real-time/real-time wearable integrated bioelectronics subsystem 1580, as an augmented reality personal assistant can enable the user to share location based real-time snapshots of the contextual world around the user—a way of viewing the world through someone else's eyes on his/her way to a place/event.

Figure 17E:
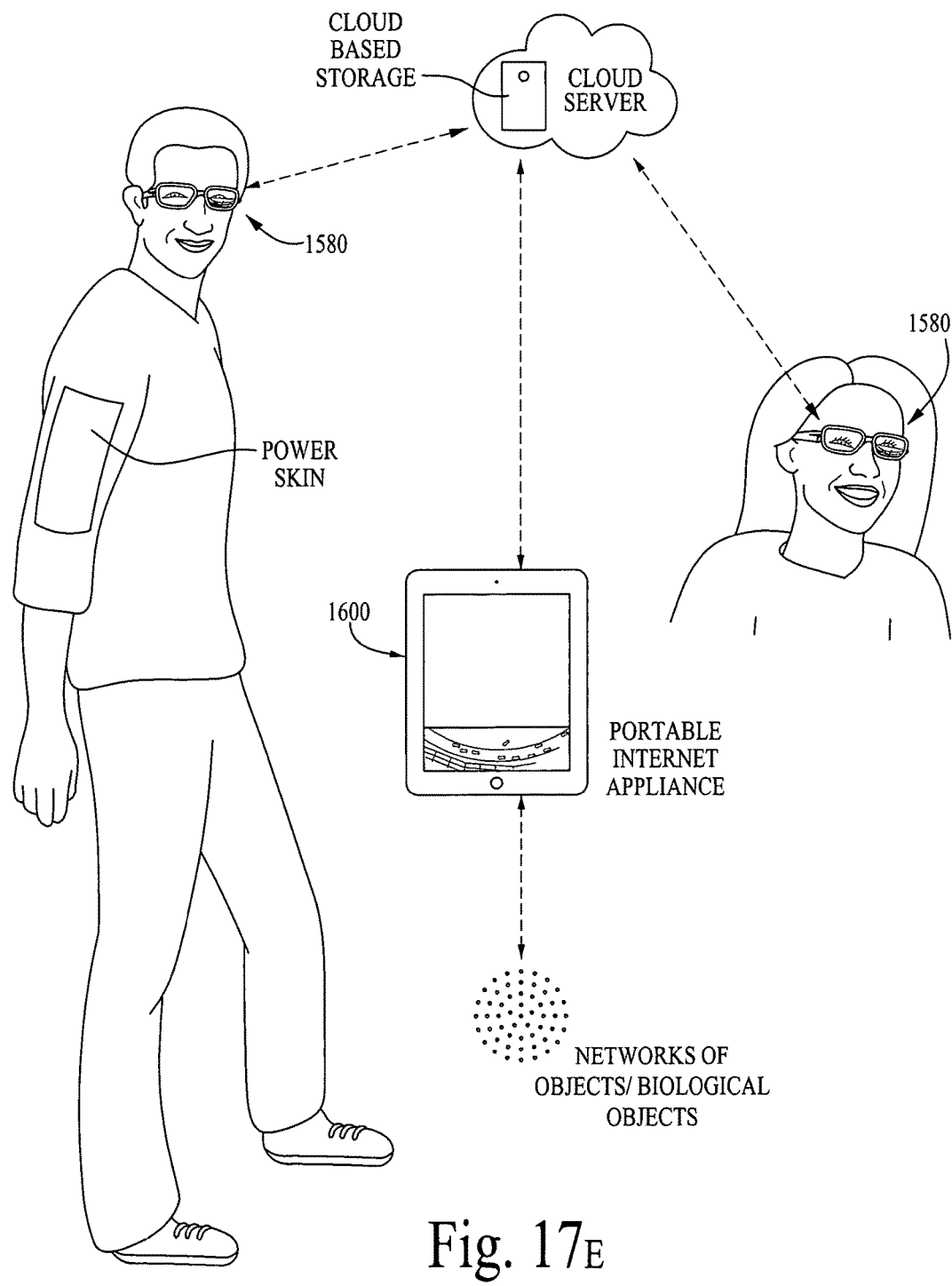
FIG. 17E illustrates interactions of a near real-time/real-time wearable bioelectronics subsystem, as an augmented reality personal assistant with another near real-time/real-time wearable bioelectronics subsystem, as an augmented reality personal assistant and a portable internet appliance via a cloud based data storage unit. The word "unit" is synonymous with the word "media unit" or with the word "media".

FIG. 17E illustrates a power skin with a thin-film printed battery or a textile nanogenerator, integrated with a textile supercapacitor (for energy storage).

Prestin protein is found in the outer hair cells of a human ear. Prestin can convert tiny vibrations into a voltage. To increase conductivity, a microbe (e.g., a bacterium Pili) can act as a conducting nanowire to transfer electrons generated by prestin. Each protein is capable of making nanowatts of electricity, but an array of prestin proteins can charge a battery. Furthermore, networks of the prestin proteins can construct a nanogenerator on the power skin, so that the user's natural movements can generate electrical power. The user's natural movements can generate electrical power in an embedded textile battery (e.g., piezoelectric zinc oxide nanowires woven in textile-fibers). Annealed (at about 125° C.)/self-assembled (aqueous-dried) thin-film of electrically conducting vanadium pentoxide fibers (with ions incorporated between the vanadium pentoxide fibers) can be utilized as a suitable electrically conducting fiber electrode for the power skin. The electrical properties and mechanical properties of annealed (at about 125° C.)/self-assembled (aqueous-dried) thin-film of electrically conducting vanadium pentoxide fibers can vary according to an amount of the water content. A direct synthesis of multi-layer graphene and porous carbon woven composite films by chemical vapor deposition on Ni gauze templates can be achieved. The composite films integrate the dual advantages of graphene and porous carbon, having not only the excellent electrical properties and flexibility of graphene, but also the porous characteristics of amorphous carbon. The multi-layer graphene/porous carbon woven fabric film can enable a textile supercapacitor.

Furthermore, the power skin can be integrated with a component to detect a radio frequency identification tag or to detect a near field communication tag or to recognize an optical identification (e.g., a barcode/quick response code).

The near real-time/real-time wearable integrated bioelectronics subsystem 1580, as an augmented reality personal assistant can (a) determine the location of the user, (b) upload a location based real-time snapshots of the contextual world around the user to a cloud based data storage unit and (c) instantly share a location based real-time snapshots of the contextual world around the user, with another near real-time/real-time wearable integrated bioelectronics subsystem 1580, as an augmented reality personal assistant and a portable internet appliance, wherein the portable internet appliance is connected with an object/an array of objects, wherein the object is fabricated/constructed with at least a sensor and a wireless transmitter.

Additionally, the components of the object can be packaged by a redistributive chip packaging (RCP) method.

The near real-time/real-time wearable integrated bioelectronics subsystem 1580, as an augmented reality personal assistant can enable a pay-per-gaze advertising model that involves billing an advertiser if the user looks at an ad online or offline while wearing the near real-time/real-time wearable integrated bioelectronics subsystem 1580.

Furthermore, the near real-time/real-time wearable integrated bioelectronics subsystem 1580, as an augmented reality personal assistant can enable a pay-per-interact advertising model that involves billing an advertiser if the user interacts with an ad online or offline while wearing the near real-time/real-time wearable integrated bioelectronics subsystem 1580.

The near real-time/real-time wearable integrated bioelectronics subsystem 1580, as an augmented reality personal assistant, can enable an application (e.g., navigation, photo capture and sharing information). Thus, a surgeon can have a patient's vital information in front of his/her eyes, while operating the patient.

The near real-time/real-time wearable integrated bioelectronics subsystem 1580, as an augmented reality personal assistant can enable the user interact with virtual items, as the camera a built-in sensor 1240, is configured to track hands for sensing, when the user touches anything along with the microphone 1200 to capture the user's voice for spoken commands in natural language.

Furthermore, the near real-time/real-time wearable bioelectronics subsystem 1580, as an augmented reality personal assistant, can be integrated with a headset to block out all external light-thus enabling a high-definition image (in front of the user's eyes) for an immersive experience. The headset can be synchronized with the near real-time/real-time wearable bioelectronics subsystem 1580 to track the user's head movement and/or eye movement. For example, the near real-time/real-time wearable bioelectronics subsystem 1580 can be utilized for:

(a) E-mails, text messages, Facebook updates, tweets, appointments & incoming phone calls;
(b) Breaking news, weather, stock data and sport results;
(c) Real-time feedback on action sports;
(d) Turn by turn directions;
(e) Aid for hearing impaired;
(f) Translations when talking in different languages;
(g) Patients' body data to a surgeon;
(h) Remote training for surgery;
(i) Teleprompter for public speaking;
(j) Subtitles at the movies (for hearing impaired and/or for different languages);
(k) Teaching and discovery;
(l) Details about art in a museum;
(m) Social graph/Personal Analytics; and
(n) Gaming.

FIG. 17E illustrates interactions of a near real-time/real-time wearable bioelectronics subsystem 1580, as an augmented reality personal assistant, with (a) another near real-time/real-time wearable bioelectronics subsystem, as an augmented reality personal assistant, and (b) the portable internet appliance 1600 via a cloud based data storage unit.

The near real-time/real-time wearable bioelectronics subsystem 1580, as an augmented reality personal assistant with a fast internet connection, real-time location data, personal information/profile, appointments/calendar, chats/e-mails (or eavesdropping on chats/e-mails/conversations in natural language in near real-time/real-time), payment/purchase history and a changing social graph (of the user) can anticipate what information the user may/will need based on context and past behavior-thus to provide it, before they have even asked for it. For example: spontaneously and predictively suggesting that the user should stay in the hotel room, because of heavy traffic in the downtown of the city and offer personalized suggestions for a dinner in the hotel.

The near real-time/real-time wearable bioelectronics subsystem 1580, as an augmented reality personal assistant with a fast internet connection, real-time location data, personal information/profile, appointments/calendar, chats/e-mails (or eavesdropping on chats/e-mails in near real-time/real-time), payment/purchase history and a changing social graph (of the user) can eavesdrop on the user's communication, utilizing (a) an intelligent learning algorithm and/or (b) an algorithm for understanding communication, wherein the intelligent learning algorithm and/or the algorithm for understanding communication can be stored in a local data storage unit or a cloud based data storage unit.

In connection with (a) another near real-time/real-time wearable bioelectronics subsystem 1580, as an augmented reality personal assistant, and (b) the portable internet appliance via a cloud based data storage unit, the near real-time/real-time wearable bioelectronics subsystem 1580, as an augmented reality personal assistant with a fast internet connection, real-time location data, personal information/profile, appointments/calendar, chats/e-mails (or eavesdropping on chats/e-mails/conversations in natural language in near real-time/real-time), payment/purchase history and a changing social graph (of the user), can anticipate what information the user may/will need based on context and past behavior-thus to provide it, before they have even asked for it. For example: spontaneously and predictively suggesting that the user should buy a new dress prior to the job interview and offer personalized suggestions for the new dress.

Portable Internet Appliance

Details of a portable internet appliance 1600 have been disclosed in U.S. Non-Provisional patent application Ser. No. 12/238,286 entitled, "PORTABLE INTERNET APPLIANCE", filed on Sep. 25, 2008 and the entire contents of this US Non-Provisional patent application are incorporated herein.

The portable internet appliance 1600 is about 125 millimeters long, 75 millimeters wide and 20 millimeters thick. It has a microprocessor (e.g., Intel's x86 based Medfield or Qualcomm's ARM based Snapdragon 800 or Nvidia Tegra) and an operating algorithm (stored in a data storage component of the portable internet appliance 1600) which can be electrically connected/coupled/interacted with: (a) a memory component, (b) a data storage component, (c) an IP address stored in the memory component, (d) an internet security algorithm (internet firewall/spyware/user-specified security control and authentication), (e) a touch/multi-touch sensitive foldable/stretchable/split/wrap-around display, wherein at least one section of the display is integrated with a component such as PCS 1280/DCS 1285 and alternatively, a touch/multi-touch sensitive stretchable/split/wrap-around display, wherein at least the back side of the display is integrated with a solar cell component to collect residual back reflected light, (f) two (2) high definition (HD) (e.g., 1 giga pixel) multi-spectral band visible/near-infrared/infrared cameras (two (2) cameras-one camera for video chat and another camera for photography, however, a 180-degrees angle rotating camera is also suitable), (g) a video conferencing system-on-chip (integrated with dynamic video compression module the video compression module could be either an electronic module and/or an algorithm), (h) a surround sound component (e.g., a micro-electrical-mechanical-systems based silicon microphone component Analog ADMP 401 or an equivalent component from akustica), (i) a personal area network (PAN) wireless transceiver module (e.g., Wibree/Bluetooth/WiFi/ultra-wideband/millimeter wave (including 60 GHz)/terahertz band with antenna(s) or a software-defined radio with a tunable antenna), (j) near field communication to enable the following: product/service discovery/initiation, peer-to-peer exchange/transfer/share/transaction, machine-to-machine exchange/transfer/share/transaction, remote access of a system/terminal and access authentication, (k) DASH 7 wireless transceiver (DASH7 is an inexpensive instant-on, long range, low power P2P wireless communications standard for applications requiring modest bandwidth like text messages, sensor readings, or source and operates on a single, global frequency 433 MHz. Unlike WiFi, DASH7 operates at a radio frequency which provides for both long range (up to 1 Km) and excellent indoor signal propagation. Dash 7 is a complement to near field communication, driven by a combination of sensing function with wireless transmission), (1) a location measurement component (e.g., an electronic compass/indoor positioning system/global positioning system with antenna(s)), (m) a radio frequency identification/one-dimensional/two-dimensional barcode/quick response code reader, (n) a communication wireless transceiver module (e.g., WiMax/LTE) with antenna(s)/metamaterial antenna(s) or a software-defined radio with a tunable antenna/tunable metamaterial antenna), (o) a sensor based communication component (e.g., low-power radio-ID presence tag that can announce a user's identity and location or can communicate to turn on the temperature of a home or can text the user's wife what things she might need from the grocery store on the way back from the user's office or can text the nearest Starbucks for the user's favorite coffee, as the user's car approaches to the nearest Starbucks or the nearest Starbucks can text an electronic coupon to the user for purchasing the user's favorite coffee, as the user/user's car approaches the nearest Starbucks), (p) a biometric component (e.g., finger print/retina scan sensor), (q) a time-shift module (e.g., the user's favorite live basketball game can be recorder to be watched at a later time), (r) a place-shift module (e.g., the user's favorite live basketball game is configured to be watched anywhere, irrespective of the user's location), (s) a personal awareness assistant module, (t) a first algorithm for content (voice, video and data)-over-IP-thus the first algorithm for content over-IP via an ambient WiFi/WiMax network, can disrupt a traditional carrier controlled cellular business model, (u) a second algorithm of a voice-to-text-to-voice conversion algorithm, (v) a third algorithm including one or more of the following: a voice recognition algorithm, a hand-writing recognition algorithm, an image authentication algorithm, a facial recognition algorithm and a biometric recognition algorithm (e.g., a heartbeat/voice signature can validate the user depositing an image of a check/banknote via digital banking), (w) a fourth algorithm for rendering intelligence (e.g., artificial intelligence, data mining, fuzzy/neuro-fuzzy logic, machine vision, neural networks, pattern recognition, reasoning modeling and self-learning), (x) a fifth algorithm for evidence-based learning, hypothesis generation and natural language processing, (y) a sixth algorithm for voice activated search engine configured by natural language processing, as a digital personal assistant, (z) a seventh algorithm including one or more of the following: algorithm-as-a-service, behavior modeling (e.g., if the user prefers to watch basketball games-such behaviour patterns can be analyzed statistically with a predictive modeling algorithm for sending a basketball ticket related coupon to the user), physical search algorithm (e.g., the portable internet appliance 1600 can scan/tag a product physically/directly to search-product manufacturer, product price, product availability, product reviews and store locations/distribution centres of the product) and a semi-autonomous or autonomous software agent (e.g., a semi-autonomous or autonomous software agent can search the internet with/without the user's input to find any useful information for the user or for the preferences/behaviour patterns of the user)-it should be noted that the semi-autonomous or autonomous software agent can be algorithmically coupled/integrated with the sixth algorithm for voice activated search engine (aa) an electrical powering component (e.g., a battery), (ab) a solar cell component, (ac) a supercapacitor (e.g., a graphene based supercapacitor) to store electrical power, (ad) a lab-on-chip/biosensor, (ae) an ionized gas cloud based cooling component for the microprocessor/system-on-chip (SoC) and (af) a fixed/reconfigurable outer case/package, wherein the portable internet appliance 1600 can morph into a smaller form factor (e.g., the size of a multi-purpose programmable smart card/wristwatch-style device).

System-on-Chip of Portable Internet Appliance

A first system-on-chip, integrates:
(a) digital microprocessor based on planar transistors/three-dimensional transistors/spin-transistors; (b) memory; (c) a graphic processor; and (d) a chip-to-chip optical interconnect; details of an optical interconnect have been described in U.S. Non-Provisional patent application Ser. No. 13/448,378 entitled "SYSTEM AND METHOD FOR INTELLIGENT SOCIAL COMMERCE", filed on Apr. 16, 2012 and the entire contents of this US Non-Provisional patent application are incorporated herein.

Additionally, the digital microprocessor in the first system-on-chip can integrate a VLSI Electronic IC for memristors elements (e.g., silver/amorphous-silicon/poly-silicon structure) for neural-like processing.

Additionally, the digital microprocessor in the first system-on-chip can integrate a VLSI Photonic IC (a photonic flip-flop based on two multi-wavelength ring lasers coupled with one semiconductor optical amplifier (SOA) or plasmonic lasers with a metallic cavity) for ultrafast information processing.

Both the VLSI Photonic IC (VLSI-PIC) and VLSI Electronic IC (VLSI-EIC) can be fabricated/constructed by co-integration epitaxy of III-V material on silicon.

A second system-on-chip integrates the first system-on-chip and an embedded Internet firewall.

A third system-on-chip integrates the second system-on-chip and an embedded spyware.

A fourth system-on-chip integrates the third system-on-chip and a user-specific security control/authentication.

A fifth system-on-chip integrates the fourth system-on-chip and a personal area network wireless component (e.g., Wibree/Bluetooth/near field communication/WiFi/ultra-wideband/millimeter wave (including 60 GHz)/terahertz band).

Interconnection within a System-on-Chip of Portable Internet Appliance

Connecting circuits (chip-to-chip) within a system-on-chip can be achieved by an optical interconnect. Details of an optical interconnect have been described in U.S. Non-Provisional patent application Ser. No. 13/448,378 entitled "SYSTEM AND METHOD FOR INTELLIGENT SOCIAL COMMERCE", filed on Apr. 16, 2012 and the entire contents of this US Non-Provisional patent application are incorporated herein.

As illustrated in FIG. 17D, stacking of circuits within a system on-chip can be realized by utilizing an array of vertical nanotubes (e.g., boron nitride/multi-walled carbon nanotubes) and a horizontal frame of two-dimensional material (e.g., graphene/molybdenum sulfide) or silicone-thus substantially eliminating interconnect wires.

Terahertz Band Transceiver of Portable Internet Appliance

It should be noted that a terahertz band transceiver can be based on silicon-germanium heterojunction bipolar transistors (HBTs) or a hybrid silicon-germanium and gallium nitride based device enhanced with graphene.

Tunable Antenna & Software-Defined Radio of Portable Internet Appliance

A tunable radio-frequency carbon nanotube cavity can tune in between 2 GHz and 3 GHz. By merging many antennas utilizing a tunable carbon nanotube cavity and an analog/digital converter, a software-defined radio can be fabricated/constructed.

Graphene or Metamaterial Based Antenna of Portable Internet Appliance

A graphene based antenna can enable faster wireless connection. The graphene based antenna can be fabricated/constructed, utilizing an array of strips of graphene material (about 10 to 100 nanometers width and 1 micron in length). Transmission and reception at a terahertz band can occur at these dimensions. Electromagnetic waves in the terahertz band can interact with plasmonic waves of electrons at the surface of the array of strips of graphene material to send and/or receive data.

Lensless Camera of Portable Internet Appliance

A lensless camera has: (a) a liquid-crystal display array that allows light to pass through, (b) a RGB photoelectric sensor and (c) a microprocessor to control the liquid-crystal display array and to process the data that is received from the RGB photoelectric sensor. To create an image, the liquid-crystal display array is placed between an item (to be imaged) and the single pixel sensor. The microprocessor sends signals to the liquid-crystal display array causing a few liquid-crystals in the liquid-crystal display array to allow light to pass through, each serves as a tiny optical aperture. The liquid-crystals in the liquid-crystal display array can be chosen by a random number generator and the end result is just a speckled pattern. The photoelectric sensor can capture the light that is allowed to pass through the liquid-crystals in the liquid-crystal display array and send the data to the microprocessor. To create a single picture, multiple image-captures can be taken with different random patterns generated on the liquid-crystal display array. The data from all of the image-captures can be processed at the microprocessor afterwards and the result is a single photograph. The more image-captures are taken, the higher is the resolution of the final image.

In another embodiment, a lensless camera can be fabricated/constructed, utilizing the principle of insect's compound eye/light field optics with over 200 photodiodes, wherein each photodiode is placed just below a microlens, wherein each microlens is configured to capture 40 by 40 pixels. The resulting image can be electronically focused/processed into a three-dimensional image afterwards.

Three-Dimensional Video Conferencing of Portable Internet Appliance

An array of (at least 4) front-facing cameras can provide stereo views and motion parallax (apparent difference in a direction of movement produced relative to its environment). Each camera can create a low dynamic range depth map. However, an array of cameras can create a high dynamic range depth map. Thus, the portable internet appliance 1600 can enable three-dimensional video conferencing.

Multi-Spectral Band Camera of Portable Internet Appliance

Nano-scaled lithography (e.g., phase mask/electron-beam lithography) and reactive ion/plasma etching of two gold electrodes can be utilized to electrically contact on graphene.

Graphene can be chemically functionalized with an array of quantum dots/nanocrystals. Quantum dots/nanocrystals can be arranged according to their size and the specific wavelength of the spectrum to be absorbed.

Silicon (Si) quantum dots/nanocrystals can be tuned in visible wavelength range.

Lead-sulphide (PbS) quantum dots/nanocrystals can be tuned in short-wavelength infrared (SWIR) and near-infrared (NIR) ranges.

The above graphene device chemically functionalized with quantum dots/nanocrystals can act like a transistor and the carrier density in the graphene can be changed by varying the gate voltage.

Graphene functionalized with an array of quantum dots/nanocrystals can act as a multi-spectral band (visible/near-infrared/infrared) photodetector/camera pixel.

In another embodiment, graphene quantum dots can trap light-generated electron particles for a much longer time, resulting in a much stronger electric signal to be processed into an image. Furthermore, graphene quantum dots themselves can be utilized to fabricate/construct a multi-spectral band camera. Fabrication of graphene quantum dots can be as follows: a monolayer graphene can be mechanically exfoliated on an ultrathin silicon dioxide/silicon substrate. The graphene photodetector can be fabricated/constructed (by photolithography and lift-off process) into a field effect transistor structure with a source metal electrode, a drain metal electrode and a gate terminal (the gate terminal is at the bottom of the silicon substrate). A nano-scaled sacrificial metal can be deposited on the graphene by electron beam evaporation and then the nano-scaled sacrificial metal can be wet etched to form graphene quantum dots of various sizes on the ultrathin silicon substrate.

Sensor Integrated with Multi-Spectral Band Camera of Portable Internet Appliance A multi-spectral band (visible/near-infrared/infrared) camera can be integrated with a sensor. The sensor can track what the user touches or sees. The sensor can capture the user's voice for spoken commands with the microphone (of the personal awareness assistant module of the portable internet appliance 1600).

Embedded Configuration of Projector, Camera & Sensor of Portable Internet Appliance The portable internet appliance 1600 can be integrated with a projector, a camera and a sensor/an array of sensors (e.g., an array of touch-sensitive sensors) in an embedded configuration (of a projector, a camera and a sensor/an array of sensors) for blurring between reality, virtual reality and augmented reality for an enhanced mixed reality experience. If a user can enlarge a portion of an image by gently touching the screen to enlarge, the projected image will make the same response.

A rear projector can be based on Texas Instrument's Digital Light Processor projector chip. A typical Texas Instrument's Digital Light Processor projector chip contains up to 8 million micromirrors. Each micromirror can be tilted at a rate of 10,000 times per second to reflect light to create a precise digital image on a surface.

Instead of Texas Instrument's Digital Light Processor projector chip, a rear projector can be fabricated/constructed, utilizing a tiltable single crystal mirror (of about 1 millimeter in diameter) or a microelectro-mechanical-system based scanning mirror. The tiltable single crystal mirror or microelectro-mechanical-system based scanning mirror deflects a color (blue, green and red) of light beam from a microelectro-mechanical-system enabled wavelength tunable surface emitting vertical cavity laser, by rapidly switching the angle of orientation-thus building pixel by pixel.

Furthermore, a rear projector can be fabricated/constructed, utilizing the principle of an insect's compound eye/light field optics with hundreds of light-emitting diodes, wherein each light-emitting diode is placed just below a microlens.

A PCS component 1280 is an embedded integration of a projector, a camera and a touch/eye motion/gesture sensor (e.g., a touch sensor can be fabricated/constructed, utilizing a large array of zinc oxide nanowire based transistors).

Figure 18A:
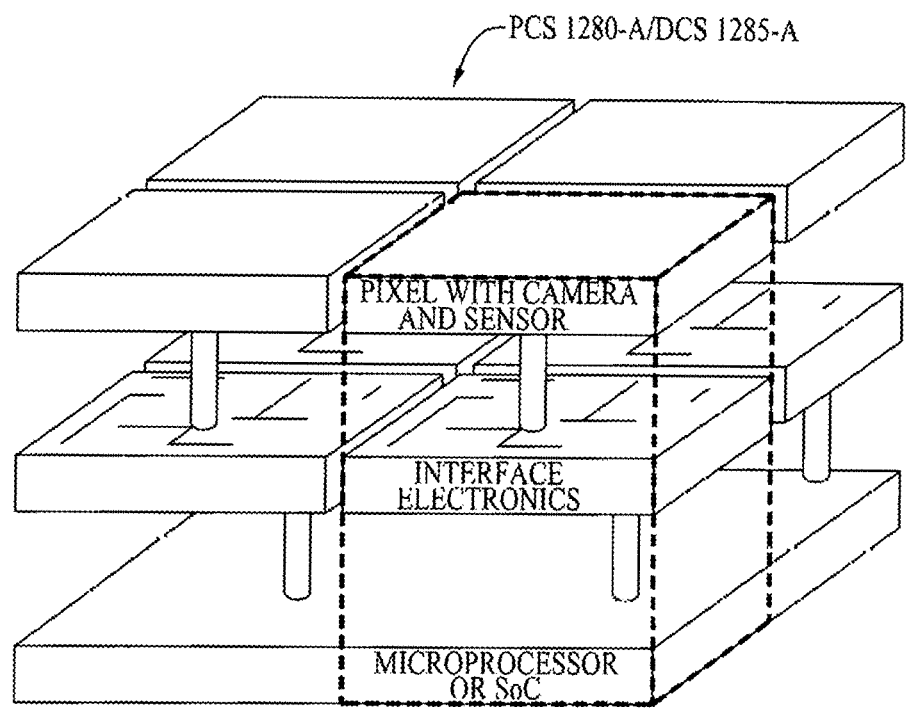
FIG. 18A illustrates a display configuration of a portable internet appliance.

FIG. 18A illustrates a display configuration with a horizontal space sharing and vertical three-dimensional stacking of PCS component 1280/1285-A and a DCS component 1285/1285-A of the portable internet appliance 1600.

Furthermore, in some cases, it may be suitable to replace the projector of the PCS component 1280 with a display pixel. A DCS component 1285 is an embedded integration of a display, a camera and a touch/eye motion/gesture sensor. Optionally, such an embedded integration can be limited to an array of display pixels.

The integrated PCS component 1280 or integrated DCS 1285 can display, record visual information and sense without an external video capture device, while the user sits in front of it.

Embedded Configuration of Projector, Camera, Sensor & Microprocessor/System-on-Chip (SoC) of Portable Internet Appliance The PCS component 1280-A is an embedded integration of a projector, a camera and a touch/eye motion/gesture sensor and a microprocessor or first/second/third/fourth/fifth system-on-chip.

Embedded Configuration of Display, Camera, Sensor & Microprocessor/System-on-Chip (SoC) of Portable Internet Appliance The DCS 1285-A is an embedded integration of a display, a camera and a touch/eye motion/gesture sensor and a microprocessor or first/second/third/fourth/fifth system-on-chip.

The display itself can have embedded integration of an array of sensors, such sensors can be fabricated/constructed (e.g., optically sensing waveguides) by a femtosecond laser. Utilizing a femtosecond laser module, a two-dimensional/three-dimensional optically sensing waveguide(s) can be fabricated/constructed at various depths of the display substrate.

The display itself can have embedded integration of (a) a transparent image sensor based on graphene, (b) a transparent microprocessor based on nanowires (e.g., zinc oxide nanowires) and (c) a transparent battery.

The display itself can have embedded integration of a transparent solar cell (e.g., $CH_3NH_3PbI_3$-xClx perovskite based solar cell utilizing indium tin oxide or fluorine-doped tin oxide and gold or graphene electrodes).

Furthermore, the above transparent solar cell can be integrated with vanadium oxide thin-film/nanoparticles for both electricity generation and electricity saving.

Additionally, the transparent microprocessor can have embedded integration of an array of transparent sensors (e.g., transparent vanadium oxide sensors). Such transparent sensors integrated with the transparent microprocessor can sense, manipulate and respond quickly, because either feedback or feed forward control happens within one integrated system-on-chip.

Furthermore, the display itself can be integrated with vanadium oxide thin-film thermochromic device, when it is activated by either voltage or temperature.

The integrated PCS component 1280-A or integrated DCS 1285-A can display, record visual information, sense and process data/information without an external video capture device, while the user sits in front of it.

Split Display/Wrap-Around Display/Dual Displays of Portable Internet Appliance

The portable internet appliance 1600 can have a split display, wherein one section of the display is a high pixel density-high brightness liquid-crystal display/organic light emitting display and the other section of the display is based on a component, such as PCS 1280/DCS 1285.

Alternatively, the portable Internet appliance 1600 can have a wrap-around display or dual displays, wherein one display is a high pixel density-high brightness liquid-crystal display/organic light emitting display and the other display is integrated with a component such as PCS 1280/DCS 1285.

The display can be reconfigured for at least two (2) different sizes, utilizing a foldable/stretchable display, which can be fabricated/constructed, utilizing a graphene sheet and/or an organic light-emitting diode connecting/coupling/interacting with a printed organic transistor or carbon nanotube based thin-film transistor and a rubbery conductor (e.g., a mixture of a carbon nanotube/gold conductor and a rubbery polymer) with a touch/multi-touch sensor.

Furthermore, a foldable/stretchable display can be fabricated/constructed, utilizing an array of flexible polymer waveguides/multi-mode plastic fibers, wherein the input of each flexible polymer waveguide/multi-mode plastic fiber can be integrated with a high brightness light source and the output of the above flexible polymer waveguide/multi-mode plastic fiber can be integrated with a high brightness white phosphor thin-film and a dense matrix of blue, green and red thin-film filters or tunable thin-film filters.

Various spatial arrangements of the flexible polymer waveguide/multi-mode plastic fiber, high brightness light source, high brightness white phosphor thin-film and thin-film filters/tunable thin-film filters are possible.

Touch Sensitive Interactive Three-Dimensional Liquid-Crystal Display of Portable Internet Appliance The display of the portable internet appliance 1600 can be a thin-film-transistor liquid-crystal three-dimensional liquid-crystal display. A thin-film-transistor liquid-crystal display is an active-matrix liquid-crystal display, a special variant of a liquid-crystal display that utilizes thin-film transistor technology to improve image qualities (e.g., contrast and addressability). Thin-film transistors are tiny switching thin-film transistors/capacitors-arranged in a matrix on a glass substrate. To address a particular pixel, the proper row is switched on and then a charge is sent down to the proper column. Since all of the other rows that the column intersects are turned off, only the capacitor at the designated display pixel receives the specified charge. The capacitor is able to hold the specified charge until the next refresh cycle. With the controlled amount of voltage supplied to a liquid-crystal, the liquid crystal can untwist only enough to allow some light to pass through.

Instead of a liquid-crystal material, a polymer stabilized liquid-crystal/photoreactive polymer stabilized liquid-crystal material can be utilized.

Additionally, utilizing plasma enhanced chemical vapor deposition (PECVD) and electron-beam lithography, an array of vertical nanotubes (e.g., multi-walled carbon nanotubes at about 5 microns apart) can be fabricated/constructed on a glass substrate. The array of vertical nanotubes can act as an array of vertical microlens-electrodes of variable focal lengths, controlled by an applied voltage. Furthermore, the array of vertical nanotubes, as an array of vertical microlens-electrodes of variable focal lengths can be switched on or off by an applied voltage.

Alternatively, an array of vertical nanowires (e.g., zinc oxide nanowires) can be utilized instead of an array of vertical nanotubes. Additionally, an array of vertical nanowires can be fabricated/constructed by spin-on-nanoprinting method.

Currently, due to larger pixel size, the field of view of the three-dimensional liquid-crystal display is limited. Vertical nanotubes/nanowires based three-dimensional liquid-crystal display incorporating millions of nano-scaled pixels can produce three-dimensional liquid-crystal display with a wider field view.

Additionally, these nano-scaled pixels can be tuned by integrating with millions of micromirrors, wherein each micromirror can be activated by a microelectro-mechanical-system actuator (e.g., Texas Instrument's Digital Light Processor projector chip).

A polymer stabilized liquid-crystal/photoreactive polymer stabilized liquid-crystal material integrated with an array of vertical nanotubes/nanowires can enable a three-dimensional liquid-crystal display, where a hologram can be changed dynamically.

Furthermore, a polymer stabilized liquid-crystal/photoreactive polymer stabilized liquid-crystal material integrated with (a) an array of vertical nanotubes/nanowires and (b) an array of micromirrors (wherein each micromirror is activated by a microelectro-mechanical-system actuator) can enable a three-dimensional tunable liquid-crystal display, where a hologram can be changed dynamically.

Furthermore, the above three-dimensional liquid-crystal display can be touch/multi-touch sensitive.

The above touch/multi-touch sensitive three-dimensional liquid-crystal display can be a foldable/stretchable/split/wrap-around display.

The above touch/multi-touch sensitive three-dimensional liquid-crystal display can be an interactive display.

Sensor-System-on-Chip (S-SoC) of Portable Internet Appliance

The portable internet appliance 1600 can be integrated with a sensor-system-on-chip. The sensor-system-on-chip integrates (a) a sensor/an array of sensors, (b) microcontroller/microprocessor and (c) a low-power radio. The sensor/array of sensors can be aware, always on, intelligent, intuitive (e.g., fuzzy logic based instructions) and wirelessly connected with other sensors. Furthermore, the sensor-system-on-chip can be embedded with the portable Internet appliance.

Personal Awareness Assistant Module of Portable Internet Appliance

The personal awareness assistant module can include: a second microprocessor component, a second memory component, a microphone component and a scrolling audio recording buffer component. Furthermore, the personal awareness assistant module can also include: a second data storage component and a second camera component.

The personal awareness assistant module can be always on. It can passively listen to what the user says in a natural language and can respond to particular contexts and situations. For example, the user can hear about a product on the radio and then the user can create a reminder by speaking to the personal awareness assistant module. The portable internet appliance 1600 can then enable further purchasing of the product at a later time.

For example, when the user is introduced to someone, the personal awareness assistant module can automatically recognize the person and may take a low resolution photo. Once the personal awareness assistant module collects the information, it can automatically categorize the information into a pre-designated database with audio, digital image, time/date stamp and indoor positioning system/global positioning system location. Because the data is stored contextually, information retrieval can be straightforward. A simple voice command inquiry, such as whom did I meet on Apr. 15, 2009 at 12 PM? The personal awareness assistant module can bring up the appropriate information about that specific person. Thus, the portable internet appliance 1600 (integrated with the personal awareness assistant module) is context-aware.

Furthermore, the voice recognition algorithm can enhance the capability of the personal awareness assistant module. Additionally, a face recognition algorithm can enhance the capability of the personal awareness assistant module.

Solar Cell Component of Portable Internet Appliance

The solar cell can be a quantum dot-nanowire-plasmon solar cell/an array of microscopic solar cells integrated with an array of refractive microlenses.

By way of an example and not by way of any limitation, a typical photovoltaic material can be copper indium gallium diselenide/CdS/CdTe/graphene/organic material/crystal line silicon/polycrystalline silicon. Furthermore, monolithically integrated lattice matched, bangdgap-optimized and current matched multi junctions of III-V semiconductor materials can be used, wherein each junction contains a p-n junction and tuned to a particular spectrum of light, reducing losses and thereby increasing efficiency.

An organic material with squaraine dye coating is based on the principle of FOrster resonance energy transfer (FRET) mechanism, wherein extra energy can migrate from one molecule to another molecule over a relatively longer distance. Squaraine dye broadens the spectral absorption of the sunlight.

In a singlet-exciton fission, an arriving photon from the sunlight can generate two (2) excitons (excited states) yielding two (2) electrons. Pentacene generates two (2) excitons (excited states) yielding two (2) electrons in a narrow visible spectrum of the sunlight. However, pentacene (an organic dye) and/or other materials for singlet-exciton fission in another spectrum of the sunlight can be integrated via coating or wafer stacking/bonding (wafer stacking/bonding is useful, when the material is not suitable for coating) for enhanced electron generation.

The top surface or back surface of the photovoltaic material (e.g., copper indium gallium diselenide/CdS/CdTe/graphene/organic material/crystalline silicon/polycrystalline silicon/monolithically integrated multi junctions of III-V semiconductor materials) can be integrated with a singlet-exciton fission material or an array of singlet-exciton fission materials, depending on the configuration of the solar cell component.

Furthermore, a photovoltaic material can be integrated (e.g., doped) with a light sensitive compound/protein.

Furthermore, a photovoltaic material can be integrated with a light trapping structure or an optical metamaterial-based light trapping structure for light collection from many incident angles. The light trapping structure or an optical metamaterial-based light trapping structure can be deposited directly onto the photovoltaic material. Alternatively, the light trapping structure or an optical metamaterial-based light trapping structure can be deposited on a suitable substrate and stacked/bonded (e.g., Soitec company's smart stacking layer transfer technology for processed wafers).

Unlike conventional solar cells, electrical contacts can run below the light trapping structure.

Graphene based photovoltaic material can be fabricated/constructed as follows: an ultrathin graphene sheet can be fabricated/constructed, by depositing carbon atoms in the form of graphene on nickel (thin-film substrate) from methane gas.

Additionally, transition metal dichalcogenides (TMDC) or aerographite (a synthetic foam consisting of a porous interconnected network of tubular carbon) monolayers can be sandwiched between/within two layers of graphene. Transition metal dichalcogenides or aerographite monolayers can act as very efficient light absorbers.

Furthermore, an array of vertical/vertically ordered plasmonic nanostructures of metal can be directly fabricated/constructed on the top surface of graphene. The plasmonic nanostructures of metal can enhance local electromagnetic fields in graphene by coupling incoming light with electrons on the surface of the metal.

Furthermore, instead of an array of vertical/vertically ordered plasmonic nanostructures of metal, nanowires of indium gallium arsenide (InGaAs) can be grown on the top surface of graphene by van der Waals epitaxy induced phase segregation.

Alternative to an array of vertical/vertically ordered nanowires integrated on the top surface of the photovoltaic material, the top surface of the photovoltaic material can have an array of vertical nanowires (e.g., zinc oxide nanowires) to concentrate rays of sunlight into a very small area of each nanowire by a factor of about ten (10) at a given wavelength of the sunlight. Because the diameter of a vertical nanowire is smaller than the wavelength of sunlight, it can cause resonances in the intensity of the sunlight in and around nanowires to produce a concentrated sunlight, at a much higher conversion efficiency of the sunlight.

Furthermore, the top surface of the array of vertical/vertically ordered nanowires or vertical nanowires can be integrated with an array of colloidal deposited/self-assembled variable sized quantum dots. These variable sized quantum dots can absorb the sunlight over a much wider range of wavelengths. These variable sized quantum dots can be arranged according to their size and according to the specific wavelength of the solar spectrum that is absorbed. Thus, the harvesting the sunlight's power (absorption) is increased.

Furthermore, instead of colloidal deposited/self-assembled variable sized quantum dots, an ultra thin-film of silicon nanoparticles (1-3 nanometers) can be deposited, forming a transparent layer of silicon nanoparticles. Large voltage enhancement with a dramatic increase in power ranging from as much as 60-70% in the ultraviolet-blue (UV) spectrum using these silicon nanoparticles and a significant boost in power by as much as 10% in the visible light spectrum can be obtained.

Instead of an array of plasmonic nanostructures of metal, an array of metamaterial structures of multi-layered metal-dielectric thin-film can be directly fabricated/constructed on the top surface of graphene.

A protective film can be deposited over the graphene and nickel (thin-film substrate on which graphene was grown) is dissolved in a suitable acid.

The unprotected back surface of graphene can be suitably coated with pentacene and then it can be attached to a flexible polymer sheet. Instead of a single layer, several layers of graphene (wherein each layer of graphene is protected on a flexible polymer sheets) can act as an efficient graphene photovoltaic material.

Furthermore, an array of plasmonic optical nanoantennas at the substrate (of the quantum dot-nanowire-plasmon solar cell) can be fabricated/constructed to enhance both light trapping and spectral efficiency.

Furthermore, sunlight can be collected by a micro-reflector and directed at a very specific angle into an array of thin-film optical filters (or nano-scaled optical filters), wherein each thin-film optical filter (or each nano-scaled optical filter) is configured to transmit a spectral band/slice of sunlight spectrum to illuminate a spectrum-matching quantum dot-nanowire-plasmon solar cell (out of an array of quantum dot-nanowire-plasmon solar cells).

Each quantum dot-nanowire-plasmon solar cell is fabricated/constructed, utilizing a different photovoltaic material, wherein each photovoltaic material is coated with pentacene. Such a configuration of an array of quantum dot-nanowire-plasmon solar cells of different photovoltaic materials coated with pentacene coating can significantly increase efficiency of the solar cell.

An alternative embodiment of the solar cell, a three-dimensional solar cell can be fabricated/constructed, by depositing a photovoltaic material: CdS/CdTe/polycrystalline silicon or alternatively roll-to-roll processing of a photovoltaic material: (e.g., graphene/organic material) on an array of vertical cubes.

Each vertical cube can consist of a large array of nanotubes (e.g., carbon nanotubes). The nanotubes are grown on a bottom metal pattern (the bottom metal film is deposited, photolithographically patterned and reactive ion-plasma etched on a substrate).

By way of an example and not by way of any limitation, a photovoltaic material such as polycrystalline silicon can be deposited on the array of cubes. Then pentacene can be deposited on the top surface of the polycrystalline silicon.

The top surface of the photovoltaic material can have an array of vertical nanowires (e.g., zinc oxide nanowires) to concentrate rays of sunlight into a very small area of each nanowire by a factor of about ten (10) at a given wavelength of the sunlight. Because the diameter of a vertical nanowire is smaller than the wavelength of sunlight, it can cause resonances in the intensity of the sunlight in and around nanowires to produce a concentrated sunlight, at a much higher conversion efficiency of the sunlight.

Furthermore, the top surface of the array of vertical nanowires can be integrated with an array of colloidal deposited/self-assembled variable sized quantum dots. These variable sized quantum dots can absorb the sunlight over a much wider range of wavelengths. These variable sized quantum dots can be arranged according to their size and according to the specific wavelength of the solar spectrum that is absorbed. Thus, the harvesting of the sunlight's power (absorption) is increased.

Furthermore, instead of colloidal deposited/self-assembled variable sized quantum dots, an ultra thin-film of silicon nanoparticles (1-3 nanometers) can be deposited, forming a transparent layer of silicon nanoparticles. Large voltage enhancement with a dramatic increase in power ranging from as much as 60-70% in the ultraviolet-blue spectrum using these silicon nanoparticles and a significant boost in power by as much as 10% in the visible light spectrum can be obtained.

Furthermore optionally, an array of plasmonic optical nanoantennas at the substrate can be fabricated/constructed to enhance both light trapping and spectral efficiency of the three-dimensional solar cell.

The photovoltaic material on the array of cubes is then encapsulated with a transparent top electrode (e.g., indium tin oxide/graphene)-thus forming the three-dimensional solar cell.

Furthermore, the three-dimensional solar cell can be a microscopic solar cell. The microscopic solar cell is about 0.25 millimeters to 1 millimeter in diameter and about 10 times thinner than the conventional solar cell.

Other Design Considerations of Portable Internet Appliance

The portable internet appliance 1600 can be dramatically thinner by utilizing (a) a metamaterial based camera, (b) an ultrathin display and (c) an ultrathin battery Ultrathin Camera of Portable Internet Appliance An ultrathin camera based on metamaterial can enable light to pass through a two-dimensional array of gold metamaterial elements. The two-dimensional array of gold metamaterial elements can be fabricated/constructed, utilizing electron-beam lithography on a 60 nanometers thick silicon wafer.

Ultrathin Display of Portable Internet Appliance

An ultrathin photonic crystal display can be constructed by optically pumping different sized photonic crystals, wherein each photonic crystal can emit blue or green or red light based on a photonic crystal's inherent diameter. An optical pump can be generated (from an optical emission) by an electrical activation of semiconductor quantum-wells. Blue, green and red light can be multiplexed to generate a white light.

Ultrathin Battery of Portable Internet Appliance

An ultrathin organic battery utilizes push-pull organic molecules, wherein after an electron transfer process, two positively charged molecules are formed which are repelled by each other like magnets. By installing a molecular switch an electron transfer process can proceed in an opposite direction. Thus, forward and backward switching of an electron flow can form a basis of an ultrathin, light weight and power efficient organic battery.

Wireless Charging of Portable Internet Appliance

The portable internet appliance 1600 can be electrically charged via a resonant electromagnetic inductive coupling energy transfer without any physical wire.

Authentication by Portable Internet Appliance

The portable internet appliance 1600 can be integrated with a miniature Raman spectrophotometer. The miniature arrayed waveguide gratings based Raman spectrophotometer can be inserted into a USB port of the portable internet appliance 1600. The Raman spectrophotometer can authenticate a product by scanning the product in Raman multispectral mode for molecular vibrational spectrum. For example, the Raman spectrophotometer can authenticate a check/banknote, wherein the check/banknote is integrated with a nano-scaled barcode. The nano-scaled barcode can be an array of a unique combination of fluorescent nanoparticles. Furthermore, each fluorescent nanoparticle can be embedded with an optical nanoantenna to increase the Raman signal, if needed. The fluorescent nanoparticles and/or fluorescent nanoparticles with embedded nanoantenna can be caged within a bit larger nanocontainer (e.g., a boron nitride nanotube/carbon nanotube). Thus, the miniature Raman spectrophotometer can enable product authentication.

Biological Lab-on-A Chip of Portable Internet Appliance

A biological lab-on-a-chip is a module that integrates a few bio-analytical functions on a single chip to perform a point-of-care disease diagnostics. A miniature biological lab-on-a-chip module manufactured by Ostendum can be integrated (by inserting into an electro-mechanical cavity of the portable internet appliance 1600) into the portable Internet appliance 1600 to perform point-of-care disease diagnostics reliably, quickly and economically. Such a lab-on-a-chip analysis can be transmitted from the portable internet appliance 1600 to a physician and/or a hospital for an interpretation without a human input.

In addition, holographic images of the complete gene sequence of the user can be stored in the portable internet appliance 1600 to enable a physician/surgeon to design a personalized medical treatment.

Ionized Gas Cloud Based Cooling Component of Portable Internet Appliance

Many algorithms, as discussed above can consume significant electrical power due to computational complexities. Alternatively, many algorithms can be processed at secure remote/cloud server/cloud based data storage unit. Details of an ionized gas cooling component for the microprocessor or system-on-chip have been described in U.S. Non-Provisional patent application Ser. No. 13/448,378 entitled "SYSTEM AND METHOD FOR INTELLIGENT SOCIAL COMMERCE", filed on Apr. 16, 2012 and the entire contents of this US Non-Provisional patent application are incorporated herein.

An ionized gas cloud based cooling component has an array of negative voltage biased nano-scaled tips (e.g., nano-scaled tips can be fabricated/constructed, utilizing boron nanotube/carbon nanotube/amorphous diamond/tungsten), wherein each nano-scaled tip is placed just below a micro-scaled hole (e.g., about 50-100 microns in diameter) of positive voltage biased surface (e.g., tungsten/two-dimensional crystal material (e.g., graphene)). Electrons emitted from the negative voltage biased array of nano-scaled tips can escape through the array of micro-scaled holes and ionize the gas molecules within the boundaries of the heat sink (e.g., aluminum/silicon/copper/carbon nanotube-copper composite/diamond). By switching the voltage polarity of the heat sink, a moving ionized gas cloud can disperse the heat from the system-on-chip.

However, it is desirable that an array of nano-scaled tips emit electrons at a much lower voltage (e.g., at 5 volts). An array of nano-scaled tungsten tips can be fabricated/constructed, utilizing a tungsten substrate. The array of nano-scaled tungsten tips can be surrounded by an insulator. The array of nano-scaled tungsten tips can be decorated with a monolayer(s) of material(s)—in particular a diamond monolayer, deposited by low temperature electron cyclotron resonance chemical vapor deposition or gold monolayer deposited by radio frequency magnetron sputtering to enable electron emission at a much lower voltage (e.g., at 5 volts) through the micro-scaled hole, which is fabricated/constructed, utilizing tungsten material.

Fixed or Reconfigurable Outer Case/Package of Portable Internet Appliance

The outer case/package of the portable internet appliance 1600 can be fabricated/constructed, utilizing a biodegradable material as described in the Table-15.

TABLE 15

Compositions Of A Biodegradable Plastic Material For Portable Internet Appliance

| Composition | Wt % Material A | Wt % Material B | Wt % Material C | Wt % Material D |
|---|---|---|---|---|
| 1 | 80% Lignin | 20% Chitin | | |
| 2 | 80% Lignin | 20% Chitosan | | |
| 3 | 80% Lignin | 10% Chitin | 10% Chitosan | |
| 4 | 80% Lignin | 20% Fibroin | | |
| 5 | 80% Lignin | 10% Chitin | 10% Fibroin | |
| 6 | 80% Lignin | 10% Chitosan | 10% Fibroin | |
| 7 | 80% Lignin | 10% Chitosan | 10% Fibroin | |
| 8 | 80% Lignin | 5% Chitosan | 5% Chitosan | 10% Fibroin |

The aluminum/magnesium alloys have small building blocks-called nanocrystal grains and crystal defects. Nanocrystal grains with crystal defects are mechanically stronger than perfect aluminum/magnesium crystals.

The outer case/package of the portable internet appliance 1600 can be fabricated/constructed from a nano-engineered aluminum/magnesium alloy or a liquid metal alloy or a carbon fiber/carbon nanotube-polymer composite material (carbon fiber/carbon nanotubes embedded within injection mold of a molten polymer) or a carbon fiber/carbon nanotube-polymer composite material with magnesium metal.

Furthermore, an antenna can be fabricated/constructed from a carbon fiber embedded with a conducting polymer or metal.

The outer case/package of the portable internet appliance 1600 can be fabricated/constructed, utilizing a suitable material matrix with an array of shape memory changing material wires (e.g., shape memory changing polymer wires).

Furthermore, the shape memory changing material matrix can be added with 1 wt % to 10 wt % graphene (or 1 wt % to 10 wt % graphene like nanostructual material) and/or 1 wt % to 10 wt % nanotubes (e.g., boron nitride/carbon) to form a nanocomposite.

Furthermore, carbon nanotubes (by stamping onto the shape memory changing material matrix/nanocomposite) can serve as a scaffold for growing zinc oxide nanostructure. Zinc oxide is a piezoelectric semiconductor material (it generates an electric potential after a mechanical motion). Zinc oxide nanostructures are nearly transparent and they can be used for touch-sensitive active matrix arrays on top a display matrix.

Furthermore, the above nanocomposite can be integrated (e.g., multi-layered/mixed) with (a) lignin (or lignen) and/or (b) chitin (a biopolymer based on the N-acetyl-glucosamine monomer) and/or (c) chitin's variant deacetylated counterpart chitosan and/or (d) fibroin (a protein derived from silk).

For flexibility/stretch-ability, a nanotube based microprocessor can be embedded in flexible/stretchable substrate, which has both conductive and non-conductive regions.

By way of an example and not by way of any limitation, a flexible substrate can be hydrogel/chitosan/fibroin/poly (lactic-co-glycolic acid (PGLA) embedded with regions of nanotubes or a suitable combination of chitosan, fibroin and poly(lactic-co-glycolic acid embedded with regions of nanotubes or a suitable combination of hydrogel, chitosan, fibroin and poly(lactic-co-glycolic acid embedded with regions of nanotubes.

By way of an example and not by way of any limitation, a flexible substrate of hydrogel/chitosan/fibroin/PGLA embedded with regions of nanotubes or a suitable combination of chitosan, fibroin and poly(lactic-co-glycolic acid embedded with regions of nanotubes or a suitable combination of hydrogel, chitosan, fibroin and poly(lactic-co-glycolic acid embedded with regions of nanotubes can act as a flexible/stretchable sensor.

The portable internet appliance 1600 can be flexible and stretchable, when it is integrated with a flexible electrophoretic plastic display, flexible transparent electronics chipset, printed battery (e.g., Zn—$MnO_2$ printed battery) and zinc oxide nanowire based solar cell component (photosensitive dye molecules can be anchored to an array of zinc oxide nanowires to fabricate/construct a solar cell component).

Other Algorithms of Portable Internet Appliance in Healthcare

The portable internet appliance 1600 includes an algorithm for interpreting a user's communication in natural language, wherein the algorithm for interpreting communication in natural language is stored in a local data storage unit of the portable internet appliance 1600 or a cloud based data storage unit.

The portable internet appliance 1600 includes an algorithm for generating social graph/personal analytics, wherein the algorithm for social graph/personal analytics generation is stored in a local data storage unit of the portable internet appliance 1600 or a cloud based data storage unit.

Example Applications of Portable Internet Appliance in Healthcare

A biosensor (integrated with a low-power wireless transceiver such as Broadcom's BCM20732) can measure a user's heart rhythm. The lab-on-chip (integrated with a low-power wireless transceiver such as Broadcom's BCM20732) can measure the user's cardiovascular rhythm pattern(s). Both the biosensor and lab-on-chip can transmit data to the portable internet appliance 1600.

The portable internet appliance 1600 can compare with previously stored data of the user and if the newly measured data is significantly abnormal, the portable internet appliance 1600 can immediately communicate (indicating the location and condition of the user) to the user's personal physician and/or directly communicate with 911 emergency without the user input.

Figure 18B:
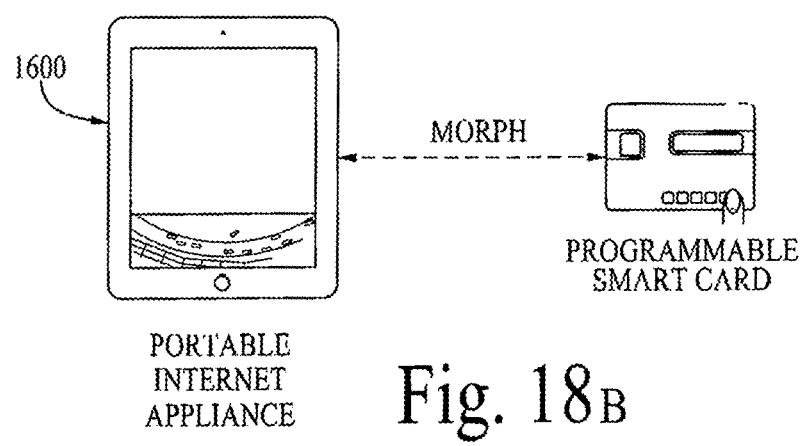
FIG. 18B illustrates how the portable Internet appliance can be morphed into a small form factor.

FIG. 18B illustrates how the portable internet appliance 1600 can be morphed into a small form factor (multipurpose) programmable smart card. Additionally, a smart card can contain a nanotube (e.g., boron nitride/carbon) based microprocessor.

Figure 18C:
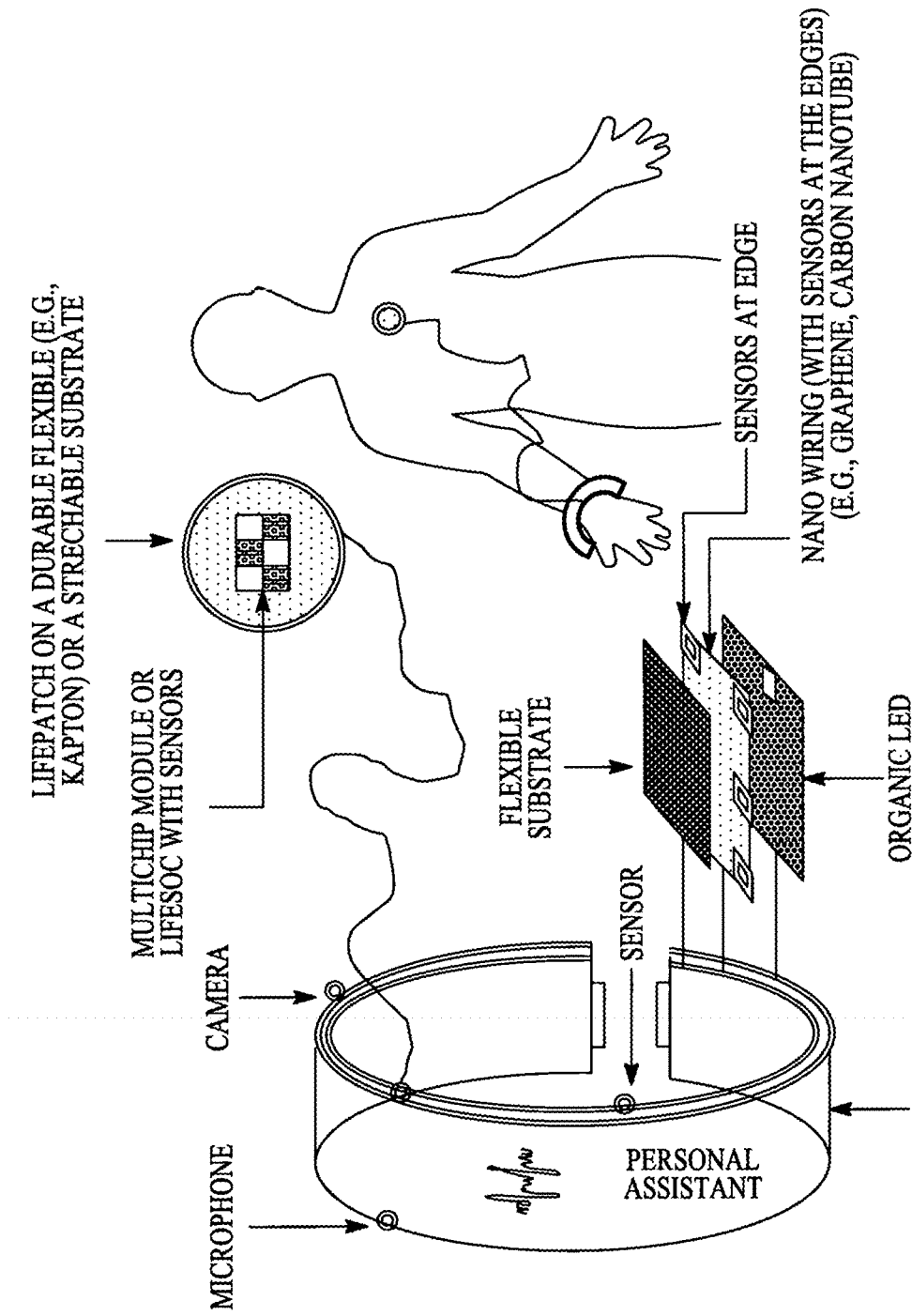
FIG. 18C illustrates how the portable internet appliance can be connected with a standalone wearable device.

Furthermore, a stand-alone wristwatch-style device as illustrated in FIG. 18C can be wirelessly tethered to the portable internet appliance 1600. The stand-alone wristwatch-style device can be fabricated/constructed, utilizing a wraparound display on a flexible substrate (e.g., DuPont Kapton or Corning Willow glass).

Organic light emitting diodes that do not need backlighting, are brighter with a wider viewing angle and better color contrast and organic light emitting diodes can be printed on the flexible substrate.

Furthermore, the above flexible substrate can be integrated with a microprocessor, memory/data storage, a sensor/an array of sensors (e.g., bio/health sensors), a low-power radio and a thin-film battery.

Additionally, the stand-alone wristwatch-style device can be integrated with an image sensor based on graphene.

Additionally, the stand-alone wristwatch-style device can be integrated with a microphone for voice activation to enable the user's voice instructions and/or authentication.

Furthermore, the standalone wristwatch-style device can pull relevant information (e.g., an appointment calendar, e-mail, twitter notification and short picture chat) from the portable internet appliance 1600, so the user can absorb information with a mere glance and can interact/communicate with the portable internet appliance 1600.

As illustrated in FIG. 18C, the stand-alone wristwatch-style device can be connected (by wire or wirelessly) with a Lifepatch of an array of bio/health sensors (e.g., sensors for blood pressure/blood sugar/heart rate/oxygen level).

Figure 18D:
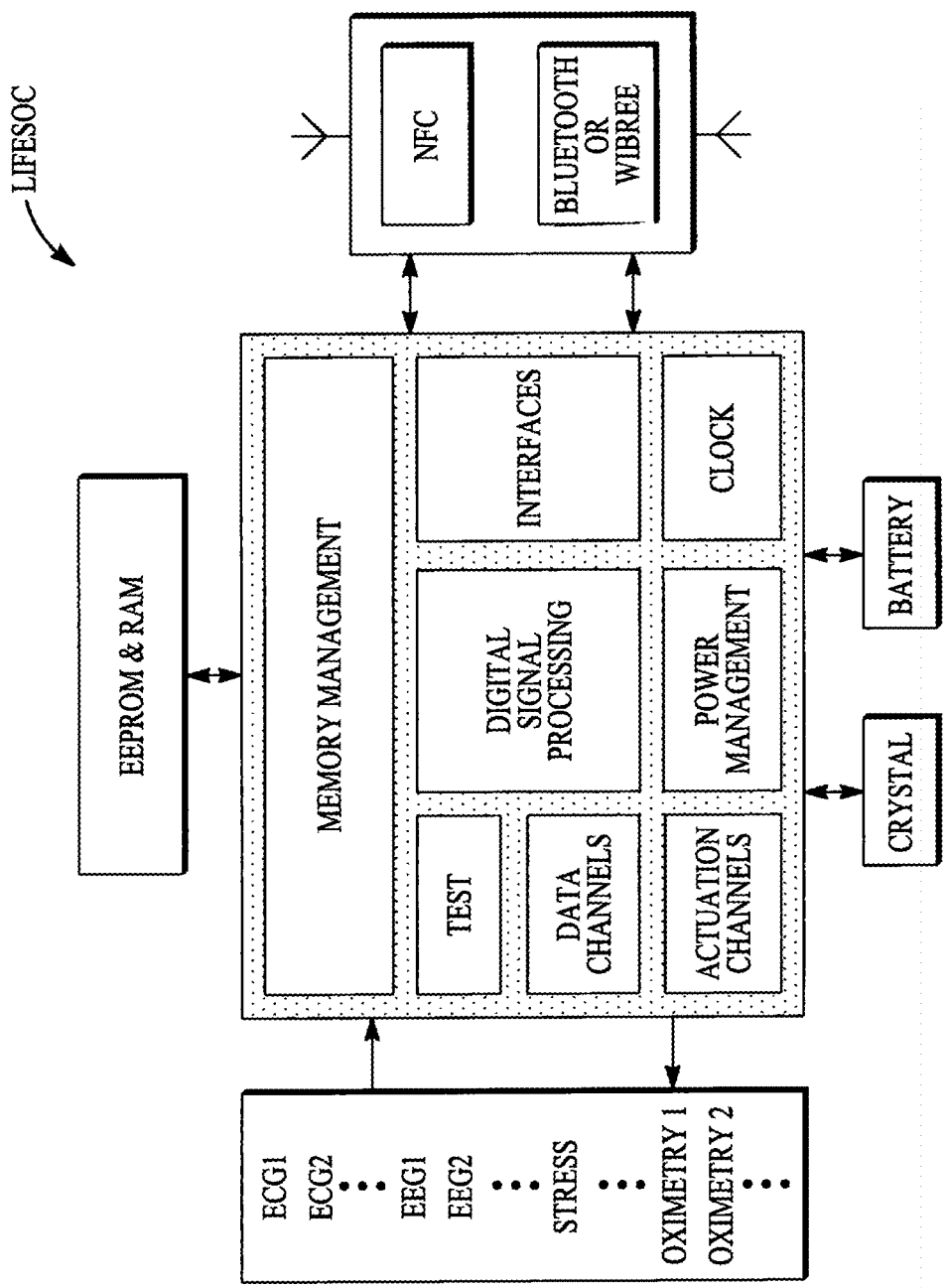
FIG. 18D illustrates a block diagram of a LifeSoC for the Lifepatch.

FIG. 18D illustrates a block diagram of a LifeSoC for the Lifepatch. LifeSoC has digital signal processing, memory management and power management capabilities, wherein LifeSoC is interfacing with various bio/health sensors (e.g., sensors for ECG, EEG, stress and oximetry) and low power wireless devices (e.g., Wibree/Bluetooth) and near field communication (NFC). Furthermore, LifeSoC can be fabricated/constructed on a flexible/stretchable substrate.

Figure 18E:
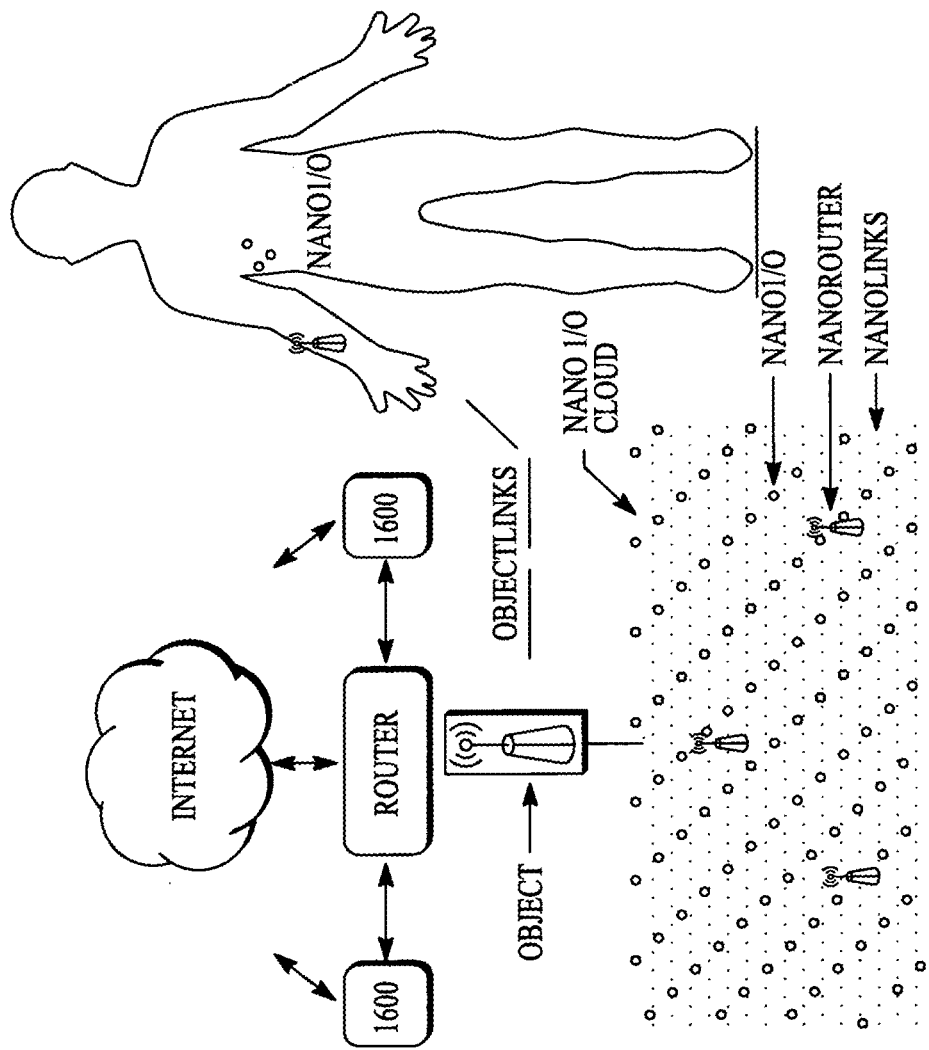
FIG. 18E illustrates how nanoI/Os (e.g., sensors on or within a human body), nanorouters and objects can connect/communicate with other nanoI/Os, nanorouters and objects in a ubiquitous/pervasive manner with an Internet.

FIG. 18E illustrates how a nanoI/O connects/communicates with other nanoI/Os via nanolinks. An array of nanoI/Os connects/communicates with a nanorouter via nanolinks. The nanorouter or the array of nanorouters connects/communicates with an object. The object or the array of objects connects/communicates with a router via objectlinks. The router or the array of routers connects/communicates with portable internet appliances 1600 via the internet. Such interactions as described in FIG. 18E can enable real-time tracking of consumer behavior, real-time awareness (of health/environment), real-time sensor-driven decision analytics and complex autonomous systems.

Figure 18F:
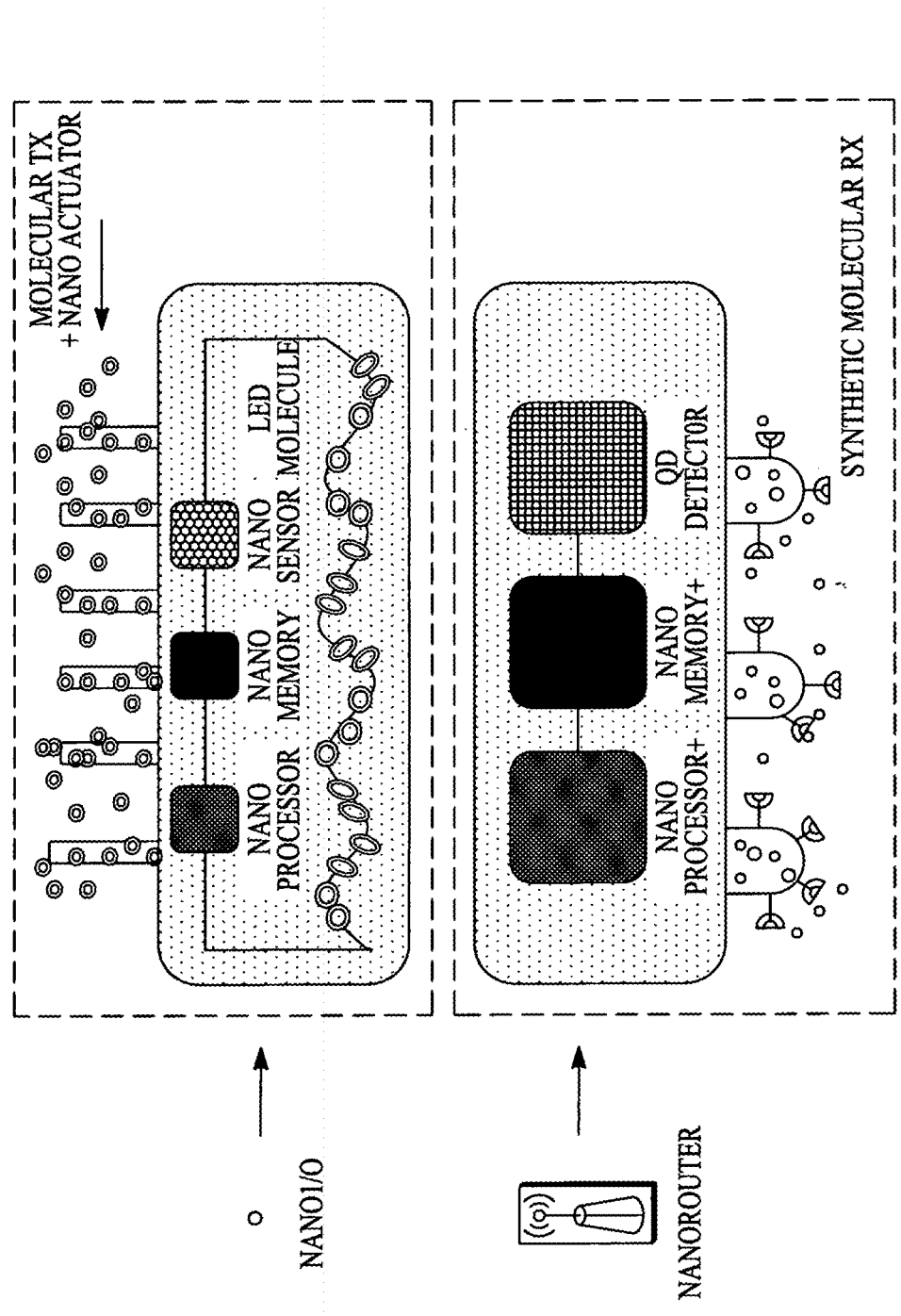
FIG. 18F illustrates a nanoI/O and a nanorouter.

FIG. 18F illustrates a block diagram of a nanoI/O and a block diagram of a nanorouter. The nanoI/O integrates a nano-scaled processor (nanoprocessor), a nano-scaled memory (nanomemory), a nano-scaled sensor (nanosensor), a nano-scaled actuator enabled molecular transmitters and a single molecule organic (e.g., polythiophene) light emitting diode. It should be noted that the single molecule organic light emitting diode and/or an array of nano-scaled actuator enabled molecular (e.g., pheromone) transmitters, can be activated upon nanosensor's signal.

The nanoprocessor, nanomemory and nanosensor can be fabricated/constructed on silicon with nanopillars of non-silicon semiconductor materials (e.g., gallium arsenide, gallium nitride and indium phosphide on silicon) and nanowires connecting between nanopillars of non-silicon semiconductor materials.

Furthermore, the nanoprocessor can be fabricated/constructed as an array of nanowire transistors/switches. The array of nanowire transistors/switches can be nonvolatile. Nonvolatile nanowire transistors/switches can remember when no electrical power is applied to nonvolatile nanowire transistors/switches-thus enabling extremely low electrical power consumption.

Furthermore, nonvolatile nanowire transistors/switches can integrate memristors enabling neuron-like analog nanoprocessor.

Nanomemory cells can be fabricated/constructed of molybdenum disulphide with graphene in a two-dimensional hetrostructure, where molybdenum disulphide acts as a channel in an intimate contact with graphene electrodes in a field-effect transistor configuration.

Alternatively, bistable rotaxane molecule based crossbar nanomemory cells can be fabricated/constructed, wherein a nanomemory cell consists of two perpendicular layers of nanowires, providing voltage, reading and writing information in bistable rotaxane molecule. A bistable rotaxane is a dumbbell-shaped molecule of a rod section and terminated by two stoppers, further encircled by a ring. The bistable rotaxane molecule behaves as a switch by incorporating two different recognition sites for the ring and the ring sits preferentially at one of the two recognition sites. The bistable rotaxane molecule can act as a switch, provided the ring can be induced to move from one recognition site to the other recognition site and then reside there for minutes. The bistable rotaxane molecules can be switched at a very modest voltage from an off (low conductivity) state to an on (high conductivity) state.

The nanorouter integrates a nanoprocessor+ (a bit more powerful than nanoprocessor), nanomemory+ (a bit more powerful than nanomemory), molecular receivers with synthetic receptors and a quantum dot detector (e.g., a nanogap quantum dot detector). Light and/or molecules (e.g., pheromone) transmitted by a nanoI/O can be detected by a quantum dot detector and an array of synthetic molecular receptors respectively.

The signals received by the nanorouter from nanoI/Os are similar to quorum sensing.

It should be noted that a nanoprocessor++ is a bit more powerful than a nanoprocessor+ and a nanomemory++ is a bit more powerful than a nanomemory+.

Figure 18G:
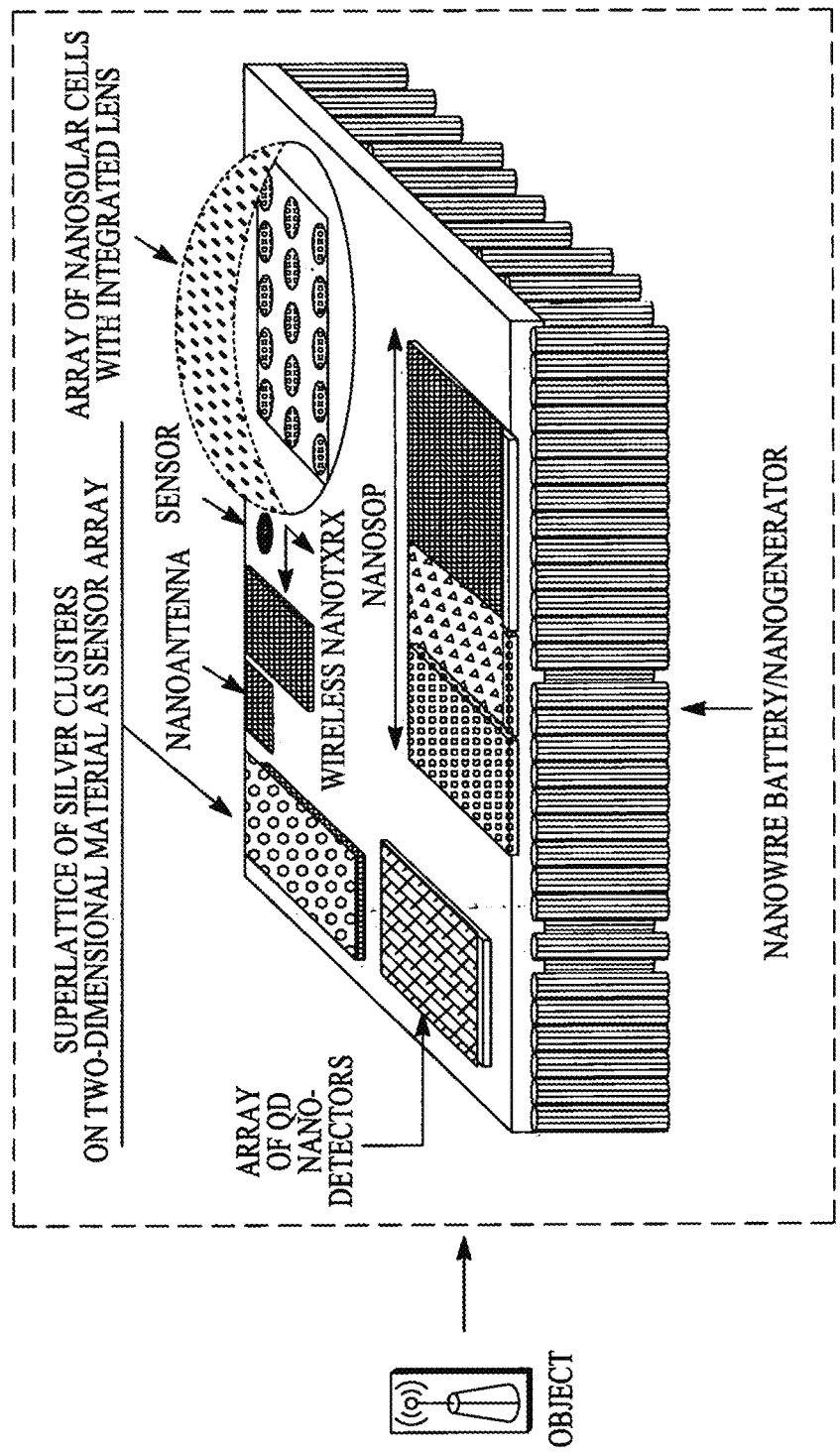
FIGS. 18G and 18H illustrate various configurations of an object.

FIG. 18G illustrates a configuration of an object, which is a nano-scaled system-on-package (SoP) of a nanoprocessor++, a nanomemory++, and a nanostorage for tiny instructions (which can be either embedded in the nanostorage at the very onset or wirelessly transmitted/reconfigured to be stored in the nanostorage at a later time), a wireless nano-transceiver (e.g., a terahertz band nanotransceiver based on silicon-germanium heterojunction bipolar transistors or a hybrid silicon-germanium and gallium nitride based device enhanced with graphene), a nanoantenna (e.g., graphene based nanoantenna), an array of quantum dot nanodetectors, an array of nano-scaled solar cells (e.g., a nanoassembly of gold nanoparticles with organic porphyin molecules) as nanosolar cells integrated with a nano-scaled lens to capture sunlight, a nano-scaled sensor, an array of self-assembled superlattices of silver clusters on a two-dimensional material (e.g., graphene) as an array of molecular sensors and a nanowire battery (e.g., piezoelectric zinc oxide nanowires based nanogenerator).

Furthermore, the nanosolar cells can be three-dimensional nanosolar cells. An array of three-dimensional nanosolar cells (each nanosolar cell is about 5 microns by 5 micron in area, 100 microns tall and separated from each other at about 10 microns) can utilize a silicon substrate, as the nanosolar cells' bottom electrode. A thin-film of iron is deposited and patterned on the silicon wafer by photolithography. Vertically aligned multi-walled carbon nanotubes can be seeded and grown on the patterns of thin-film of iron, utilizing 700 degrees Celsius chemical vapor deposition with hydrocarbon gases, wherein the carbon and hydrogen are separated. Upon formation of arrays of vertical carbon nanotubes, a p-type photovoltaic layer (e.g., cadmium telluride) and an n-type photovoltaic layer (e.g., cadmium sulfide) can be conformally grown by molecular beam epitaxy.

In a singlet-exciton fission, an arriving photon from the sunlight can generate two (2) excitons (excited states) yielding two (2) electrons. Pentacene generates two (2) excitons (excited states) yielding two (2) electrons in a narrow visible spectrum of the sunlight. Pentacene and/or other suitable materials for singlet-exciton fission in another spectrum of the sunlight can be integrated via coating or wafer stacking/bonding (wafer stacking/bonding is useful, when the material is not suitable for coating) for enhanced electron generation.

A thin-film of conducting transparent indium tin oxide/graphene layer can act as the top electrode.

Furthermore, a photovoltaic material can be integrated (e.g., doped) with a light sensitive compound/protein.

Furthermore, a photovoltaic material can be integrated with a light trapping structure or an optical metamaterial-based light trapping structure for light collection from many incident angles. The light trapping structure or an optical metamaterial-based light trapping structure can be deposited directly onto the photovoltaic material. Alternatively, the light trapping structure or an optical metamaterial-based light trapping structure can be deposited on a suitable substrate and stacked/bonded (e.g., Soitec company's smart stacking layer transfer technology for processed wafers).

A nanostorage for instructions in the form of write-once-read-many times can be fabricated/constructed of a DNA based memory cell, which is DNA embedded with silver nanoparticles sandwiched between two transparent electrodes. Incident UV light (through one of the transparent electrodes) can cause the silver atoms to nanocluster for data encoding. When low voltage is applied through the electrodes to the ultraviolet-irradiated DNA, only a low current is able to pass through the memory cell. This corresponds to the off state. But, when the applied voltage exceeds a certain threshold, increased current is able to pass through the memory cell corresponding to the on state. It is reversible from the off state to the on state. Once the memory cell is turned on, it stays on, no matter what voltage is applied to the memory cell.

A self-assembled superlattice consists of silver clusters, wherein each silver cluster has a core of 44 silver atoms. 33 molecules of mercaptobenzoic acid (p-MBA) can be utilized to protect the silver clusters. Mercaptobenzoic acid molecules are attached to the silver atom by sulfur atoms. By compressing the self-assembled superlattice, the hydrogen bonds attached to the mercaptobenzoic acid molecules, rotate about 25-degrees in angle and return to its original position—creating a molecular gear machine.

By integrating conductive polymers with the self-assembled superlattice of silver clusters on a substrate of two-dimensional material, the self-assembled superlattice of silver clusters can be utilized as molecular sensors.

DNA nanostructures preferentially attached to lithographically patterned binding/assembly sites can be utilized as nanoprinted circuit board (nanoPCB) to fabricate/construct a nanoI/O, a nanorouter and an object by sticking nano-scaled components of the nanoI/O or the nanorouter or the object.

Figure 18H:
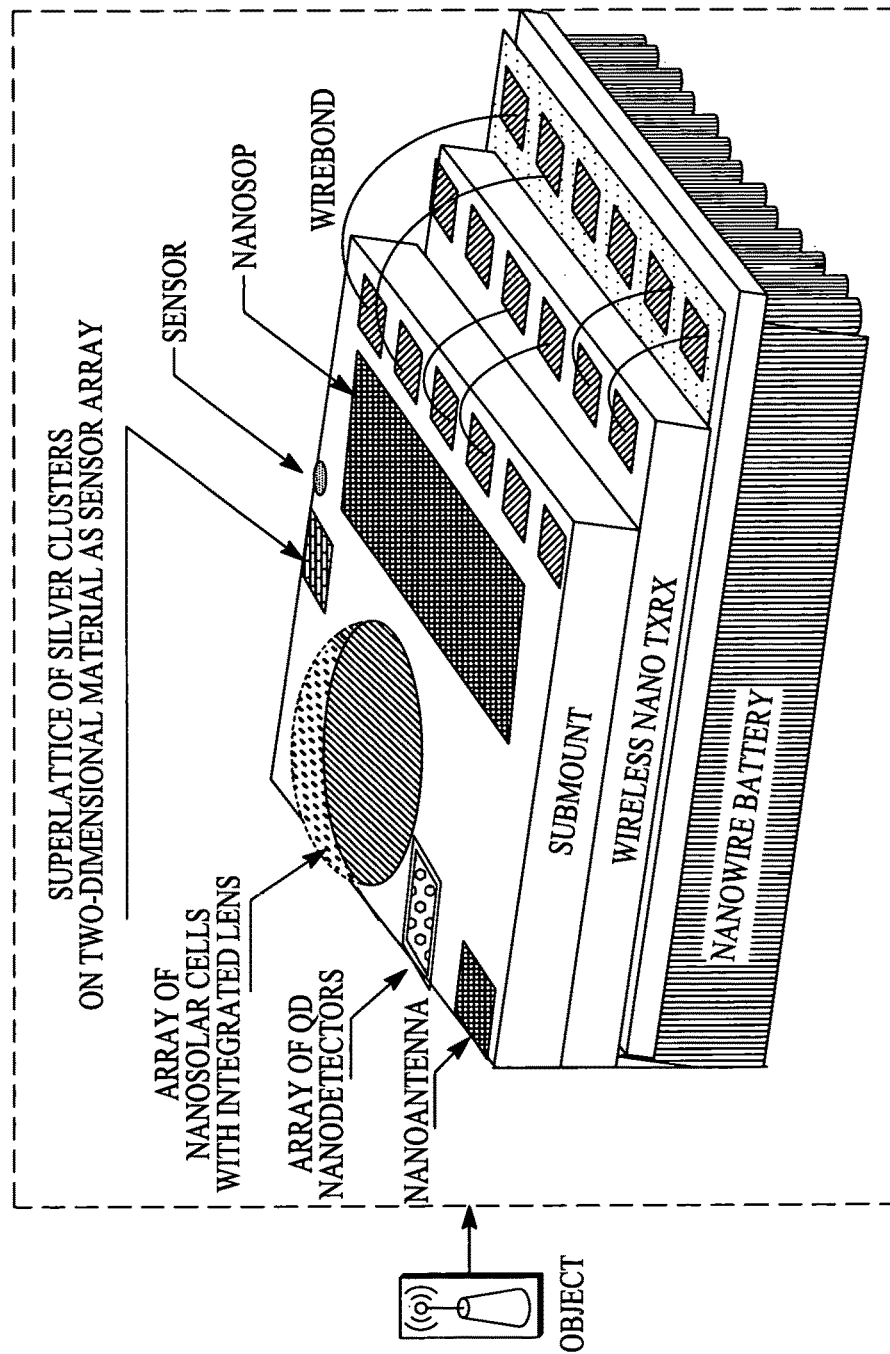

FIG. 18H illustrates another configuration of the object, wherein the stacked package is realized by standard microelectronics packaging method.

Furthermore, the object can be encapsulated for protection from environment.

Furthermore, ambient backscattering of existing wireless signal(s) can enable an object as a sensor to communicate with another object as a sensor without an electrical powering device.

The object can sense/measure/coordinate its actions via a shared language (e.g., AllJoyn or Message Queue Telemetry Transport (MQTT)). AllJoyn provides a universal software framework. Message Queue Telemetry Transport is an open message protocol. Collective intelligence (e.g., swarm intelligence) can be derived from inputs of networks of objects.

Example Applications of Portable Internet Appliance for Point of Care Detection of a Disease/an Array of Diseases The portable internet appliance 1600 can be suitably integrated with a photonics-lab-on chip for point of care detection of a disease/an array of diseases.

Various embodiments of a photonics-lab-on-chip are illustrated in FIGS. 19A, 19B, 19C, 19D, 19E, 19F, 19G, 19H, 19I and 19J.

Figure 19A:
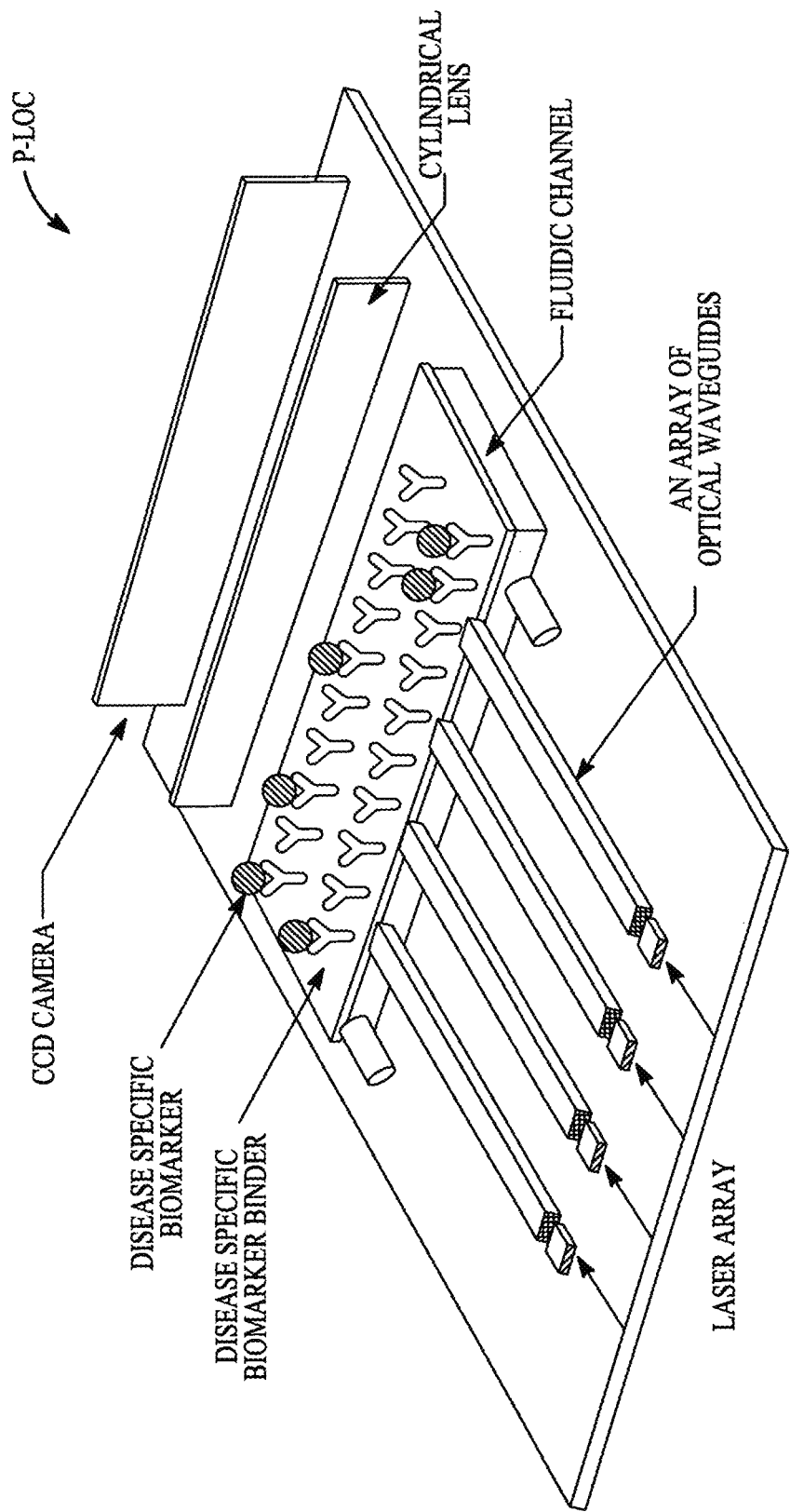
FIGS. 19A, 19B, 19C, 19D, 19E, 19F, 19G, 19H, 19I and 19J illustrate various (block diagram) embodiments of a photonics-lab-on chip (P-LOC).

In FIG. 19A an array of light sources (e.g., an edge emitting distributed feedback (DFB) wavelength tunable laser or a microelectro-mechanical-system enabled wavelength tunable surface emitting vertical cavity laser-integrated with a 45-degrees mirror) is guided via an array of optical waveguides.

The array of optical waveguides is connected with a fluidic channel, which contains disease specific fluorescent biomarker binders to chemically bind with disease specific biomarkers in a human body's blood/biological fluid.

Furthermore, each fluorescent biomarker binder can be integrated with an optical antenna to enhance fluorescence significantly.

The fluidic channel is optically connected with a cylindrical lens to collimate the output fluorescent beam to a charged-coupled detector based camera for spectrum analysis.

Figure 19B:
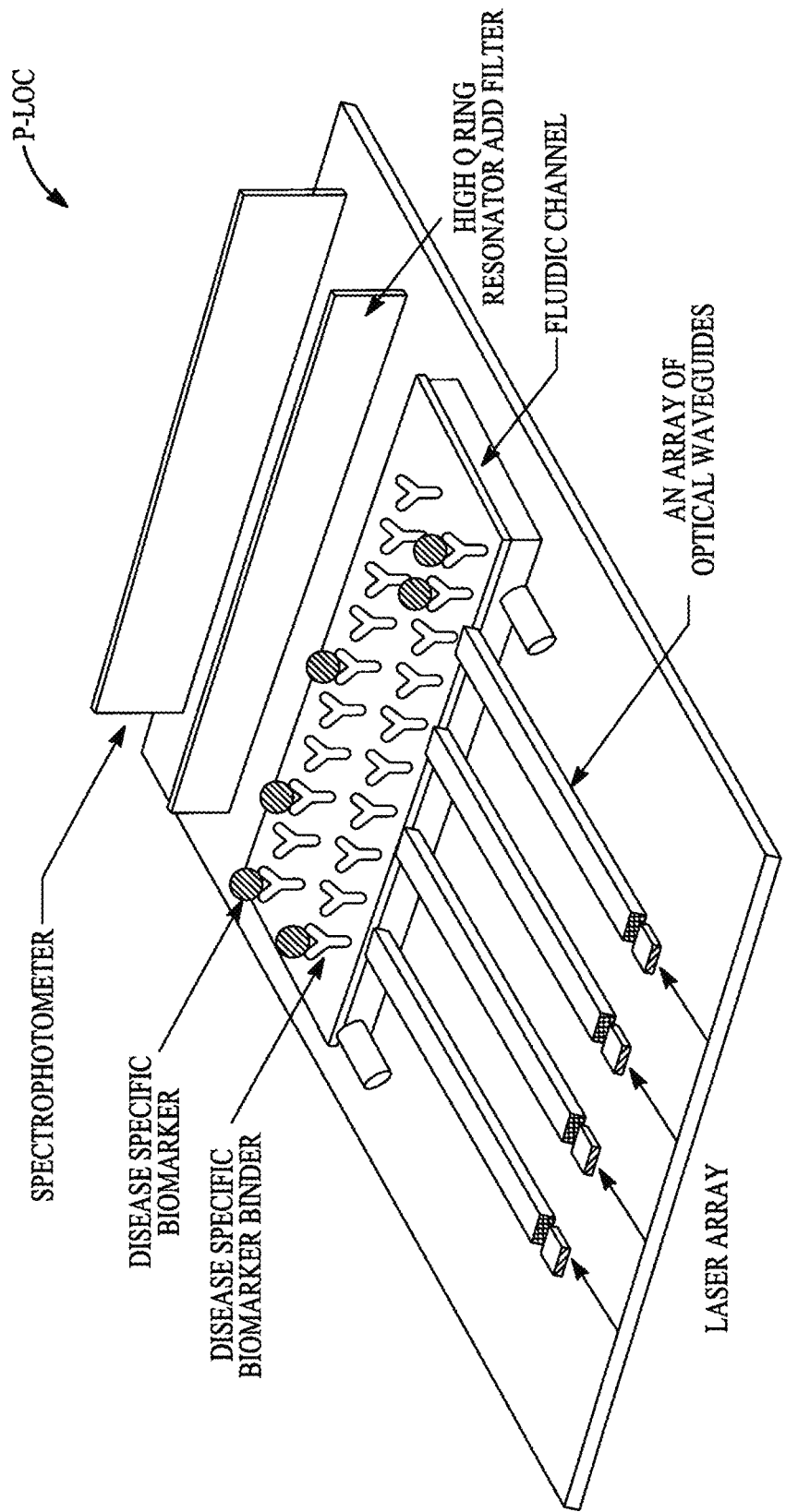

Alternatively, in FIG. 19B, the cylindrical lens can be replaced by an array of high Q ring resonator based add filters. The outputs of the high Q ring resonators based add filters can be combined at one port. This combined port can be the input of a high-resolution spectrophotometer for spectrum analysis.

Figure 19C:
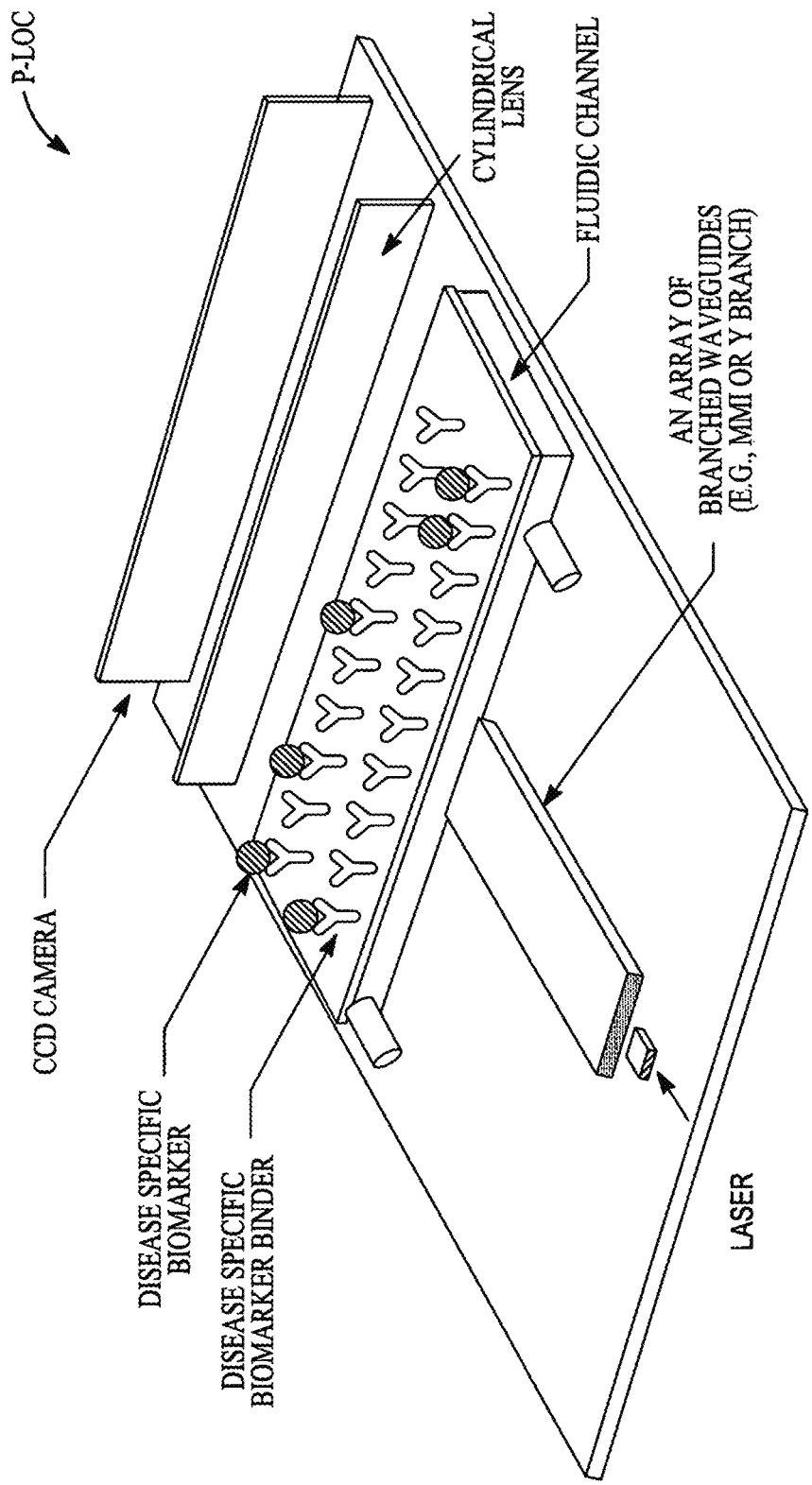

In FIG. 19C, a light source is guided via an array of optical waveguides (e.g., MMI/Y-branched waveguides). The array of optical waveguides is connected with a fluidic channel, which contains disease specific fluorescent biomarker binders to chemically bind with disease specific biomarkers in a human body's blood/biological fluid.

Furthermore, each fluorescent biomarker binder can be integrated with an optical antenna to enhance fluorescence significantly.

The fluidic channel is optically connected with a cylindrical lens to collimate the output fluorescent beam to a charged-coupled detector based camera for spectrum analysis.

Figure 19D:
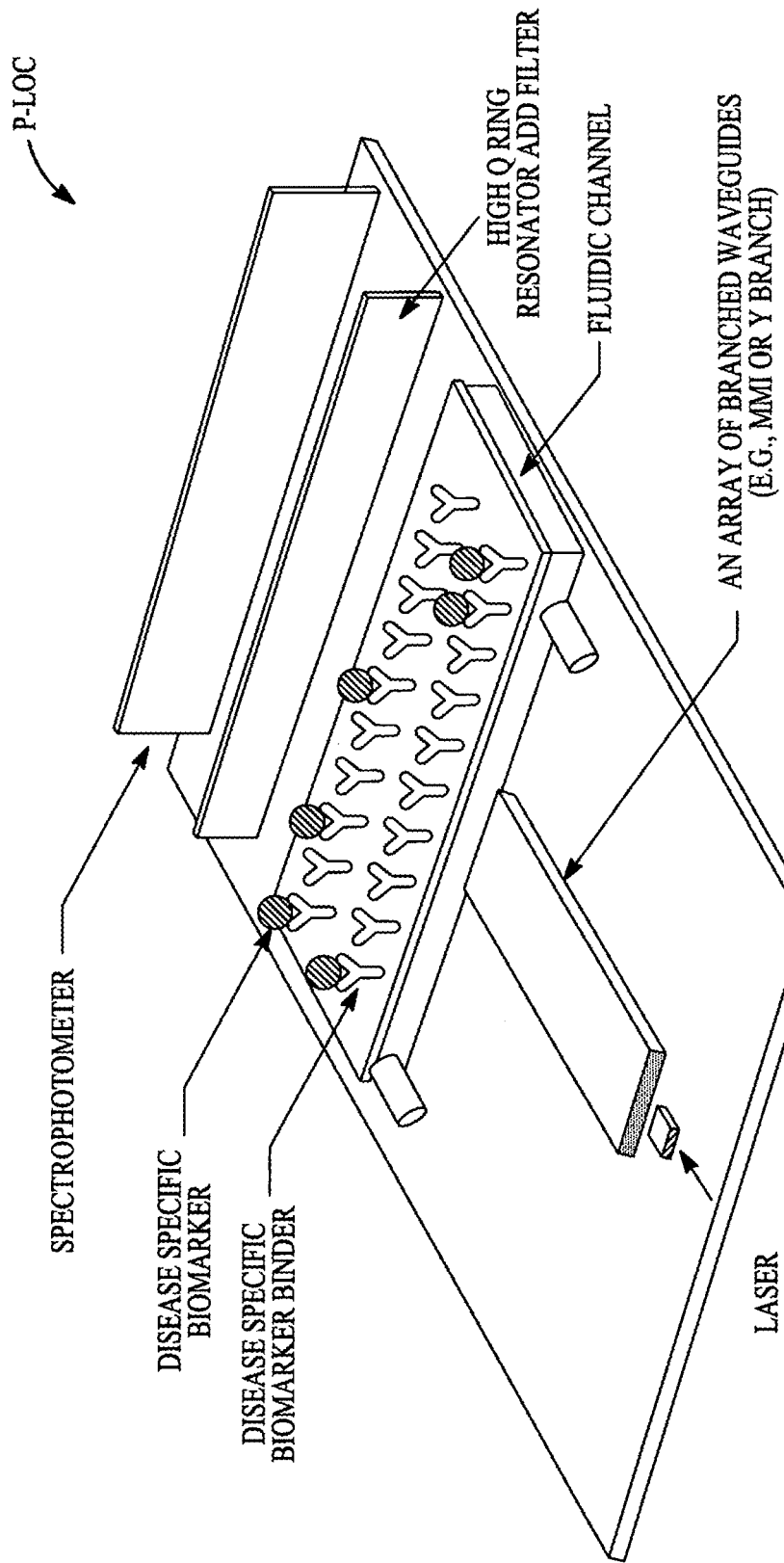

Alternatively, in FIG. 19D, the cylindrical lens can be replaced by an array of high Q ring resonator based add filters. The outputs of the ring resonators based add filters can be combined at one port. This combined port can be the input of a high resolution spectrophotometer for spectrum analysis.

By way of an example and not by way of any limitation, a high resolution spectrophotometer can be an echelle gratings based demultiplexer/microspectrophotometer-on-a-chip/photonic crystal/planar lightwave circuit based demultiplexer/microring resonator based/silicon nanowire waveguide based demultiplexer spectrophotometer.

Alternatively, a high resolution spectrophotometer can be a Fourier-transform (FT) Michelson-type arrayed waveguide gratings spectrophotometer. The spectral resolution of the Fourier-transform (FT) Michelson-type arrayed waveguide gratings spectrophotometer can be increased by inserting a triangular photonic bandgap waveguide section into the waveguide array. Furthermore, the Fourier-transform Michelson-type arrayed waveguide gratings spectrophotometer can be fabricated/constructed by two interleaved arrayed waveguide gratings that produce interference fringes with different spacing for different wavelengths.

Figure 19E:
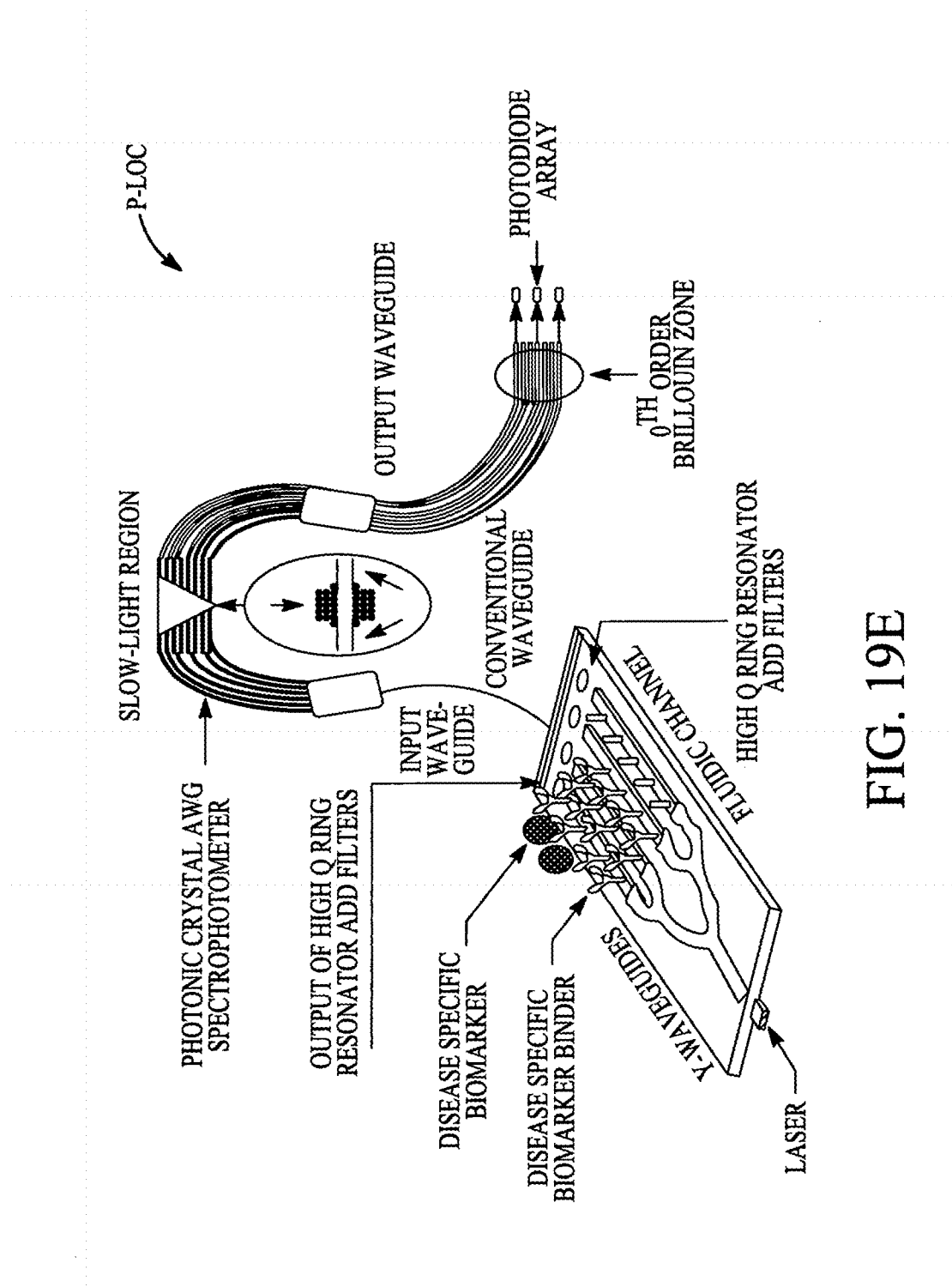

FIG. 19E illustrates a specific embodiment of 19D. Y-branched optical waveguides are connected to array of fluidic channels, wherein each fluidic channel contains disease specific fluorescent biomarker binders to chemically bind with disease specific biomarkers in a human body's blood/biological fluid. Furthermore, any branched optical waveguides (e.g., a multimode interference (MMI) waveguide) can function instead of Y-branched optical waveguides.

Furthermore, each fluorescent biomarker binder can be integrated with an optical antenna to enhance fluorescence significantly.

Laser light propagating through Y-branched optical waveguides can induce fluorescence signals in the array of fluidic channels. The fluidic channels are separated spatially enough to reduce fluorescence related cross-talk from one fluidic channel to another fluidic channel. Fluorescence from each fluidic channel is picked up by a suitable high Q ring-resonator filter and multiplexed/combined at the exit port of the ring-resonator filter device, which is coupled with the Fourier-transform Michelson-type arrayed waveguide gratings spectrophotometer/an array of photodiodes for spectrum analysis.

However, it should be noted that simply a ring resonator based spectrophotometer/an array of photodiodes can be utilized for spectrum analysis.

Figure 19F:
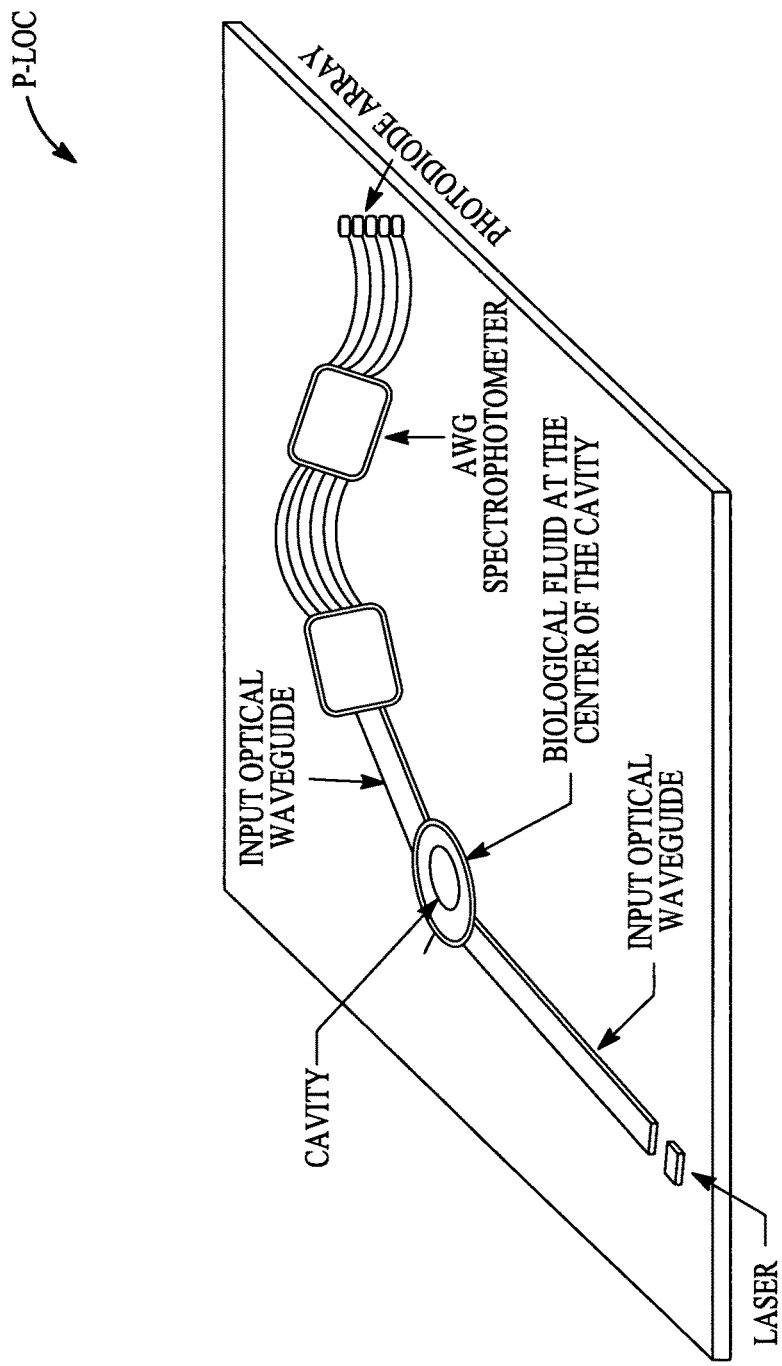

FIG. 19F illustrates a planar design of a photonics-lab-on chip. The planar design has a fluid cavity which contains a human body's blood/biological fluid and disease specific fluorescent biomarker binders to chemically bind with disease specific biomarkers in a human body's blood/biological fluid.

The fluid cavity is optically connected by an input optical waveguide and an output optical waveguide. The input optical waveguide is connected with an optical excitation source (e.g., a laser). The output optical waveguide is connected to an arrayed waveguide gratings spectrophotometer and an array of photodiodes for spectrum analysis.

Figure 19G:
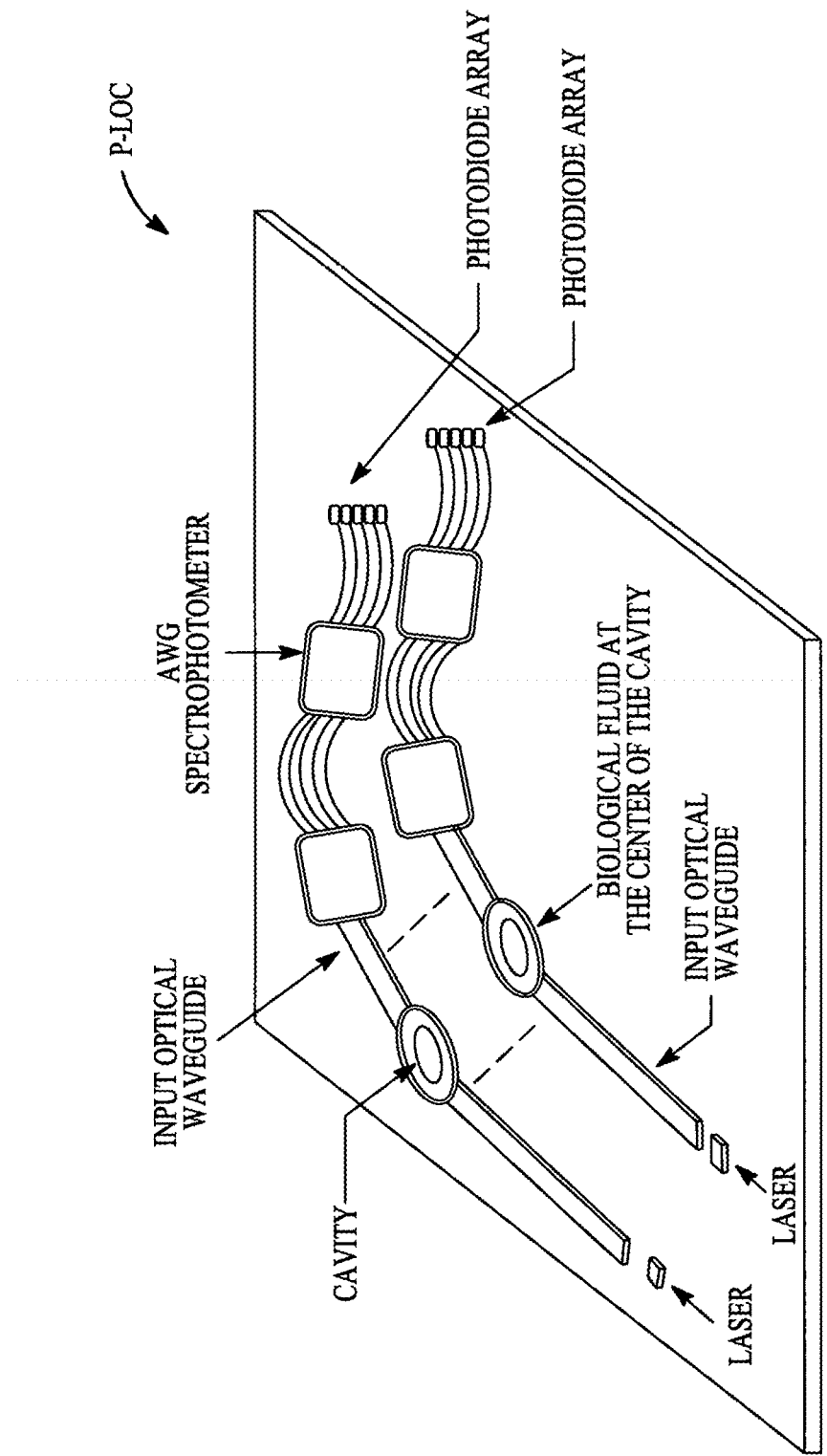

The planar design in FIG. 19F can be scaled to an array of fluid cavities, an array of input optical waveguides, an array of output optical waveguides, an array of arrayed waveguide gratings router spectrophotometers and multiple arrays of photodiodes. The scaled version of the planar design is illustrated in FIG. 19G.

Figure 19H:
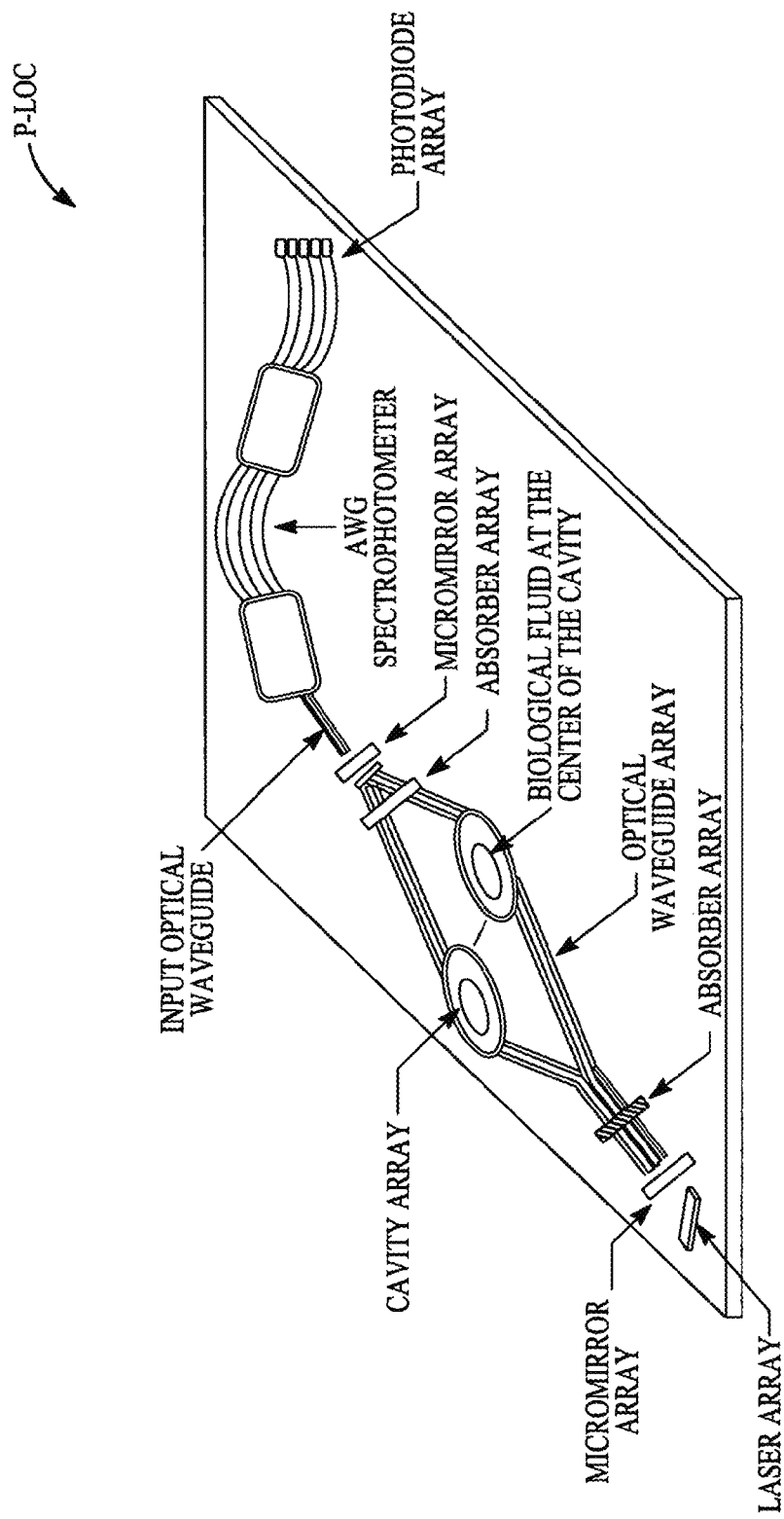

Alternatively, as illustrated in FIG. 19H just one arrayed waveguide gratings router spectrophotometer/an array of photodiodes can be utilized in conjunction with an array of lasers, an array of micromirrors, an array of absorbers, an array of optical waveguides, an array of fluid cavities-containing a human body's blood/biological fluid and disease specific fluorescent biomarker binders to chemically bind with disease specific biomarkers in a human body's blood/biological fluid.

Figure 19I:
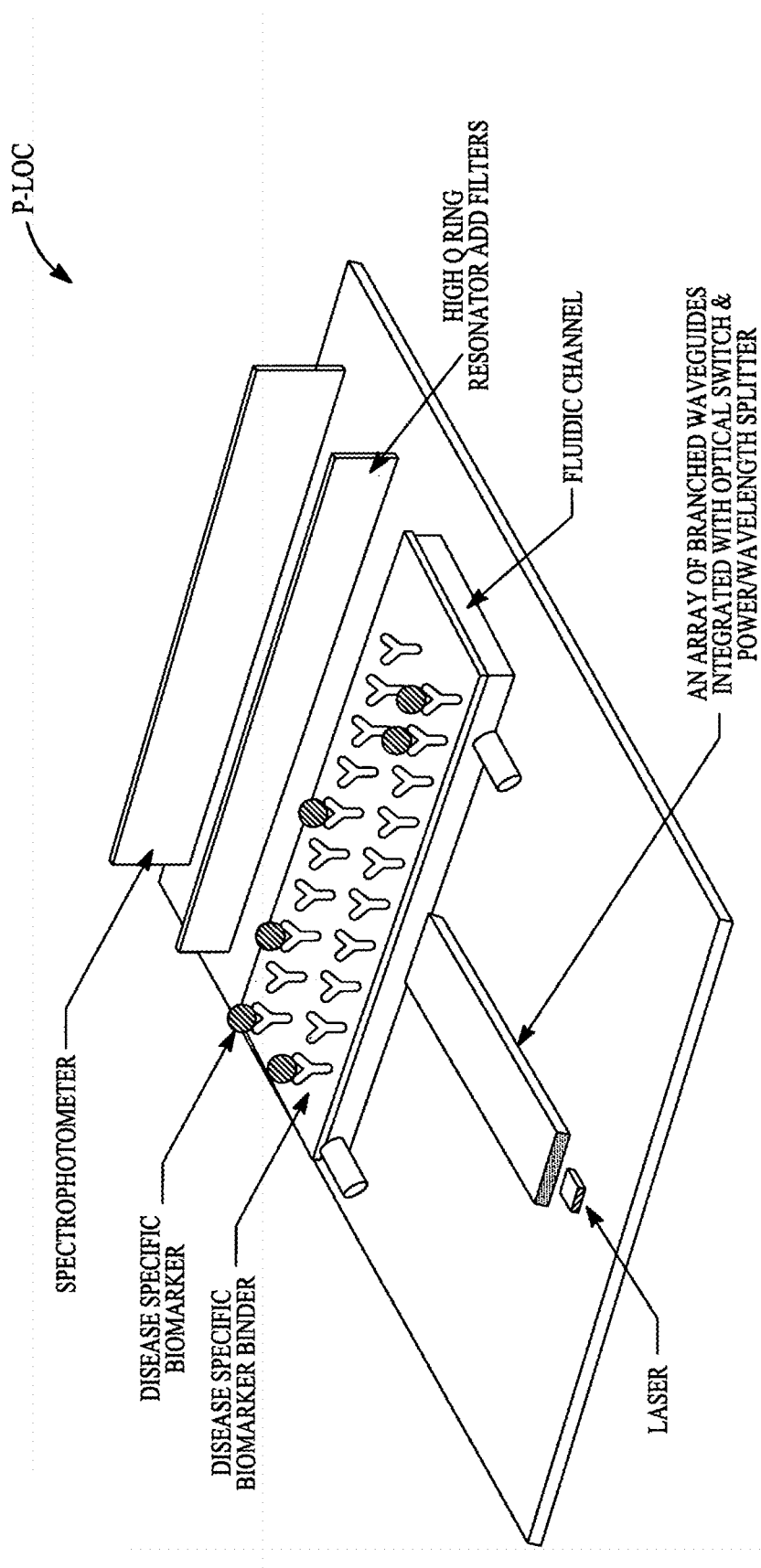

FIG. 19I illustrates another embodiment of 19D, wherein an array of branched optical waveguides is replaced by an array of optical waveguides, integrated with an optical switch and a power/wavelength splitter.

Figure 19J:
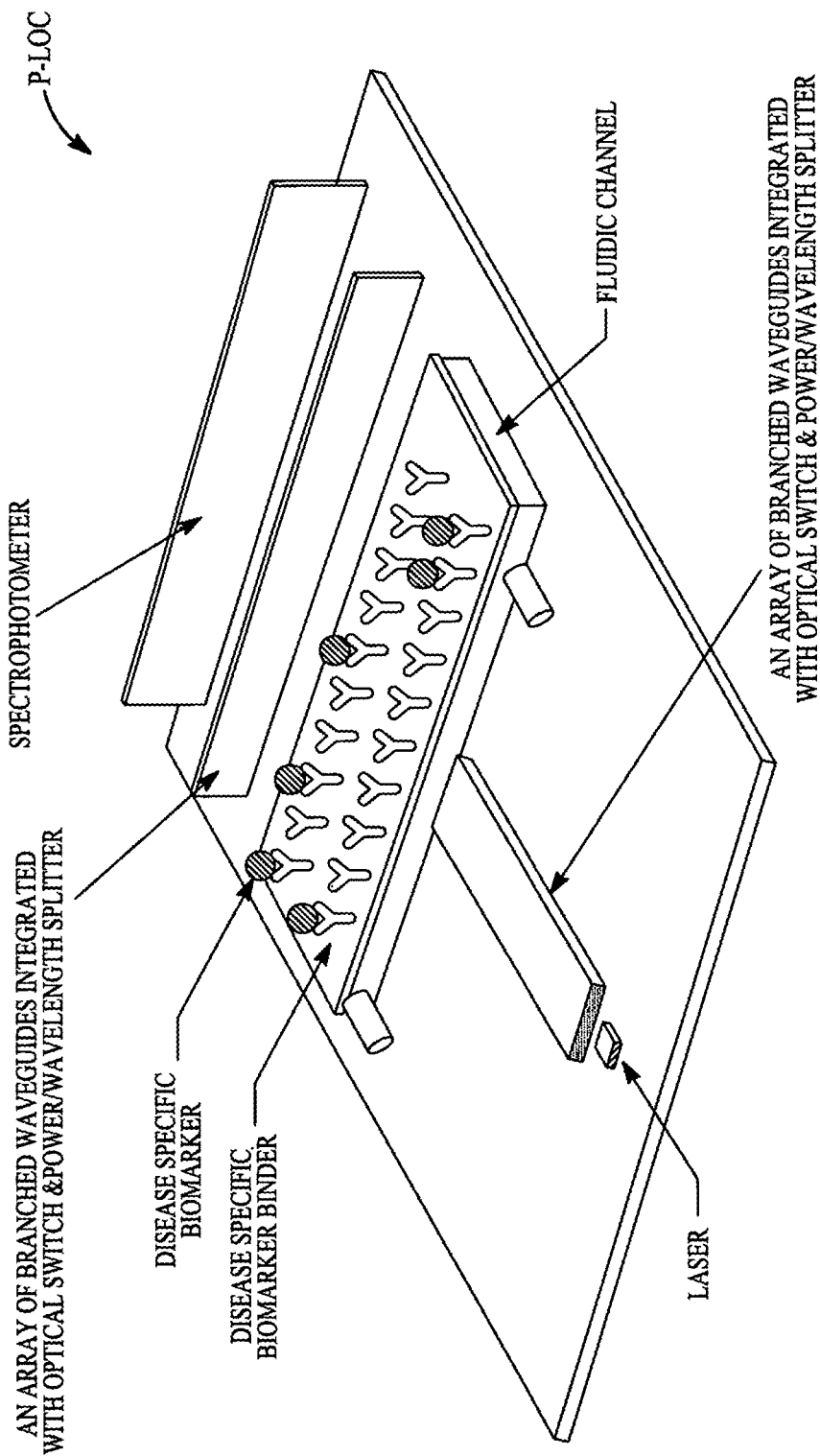

FIG. 19J illustrates another embodiment of 19I, wherein an array of high Q ring resonator based add filters is also replaced by an array of optical waveguides, integrated with an optical switch and a power/wavelength splitter.

Additionally, a metamaterial waveguide (e.g., a hyperbolic waveguide) of alternating ultra thin-films of semiconductors and/or insulators and metals can be fabricated/constructed to absorb each wavelength of light, at slightly different places in a vertical direction.

Additionally, various devices can be connected by a multi-optical fiber connector, making the fluid/cavity section(s) containing a human body's blood/biological fluid disposable.

Alternatively, optical fibers can be aligned passively with precise metal alignment pins seated into v-grooves on a precise silicon optical bench substrate. The precise metal alignment pins are utilized top mate with a pluggable optical fiber connector integrated with a molded plastic lens.

Figure 19K:
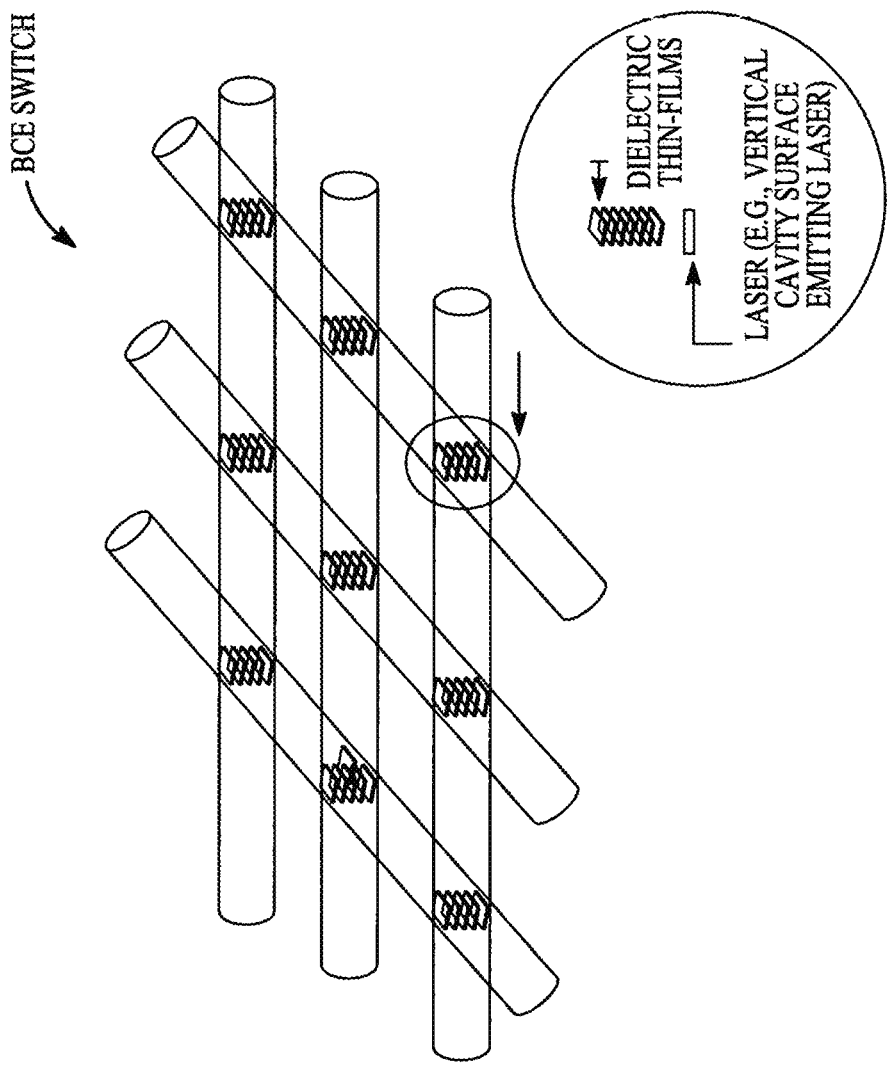
FIG. 19K illustrates a specific embodiment of Bose-Einstein condensate (BCE) based ultrafast optical switch for applications in biology.

FIG. 19K illustrates an embodiment of an ultra-fast Bose-Einstein Condensate based ultra-fast optical switch for applications in biology. An ultra-fast N×N Bose-Einstein Condensate based optical switch can be realized utilizing an array of single-mode/multi-mode waveguides on the left-hand side and an array of single-mode/multi-mode waveguides on the right hand side, wherein the array of single-mode/multi-mode waveguides on the left-hand side and the array of single-mode/multi-mode waveguides on the right hand side are optically coupled with polariton Bose-Einstein condensate. Short-lived room temperature polariton Bose-Einstein condensate can be created through interaction of a laser light (bouncing back and forth within multiple dielectric thin-films) and a luminescent polymeric thin-film of about 30 nanometers in thickness. The luminescent polymeric thin-film is embedded within multiple dielectric thin-films, wherein the multiple dielectric thin-films is then illuminated from the bottom (of the multiple dielectric thin-films, each dielectric thin-film is about 40 nanometers in thickness) by a vertical surface emitting laser or an in-plane laser integrated with a mirror and a lens.

Figure 19L:
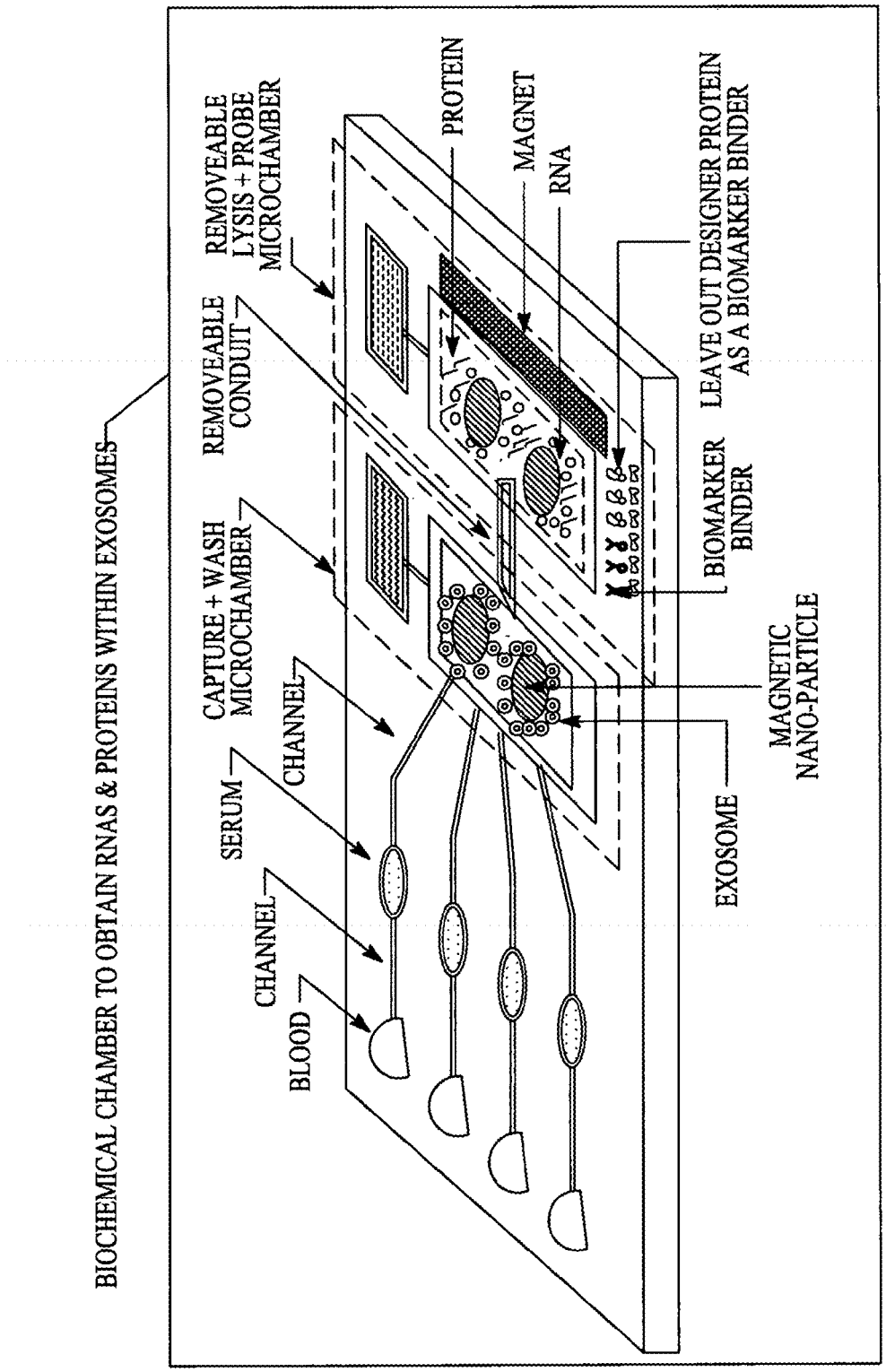
FIGS. 19L, 19M and 19N illustrate an integrated device to obtain various RNAs and proteins within exosomes from a human body's blood.
Figure 19M:
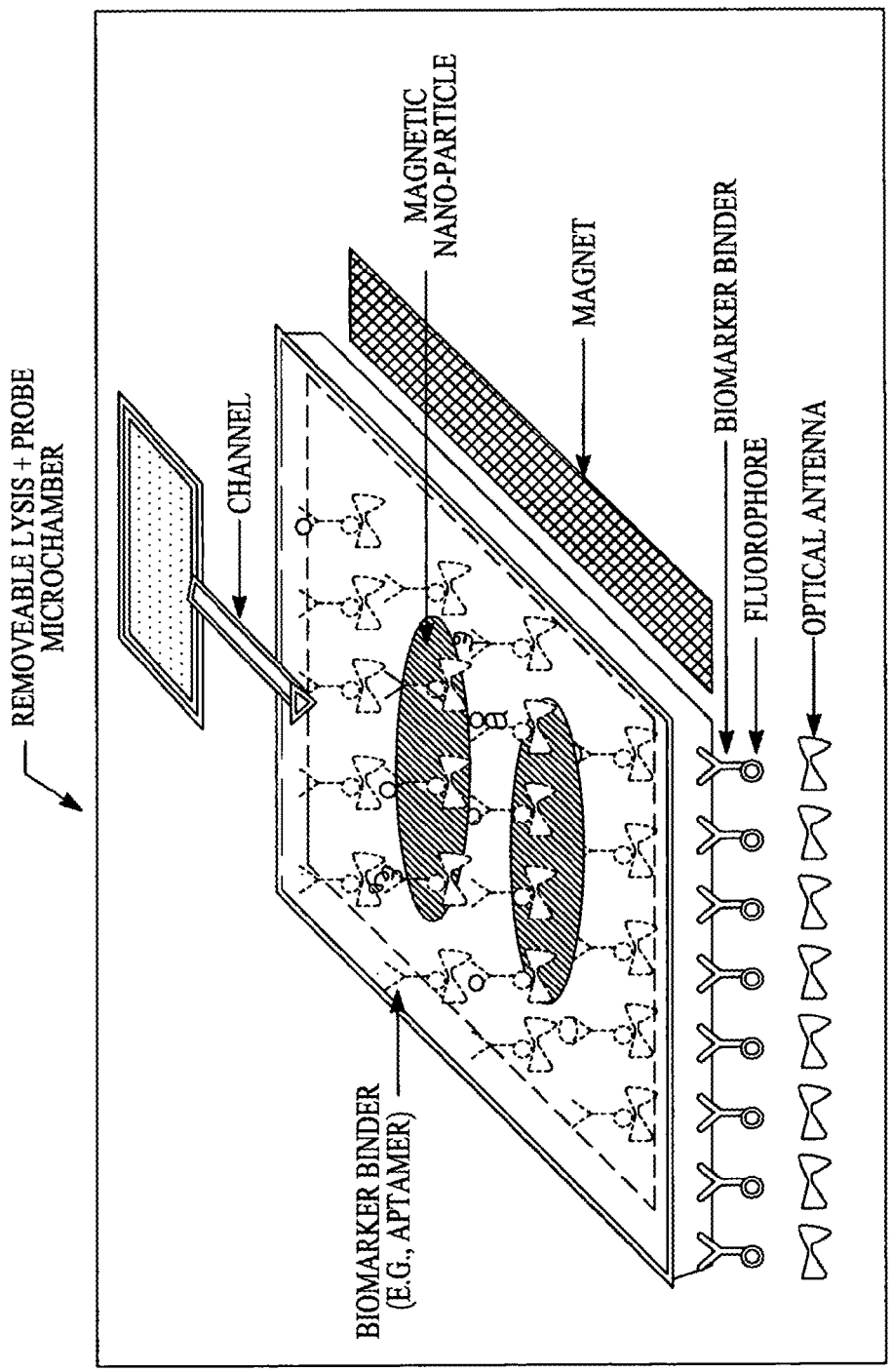
Figure 19N:
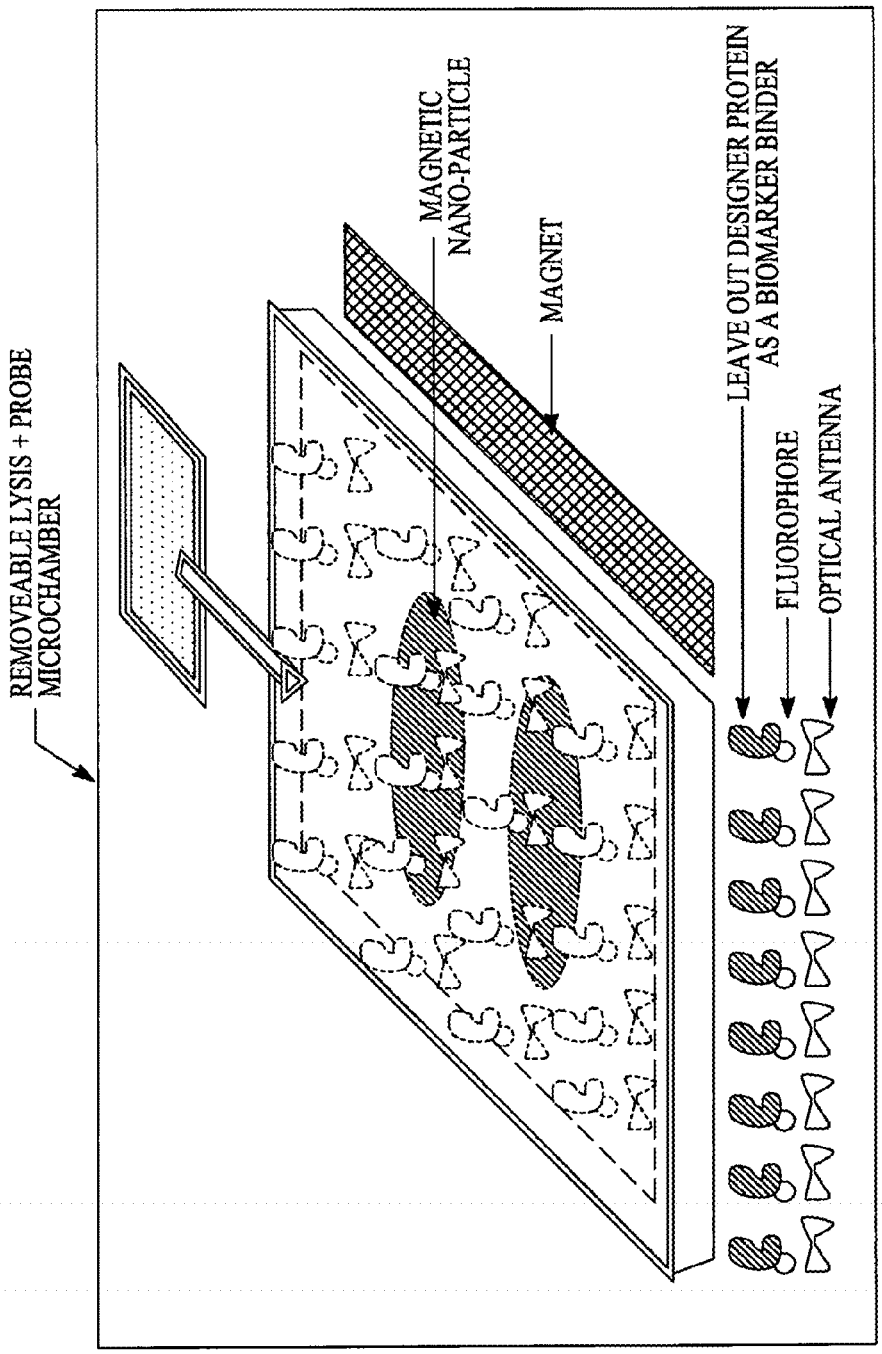
Figure 19O:
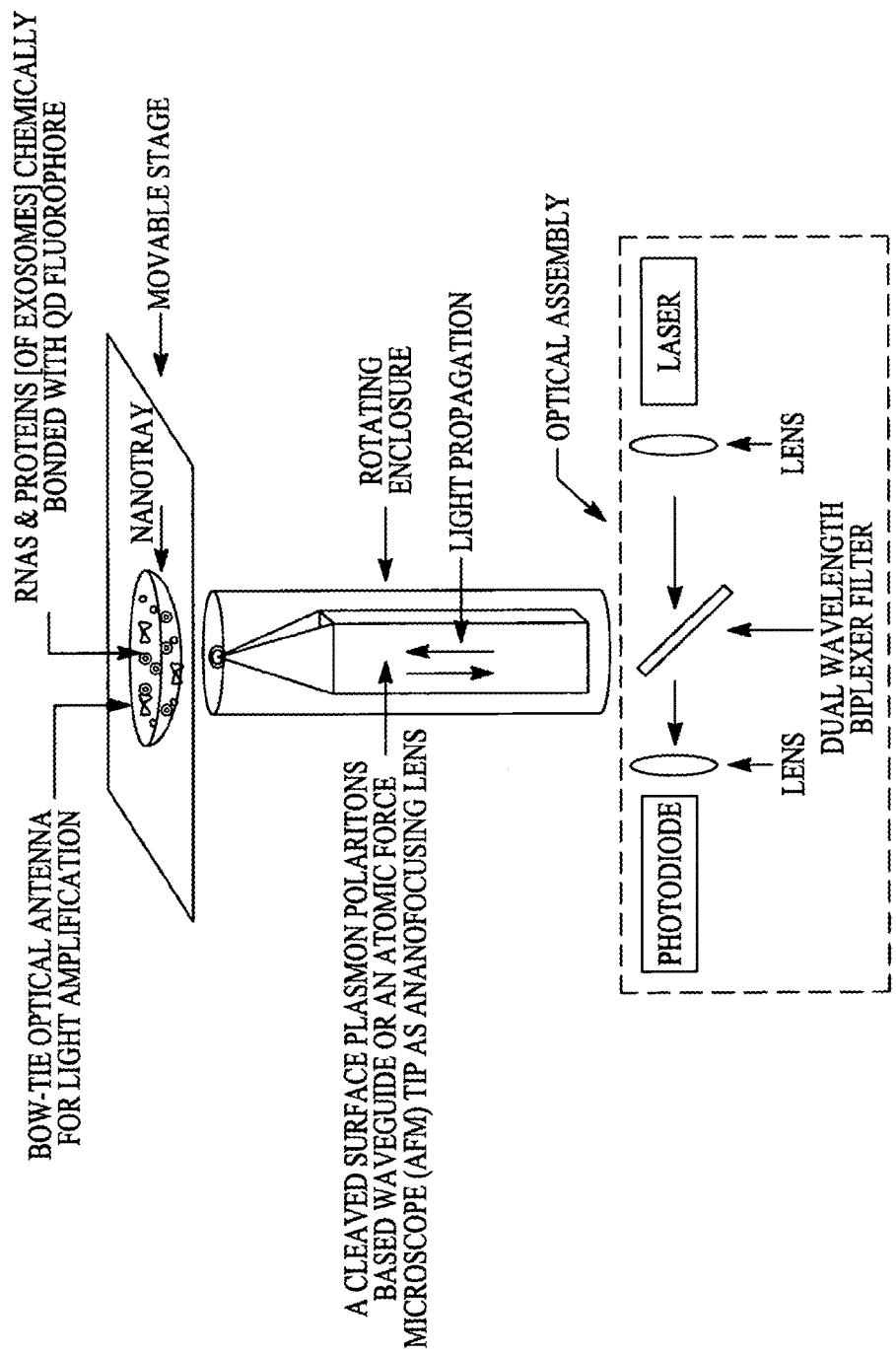
FIG. 19O illustrates a nanoscope for detecting various RNAs and proteins within exosomes from a human body's blood.

FIGS. 19L, 19M and 19N illustrate an integrated device to obtain various RNAs and proteins within exosomes from a human body's blood.

FIG. 19L illustrates a biochemical chamber to obtain RNAs or proteins caged within exosomes. The biochemical chamber can be molded in poly(dimethylsiloxane). The biochemical chamber is degassed via vacuum prior to its use and the absorption of gas by poly(dimethylsiloxane) provides the mechanism for actuating and metering the flow of fluid in the microfluidic channels and between various parts of the biochemical chamber. The biochemical chamber can take in a human body's blood at inlets. The biochemical chamber can use tiny microfluidic channels of 30 micron in diameter underneath the inlets to separate the serum from a human body's blood by utilizing laws of microscale physics. The serum moves through the biochemical chamber via a process called degas-driven flow.

Superparamagnetic nanoparticles iron oxide can be synthesized with a positive electrical charge to bond onto the membrane surface of exosomes (within a human body's blood/biological fluid) of negative electrical charge due to electrostatic interactions. Capture of exosomes by superparamagnetic nanoparticles iron oxide is realized in Capture+Wash Microchamber.

The biochemical chamber can be integrated with a magnet. Exposure to a magnetic field can separate superparamagnetic nanoparticles iron oxide bonded with exosomes. Alternatively, the biochemical chamber can be integrated with a nanosieve/nanomembrane (e.g., a carbon nanomembrane) of about 100 nanometers pore diameter to filter exosomes—this is not illustrated in the Lysis+Probe Microchamber of the FIG. 19L.

Alternatively, the biochemical chamber can be integrated with a nanofilter (e.g., a carbon nanomembrane) of about 100 nanometers pore diameter to filter exosomes.

For example, a nano filter can be graphene based nanofilter. Nanoholes in graphene-a hexagonal array of carbon atoms can be fabricated/constructed in a two-stage process. First, a graphene sheet is bombarded with gallium ions or helium ions, which disrupt the carbon bonds. Second, the graphene sheet is etched in an oxidizing solution that reacts strongly with the disrupted carbon bonds-producing a nanohole at each spot where the gallium ions or helium ions struck. By controlling how long the graphene sheet is left in the oxidizing solution, one can control the average size of the nanoholes.

Furthermore, the Lysis+Probe Microchamber is removable. Furthermore, a suitable chemical (e.g., System Bio company's Micro SeraMir) can be added in the removable Lysis+Probe Microchamber to break the membrane of exosomes to obtain embedded RNAs and proteins within the exosomes.

The removable Lysis+Probe Microchamber has a disease specific aptamer (integrated with a fluorescent protein or a fluorophore) to bind with a disease specific mRNA, which was once caged within the exosomes.

Furthermore, the removable Lysis+Probe Microchamber has a disease specific designer protein (integrated with a fluorescent protein or a fluorophore) with a leave-one-out configuration, wherein each protein has an omitted segment to create a binding site to fit a disease specific protein, which was once caged within the exosomes.

Plasmonic optical nanoantennas can be integrated with the fluorescent protein or the fluorophore (e.g., quantum dot fluorophore) to enhance fluorescence.

Alternatively, the removable Lysis+Probe Microchamber has an array (e.g., billions) of plasmonic optical nanoantennas on the floor of the Removable Lysis+Probe Microchamber to enhance fluorescence.

FIG. 19M illustrates an embodiment of the removable Lysis+Probe Microchamber with a biomarker binder (e.g., an aptamer integrated with a fluorescent protein or a fluorophore). Furthermore, plasmonic optical nanoantennas can be integrated with the fluorescent protein or the fluorophore (e.g., quantum dot fluorophore) to enhance fluorescence.

FIG. 19N illustrates an embodiment of the removable Lysis+Probe Microchamber with a biomarker binder such as a designer protein integrated with the fluorescent protein or the fluorophore. The designer protein is a leave-one-out configuration, wherein each protein has an omitted segment to create a binding site to fit a disease specific protein, which was once caged within the exosomes Furthermore, plasmonic optical nanoantennas can be integrated with the fluorescent protein or the fluorophore (e.g., quantum dot fluorophore) to enhance fluorescence The fluidic channel as described in FIGS. 19A, 19B, 19C, 19D, 19E, 19I and 19J can be replaced with the removable Lysis+Probe Microchamber, as described in either FIG. 19M or FIG. 19N.

The cavity, as described in FIGS. 19F, 19G and 19H, can be replaced with the removable Lysis+Probe Microchamber, as described in either FIG. 19M or FIG. 19N.

A femtosecond laser (as a single machining tool) can be utilized to fabricate/construct three-dimensional optical waveguides and fluidic channels of the photonics-lab-on chip. Thus, the photonics-lab-on chip can be utilized for point of care detection of a disease/an array of diseases.

FIG. 19O illustrates (both in top view and cross-sectional view) a nanoscope for detecting various RNAs and proteins within exosomes from a human body's blood/biological fluid. A specific RNA and/or protein can bind with a specific aptamer, wherein the aptamer is chemically coupled with a quantum dot fluorophore. Incident light from a laser, collimated by a lens and transmitted through an optical filter, then focused onto a nanotray containing exosomes, by surface plasmon polaritons based a nanofocusing waveguide lens.

Alternatively, an atomic force microscopy (AFM) tip with high resolution optics (100×, resolving power ≤400 nanometer) can be utilized as a nanofocusing waveguide lens.

The bottom of the nanotray can be integrated with an array of gold nanoantennas for light amplification. The nanotray can be mounted on a movable stage.

The nanofocusing waveguide lens is fabricated/constructed, utilizing amorphous silicon dioxide. The waveguide is coated with an ultra thin-film of gold. The nanofocusing waveguide lens is about five microns long and rectangular in shape tapering to a point at one end. Because the nanofocusing waveguide lens concentrates light into a nanosized point, it can create a high-resolution map of RNAs and proteins within exosomes. The nanofocusing waveguide lens is mounted and enclosed within a rotating enclosure.

Fluorescence light can also travel in the reverse/opposite direction through the nanofocusing waveguide lens, then through the optical filter, the lens and the photodiode. Thus, collecting light through the narrow point can turn the nanofocusing waveguide lens into a high resolution nanoscope.

However, it should be noted that FIG. 19O illustrates the nanoscope in a vertical configuration. Other configurations (e.g., an upright or an inverted or a planar configuration) of the nanoscope are possible, without departing from the scope and spirit of this nanoscope.

Figure 19P:
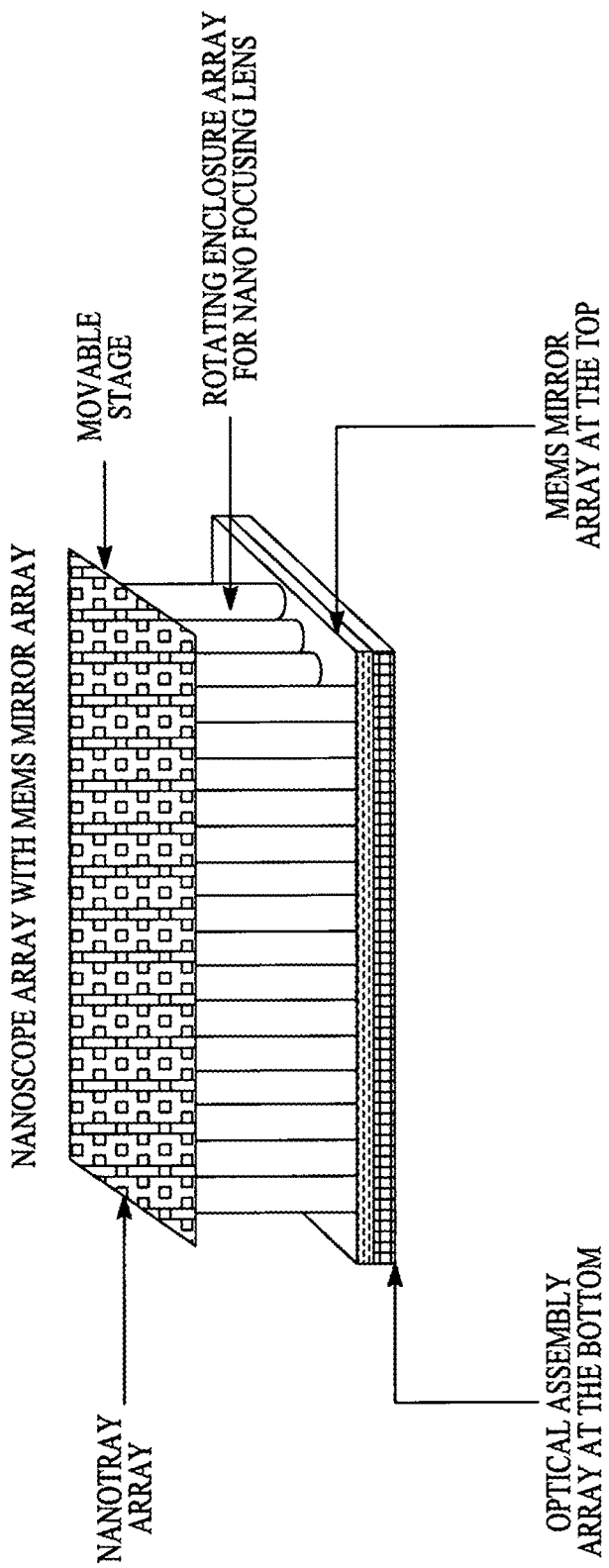
FIG. 19P illustrates an array of nanoscopes for detecting various RNAs and proteins within exosomes from a human body's blood.

FIG. 19P illustrates an array of nanoscopes enabled by microelectro-mechanical-system mirror array (e.g., Texas Instrument's Digital Light Processor projector chip) and rotating array of enclosures for nanofocusing waveguide lens.

Figure 19Q:
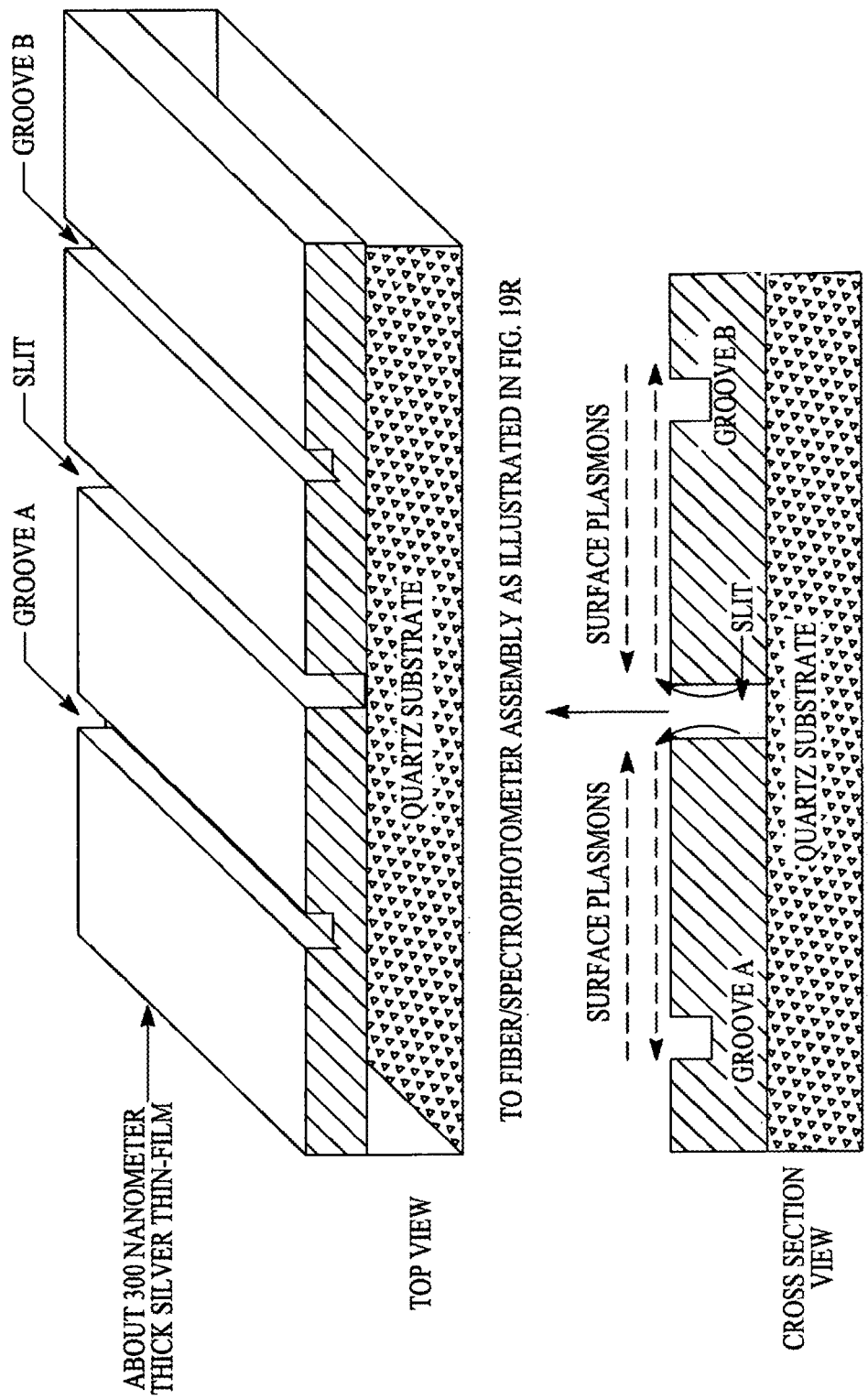
FIG. 19Q illustrates a plasmonic interferometer for detecting various RNAs and proteins within exosomes from a human body's blood.

FIG. 19Q illustrates a plasmonic interferometer for detecting various RNAs and proteins within exosomes from a human body's blood/biological fluid. A quartz substrate coated with a thin-film of silver (about 300 nanometers in thickness). Fabricated/constructed in the silver thin-film is a nano-scaled plasmonic interferometer, wherein the nano-scaled plasmonic interferometer has a center slit (about 100 nanometers in depth and 30 microns in length) with a groove (about 70 nanometers in depth, 130 nanometers in width and 30 microns in length) on each side of the groove. When light (e.g., light from a narrow-band light source) is shined through the quartz substrate, the groove cause a wave of free electrons in the silver thin-film, a surface plasmon polariton to propagate toward the center slit. Those waves interfere with light that passes through the center slit. A sensitive spectrophotometer/optical fiber assembly (as described in the FIG. 19R) can be utilized to measure the patterns of interference generated by the grooves and slit. When a human body's blood/biological fluid is deposited on the above nano-scaled plasmonic interferometer; the light and the surface plasmon waves propagate through a human body's blood/biological fluid before they interfere with each other-thus altering the interference pattern detected by a sensitive spectrophotometer.

Furthermore, by adjusting the distance between the grooves and center slit, the above nano-scaled plasmonic interferometer can be calibrated to detect the signature of a disease specific biomarker and/or bioactive compound and/or bioactive biomolecule with high sensitivity in an extremely small volume of a human body's blood/biological fluid.

For example, a first enzyme-glucose oxidase can chemically react with glucose (from a human blood/biological fluid) to generate hydrogen peroxide. A second enzyme-horseradish peroxidase can chemically react with hydrogen peroxide to generate resorufin. Both reactions can be facilitated by microfluidic channels. Resorufin is a colored liquid, which can absorb/emit red light. Thus, the above nano-scaled plasmonic interferometer can be calibrated to detect the signature of resorufin, as a measure of glucose concentration in a human body's blood/biological fluid.

Furthermore, thousands of nano-scaled plasmonic interferometers can be fabricated in the thin-film of silver, wherein each nano-scaled plasmonic interferometer can be calibrated to detect only the signature of a disease specific biomarker and/or bioactive compound and/or bioactive biomolecule with high sensitivity in an extremely small volume of a human body's blood/biological fluid without any need of a fluorophore.

Figure 19R:
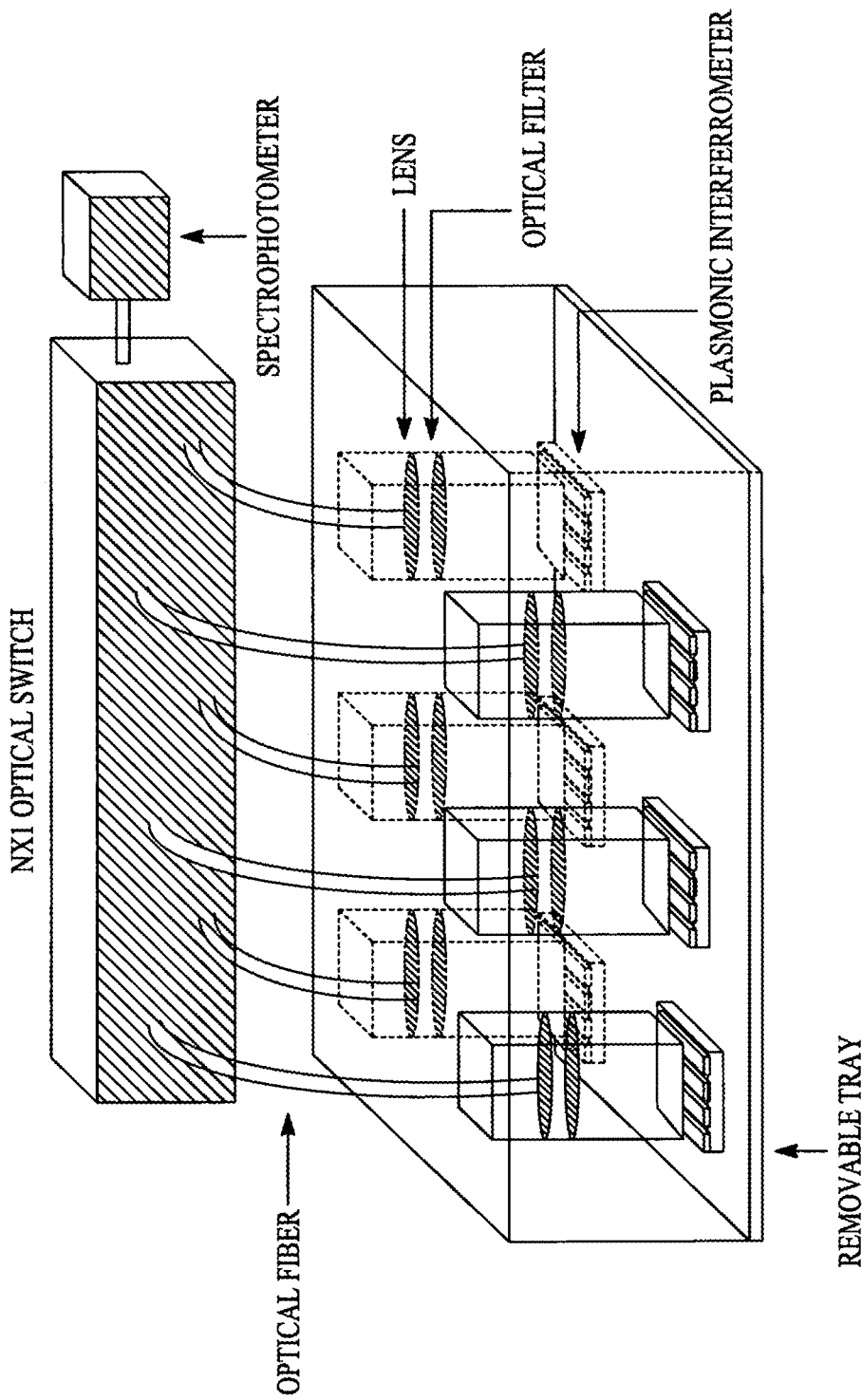
FIG. 19R illustrates an optical assembly of plasmonic interferometer-optical fiber-optical switch-spectrophotometer to measure the interference patterns generated by an array of plasmonic interferometers.

FIG. 19R illustrates an optical assembly of plasmonic interferometer-optical fiber-optical switch-spectrophotometer to measure the interference patterns generated by an array of plasmonic interferometers.

The interference patterns generated by the grooves and center slit is propagated through an optical thin-film filter (to reduce cross-talk from other plasmonic interferometers) and focused by a focusing lens onto an optical fiber. The array of optical fibers is connected with a N×1 optical switch, which is optically connected with a spectrophotometer for spectrum analysis.

FIG. 20 illustrates the photonics-lab-on chip, which can be inserted into the portable internet appliance 1600.

FIG. 20 also illustrates interactions of the portable internet appliance 1600 with a hologram. A hologram is an optical illusion enabling a two-dimensional image to appear in a three-dimensional form, out of the portable internet appliance 1600 and it can add a new dimension in video calls and/or multimedia texts.

Furthermore, haptic feedback can be added to the hologram. A user can touch and interact with the hologram and receive tactile responses, as if the hologram were real.

Example Applications of Portable Internet Appliance in Daily Life

The portable internet appliance 1600 can book the user on the next flight when the portable internet appliance 1600 finds out from the internet and other resources that the previous flight is canceled. The portable internet appliance 1600 can communicate with the user's family about the delay in arrival, newly booked flight and then notify/reorder the airport shuttle/taxicab accordingly to pick up the user from the airport. Besides the internet, the other resources may include various search engines (e.g., Bing, Google, Yahoo and Yelp), expert databases, data from existing Question & Answer forums (e.g., ChaCha) and answers drawn from a real-time application that would simply ask relevant people if they know they answer. What makes Question & Answer forums powerful is that they keep track of each and every question and answer pairing ever asked and every answer ever given.

The portable internet appliance 1600 can order and pay (with near-field communication for a coffee and downloadable movie (from a movie kiosk utilizing WiFi/millimeter wave (including 60 GHz)/terahertz band transceiver) of the user's preference at the airport terminal without the user input, where the digital signature of the movie can expire after a few days, making the movie unusable, after expiration of the digital signature.

A location positioning system can track/map how and where the user spends time both online and offline and if these times are happy or sad.

Example Other Applications of Portable Internet Appliance in Daily Life

The portable internet appliance 1600 can be integrated with a suitable software application program ("app") to convert/merge both a cell phone number and an e-mail identification into one integrated user identification.

Figure 21:
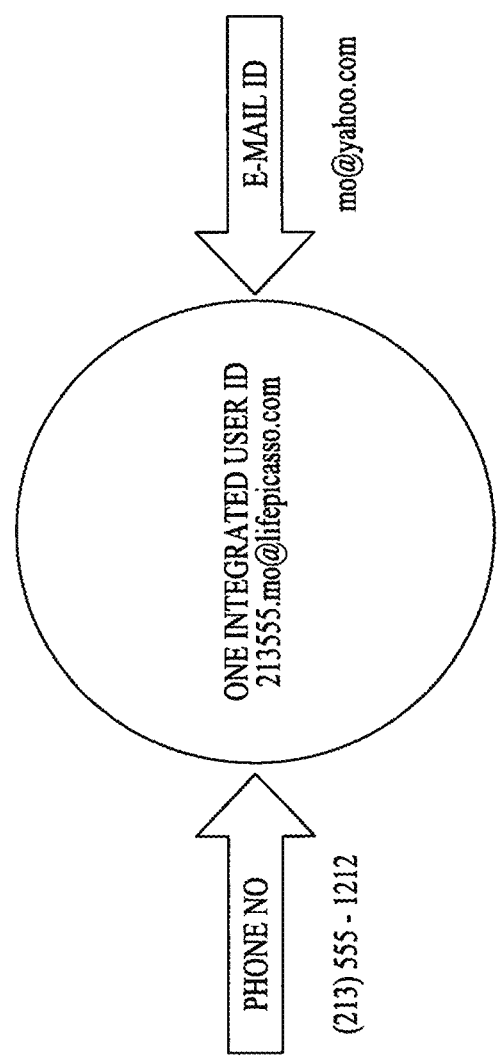
FIG. 21 illustrates realization of one integrated user identification merging a cell phone number and e-mail identification.

FIG. 21 illustrates a merger of a cell phone number (213) 555-1212 and an e-mail identification mo@yahoo.com into one integrated user identification: 213555.mo@lifepicasso.com. Thus, one integrated user identification can be utilized as a focal point for (a) voice-over-IP, (b) texting with an attachment, (c) microtexting, (d) e-mail with an attachment and (e) convergence of various internet related services. As an example, the focal point of near real-time/real-time convergence of various internet related services are: online files, VOIP phone calls, e-mail with an attachment/text message with an attachment/voice/video messages, social media/message, IPS/GPS locations, secure payments/purchases (offline/online) and digital banking. The above convergence can be configured with encryption, time-shifted and follow-up capabilities.

Furthermore, the one integrated user identification can be utilized as a platform for sending and receiving messages with another user.

Figure 22A:
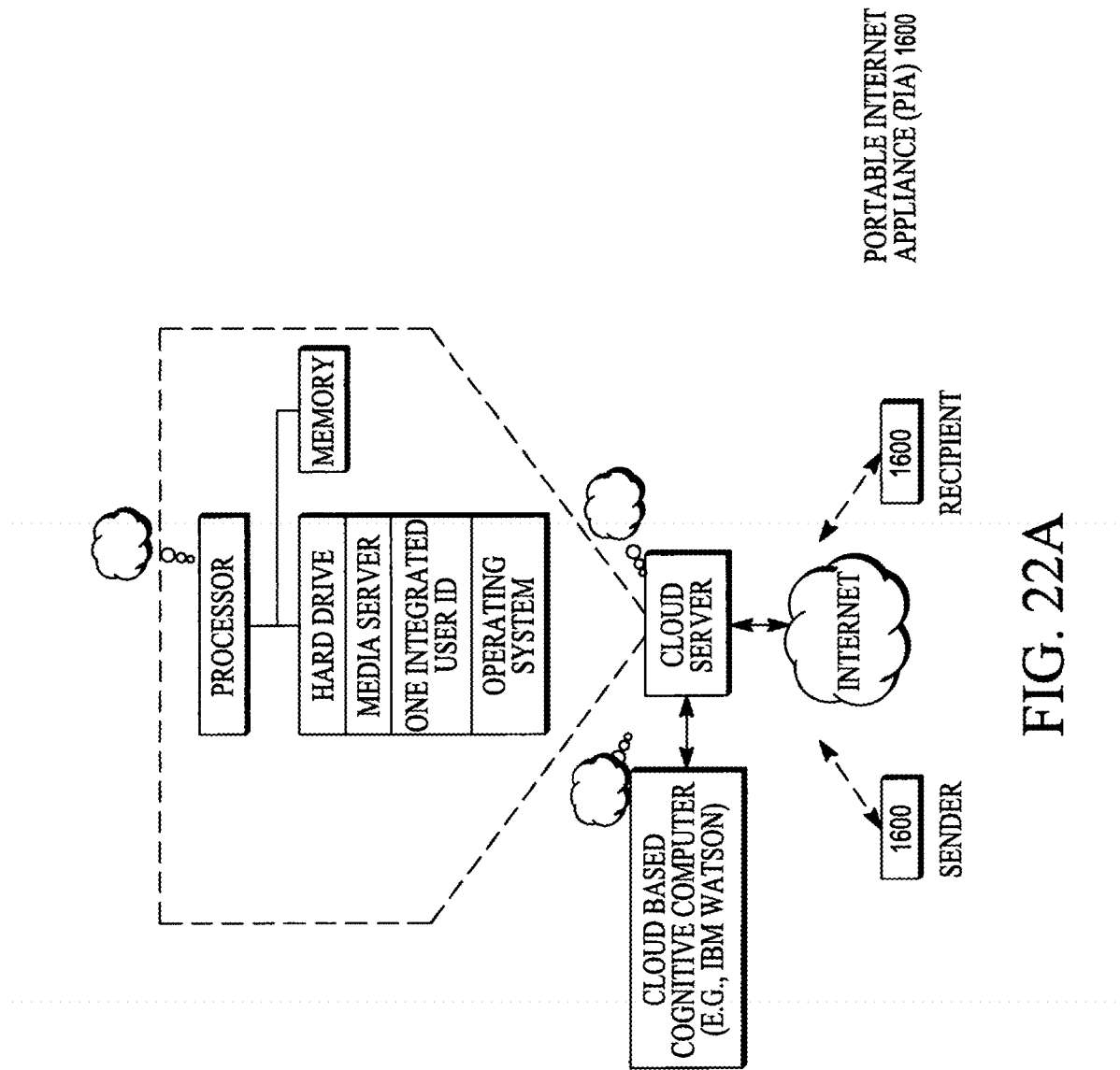
FIG. 22A illustrates a sender's portable internet appliance with a recipient's portable internet appliance via a cloud based server.

FIG. 22A illustrates a hardware configuration of the one integrated user identification with a processor, memory, hard drive (storage device), media server, operating system, stored in a cloud baser server. The cloud based server also connects with a cloud based cognitive computer and the portable internet appliance 1600. The one integrated user identification as a platform is shared between the sender's portable internet appliance 1600 and the recipient's portable internet appliance 1600 over the Internet.

Interactions of the users can be stored in a cloud based storage unit and analyzed by a cloud based expert cognitive computer (e.g., IBM Watson) in near real-time/real-time.

Figure 22B:
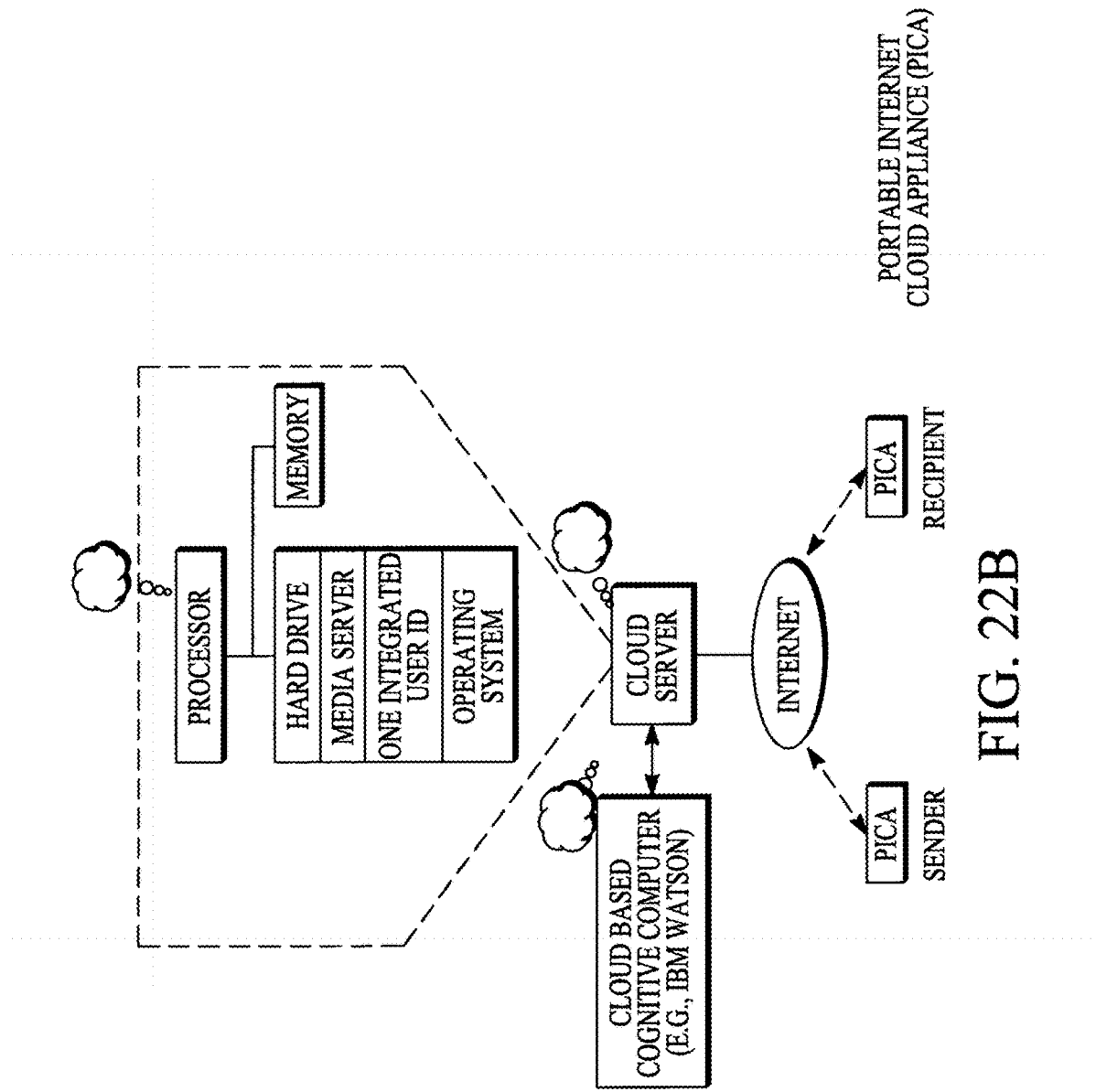
FIG. 22B illustrates a sender's portable internet cloud appliance with a recipient's portable internet cloud appliance via a cloud based server.

FIG. 22B illustrates a sender's portable internet cloud appliance (PICA) with a recipient's portable internet cloud appliance via a cloud based server, where the portable internet cloud appliance could be an Internet connected terminal device. The portable internet cloud appliance can replace the portable internet appliance, 1600.

Figure 23:
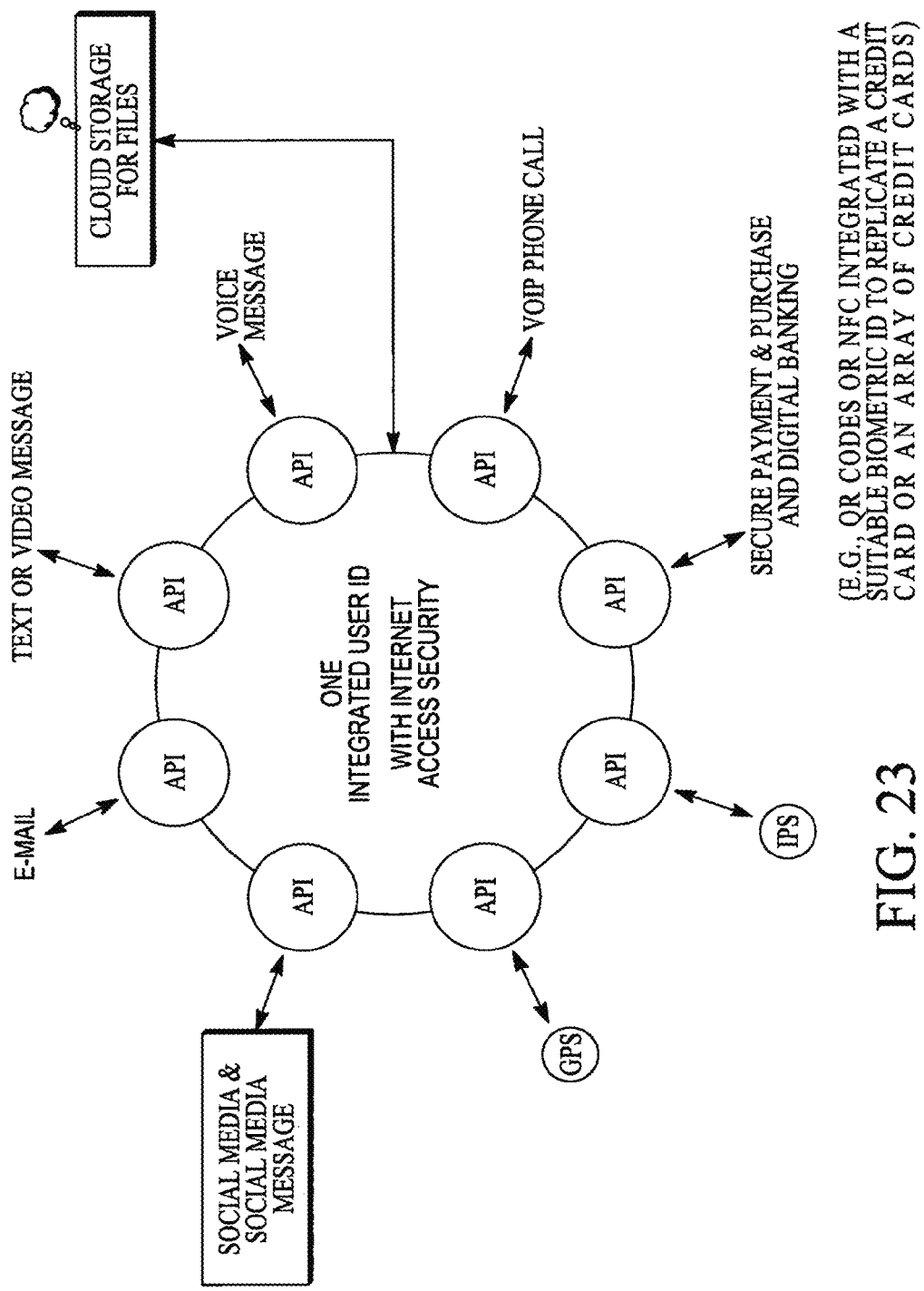
FIG. 23 illustrates a near real-time/real-time focal point convergence of various applications or functions with one integrated user identification.

FIG. 23 illustrates a near real-time/real-time focal point convergence of various applications or functions with one integrated user identification. APIs of many service links can be created by import.io and converged into the one integrated user identification For example, after properly authenticating the user's profile via suitable biometric verification, the user can open a digital bank account entirely online. The digital bank account with a search box can enable the user to type in queries in a question-answer format (e.g., "how much did I spend on travel last week?").

Furthermore, the question-answer format can be enhanced by a fuzzy logic algorithm/neuro-fuzzy logic algorithm. A fuzzy logic algorithm can be implemented as follows: (a) define linguistic variables and terms, (b) construct membership functions, (c) construct rule base, (d) convert crisp inputs into fuzzy values, utilizing membership functions (fuzzification), (e) evaluate rules in the rule base (inference), (f) combine the results of each rules (inference) and (g) convert outputs into non-fuzzy values (de-fuzzification). The key idea of fuzzy logic algorithm is that it uses a simple/easy way to secure the output(s) from the input(s), wherein the outputs can be related to the inputs by using if-statements. Neural networks can approximate a function, but it is impossible to interpret the result in terms of natural language. The fusion of neural networks and fuzzy logic in neuro-fuzzy algorithm can provide both learning as well as readability. Neuro-fuzzy algorithm is based on combinations of artificial neural networks and fuzzy logic.

Figure 24:
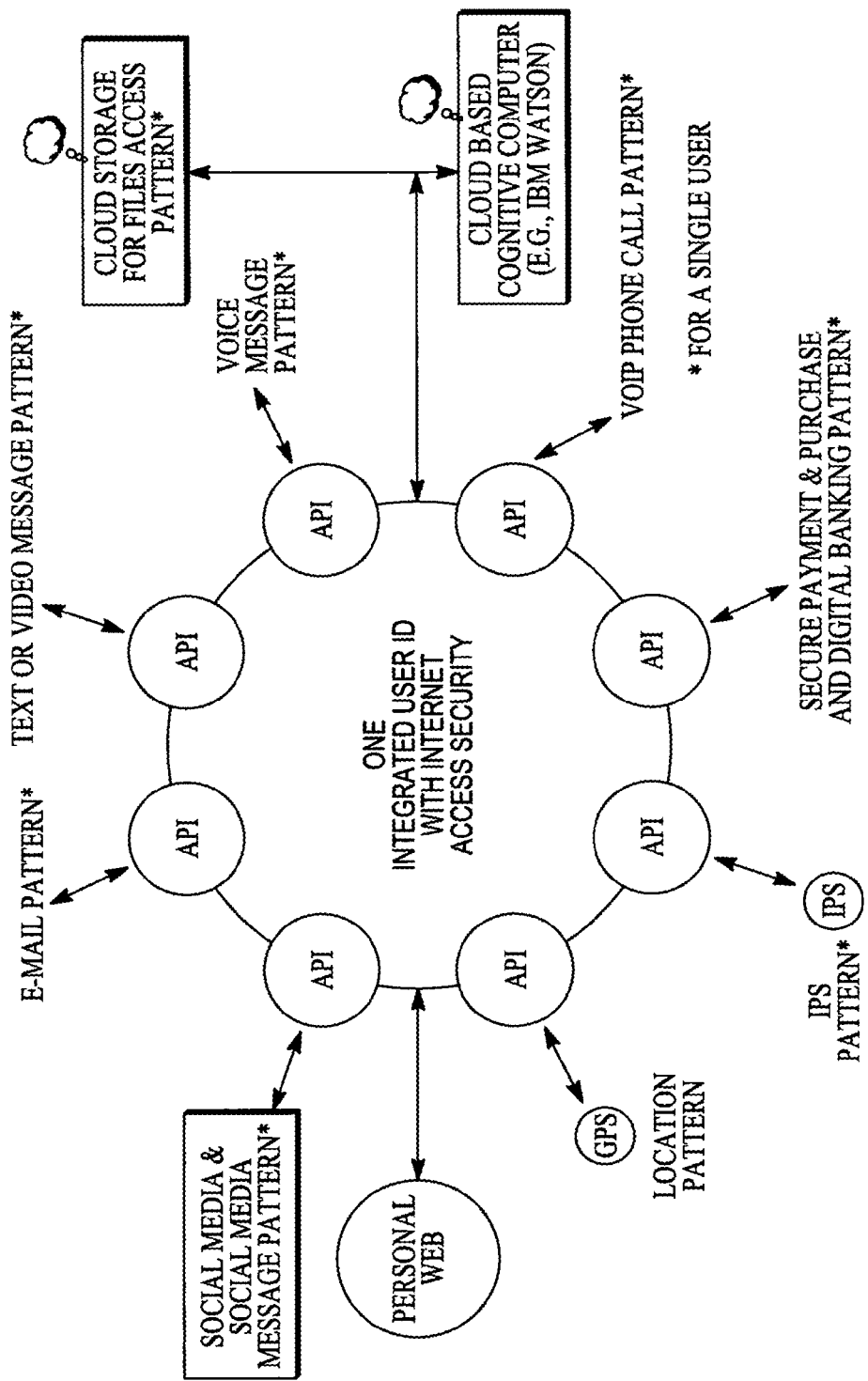
FIG. 24 illustrates patterns of various applications or functions of a single user with a user-centric personal web.

FIG. 24 illustrates patterns of various applications or functions of a single user (as described in FIG. 23) with a user-centric personal web. A user-centric personal web can make life easier in automating routine actions/decisions for the user.

The personal web can relate to (a) social (the people, a user interacts with and the content the user exchanges in social networks), (b) location (the user checks into), (c) product (the things the user buys on Amazon or eBay, the movies the user watches on Netflix/You Tube or the hotels the user books online) and (d) interest (the sort of things the user searches for on Google/You Tube or the things the user like on Facebook)-thus the personal web can reveal a lot about the user.

Building a statistical history, learning and relearning about the user data of social, location, product and interest, the usefulness of a personal web can be enhanced.

Thus, the portable internet appliance 1600 can be configured to know what time the user wants to wake up at, even before the user set an alarm. It knows the user's route to work and monitors traffic along the way, guiding the user through the most efficient route. In user's lunch break, the user can get food recommendations based on his/her past eating habits and current health conditions. When the user gets home, a smart thermostat has heated the home to the user's preferred temperature and a smart TV has remembered that the user loves to watch the evening news with CBS Dan Rather after work.

Furthermore, the usefulness of a personal web can be enhanced by connecting it with sensors, wherein the sensors are also connected with the internet and the portable internet appliance 1600.

The user has multiple passwords, identifications, services and devices. But security across them is fragmented. A digital security protector will sort through contextual, situational and historical data to verify the user's identity on different devices including the user's identity with biometric data in near real-time/real-time. The digital security protector can learn about the user's social graph (as described in FIG. 25) and make an inference about the user behavior that is out of the norm or may be due to someone stealing that user's identity. Based on the user's social graph, the digital security protector will know the user intimately, for example a particular user is a vegetarian, but someone is buying a non-vegetarian food with the user's credit card, the digital security protector will automatically close the credit card in question. Thus, the online security is based on intimacy with the user's social graph; rather than a collection of various fragmented passwords.

Furthermore, the one integrated user identification can be embedded with his/her digital security protector.

Figure 25:
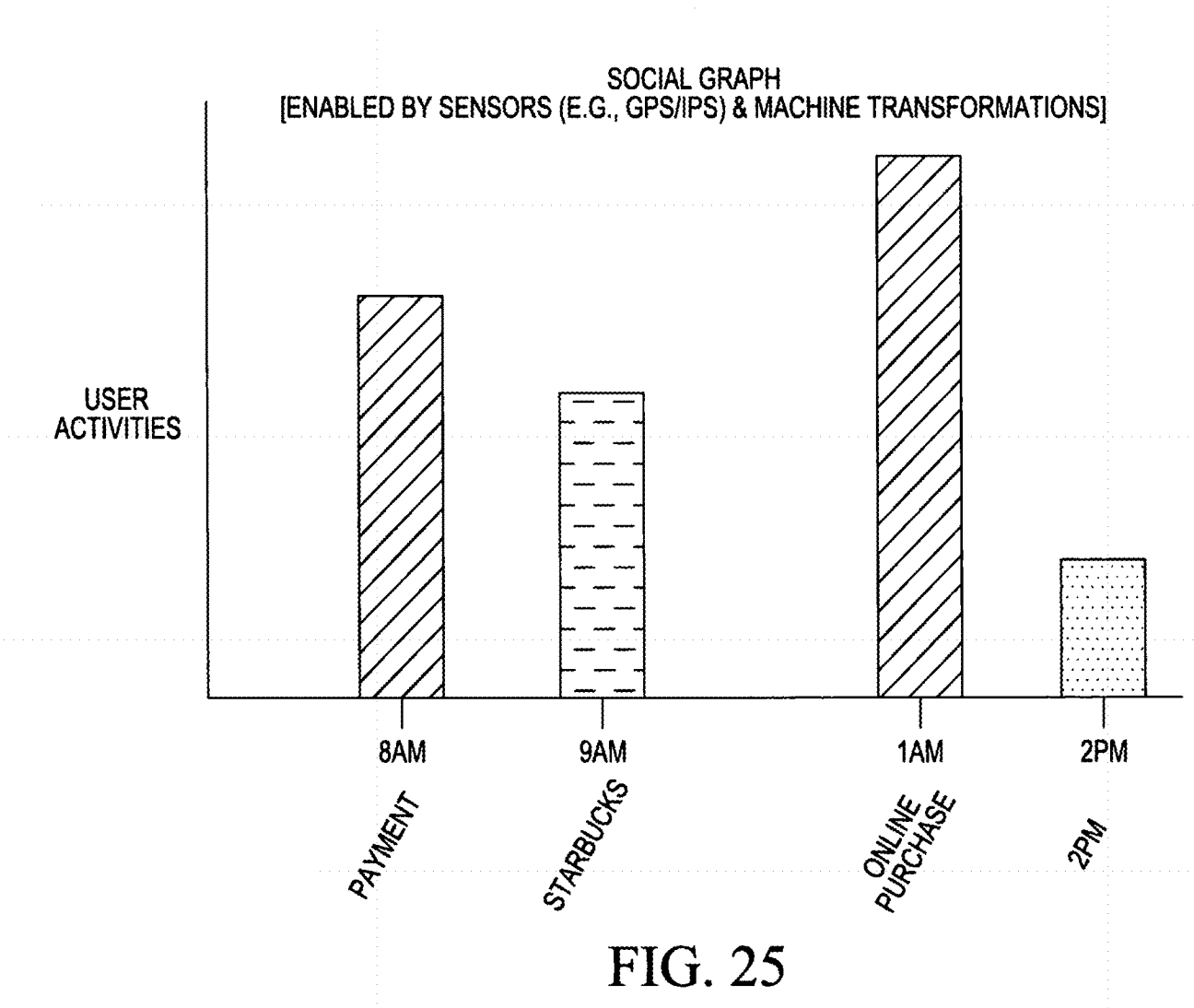

FIG. 25 illustrates a social graph of a user, enabled by (a) sensors (e.g., location determination module-indoor positioning system/global positioning system), (b) individual data patterns of the user, (c) an algorithm for generating the user's social graph with machine transformations, wherein the algorithm for generating the composite social graph with machine transformations can be stored in a local data storage unit of the portable Internet appliance 1600 or a cloud based data storage unit and (d) mathematical/statistical algorithm of Big Data stored in a cloud based data storage unit.

The user can auction his/her social graph or opt out. The auction price of his/her social graph can be based on the utility function of the user's social graph.

Figure 26:
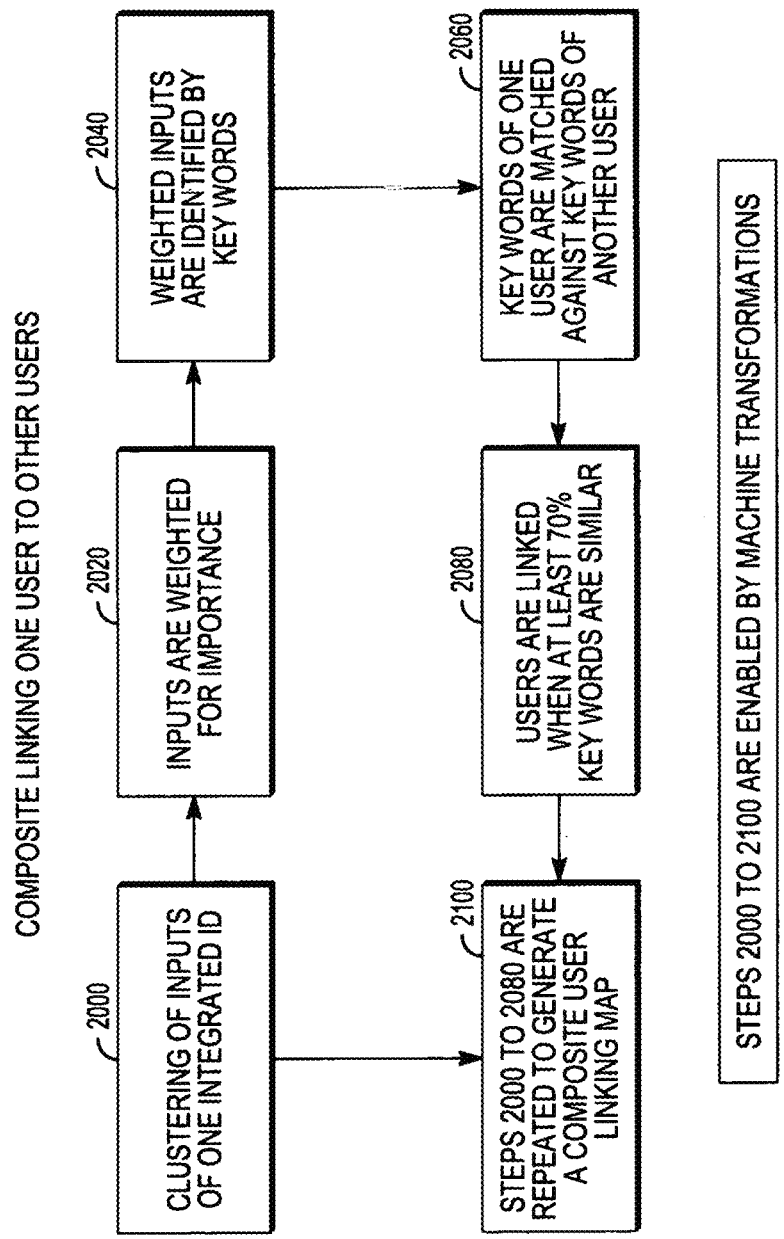
FIG. 26 illustrates a flow chart method of linking many users, utilizing machine transformations.

FIG. 26 illustrates a flow chart linking one user with many users, utilizing machine transformations. In step 2000, an algorithm performs clustering of inputs from one integrated user identification. In step 2020, the algorithm weighs inputs for importance. In step 2040, weighted inputs are identified for key words. In step 2060, key words of one user is matched with key words of another user. In step 2080, a user is linked with another user, when 70% of key words are matched. In step 2100, all previous steps (from 2000 to 2080) are repeated until there is a composite linking map.

Figure 27:
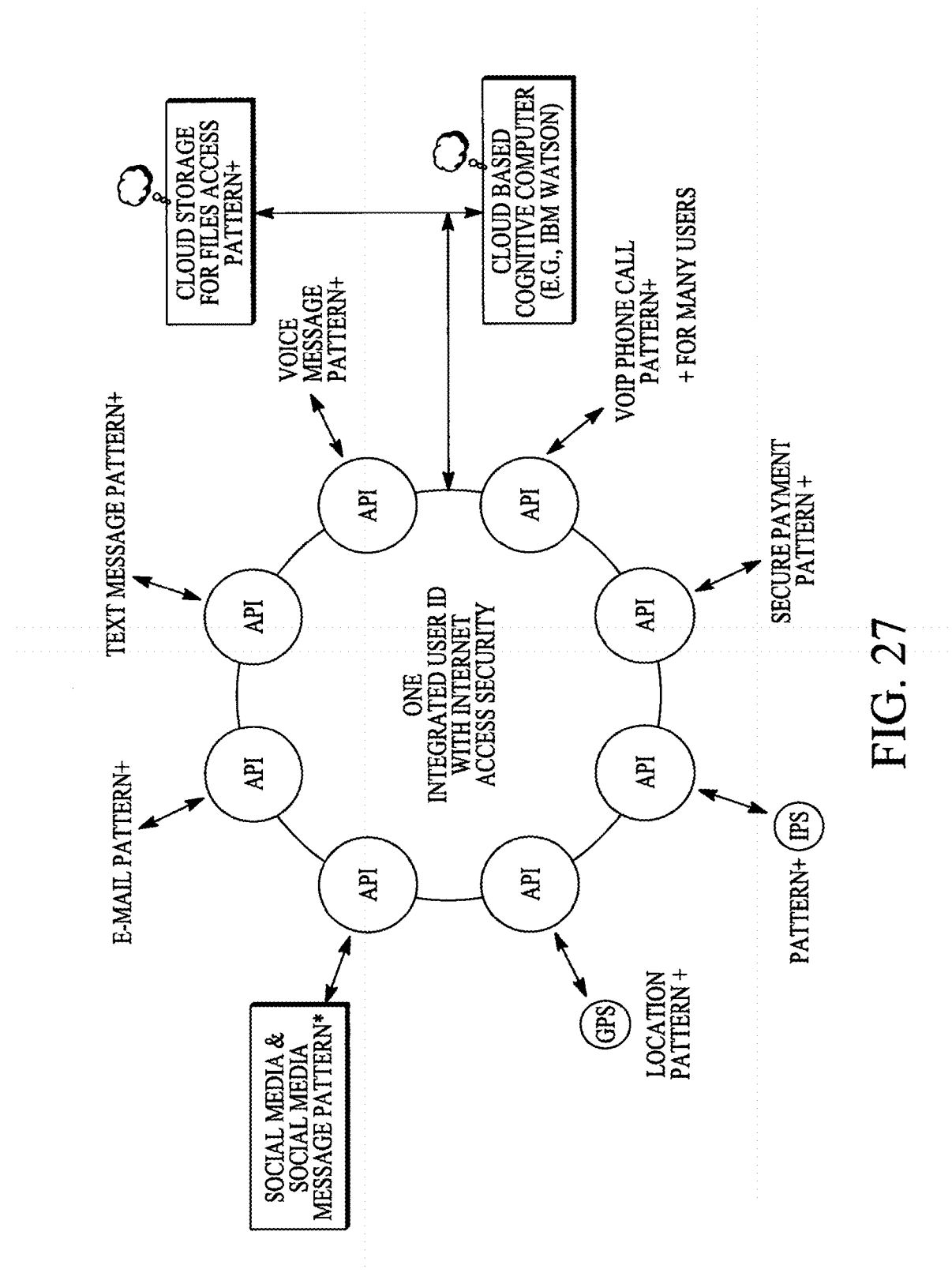
FIG. 27 illustrates patterns of various applications or functions of many users and analysis of such patterns by a cloud based machine learning/relearning interactive expert cognitive computer (e.g., IBM Watson).

FIG. 27 illustrates patterns of various applications or functions of many users and analyzes such patterns by a cloud based machine learning/relearning interactive expert cognitive computer (e.g., IBM Watson). Collective complex patterns of many users can be analyzed by topological analysis for data shape/structure and predictive modeling.

Figure 28:
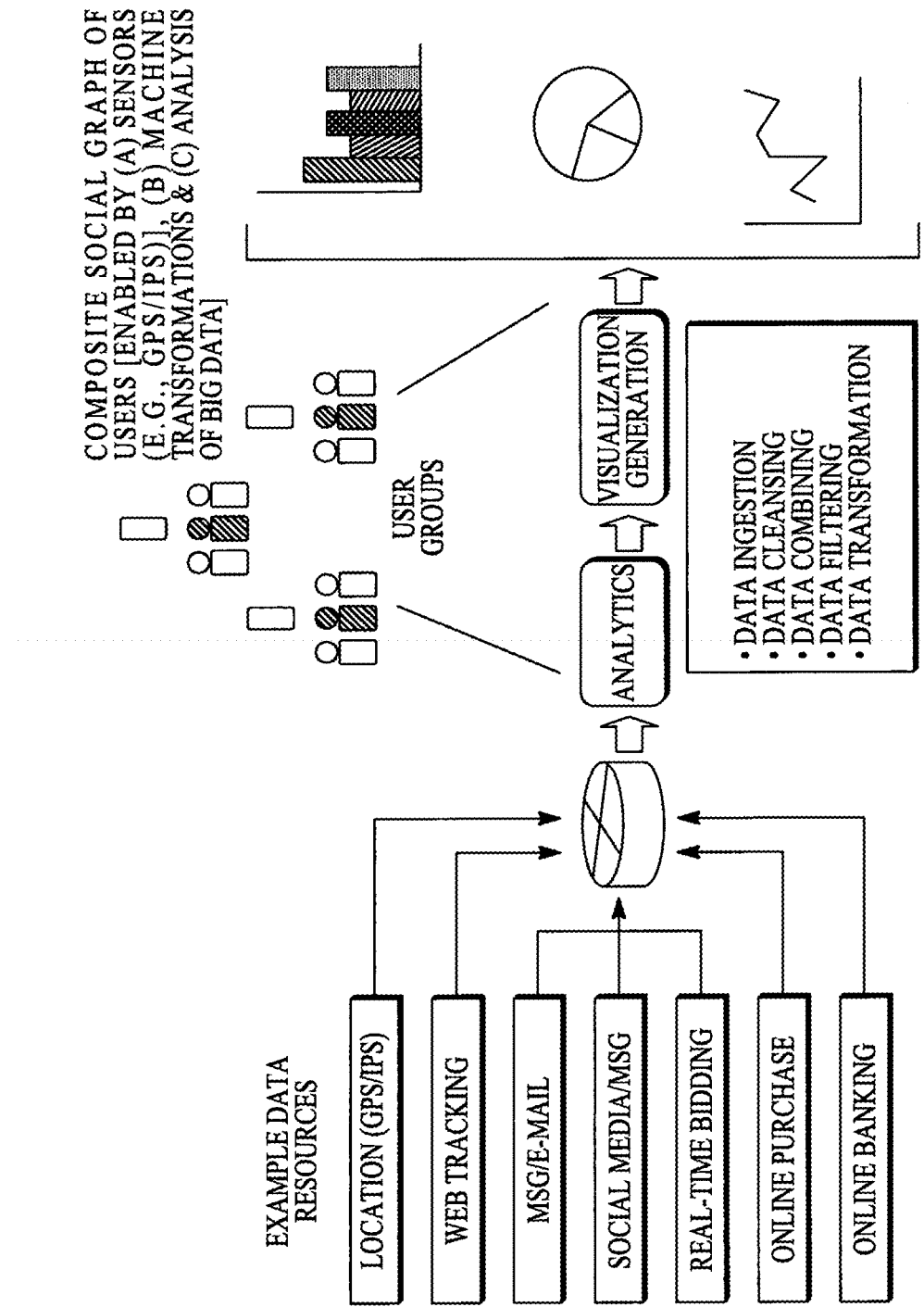
FIG. 28 illustrates a composite social graph of many users.

FIG. 28 illustrates a composite social graph of many users, enabled by (a) sensors (e.g., location determination module-indoor positioning system/global positioning system), (b) collective data patterns, (c) an algorithm for generating the composite social graph with machine transformations, wherein the algorithm for generating the composite social graph with machine transformations can be stored in a local data storage unit of the portable Internet appliance 1600 or a cloud based data storage unit and (d) mathematical/statistical algorithm of Big Data stored in a cloud based data storage unit.

The collective data patterns may include location, web tracking, message/e-mail, social media/message, real-time bidding, online purchase and online/digital banking.

Figure 29:
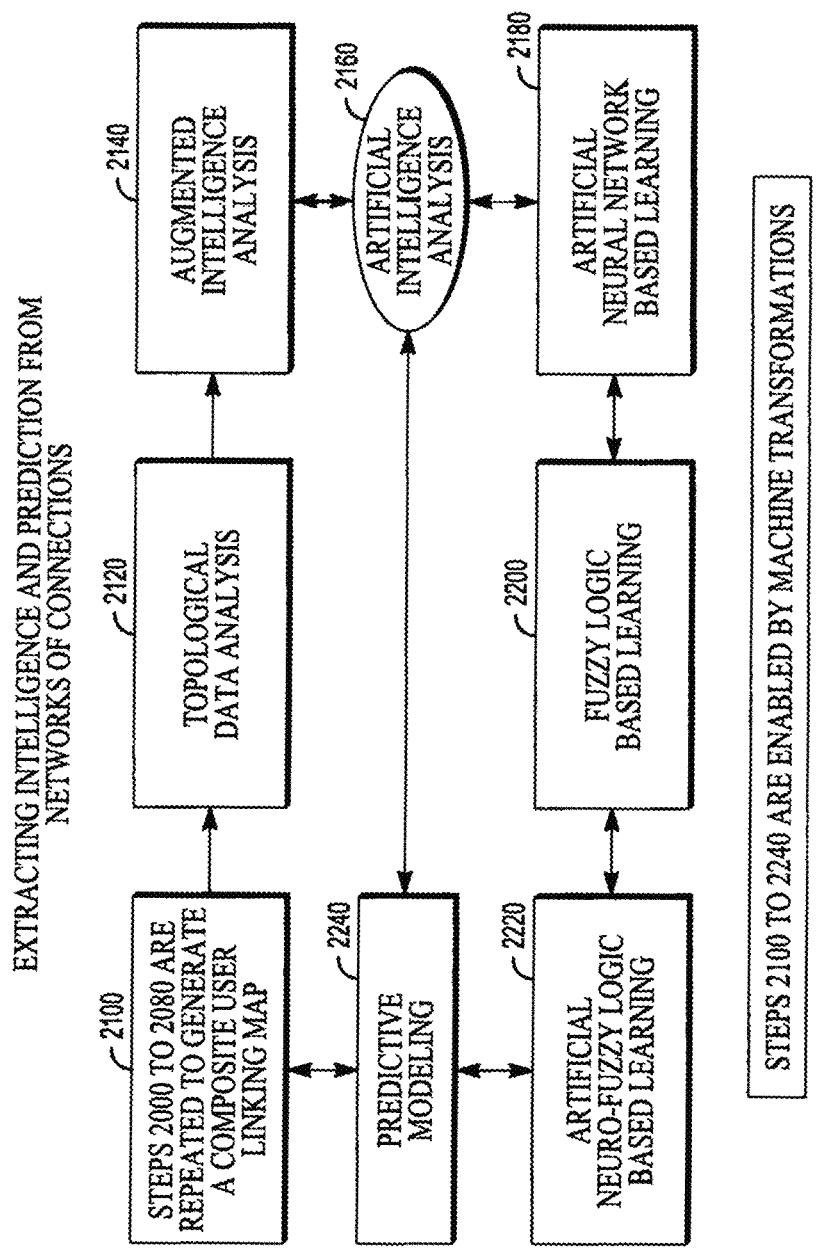
FIG. 29 illustrates a flow chart method of extracting intelligence and prediction from the collective data patterns, utilizing machine transformations.

FIG. 29 illustrates a method of extracting intelligence and prediction from the collective data patterns, utilizing machine transformations. In step 2100, a composite linking map is produced. In step 2120, the structure or shape of data is analyzed by topological data analysis. In step 2140, augmented intelligence analysis is performed. In step 2160, artificial intelligence based analysis is performed. In step 2180, artificial neural network based learning is performed. In step 2200, fuzzy logic based learning is performed. In step 2220, artificial neuro-fuzzy logic based learning is performed. In step 2240, predictive modeling is performed. Furthermore, step 2240 of predictive modeling is linked with the step 2160 of artificial intelligence based analysis. Steps 2100 to 2240, are realized by a series of machine transformations.

Fuzzy logic is a form of approximate reasoning, that can represent variation or imprecision in logic by making use of natural language (NL) in logic. An artificial neural network can approximate a function, but it is impossible to interpret the result in terms of natural language. Artificial neuro-fuzzy system is based on combinations of artificial neural networks and fuzzy logic.

The one integrated used identification can also enable collaboration, without needing to download any software. A user can click to join for collaboration (with many users) on one integrated used identification platform.

By way of an example of an application and not by way of any limitation, utilizing steps 2120, 2140, 2160, 2180, 2200, 2220 and 2240, a targeted marketing campaign via viral meme can be realized. Furthermore, the marketer can enhance user response to a particular advertisement by utilizing augmented reality. In another example, a marketer can anticipate what a particular user wants and needs for a car. A marketer can ask if the user would like to see a certain model of a car and then have a salesperson meet the user at a place, where that model of the car is located. Thus, the shopping experience can integrate both online and offline. Analysis of Big Data Related to Users' Social Graphs/Personal Analytics Big Data can be converted into a smaller data set utilizing linear simplification and/or signal clustering, as the underlying data has geometrical structures and patterns (repeated over time). Furthermore, signal clustering can be categorized and weighted for importance.

Alternatively, topological data analysis or Bayesian analysis coupled with Markov chain Monte Carlo methods can be utilized for analysis of Big Data.

Analysis of Big Data can be coupled with an augmented intelligence modeling algorithm and/or predictive modeling algorithm.

Furthermore, analysis of Big Data in unstructured format/natural language can be realized by a cloud based machine learning/relearning interactive expert cognitive computer (e.g., IBM Watson).

Furthermore, analysis of Big Data can be coupled with an intelligent learning set of instructions. A first intelligent learning set of instructions can include: artificial intelligence, data mining, fuzzy/neuro-fuzzy logic, machine vision, natural language processing, neural networks, pattern recognition, reasoning modeling and self-learning. A second intelligent learning set of instructions can include: algorithm-as-a-service, behavior modeling, physical search algorithm and software agent.

The behavior modeling can be described as-a user's behavior patterns are stored in a data storage module of the portable internet appliance 1600 or in a cloud based data storage unit. A data mining algorithm and/or a data interpretation algorithm can analyze the user's behavior patterns. Furthermore, a statistical machine learning software module can learn and relearn the user's behavior patterns to intimately identify the user.

A physical search algorithm can be utilized to search or search about a physical item (e.g., "Google my wallet?").

A software agent can search the internet for a particular topic/physical item with/without a human input. The software agent can further recommend information about the particular topic/physical item to the user.

Interactions of Networks of Objects/Biological Objects with the Portable Internet Appliance "Google my wallet?" would give the user the right answer, if the user's wallet is embedded with an object. (an object is illustrated in FIGS. 18E, 18F, 18G and 18H)

Furthermore, the object can be fabricated/constructed, as nanostructured mesh (as described in Table-16A and Table-16B), wherein each nanostructured mesh can be integrated with other suitable circuits and sensors.

TABLE 16A

Compositions For A Nanostructured Mesh For An Object

| Composition | Wt % Material A | Wt % Material B | Wt % Material C | Wt % Material D |
|---|---|---|---|---|
| 1 | 80% Hydrogel | 20% Chitin | | |
| 2 | 80% Hydrogel | 20% Chitosan | | |
| 3 | 80% Hydrogel | 20% Fibroin | | |
| 4 | 80% Hydrogel | 10% Chitin | 10% Chitosan | |
| 5 | 80% Hydrogel | 10% Chitin | 10% Fibroin | |
| 6 | 80% Hydrogel | 10% Chitosan | 10% Fibroin | |
| 7 | 80% Hydrogel | 10% Chitin | 10% PGLA | |
| 8 | 80% Hydrogel | 10% Chitosan | 10% PGLA | |
| 9 | 80% Hydrogel | 10% Fibroin | 10% PGLA | |
| 10 | 70% Hydrogel | 10% Chitin | 10% Fibroin | 10% PGLA |
| 11 | 70% Hydrogel | 10% Chitosan | 10% Fibroin | 10% PGLA |

TABLE 16B

Nanostructured Mesh (For An Object) Integrated With
Various Nanowire Field Effect Transistors (FETs)

| Compositions From Table-16A | Integrated With An Array Of Nanowire FETs |
|---|---|
| 1 | Nanowire$^{P1}$/Nanowire$^{P2}$/Nanowire$^{P3}$/Nanowire$^{z}$/Nanowire$^{c}$ |
| 2 | Nanowire$^{P1}$/Nanowire$^{P2}$/Nanowire$^{P3}$/Nanowire$^{z}$/Nanowire$^{c}$ |
| 3 | Nanowire$^{P1}$/Nanowire$^{P2}$/Nanowire$^{P3}$/Nanowire$^{z}$/Nanowire$^{c}$ |
| 4 | Nanowire$^{P1}$/Nanowire$^{P2}$/Nanowire$^{P3}$/Nanowire$^{z}$/Nanowire$^{c}$ |
| 5 | Nanowire$^{P1}$/Nanowire$^{P2}$/Nanowire$^{P3}$/Nanowire$^{z}$/Nanowire$^{c}$ |
| 6 | Nanowire$^{P1}$/Nanowire$^{P2}$/Nanowire$^{P3}$/Nanowire$^{z}$/Nanowire$^{c}$ |
| 7 | Nanowire$^{P1}$/Nanowire$^{P2}$/Nanowire$^{P3}$/Nanowire$^{z}$/Nanowire$^{c}$ |
| 8 | Nanowire$^{P1}$/Nanowire$^{P2}$/Nanowire$^{P3}$/Nanowire$^{z}$/Nanowire$^{c}$ |
| 9 | Nanowire$^{P1}$/Nanowire$^{P2}$/Nanowire$^{P3}$/Nanowire$^{z}$/Nanowire$^{c}$ |
| 10 | Nanowire$^{P1}$/Nanowire$^{P2}$/Nanowire$^{P3}$/Nanowire$^{z}$/Nanowire$^{c}$ |
| 11 | Nanowire$^{P1}$/Nanowire$^{P2}$/Nanowire$^{P3}$/Nanowire$^{z}$/Nanowire$^{c}$ |

Nanowire$^{P1}$ FET is a polymer nanowire FET (optionally coated with a lipid layer).
Nanowire$^{P2}$ FET is an engineered protein nanowire FET (optionally coated with a lipid layer). An engineered protein based field effect transistor (FET) can be fabricated/constructed, utilizing a suitable material decorated on engineered protein (e.g., a three-dimensional (3-D) ball and spike engineered protein-synthesized by a fusion of both Dps and gp5c genes).
Nanowire$^{P3}$ FET is a proton nanowire H+ FET (optionally coated with a lipid layer). A natural biopolymer chitosan/melanin based proton field effect transistor (H+ FET) and it incorporates a polymer substrate as a gate, a gate oxide insulator film, a source metal thin-film and a drain metal thin-film for proton current.
Nanowire$^{z}$ FET is zinc oxide wire nanowire FET (optionally coated with a lipid layer).
Nanowire$^{c}$ FET is carbon nanotube nanofiber FET (optionally coated with a lipid layer).

Similarly, a biological object can be fabricated/constructed, utilizing a nanostructured mesh (as described in Table-16A and Table-16B) integrated with suitable biocompatible circuits and biosensors. A biological object can be fabricated/constructed as biodissolvable, utilizing electronic circuits based on silicon nanowires and/or silk nanowires.

Furthermore, an object/biological object can be decorated/tagged with a nano-scaled label (an array of quantum dots or semiconductor nanocrystals) to absorb and emit light at a specific wavelength for identification. The nano-scaled label can be suitably excited by an invisible ultraviolet laser from a distance and detected by an infrared camera from a distance.

Furthermore, an object/biological can be integrated with a microelectro-mechanical-system-piezoelectric based actuator for movement or a propeller.

Networks of objects/biological objects can be utilized for recording and/or transmitting audio-visual information in a battlefield.

Networks of objects/biological objects can be utilized as collective assassins (wherein a nano-scaled reservoir within an object/biological object is filled with a toxic chemical) in a battlefield.

All the algorithms and/or software programs and/or software application programs ("apps") in the above disclosed specifications reside in a computer system, wherein the computer system generally includes: a premise based computer system and/or a cloud based computer and/or a cloud based machine learning/relearning interactive expert cognitive computer system (e.g., IBM Watson); and wherein the computer system includes: one or more hardware (e.g., super-processors/processors/microprocessors/nanoprocessors) in communication with a computer readable medium storing one or more algorithms and/or software programs and/or software application programs ("apps") including instructions that are executable by one or more hardware (e.g., super-processors/processors/microprocessors/nanoprocessors).

In the above disclosed specifications "/" has been used to indicate an "or". Any example in the above disclosed specifications is by way of an example only and not by way of any limitation.

The above disclosed specifications are the preferred best mode embodiments of the present invention. However, they are not intended to be limiting only to the preferred best mode embodiments of the present invention. Numerous variations and/or modifications are possible within the scope of the present invention. Accordingly, the disclosed preferred best mode embodiments are to be construed as illustrative only. Those who are skilled in the art can make various variations and/or modifications (e.g., a light source can be utilized instead of a laser, when it is applicable) without departing from the scope and spirit of this invention. The inventors of the present invention are not required to describe each and every conceivable and possible future embodiment in the preferred best mode embodiments of the present invention. See *SRI Int'l v. Matsushita Elec. Corp. of America*, 775F.2d 1107, 1121, 227 U.S.P.Q. (BNA) 577, 585 (Fed. Cir. 1985) (enbanc).

The scope and spirit of this invention shall be defined by the claims and the equivalents of the claims only. The exclusive use of all variations and/or modifications within the scope of the claims is reserved. Unless a claim term is specifically defined in the preferred best mode embodiments, then a claim term has ordinary meaning, as understood by a person with an ordinary skill in the art (e.g., a BS with 3 years of experience in the art), at the time of the present invention. As noted long ago: "Specifications teach. Claims claim". See *Rexnord Corp. v. Laitram Corp.*, 274 F.3d 1336, 1344 (Fed. Cir. 2001). Furthermore, the rights of claims (and rights of the equivalents of the claims under the Doctrine of Equivalents-meeting the "Triple Identity Test" (a) performing substantially the same function, (b) in substantially the same way and (c) yielding substantially the same result See *Crown Packaging Tech., Inc. v. Rexam Beverage Can Co.*, 559 F.3d 1308, 1312 (Fed. Cir. 2009)) of the present invention are not narrowed or limited by the selective import of the specifications (of the preferred embodiments of the present invention) into the claims.

We claim:
1. A subsystem, as an augmented reality personal assistant comprising:
   (a) a first sensor, wherein the first sensor is an eye motion sensor;
   (b) a camera sensor;
   (c) a decoder;
   (d) a display and a projector, wherein one or more pixels or three-dimensional (3-D) pixels of the display are integrated with a second sensor; and
      wherein the first sensor is electrically coupled with the camera sensor,
      wherein the camera sensor is electrically coupled with the decoder,
      wherein the decoder is electrically coupled with the display or the projector,
      wherein the first sensor is determining an item or a person that a user is looking at within the user's field of view,
      wherein the decoder is converting the camera sensor's reading of the item or the person targeted by the first sensor in the user's field of view into a text or a picture image or a video image,
      wherein the text or the picture image or the video image, converted by the decoder is either viewed on the display or projected by the projector on a surface,
   (e) a first microprocessor, wherein the first microprocessor comprises memristors, wherein the first microprocessor further electrically couples with a first non- transitory local data storage media of the subsystem, as the augmented reality personal assistant storing a system operating algorithm,
    wherein the memristors are arranged in two-dimension (2-D) or in three-dimension (3-D),
    wherein the first microprocessor is electrically coupled with the first sensor, the camera sensor, the decoder, the display and the projector,
wherein the subsystem, as the augmented reality personal assistant and a portable Internet appliance are electrically or wirelessly coupled with a cloud based server or a cloud based data storage media,
    wherein the portable internet appliance comprises: a second microprocessor or a neural microprocessor,
    wherein the second microprocessor or the neural processor electrically couples with a second non-transitory local data storage media of the portable internet appliance storing an intelligent rendering algorithm.

2. The subsystem, as the augmented reality personal assistant according to claim 1, further comprises: a contact lens or a contact lens integrated with a nanoscaled optical structure.

3. The subsystem, the augmented reality personal assistant according to claim 1, further electrically or wirelessly couples with or comprises: a third sensor selected from the group consisting of: a gesture sensor and a touch sensor.

4. A subsystem, as an augmented reality personal assistant for social graph or personal analytics comprising:
(a) a first sensor, wherein the first sensor is an eye motion sensor;
(b) a camera sensor;
(c) a decoder;
(d) a display and a projector, wherein one or more pixels or three-dimensional (3-D) pixels of the display are integrated with a second sensor;
(e) a microphone;
(f) a location determination module;
(g) a first microprocessor;
(h) an electrical powering component; and
    wherein the first sensor is electrically coupled with the camera sensor,
    wherein the camera sensor is electrically coupled with the decoder,
    wherein the decoder is electrically coupled with the display or the projector,
    wherein the first sensor is determining an item or a person that a user is looking at within the user's field of view,
    wherein the decoder is converting the camera sensor's reading of the item or the person targeted by the first sensor in the user's field of view into a text or a picture image or a video image,
    wherein the text or the picture image or the video image, converted by the decoder is either viewed on the display or projected by the projector of on a surface,
    wherein the first microprocessor is electrically coupled with the first sensor, the camera sensor, the decoder, the display, the projector, the microphone, the location determination module and the electrical powering component,
    wherein the first microprocessor further comprises memristors, wherein the first microprocessor further electrically couples with a first non-transitory local data storage media of the subsystem, as the augmented reality personal assistant storing a system operating algorithm,
    wherein the memristors are arranged in two-dimension (2-D) or in three-dimension (3-D),
    wherein the first microprocessor further electrically couples with or comprises: a set of computer implementable instructions to interpret or analyze or learn activities or contextual information of the user,
    wherein the said set of computer implementable instructions is stored in the first non-transitory local data storage media of the subsystem, as the augmented reality personal assistant or in a cloud based data storage media or a cloud based server,
    wherein the first microprocessor further electrically couples with or comprises: a set of computer implementable instructions to interpret or analyze or learn a location of the user,
    wherein the said set of computer implementable instructions is stored in the first non-transitory local data storage media of the subsystem, as the augmented reality personal assistant or in the cloud based data storage media or the cloud based server,
wherein the subsystem, as the augmented reality personal assistant and a portable internet appliance are electrically or wirelessly coupled with the cloud based data storage media or the cloud based server,
    wherein the portable internet appliance comprises: a second microprocessor or a neural microprocessor,
    wherein the second microprocessor or the neural processor electrically couples with a second non-transitory local data storage media of the portable internet appliance storing an intelligent rendering algorithm.

5. The subsystem, as the augmented reality personal assistant according to claim 4, further comprises: a contact lens or a contact lens integrated with a nanoscaled optical structure.

6. The subsystem, as the augmented reality personal assistant according to claim 4, further electrically or wirelessly couples with or comprises: a third sensor selected from the group consisting of: a gesture sensor and a touch sensor.

7. The subsystem, as the augmented reality personal assistant according to claim 4, further comprises: a component selected from the group consisting of: a radio frequency identification device (RFID) and a near field communication (NFC) transceiver.

8. The subsystem, as the augmented reality personal assistant according to claim 4, further comprises: a transceiver module selected from the group consisting of: a radio transceiver, a millimeter wave transceiver and a terahertz band transceiver.

9. The subsystem, as the augmented reality personal assistant according to claim 4, further comprises: coupling with an algorithm selected from the group consisting of: a face recognition algorithm, a gesture recognition algorithm, a sound recognition algorithm, a voice recognition algorithm and a voice-to-text conversion algorithm stored in the first non-transitory local data storage media of the subsystem, as the augmented reality personal assistant or in the cloud based data storage media or the cloud based server.

10. The subsystem, as the augmented reality personal assistant according to claim 4, further comprises: coupling with a pattern recognition algorithm or a data mining algorithm stored in the first non-transitory local data storage media of the subsystem, as the augmented reality personal assistant or in the cloud based data storage media or the cloud based server.

11. The subsystem, as the augmented reality personal assistant according to claim 4, further comprises: coupling with a predictive algorithm stored in the first non-transitory local data storage media of the subsystem, as the augmented reality personal assistant or in the cloud based data storage media or the cloud based server.

12. A subsystem, as an augmented reality personal assistant for recommending a user comprising:
   (a) a first sensor, wherein the first sensor is an eye motion sensor;
   (b) a camera sensor;
   (c) a decoder;
   (d) a display and a projector, wherein one or more pixels or three-dimensional (3-D) pixels of the display are integrated with a second sensor;
   (e) a microphone;
   (f) a location determination module;
   (g) a first microprocessor;
   (h) an electrical powering component; and
      wherein the first sensor is electrically coupled with the camera sensor,
      wherein the camera sensor is electrically coupled with the decoder,
      wherein the decoder is electrically coupled with the display or the projector,
      wherein the first sensor is determining an item or a person that a user is looking at within the user's field of view,
      wherein the decoder is converting the camera sensor's reading of the item or the person targeted by the first sensor in the user's field of view into a text or a picture image or a video image,
      wherein the text or the picture image or the video image, converted by the decoder is either viewed on the display or projected by the projector of on a surface,
      wherein the first microprocessor is electrically coupled with the first sensor, the camera sensor, the decoder, the display, the projector, the microphone, the location determination module and the electrical powering component,
      wherein the first microprocessor comprises memristors, wherein the first microprocessor further electrically couples with a first non-transitory local data storage media of the subsystem, as the augmented reality personal assistant storing a system operating algorithm,
      wherein the memristors are arranged in two-dimension (2-D) or in three-dimension (3-D),
      wherein the first microprocessor further electrically couples with or comprises: a set of computer implementable instructions to interpret or analyze or learn activities or contextual information of the user,
      wherein the said set of computer implementable instructions is stored in the first non-transitory local data storage media of the subsystem, as the augmented reality personal assistant or in a cloud based data storage media or a cloud based server,
      wherein the first microprocessor further electrically couples with or comprises: a set of computer implementable instructions to interpret or analyze or learn personal communication of the user in a natural language,
      wherein the said set of computer implementable instructions is stored in the first non-transitory local data storage media of the subsystem, as the augmented reality personal assistant or in the cloud based data storage media or the cloud based server,
      wherein the personal communication of the user is selected from the group consisting of: voice communication, text communication, e-mail communication and video communication,
   wherein the subsystem, as the augmented reality personal assistant and a portable internet appliance are electrically or wirelessly coupled with the cloud based data storage media or the cloud based server,
      wherein the portable internet appliance comprises: a second microprocessor or a neural microprocessor,
      wherein the second microprocessor or the neural processor electrically couples with a second non-transitory local data storage media of the portable internet appliance storing an intelligent rendering algorithm.

13. The subsystem, as the augmented reality personal assistant according to claim 12, further comprises: a contact lens or a contact lens integrated with a nanoscaled optical structure.

14. The subsystem, as the augmented reality personal assistant according to claim 12, further electrically or wirelessly couples with or comprises: a third sensor selected from the group consisting of: a gesture sensor and a touch sensor.

15. The subsystem, as the augmented reality personal assistant according to claim 12, further comprises: a component selected from the group consisting of: a radio frequency identification device (RFID) and a near field communication (NFC) transceiver.

16. The subsystem, as the augmented reality personal assistant according to claim 12, further comprises: a transceiver module selected from the group consisting of: a radio transceiver, a millimeter wave transceiver and a terahertz band transceiver.

17. The subsystem, as the augmented reality personal assistant according to claim 12, further comprises: coupling with an algorithm selected from the group consisting of: a face recognition algorithm, a gesture recognition algorithm, a sound recognition algorithm, a voice recognition algorithm and a voice-to-text conversion algorithm stored in the first non-transitory local data storage media of the subsystem, as the augmented reality personal assistant or in the cloud based data storage media or the cloud based server.

18. The subsystem, as the augmented reality personal assistant according to claim 12, further comprises: coupling with a pattern recognition algorithm or a data mining algorithm stored in the first non-transitory local data storage media of the subsystem, as the augmented reality personal assistant or in the cloud based data storage media or the cloud based server.

19. The subsystem, as the augmented reality personal assistant according to claim 12, further comprises: coupling with a predictive algorithm stored in the first non-transitory local data storage media of the subsystem, as the augmented reality personal assistant or in the cloud based data storage media or the cloud based server.

20. The subsystem, as the augmented reality personal assistant according to claim 12, further comprises: coupling with a set of computer implementable instructions for recommending or advising the user stored in the first non-transitory local data storage media of the subsystem, as the augmented reality personal assistant or in the cloud based data storage media or the cloud based server.

\* \* \* \* \*